US007781565B2

(12) United States Patent
Pasqualini et al.

(10) Patent No.: US 7,781,565 B2
(45) Date of Patent: Aug. 24, 2010

(54) COMPOSITIONS AND METHODS RELATED TO PROFILING A PLURALITY OF CELLS BASED ON PEPTIDE BINDING

(75) Inventors: Renata Pasqualini, Houston, TX (US); Wadih Arap, Houston, TX (US); Mikhail Kolonin, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 11/684,379

(22) Filed: Mar. 9, 2007

(65) Prior Publication Data

US 2007/0248952 A1 Oct. 25, 2007

Related U.S. Application Data

(60) Provisional application No. 60/780,893, filed on Mar. 9, 2006.

(51) Int. Cl.
*A61K 38/00* (2006.01)
*A61K 39/00* (2006.01)

(52) U.S. Cl. .................................... 530/300; 424/192.1

(58) Field of Classification Search ....................... None
See application file for complete search history.

(56) References Cited

U.S. PATENT DOCUMENTS

| | | | | |
|---|---|---|---|---|
| 6,372,473 | B1 * | 4/2002 | Moore et al. | 435/212 |
| 2002/0142981 | A1 | 10/2002 | Horne et al. | 514/44 |
| 2003/0143539 | A1 | 7/2003 | Bertucci et al. | 435/6 |
| 2004/0048243 | A1 | 3/2004 | Arap et al. | 435/5 |

FOREIGN PATENT DOCUMENTS

| | | |
|---|---|---|
| WO | WO 02/20722 | 3/2002 |
| WO | WO 02/20822 | 3/2002 |
| WO | WO 03/086289 A2 * | 10/2003 |
| WO | WO 2004/038020 | 5/2004 |

OTHER PUBLICATIONS

Tsumoto et al (FEBS Letters, 2002, 525:77-82).*
Adam et al., "Comprehensive proteomic analysis of breast cancer cell membranes reveals unique proteins with potential roles in clinical cancer," *J. Biol. Chem.*, 278:6482-6489, 2003.
Arap et al., "Cancer Treatment by Targeted Drug Delivery to Tumor Vasculature in a Mouse Model," *Science*, 279:377-80, 1998.
Arap et al., "Steps toward mapping the human vasculature by phage display," *Nature Med.*, 8:121-127, 2002.
Bals and Jany, "Identification of disease genes by expression profiling," *Eur. Respir. J.*, 18:882-889, 2001.
Blower et al., "Pharmacogenomic analysis: correlating molecular substructure classes with microarray gene expression data," *Pharmacogenomics J.*, 2:259-271, 2002.
Brown, "NCI's anticancer drug screening program may not be selecting for clinically active compounds," *Oncol. Res.*, 9:213-5, 1997.
Celis and Gromov, "Proteomics in translational cancer research: Toward an integrated approach," *Cancer Cell*, 3:9-15, 2003.
Cloutier et al., "Profiling of Proteolytic Activities Secreted by Cancer Cells using Phage Display Substrate Technology," *Tumor Biol.*, 25:24-30, 2004.
Das, "Phage display: Brussels Symposium highlights the gains made on both basic and applied fronts," *American Biotechnology Laboratory*, pp. 16, 18, Dec., 1999.
Drapkin et al., "expression of Candidate Tumor Markers in Ovarian Carcinoma and Benign Ovary: Evidence for a Link Between Epithelial Phenotype and Neoplasia," *Human Pathol.*, 35:1014-1021, 2004.
Efferth et al., "Expression profile of proteins involved in the xenotransplantability of non-small cell lung cancers into athymic nude mice," *Int. J. Oncology*, 20:391-395, 2002.
Farmer, "Targeted lung cancer therapies," *Nat. Reviews*, 3:547-548, 2004.
Fojo et al., "Identification of non-cross-resistant platinum compounds with novel cytotoxicity profiles using the NCI anticancer drug screen and clustered image map visualizations.," *Crit. Rev. Oncol. Hematol.*, 53:25-34, 2005.
Giordano et al., "Biopanning and rapid analysis of selective interactive ligands," *Nat. Med.*, 7:1249-1253, 2001.
Hanash et al., "A proteomic approach to the identification of lung cancer markers," *Disease Markers*, 17:295-300, 2001.
Holbeck, "Update on NCI in vitro drug screen utilities," *Eur. J. Cancer*, 40:785-793, 2004.
Kolonin et al., "Ligand-Directed Surfaced Profiling of Human Cancer Cells with Combinatorial Peptide Libraries," *Cancer Res.*, 66(1):1-7, 2006.
Kolonin et al., "Molecular addresses in blood vessels as targets for therapy," *Curr. Opin. Chem. Biol.*, 5:308-13, 2001.
Kolonin et al., "Reversal of obesity by targeted ablation of adipose tissue," *Nat. Med.*, 6:625-632, 2004.
Kolonin et al., "Teratogenicity induced by targeting a placental immunoglobulin transporter," *Proc. Natl. Acad. Sci. USA*, 99:13055-13060, 2002.
Lage, "Proteomics in cancer cell research: An analysis of therapy resistance," *Pathology*, 200:105-117, 2004.
Landon and Deutscher, "Combinatorial discovery of tumor targeting peptides using phage display," *J. Cell Biochem.*, 90:509-517, 2003.
Monks et al., "Feasibility of a high-flux anticancer drug screen using a diverse panel of cultured human tumor cell lines," *J. Natl. Cancer Inst.*, 83:757-66, 1991.
Mori, "Cancer-Specific Ligands Identified from Screening of Peptide-Display Libraries," *Current Pharma. Design*, 10:2335-2343, 2004.
Myers et al., "A protein expression database for the molecular pharmacology of cancer," *Electrophoresis*, 18:647-653, 1997.
Nishizuka et al., "Proteomic profiling of the NCI-60 cancer cell lines using new high-density reverse-phase lysate microarrays," *Proc. Natl. Acad. Sci. USA*, 100:14229-14234, 2003.
Pasqualini and Ruoslahti, "Organ targeting in vivo using phage display peptide libraries," *Nature*, 380:364-366, 1996.
Pasqualini et al., "Aminopeptide N Is a Receptor for Tumor-homing Peptides and a Target for Inhibiting Angiogenesis," *Cancer Res.*, 60:722-727, 2000.

(Continued)

*Primary Examiner*—Sean E Aeder
(74) *Attorney, Agent, or Firm*—Fulbright & Jaworski LLP

(57) ABSTRACT

Methods and compositions are described for classifying cells and/or peptides that associate or bind with a particular characteristic pattern to a plurality of cells or cell lines. Aspects of the invention also include the use of peptide(s) having an appropriate binding characteristic to deliver a drug to a cell or cell population.

35 Claims, 12 Drawing Sheets

OTHER PUBLICATIONS

Pasqualini et al., "Chapter 22: In Vivo Selection of Phage-display Libraries," In: *Phage Display*, A Laboratory Manual, Barbas et al. (Eds.), NY, Cold Spring Harbor Laboratory Press, 22.1-22.24, 2001.

Rabow et al., "Mining the National Cancer Institute's tumor-screening database: identification of compounds with similar cellular activities," *J. Med. Chem*., 45:818-40, 2002.

Sato et al., "Discovery of Novel Targets for Aberrant Methylation in Pancreatic Carcinoma Using High-Throughput Microarrays," *Cancer Res*., 63:3735-3742, 2003.

Scherf et al., "A gene expression database for the molecular pharmacology of cancer," *Nat. Genet*., 24:236-244, 2000.

Sheldon, "Cell Signalling Pathways: Market for Novel Cancer Therapies," *Drug and Market Development*, Sep. 24, 2004.

Shin et al., "Global profiling of the cell surface proteome of cancer cells uncovers an abundance of proteins with chaperone function," *J. Biol. Chem*., 278:7607-7616, 2003.

Somers, "Profiling the Cancer Immunome Using Phage cDNA Display," In: Cambridge Healthtech Institute's Fourth Annual Phage Display: The Chemistry Set for Proteins, 2003 Program, Apr. 22-23, 2002.

Szakacs et al., "Predicting drug sensitivity and resistance: profiling ABC transporter genes in cancer cells," *Cancer Cell*, 6:129-37, 2004.

Tammen et al., "Expression profiling of breast cancer cells by differential peptide display," *Breast Cancer Res. Treat*., 79:83-93, 2003.

Tomlinson and Holt, "Protein profiling comes of age," *Genome Biology*, 2:1004.1-1004.3, 2001.

Van Beijnum et al., "Target validation for genomics using peptide-specific phage antibodies: a study of five gene products overexpressed in colorectal cancer," *Int. J. Cancer*., 101:118-127, 2002.

Vogelstein and Kinzler, "Cancer genes and the pathways they control," *Nat. Med*., 10:789-799, 2004.

Volm et al., "Protein expression profiles indicative for drug resistance of non-small cell lung cancer," *Br. J. Cancer*, 87:251-257, 2002.

Walloyist et al., "Linking the growth inhibition response from the National Cancer Institute's anticancer screen to gene expression levels and other molecular target data," *Bioinformatics*, 19:2212-24, 2003.

Wallqvist et al., "Establishing connections between microarray expression data and chemotherapeutic cancer pharmacology," *Mol. Cancer Ther*., 1:311-20, 2002.

Weinstein et al., "An Information-Intensive Approach to the Molecular Pharmacology of Cancer," *Science*, 275:343-349, 1997.

Weinstein et al., "The bioinformatics of microarray gene expression profiling," *Cytometry*, 47:46-49, 2002.

Weinstein, "Integromic Analysis of the NCI-60 Cancer Cell Lines," *Breast Disease*, 19:11-22, 2004.

Wong et al., "Profiling of protein kinases in the neoplastic transformation of human ovarian surface epithelium," *Gynecologic Oncology*, 82:305-311, 2001.

Yanagisawa et al., Proteomic patterns of tumour subsets in non-small-cell lung cancer,: *Lancet*, 362:433-439, 2003.

Zaharevitz et al., "Compare: A web accessible tool for investigating mechanisms of cell growth inhibition," *J. Mol. Graph. Model*, 30:297-303, 2002.

Zhang et al., "Neuroblastoma tumor cell-binding peptides identified through random peptide phage display," *Cancer Lett*., 171:153-164, 2001.

Zurita et al., "Combinatorial Screenings in Patients: The Interleukin-11 Receptor αas a Candidate Target in the Progression of Human Prostate Cancer," *Cancer Res*., 2004:64:435-9, 2004.

* cited by examiner

| Panel | Cell Line | Value | I Lowest value Highest value I |
|---|---|---|---|
| Leukemia | CCRF-CEM | 3000 | |
| Leukemia | K-562 | 3000 | |
| Leukemia | MOLT-4 | 3000 | |
| Leukemia | RPMI-8226 | 3000 | |
| Leukemia | SR | 3000 | |
| Non-Small Cell Lung Cancer | AS49/ATCC | 38195 | |
| Non-Small Cell Lung Cancer | EKVX | 122865 | |
| Non-Small Cell Lung Cancer | HOP-62 | 8207 | |
| Non-Small Cell Lung Cancer | HOP-92 | 106423 | |
| Non-Small Cell Lung Cancer | NCI-H226 | 27396 | |
| Non-Small Cell Lung Cancer | NCI-H23 | 3000 | |
| Non-Small Cell Lung Cancer | NCI-H322M | 3000 | |
| Non-Small Cell Lung Cancer | NCI-H460 | 128674 | |
| Non-Small Cell Lung Cancer | NCI-H522 | 3000 | |
| Colon Cancer | COLO 205 | 3000 | |
| Colon Cancer | HCC-2998 | 3000 | |
| Colon Cancer | HCT-116 | 3000 | |
| Colon Cancer | HCT-15 | 3000 | |
| Colon Cancer | HT29 | 3000 | |
| Colon Cancer | KM12 | 3000 | |
| Colon Cancer | SW-620 | 3000 | |
| CNS Cancer | SF-268 | 3000 | |
| CNS Cancer | SF-295 | 23095 | |
| CNS Cancer | SF-539 | 32026 | |
| CNS Cancer | SNB-19 | 5565 | |
| CNS Cancer | SNB-75 | 45489 | |
| CNS Cancer | U251 | 3000 | |
| Melanoma | LOX IMVI | 3000 | |
| Melanoma | MALME-3M | 3000 | |
| Melanoma | M14 | 3000 | |
| Melanoma | SK-MEL-2 | 3000 | |
| Melanoma | SK-MEL-28 | 3000 | |
| Melanoma | SK-MEL-5 | 3000 | |
| Melanoma | UACC-257 | 3000 | |
| Melanoma | UACC-62 | 3000 | |
| Ovarian Cancer | IGROV1 | 56354 | |
| Ovarian Cancer | OVCAR-3 | 3000 | |
| Ovarian Cancer | OVCAR-4 | 3000 | |
| Ovarian Cancer | OVCAR-5 | 3000 | |
| Ovarian Cancer | OVCAR-8 | 3000 | |
| Ovarian Cancer | SK-OV-3 | 3000 | |
| Renal Cancer | 786-0 | 3000 | |
| Renal Cancer | A498 | 3000 | |
| Renal Cancer | ACHN | 3000 | |
| Renal Cancer | CAKI-1 | 3000 | |
| Renal Cancer | RXF 393 | 3000 | |
| Renal Cancer | SN12C | 3000 | |
| Renal Cancer | TK-10 | 3000 | |
| Renal Cancer | UO-31 | 3000 | |
| Prostate Cancer | PC-3 | 3000 | |
| Prostate Cancer | DU-145 | 3000 | |
| Breast Cancer | MCF7 | 3000 | |
| Breast Cancer | NCI/ADR-RES | 27835 | |
| Breast Cancer | MDA-MB-231/ATCC | 3000 | |
| Breast Cancer | HS 578T | 3000 | |
| Breast Cancer | MDA-MB-435 | 3000 | |
| Breast Cancer | MDA-N | 22411 | |
| Breast Cancer | BT-549 | 4129 | |
| Breast Cancer | T-47D | 3000 | |

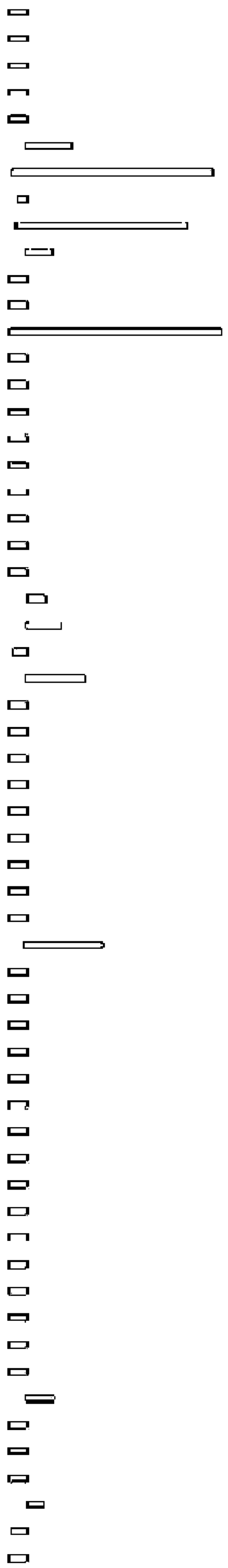

Fig. 4

FIG. 8
CSGIGSGGC - phage
CRFESSGGC - phage
insertless phage

COMPOSITIONS AND METHODS RELATED TO PROFILING A PLURALITY OF CELLS BASED ON PEPTIDE BINDING

This application claims the benefit of U.S. Provisional Patent Application No. 60/780,893, filed on Mar. 9, 2006.

The United States Government owns rights in present invention pursuant to grant number DAMD17-03-1-0638 from the Department of Defense, and grant CA103056 from the National Institutes of Health.

1. TECHNICAL FIELD

The present invention is directed generally to method and compositions related to molecular biology, virology, and oncology. In certain aspects it is directed to compositions comprising and methods of profiling and/or classifying a plurality of cells or cell lines based on peptide binding characteristics.

BRIEF SUMMARY OF THE INVENTION

An embodiment of the invention includes methods of profiling cell lines and/or identifying peptide sequences or structures that bind a target population or family of cells. The methods include providing a plurality of cell lines; contacting each cell line with a library of phage displaying random heterologous peptides on their surface; obtaining phage that bind each of the cell lines; identifying peptides that bind each cell line; and classifying each cell line based on the identified peptides. The method can further comprise classifying each identified peptide based on the cell lines that bind each identified peptide. In one aspect, the cell lines include cancer cell lines. Cancer cell lines may include, but are not limited to kidney, breast, colon, lung, prostate, brain, liver, pancreatic, uterine, neuronal, skin, head and neck, leukemic, lymphocytic, or ovarian cancer cell lines. In another aspect, the panel is cancer cell lines. In a particular aspect, the panel is a NCI 60 panel of cancer cell lines. The methods further include identifying a peptide that binds to a majority of the cancer cell lines or cancer cells of common origin. Furthermore, methods can also include analyzing the identified peptides to identify similarities with known receptor ligands.

In certain aspects, classifying the cell line is performed by clustering analysis. Clustering analysis can be used to construct a clustered image map (CIM). In a particular aspect, classifying the identified peptide is performed by clustering analysis. Clustering analysis can be used to construct a clustered image map. In another aspect, the methods may also include identifying receptors for at least one of the identified peptides comprising the steps of providing an identified peptide; labeling the identified peptide; contacting an appropriate cell line with the labeled peptide; isolating a receptor—peptide complex; and identifying the receptor bound to the labeled peptide.

In another embodiment, a group of peptides comprising five or more peptides can be classified or identified as selectively bind to a sub-population of cell lines, wherein the peptides include, but are not limited to those listed in Table 3 and described herein. In certain aspects, a sub sequence of the peptide may be identified as conferring to the peptide a certain binding characteristic.

In still further embodiments, methods of the invention can be used to classify a cell or cell line. Methods of classifying a cell line include, but are not limited to steps comprising: contacting a cell with a group of selected peptides or polypeptides that differentially bind cells of a known origin; detecting the peptides that bind the cell line; and assessing the classification of the cell line based on the peptide(s) that bind the cell line. Thus, in certain aspects, classifying a cell may comprise determining whether as cell expresses a certain receptor polypeptide, is susceptible to a particular therapy or determining the tissue of origin for the cell. In certain aspects of the invention, a group of selected peptide for use according to the invention are further defined as cyclic or partially peptides, such as peptides comprising a disulfide bond. In certain cases, a group of selected peptides or polypeptides may comprise at least 3, 4, 5, 6, 7, 8, 9, 10, 15, 20, 25, 30 or more distinct peptides or polypeptides.

Thus, in a further specific embodiment there is provided a method for classifying a cell comprising obtaining or having a sample comprising a cell; contacting the cell with a group of peptides or polypeptides that differentially bind cells of a known origin or type; detecting the peptides that bind to the cell and classifying the cell based on the peptide binding. As described supra, in certain aspects, a group of selected peptides or polypeptides comprise amino acid sequences selected from those provided in Table 3. Thus, in certain cases a group of selected peptides or polypeptides comprise 3, 4, 5, 6, 7, 8, 9, 10, 15, 20, 25, 30 or more members that comprising an amino acid sequence according to Table 3. The skilled artisan will recognize that selected peptide or polypeptides of the invention may in some aspects be labeled for example with an enzyme, a fluorophor or a radio isotope.

In some aspects, a selected peptide or polypeptide may be a cyclic or partially polypeptide such as a peptide or polypeptide comprising a disulfide bond. In some preferred aspects, the cyclic region of a peptide or polypeptide comprises 5, 6, 7, 8, 9, 10 or more amino acids. For example, in certain aspects, a selected peptide or polypeptide comprises an amino acid sequence provided in Table 3 wherein the given amino acid sequence is comprised in the cyclic region of the polypeptide. Thus, it is contemplated that a selected peptide or polypeptide may comprise an amino acid sequence of Table 3 wherein the sequence is flanked by cysteine residues such that the cysteine residues may be linked by a disulfide bond.

In some aspects of the invention a method for classifying a cell according to the invention may comprise comparing the binding profile of a group of selected peptides or polypeptides to a cell to a similar binding profile from a cell with a known classification. Such a comparison may be performed directly or may performed by consulting a chart or database of binding profiles. For example, a chart or database of binding profiles may comprise binding profiles from cells of 5, 10, 15, 20, 25 or more different classifications. In certain aspects, a chart or database of binding profiles may comprise clustering analysis of the binding of selected peptides or polypeptide to cells of different classification. Thus, in some cases a chart or database of binding profiles may comprise a clustered image map (CIM). Thus, classifying a cell may be performed by for example clustering analysis.

In still further aspects of the invention there is provided a method for treating a subject comprising obtaining or having a sample from the subject comprising a cell; classifying the cell (e.g., by the methods described supra); and treating the subject with a therapeutic based upon the classification of the cell. For example, in some cases a subject may be defined as a cancer patient. In this case a cancer cell from the subject may be classified. Classification of the cell may for example comprising determining the tissue of origin, receptor status or susceptibility of the cell to particular anticancer therapy. Thus, based upon the classification of the cell the subject may be treated with an appropriate anticancer therapy. For example, methods of the invention may be used to classify a cell as susceptible or resistant to radiation therapy, immunotherapy, surgical therapy or chemotherapy. Furthermore, methods of the invention may be used to classify the cell as susceptible or resistant to a particular chemotherapeutic agent or class of chemotherapeutic agents. Thus, methods of the invention may involve classifying a cancer cell from a subject as susceptible or resistant to an anticancer therapy and treating the subject with one or more anticancer therapies that the cell is susceptible to.

In certain aspects the invention concerns obtaining or having a sample such as a cell. It is contemplated that in cases where a sample is from a subject the sample may be directly obtained or may be obtained by a third party and subsequently subjected to methods described herein. Furthermore, in certain aspects it is contemplated that methods of the invention may be defined as a method for aiding in the therapy of a subject comprising classify a cell from the subject (e.g., as having certain protein receptor expression or being from a tissue of a particular origin) and providing the classification information to a third party such as a medical professional to aid in the therapy of the subject.

In yet another embodiment of the invention includes a method of classifying a peptide(s). Methods of peptide classification include, but are not limited to steps comprising: contacting a plurality of cell lines with a library of peptides that differentially bind the cells; detecting the peptides that bind the cell line; and classifying the peptides based on the cells that bind the peptide.

In certain aspects an EphA5 receptor can be targeted by using a composition comprising a peptide sequence of CSGIGSGGC (SEQ ID NO:2) or CRFESSGGC (SEQ ID NO:3). The skilled artisan will further recognize that in certain aspects a peptide targeting sequence of the invention is cyclic. Thus, there is provided EphA5 receptor targeting composition comprising a cyclic polypeptide wherein the cyclic polypeptide comprises the amino acid sequence SGIGSGG (SEQ ID NO:4) or RFESSGG (SEQ ID NO:5). As exemplified herein in certain aspects an cyclic EphA5 targeting composition may comprise a peptide sequence according to SEQ ID NO:4 or SEQ ID NO:5 flanked by cysteine residues thereby forming a cyclic targeting agent via disulfide bonds between the cysteine residues. As used herein the termed flanked means that the indicated amino acid sequence are between two cysteine residues however it is contemplated that in some cases additional amino acids may also be comprised between the two cysteine residues.

A composition of the invention can be coupled (either non-covalently or covalently, or indirectly via an intermediate such as a liposome or directly) to a therapeutic or imaging agent. The therapeutic can include, but is not limited to a small molecule, a drug, or a therapeutic peptide. For example, in certain aspects, a therapeutic composition of the invention comprises a polypeptide. In these aspects the therapeutic Eph5A receptor targeting composition may comprise a fusion protein. Thus, in some very specific cases the therapeutic polypeptide may be a toxin or other cytotoxic molecule capable of inducing cell death in Eph5A receptor expressing cells. Imaging agents for use in the invention include but are not limited to MRI contrast agents, radio isotopes, fluorophors and mass tags (e.g., for detection via mass spectrometry).

In certain aspects there is provided an EphA5 receptor agonist comprising the amino acid sequence SGIGSGG (SEQ ID NO:4) or RFESSGG (SEQ ID NO:5). As described above in some cases the EphA5 receptor agonist is a cyclic peptide or polypeptide wherein the cyclic region comprises the amino acid sequence of SEQ ID NO:4 or SEQ ID NO:5. Thus, in some case the agonist is a cyclic peptide or polypeptide comprising a disulfide bond such as a peptide or polypeptide wherein the amino acid sequence of SEQ ID NO:4 or SEQ ID NO:5 are flanked by cysteine residues (e.g., as in SEQ ID NO:2 or SEQ ID NO:3).

Thus, in still further aspects of the invention there is provided a method for treating an Eph5A receptor positive cell comprising administering to the cell an EphA5 receptor targeting therapeutic as described supra. Thus, in some aspects a method of the invention may be further defined as a methods for treating a subject comprising an EphA5 receptor positive cell by administering an effective amount of an EphA5 receptor targeting therapeutic. For example, in certain cases a subject may be a cancer patient comprising an EphA5 receptor positive positive cancer such as a lung cancer or neuronal cancer. In still further aspects there is provided a method for treating a subject with a an EphA5 receptor positive cancer by administering an EphA5 receptor targeting therapeutic wherein the therapeutic comprising a cytotoxic agent or an anticancer agent.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

For a more complete understanding of the present invention, reference is now made to the following descriptions taken in conjunction with the accompanying drawing, in which:

FIG. 2A, EGFR-binding peptide sequences isolated from the SKOV-3 selected phage pool were matched in each orientation to protein sequences of biological human EGFR ligands (leader peptide sequence underlined). Matches displayed are peptides with three or more amino acids being identical (red) and one or more being from the same class (green) as the correspondingly positioned protein amino acids. Tripeptides listed in Table 1 (yellow). FIG. 2B, isolation of peptides targeting EGFR. Binding of SKOV3-selected phage pool to immobilized EGFR compared with BSA in rounds 1 and 2 of biopanning of SKOV3-selected phage pool on immobilized human EGFR.

FIG. 3A, Ephrin-mimic phage displaying the enriched motif GGS were selected on EphA5-coated microtiter wells. Phage showing specific binding to EphA5 was analyzed for its distinctive binding to EphA5 compared to EphA4 receptor (FIG. 3B). BSA and fd-tet insertless phage were used as negative controls.

FIG. 4: EphA5 receptor expression in the NCI-60. From microarray analysis reported at dtp.nci.nih.gov/mtweb/servlet/moltidsearch?moltid=MT894.

FIG. 7A, Two-dimensional hierarchical clustering was applied to the frequencies of 3,280 unique tripeptides (rows) found in cell-binding CX7C peptides selected on the NCI-60 cells (columns). Tripeptides were clustered based on their correlations with cell lines; cell lines were clustered based on their correlations with tripeptides. Tripeptide frequencies were mean-subtracted and average-linkage clustered with correlation metric (the data were transformed to the mean of 0; variance of 1). The color in each CIM segment ranges from blue (high negative correlation) to red (high positive correlation), as indicated by the scale bar. Cell lines are color-coded based on previously defined histological tumor origin. FIG. 7B, A control two-dimensional hierarchical clustering applied under the Poisson assumption to 3,280 randomly simulated tripeptide frequencies (rows) showed no obvious pattern, thus indicating that clusters in A were not generated at random.

DETAILED DESCRIPTION OF THE INVENTION

Figure 1:
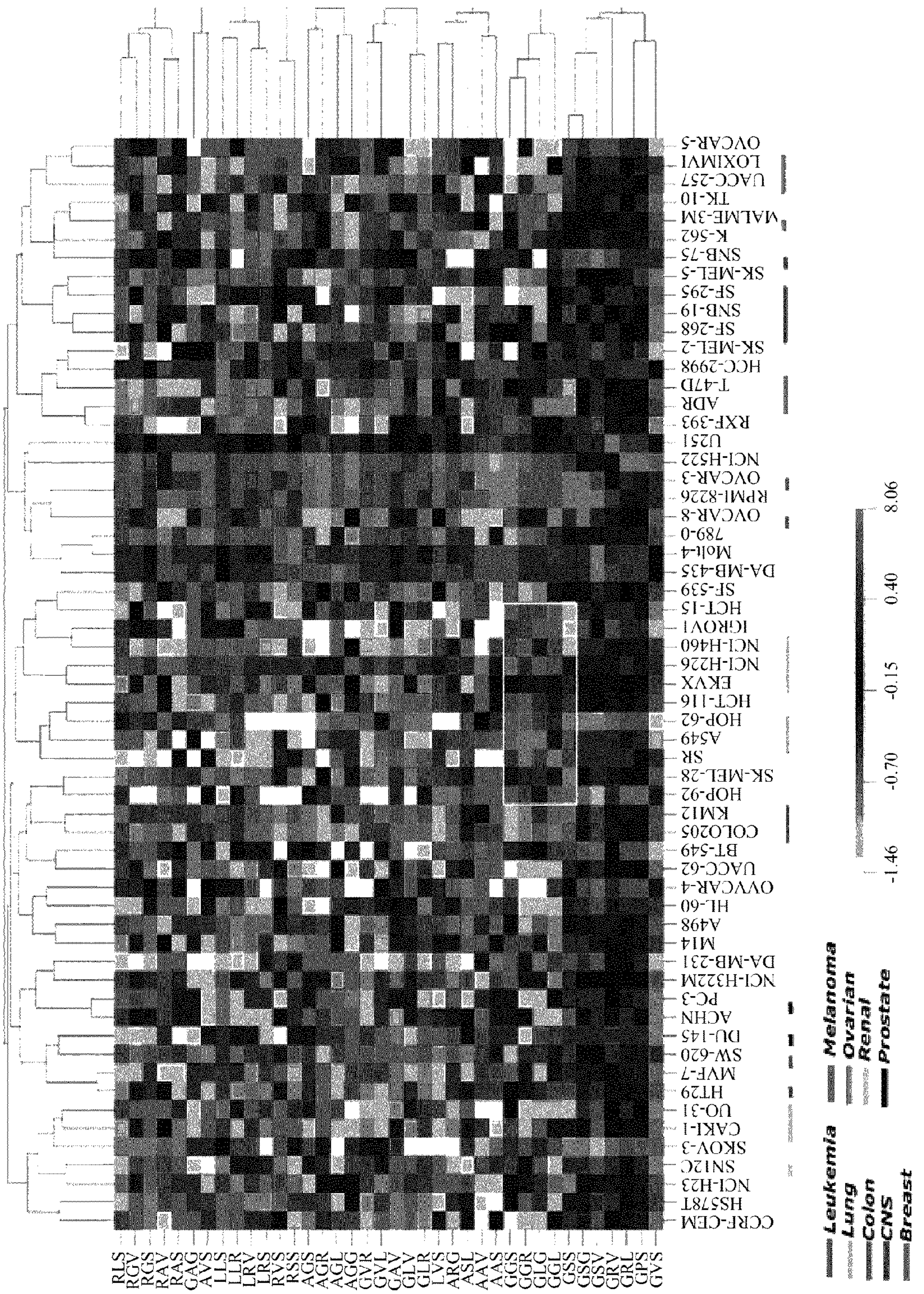
FIG. 1: Selectivity of broad-specificity tripeptides for clusters of NCI-60 cell lines. Two-dimensional hierarchical clustering was applied to the frequencies of 38 tripeptides (rows) encountered in $CX_7C$ peptides selected on NCI-60 cell lines (columns). Tripeptides selected on all but one cell line of common origin were clustered based on their correlations with cell lines; cell lines were clustered based on their correlations with the tripeptides. Tripeptide frequencies were mean subtracted and average linkage clustered with correlation metric. Amino acid color code: red, hydrophobic; green, neutral and polar; purple, basic. The color in each CIM segment ranges from blue (negative correlation) to red (positive correlation), as indicated by the scale bar. Cell lines are color-coded based on previously defined histologic tumor origin (Monks et al., 1991, Weinstein et al., 1997. Bars underneath dendrogram, clusters of cells of similar tumor tissue origin (one exception allowed). Boxed, cluster of lung cancer-derived cell lines and associated/dissociated tripeptides.

A collection of 60 cell lines derived from human tumors (NCI-60) has been widely explored as a tool for anticancer drug discovery. In one aspect of the invention, the cell surface of the NCI-60 was profiled by high-throughput screening of a phage-displayed random peptide library and classified the cell lines according to the binding selectivity of 26,031 recovered tripeptide motifs. By analyzing selected cell-homing peptide motifs and their NCI-60 recognition patterns, the inventors established that some of these motifs (a) are similar to domains of human proteins known as ligands for tumor cell receptors and (b) segregate among the NCI-60 in a pattern correlating with expression profiles of the corresponding receptors. The inventors biochemically validated some of the motifs as mimic peptides of native ligands for the epidermal growth factor receptor. The results indicate that ligand-directed profiling of tumor cell lines can select functional peptides from combinatorial libraries based on the expression of tumor cell surface molecules, which in turn could be exploited as "druggable" receptors in specific types of cancer (Kolonin et al., 2006).

The National Cancer Institute panel of human cancer cell lines from different histologic origins and grades (NCI-60) has been extensively used to screen compounds for anticancer activity (Monks et al., 1991; Weinstein et al., 1997). The NCI-60 includes carcinomas of several origins (kidney, breast, colon, lung, prostate, and ovarian), tumors of the central nervous system, malignant melanomas, leukemias, and lymphomas. Gene expression determined by high-throughput microarrays has been used to survey the variation in abundance of thousands of distinct transcripts in the NCI-60; such data provided functional insights about the corresponding gene products in tumor cell transformation (Weinstein et al., 1997; Scherf et al., 2000; Nishizuka et al, 2003). This information-intensive genomic approach has yielded candidate diagnostic tumor markers to be validated at the protein level in prospective studies (Nishizuka et al., 2003). Moreover, systematic proteomic studies based on two-dimensional PAGE (Myers et al., 1997) and protein microarrays (Nishizuka et al., 2003) have also been implemented. Finally, in parallel with the NCI-60 transcriptome and proteome initiatives, pharmacologic sensitivity of the cells to $>10^5$ different chemical compounds has been registered (Monks et al., 1991; Weinstein et al., 1997). Indeed, for some genes, correlation of expression data to drug sensitivity profiles has uncovered the mechanistic basis for the drug activity (Scherf et al., 2000; Zaharevitz et al., 2002; Blower et al., 2002; Rabow et al., 2002; Wallqvist et al., 2002; Szakacs et al., 2004). Thus, conventional genomic and proteomic approaches have identified several potential tumor markers and drug targets. However, despite such advances, correlation between drug activity and gene expression profiles has not as yet been established for most of the compounds tested (Wallqvist et al., 2002; Brown, 1997; Walloyist et al., 2003). This suggests the likely existence of unknown factors and the need to develop alternative methodology to discover "druggable" molecular targets.

Over the past few years, it has been proposed that (a) characterization of molecular diversity at the tumor cell surface level (represented primarily by membrane-associated proteins that are often modified by lipids and carbohydrates) is required for the development of ligand-directed anticancer therapies, and that (Zaharevitz et al., 2002) peptides binding to surface receptors preferentially expressed on tumor cells may be used to ligand-direct therapeutics to sites of disease with potential for increased therapeutic windows (Arap et al., 1998; Kolonin et al., 2001). It has become increasingly clear that selective cell surface features can be mapped by screening libraries of peptides (Kolonin et al., 2001; Pasqualini and Ruoslahti, 1996; Giordano et al., 2001; Arap et al., 2002). In fact, combinatorial peptide libraries displayed from pIII protein of an M13-derived phage have now been successfully screened on intact cells and in vivo (Arap et al., 1998; Kolonin et al., 2001; Pasqualini and Ruoslahti, 1996). Peptide ligands selected from unbiased screens without any predetermined notions about the nature of the cellular receptor repertoire have been used for the subsequent identification of the corresponding target cell surface receptors (Giordano et al., 2001; Arap et al., 2002; Pasqualini et al., 2000; Kolonin et al., 2002; Kolonin et al., 2004; Pasqualini et al., 2001). In addition, novel techniques, such as the biopanning and rapid analysis of selective interactive ligands (BRASIL), have enabled high-throughput phage library screening on cells (Giordano et al., 2001). Here, the BRASIL method is used to systematically screen combinatorial libraries on tumor cells of the NCI-60 panel. Results of this feasibility study suggest that tumor cells can be grouped by profiles of their peptide ligands directed to differentially expressed cell surface receptors. The data support the notion that many tumor cell surface-exposed receptors are expressed irrespective of tumor origin, thus suggesting they could be developed as broad tumor targets. Integration of ligand-directed surface profiling with other approaches related to the NCI-60 may uncover functional ligand-receptor pairs for the targeted drug delivery.

I. CELL TARGETING MOLECULES

Modified cell targeting molecules of the present invention may be produced by chemical synthetic methods, by chemical linkage between the two moieties or in some cases by fusion of a second polypeptide coding sequence to the targeting moiety. It is contemplated that modified cell targeting molecules of the invention may be used as therapeutics and/or as imaging agents to target specific classes of cells.

As mentioned above, in certain aspects of the invention, a modified cell targeting moiety may comprise a second polypeptide wherein the two polypeptides together comprise a fusion protein. For example, in certain aspects the second polypeptide may be a therapeutic or cytotoxic (e.g., a toxin) polypeptide as exemplified below. A fusion of two polypeptide coding sequences can be achieved by methods well known in the art of molecular biology. It is preferred that a fusion polynucleotide contain only the AUG translation initiation codon at the 5' end of the first coding sequence without the initiation codon of the second coding sequence to avoid the production of two separate encoded products. In addition, a leader sequence may be placed at the 5' end of the polynucleotide in order to target the expressed product to a specific site or compartment within a host cell to facilitate secretion or subsequent purification after gene expression. The two coding sequences can be fused directly without any linker or by using a flexible polylinker.

A. Cell Targeting Moieties

Cell targeting moities as provided here may, in some aspects, comprise peptides or polypeptides that exhibit binding to a specific class of cells. For example, in some cases the cell targeting moiety is selected from one of the polypeptide sequences provided in Table 3. The skilled artisan will understand that such sequences may comprise additional amino acids or other covalent modifications. For instance, in preferred embodiments a polypeptide sequence from Table 3 is provided a cyclic polypeptide. Thus, in some specific examples, an amino acid sequence from Table 3 is flanked by cysteine residues that may form a disulfide bond thereby providing a cyclic polypeptide. Thus, in some aspects the invention provides compositions and methods for targeting any of the classes of cells that bind to the peptides and polypeptides provided herein (e.g., as indicated in Table 3) such as leukemia cells, lung cancer cells, colon cancer cells, CNS cancer cells, melanoma cells, ovarian cancer cells, prostate cancer cells, renal cancer cells or breast cancer cells.

B. Therapeutic Moieties

As mentioned above in certain aspects, a therapeutic moiety may be a toxin such as radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Z, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin. Furthermore, a therapeutic moiety may be a pro-apoptotic protein such as a BCL2 family member, a caspase or a granzyme.

II. CANCER THERAPIES

A variety of conventional cancer therapies are currently used in the treatment of cancer. Thus, in some aspects of the invention there are provided methods for classifying cancer cells such as cells that are sensitive or resistant to an anticancer therapy. Some examples of conventional cancer therapies discussed below. It is contemplated that methods according to the invention may be used to identify cells that are sensitive or resistant to any particular cancer treatment. Furthermore, some aspects of the invention concern compositions and methods for cell targeted anticancer therapy. Thus, it is contemplated that any anticancer method known to those in the art (as exemplified below) may be used in combination or conjunction with compositions and methods provided herein.

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

III. EXAMPLES

Example 1

Combinatorial Library Screening on Cells

All the NCI-60 cell lines (1), except MDA-N (unavailable), were grown in RPMI 1640 supplemented with 5% fetal bovine serum (FBS) and 5 mmol/L L-glutamine. A phage display random peptide library based on the vector fUSE5 displaying the insert $CX_7C$ (SEQ ID NO:1) was screened by using BRASIL as described (Giordano et al., 2001). Exponentially growing cells were harvested with 0.5 mmol/L EDTA, 0.4 g/L KCl, 8 g/L NaCl, and 1 g/L dextrose, washed once with phosphate buffer saline (PBS), and resuspended in RPMI containing 1% bovine serum albumin (BSA) and 1 mmol/L HEPES. Cells (~$10^6$) were incubated for 2 hours on ice with $10^9$ transduction units (T.U.) of $CX_7C$ phage in 200-μL suspension, transferred to the top of a nonmiscible organic lower phase (dibutyl phtalate/cyclohexane, 9:1), and centrifuged at 10,000×g for 10 minutes. The phage-bound cell pellet was incubated with 200 μL of K91 bacterial culture, and the bound phages were amplified and used in the following round. To prevent preferential isolation of peptides containing the RGD motif, which is selected on tissue-cultured cells due to expression of cell adhesion molecules binding to vitronectin, library screening was done in the presence of 1 mg/mL of the synthetic peptide RGD-4C (AnaSpec, San Diego, Calif.) in each round. After three rounds of selection, phage peptide-encoding inserts were sequenced as described (Pasqualini and Ruoslahti, 1996; Arap et al., 2002; Pasqualini et al., 2001).

Example 2

Hierarchical Cluster Analysis of Peptide Motif/Cell Line Association

The inventors created an interactive sequence management database of all peptide sequences isolated in the screen. Calculation of tripeptide motif frequencies in $CX_7C$ peptides (in both directions) was done by using a character pattern recognition program based on SAS (version 8.1.2, SAS Institute, Cary, N.C.) and Perl (version 5.6.1) as described (Arap et al., 2002). To identify the most closely related tripeptides and cell lines, clustered image maps (CIM) were generated by using online software CIMminer available at discover.nci.nih.gov/toolsjsp. Data were centered (mean subtracted and divided by SD) on both cell lines and tripeptide motifs; correlation coefficient metric with average linkage algorithm was used as distance measurement. The tripeptide motif frequencies across the NCI-60 cell lines formed a two-dimensional data matrix that was used to correlate motif enrichment with groups of cell lines. To evaluate whether CIMMiner algorithm is appropriate for clustering analysis of peptide frequency data, a simulation test was devised assuming that the frequencies of tripeptide motifs in a given data set follow an independent Poisson distribution. The inventors simulated a random 3,280×59 data matrix of the dimension identical to that of tripeptide motif frequency data matrix (corresponding to the set of 3,280 tripeptides and 59 cell lines). These simulated data were centered the same way as the experimental data by transforming to mean of 0, variance of 1. For CIM in FIG. 1, tripeptides selected on all but one cell line of common origin (Arap et al., 2002) were used. Specificity of five tripeptides selectively overrepresented or underrepresented in lung tumor cell binding peptides for the 11 boxed cell lines (against the other 48 cell lines) was evaluated by using the R Package, version 2.0.0 (www.r-project.org) by performing two-sample t test (one tailed), as well as using Wilcoxon rank sum test (one tailed) and Fisher exact test (one tailed) as described (Arap et al., 2002).

Example 3

Identification of Candidate Targeted Receptors

To identify lead receptors targeted by tripeptide motifs, the Molecular Target Database (found on the world wide web at dtp.nci.nih.gov) was screened to identify proteins, expression levels of which in individual cell lines of the NCI-60 correlated with frequencies of individual tripeptides from FIG. 1 in the corresponding cell lines. The inventors used the COMPARE software (found on the world wide web at dtp.nci.nih.gov/docs/compare/compare.html) to calculate pairwise Pearson correlations between tripeptide frequencies in cell lines and the protein expression patterns in the database. Minimum Pearson correlation coefficient of 0.2 served as cutoff for the selection of lead receptors, as it provided a reasonable number of candidate molecular targets for which NCI-60 expression profiles and tripeptide frequency distribution profiles correlated. To initially restrict the candidate targets analyzed to broad-specificity receptors, only putative cell surface molecules (Table 1) were included, expression of which in the NCI-60 was found to correlate with the frequency profile of at least 25% of the tripeptides.

Example 4

Protein Database Screening for Peptide Motif Similarity

To identify natural prototype ligands of candidate receptors that are mimicked by selected peptides, the inventors screened all 7-mer peptides selected in the screen by using online ClustalW software (www.ebi.ac.uk/clustalw/) to identify extended (four or longer amino acids) motifs shared between multiple peptides containing the broad-specificity tripeptides (FIG. 1). Nonredundant databases of human proteins were searched by the BLAST software (www.ncbi.nlm-.nih.gov/BLAST/) for proteins containing the cell-targeting 4-mers under the condition that at least the tripeptide part of the motif is identical to the part of the BLAST match.

Example 5

Validation of Epidermal Growth Factor Receptor as One of the Peptide Targets

Figures 2A, 2B:
FIGS. 2A-B: Identification of peptides mimicking EGFR ligands.

To isolate peptides binding to epidermal growth factor receptor (EGFR), phage clones selected on SKOV3 in rounds 2 and 3 of the screening were individually amplified and pooled, and $10^9$ transduction units of the mixed phage were incubated overnight at 4° C. with 10 μg of purified human EGFR (Sigma, St. Louis, Mo.), or BSA control immobilized on plastic. Unbound phages were extensively washed off with PBS, and then the bound phages were recovered by infecting host K91 *Escherichia coli* directly on the plate, and tetracycline-resistant clones were selected, quantified, and sequenced. To identify EGFR ligand-matching motifs among phage-displayed SKOV3-binding peptides, custom-designed Perl 5.8.1-based software was used to run peptide sequences against biological EGFR ligand sequences. Each 7-mer peptide sequence was aligned in each orientation against the EGFR ligand sequences from the $NH_2$ to COOH terminus in one-amino-acid shifts. The peptide/protein similarity scores for each residue were calculated based on a BLOSUM62 matrix modified to identify peptide matches of at least three amino acids in any position being identical and one being similar to the corresponding amino acid positions in the EGFR ligands (FIG. 2A).

Example 6

Isolation of Peptides Binding to Surface of the NCI-60 Cancer Cells

As an initial attempt to profile cell surface of the tumor cell panel, a large ($2\times10^8$ unique sequences) cyclic random peptide library was screened with the basic structure $CX_7C$ (C, cysteine; X any residue) on every cell line of the NCI-60. Phage selection was done in the excess of a competing Arg-Gly-Asp (RGD) synthetic integrin-binding peptide (Arap et al., 1009) to minimize the recovery of RGD-containing peptides. This strategy was designed to facilitate the recovery of ligands binding to nonintegrin families of cell surface receptors because RGD tends to become dominant in the screening due to the high levels of integrin expression in adherent cells (unpublished observation). Preferential cell binding of specific cell-targeting peptides results in enrichment, defined by the increased recovery frequency of these peptide motifs in each subsequent round of the screen (Kolonin et al., 2001; Pasqualini et al., 2001). Thus, the inventors set out to profile the expression of nonintegrin cell surface molecules among the cell lines of the NCI-60 according to the differential selection of motifs enriched in the screen.

Example 7

Hierarchical Cluster Analysis of Peptides Binding to the NCI-60 Cells

To analyze the spectrum of the peptides resulting from the screening and compare those among different cell lines of the panel, a combinatorial statistical approach was adopted based on the premise that three residue motifs (tripeptides) provide a sufficient structure for protein-peptide interactions in the context of phage display (Arap et al., 2002). For each NCI-60 cell line, $CX_7C$ peptide-encoding DNA inserts from 96 phage clones recovered after three rounds of selection were sequenced. A computer-assisted survey of all tripeptides within the library-derived sequences selected on each cell line by analyzing a database of 26,031 tripeptides contained within the 5,270 $CX_7C$-encoded 7-mer peptides isolated (an average of eighty-nine 7-mer peptide sequences analyzed per each NCI-60 cell line) was performed. Thus, each cell line was assigned a unique set of tripeptides that was identified during the selection for cell surface binders, and the frequencies of each motif among all peptides for a given cell line were calculated.

To classify cell lines according to their association with particular motifs, which might provide inference on the targeted surface molecules, a hierarchical clustering analysis of the 3,280 nonredundant tripeptides was done based on the frequency of association with the NCI-60 cell lines. For the construction of a CIM, the inventors adapted a hierarchical clustering algorithm and a pseudo-color visualization matrix initially designed to address differential gene expression among the cells of the panel (Scherf et al., 2000; Zaharevitz et al., 2002; Blower et al., 2002; Rabow et al., 2002). CIMMiner (Weinstein et al., 1997) was used for inference of the variation in peptide binding specificity across the cell lines by comparing relative frequencies of tripeptides found in 7-mer peptides binding to each cell. Clustering of peptide motifs with similar cell selectivity revealed that the peptide distribution of the combinatorial library within the NCI-60 set was nonrandom. Computer simulations of the permutated data set show that the observed pattern could not be generated by random chance, thus indicating that the discontinuous tripeptide frequency data is applicable for cluster analysis.

The selective spectra of peptide motifs interacting with the clustered cell lines suggest the existence of shared targeted surface receptor(s) expressed in these lines. In this study, the inventors chose to focus on putative peptide-targeted receptors with broad cell line specificity, which would be more informative for an initial peptide binding/receptor expression correlation analysis. the inventors therefore excluded from the data set motifs selected only on a single or few cell lines. Instead, the inventors focused on 38 tripeptides that showed a semiubiquitous distribution among the NCI-60 lines (FIG. 1). A CIM constructed according to the isolation frequency of these broader-specificity tripeptides from each cell line revealed several apparent clusters of cell lines that displayed distinct profiles of association with certain classes of peptide motifs. For example, the majority of lung cancer-derived cell lines segregated as a separate group, suggesting that some of the receptors targeted may be conserved among cell lines derived from a common origin (FIG. 1). Thus, although the analysis was severely restricted by limiting it to semiubiquitous tripeptides, clustering of some of them (predominantly with cell lines derived from the same tumor type) is consistent with their relative tissue specificity. To evaluate individual motifs for selectivity, a distinct cluster of five tripeptides associated with lung tumor-derived cell lines (FIG. 1, boxed) were identified. The inventors compared tripeptide frequencies for the 11 cell lines within this cluster with their frequencies for the rest of NCI-60 lines by using statistical tests (Fisher exact, Wilcoxon rank-sum, and t test). Consistently, the GGS motif was isolated for the clustered lines significantly ($P<0.05$) more frequently than for the other NCI-60 cell lines.

Notably, the distribution of cell lines in the dendrogram (FIG. 1) was partially consistent with the reported association of cells derived from tumors with common tissue origin (Scherf et al., 2000; Nishizuka et al., 2003). This suggests that some of the receptors, such as the one presumably recognized by the lung tumor-specific tripeptide GGS (FIG. 1), may be up-regulated only in certain cancer origins. However, the tumor cell phylogeny was recapitulated only to an extent; the majority of the observed clusters contained cell lines derived from unrelated tumor types (FIG. 1). The limited grouping of lines derived from tumors of common origin is perhaps not surprising: the relationship between different cell lines in the study is based on peptide binding to putative cell surface molecules, many of which may be tumor induced rather than characteristic of the tissue of origin. If so, the analysis of broad-specificity motif distribution may be well suitable for identification of specific surface molecules that are generally up-regulated by tumors and thus may constitute broad drug targets against cancer.

Example 8

Identification of Candidate Receptor Targets for Peptide Motifs

The inventors proceeded to identify the targets for the 38 broad-specificity tripeptides, most of which presumably bind to receptors expressed by multiple NCI-60 cell lines. The NCI Molecular Targets Database that contains detailed information on the expression and activity of 1,218 human proteins measured by nonarray methods was used (Holbeck, 2004). By using the COMPARE algorithm (Zaharevitz et al., 2002), the inventors correlated the selectivity profiles of the 38 tripeptide motifs with the expression profiles of the characterized molecular targets. It was observed that several of the qualifying proteins, expression of which correlated with enrichment profiles of certain motifs, represented tyrosine kinase receptors, such as those for ligands belonging to families of EGFs, fibroblast growth factors (FGF), nerve growth factors (NGF), and ephrins (Table 1). When transferred to molecular target correlation data, the order of the 38-tripeptide motif set in the dendrogram (FIG. 1) revealed clusters of tripeptides for which cell line association profile correlated with expression profiles of EGF, FGF, NGF, or ephrin receptors (Table 1).

The peptide distribution-correlating tyrosine kinase receptors, belonging to EGFR, FGFR, NGFR, and ephrin receptor families (Table 1), are often up-regulated in many types of cancer (Vogelstein and Kinzler, 2004). To determine if the cell-binding peptides may target these tyrosine kinases, the inventors employed the notion that receptor-binding peptide motifs often mimic natural ligands for these receptors (Giordano et al., 2001; Arap et al., 2002; Kolonin et al., 2002). Thus, the selected motifs mimic ligands for the candidate tyrosine kinases were tested by determining whether tripeptides listed in Table 1 are embedded into longer peptides that may be responsible for cell surface binding. The inventors analyzed the $CX_7C$ (SEQ ID NO:1) phage inserts containing the 38 tripeptides by using the ClustalW software and compiled extended motifs containing the tripeptides shared among multiple peptides selected during the screen (data not shown). To identify candidate prototype human ligands, epitopes of which could be mimicked, each of the ClustalW-extended motifs were screened against the nonredundant database of human proteins by using the BLAST software (National Center for Biotechnology Information). As a result of this analysis, the inventors found the motifs containing 34 of 38 tripeptides (89%) to be identical or very similar to segments of proven or putative ligands for the tyrosine kinase receptors listed (Table 1).

Example 9

Validation of EGFR as a Targeted Receptor

To show that the approach taken can lead to actual targetable tumor cell surface proteins, the inventors chose to test if the EGFR is bound by any of the tripeptide motifs distributed in the panel in a profile correlating with EGFR expression. Consistently, 24 of 38 tripeptides surveyed displayed NCI-60 cell line association pattern consistent with that of EGFR expression (Table 1). Of these tripeptides, 22 were isolated in the screens on ovarian cancer cell lines SKOV3 and OVCAR4 (data not shown). Because EGFR is well known to be associated with ovarian cancer (Vogelstein and Kinzler, 2004), the inventors deemed these cell lines to be likely expressers of targetable EGFR, which would account for the selection of EGFR ligand-mimicking motifs. To validate EGFR binding by the selected motifs, the SKOV3-binding phage sublibrary (pooled clones recovered in rounds 2 and 3) were screened against immobilized human EGFR. After two rounds of selection, phage displaying the EGFR-binding peptides were analyzed: the majority were comprised by different 7-mer peptides (FIG. 2A) that contained 17 of 22 SKOV3-selected tripeptide motifs distributed in the panel in a profile correlating with EGFR expression (Table 1). Phage displaying these peptides had specific affinity to EGFR, as determined by subjecting the same sublibrary to immobilized BSA control binding (FIG. 2B). Remarkably, computer-assisted analysis of sequences (FIG. 2A) revealed that 12 of the 7-mer EGFR-binding peptides contained amino acid motifs similar to those present in some of the biological EGFR ligands (Vogelstein and Kinzler, 2004). These peptides, containing eight of the candidate tripeptides (RVS, AGS, AGL, GVR, GGR, GGL, GSV, and GVS), were found highly similar to fragments of EGF, amphiregulin, heparin-binding EGF-like growth factor, and epiregulin (FIG. 2A). Similarity search using the same algorithm on the same twelve 7-mers did not reveal any matches to two other EGFR ligands, transforming growth factor-α and β-cellulin, or randomly chosen control ligands of tyrosine kinase receptors from the three other candidate families listed in Table 1: ephrin A, NGF-β, and FGF6 (data not shown). Taken together, these data suggest that at least some of the peptides selected on the NCI-60 cells target EGFR, whereas others may bind to different tyrosine kinases, possibly including those from TRK, ephrin, or FGF receptor families.

Expression profiles of the candidate receptor targets for peptides identified in the screen illustrate the concept that in cancer, at least some tumor-associated cell surface molecules seem up-regulated regardless of cancer tissue origin. As such, this is the case for the EGFR and other tyrosine kinases possibly targeted by peptide ligands selected on the NCI-60 cell panel. This may also be the case for many other receptors with a role in tumorigenesis, expression profiles of which may not correlate with the overall proteomic profile of the original tumor tissue. In fact, these observations may account for the relatively limited success in correlating drug toxicity profiles with the genomic and/or proteomic profiles of the NCI-60 panel (Walloyist et al., 2003). On the other hand, some of the receptors, such as EphA5 presumably targeted by GGS tripeptide and its derivatives predominantly selective for lung tumor-derived cell lines (FIG. 1), seem to be at least partially specific for the progenitor cancer type.

The candidate ligand-receptor leads identified in this study can be characterized further for the development of targeted agents selective for tumors. Moreover, the peptides identified by the approach described here may map receptor interaction domains of biological (native) ligands. Similarity of peptides to the corresponding receptor-binding ligands has already been used for validation of the IL-11Rα receptor as a target of an interleukin-11 mimic peptide homing to blood vessels in the prostate (Arap et al., 2002; Zurita et al., 2004). The inventors and others have modeled the usage of peptides homing to receptors expressed by tumors (Pasqualini et al., 2000) or non-malignant tissues (Kolonin et al., 2002; Kolonin et al., 2004) for directing the delivery of cytotoxics, proapoptotic peptides, metalloprotease inhibitors, cytokines, fluorophores, and genes (Arap et al., 1998; Kolonin et al., 2001). Thus, the approach provides a straightforward way to identify drug-accessible tumor cell surface receptors and to discover peptide ligands that can serve as mimetic prototype drugs. Unlike genomic or proteomic-based approaches that rely on differential expression levels of transcripts or protein products, this discovery platform directly addresses functional protein-protein interactions at the level of physical binding. In contrast to protein array systems, it is possible to select binding peptides even if the ligand-receptor interaction is mediated by conformational (rather than linear) epitopes. Ligand-directed screening of combinatorial libraries on tumor cell surfaces can lead to improved selection of functionally relevant peptides that can be developed for targeting "druggable" molecular targets.

Chart 1: Platform strategy for systematic identification ligand/receptor pairs operating on cancer cell surface using ligand-mimicking peptides isolated from combinatorial phage display libraries

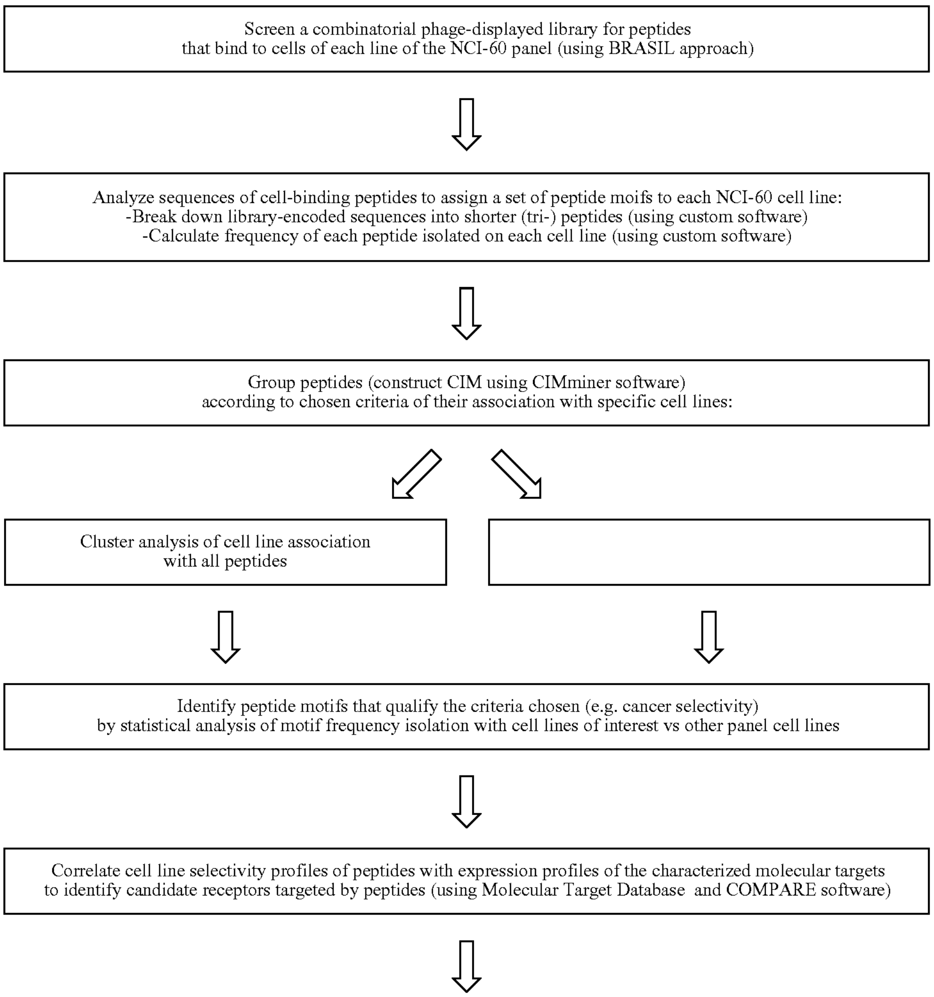

-continued

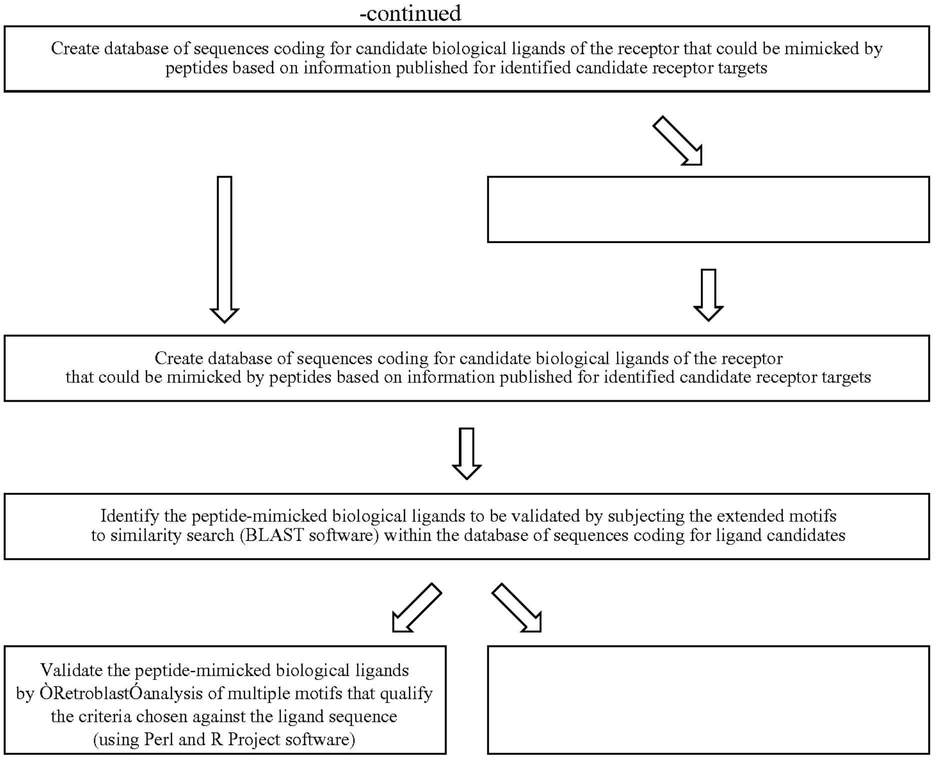

TABLE 1

| | Candidate ligand-receptor interactions mimicked* | | | | |
|---|---|---|---|---|---|
| RLS | ErbB2, ErbB4 | FGF2, 4 | | | EGF-TM7 |
| RGV | | | | | |
| RGS | ErbB4 | FGF2 | | EphA2, A3, A4, A8, B1 | EGF-TM7, FGF-12b, FGF-5, NGF-beta |
| RAV | ErbB2 | | | | MEGF7, NGF-beta. NTF 6 alpha |
| RAS | | | TRKA | | FGF-20, NRG-3 |
| GAG | EGFR | FGF1, 2, 3 | | | MEGF4. FGF6, NGF-beta |
| AVS | EGFR, ErbB2, ErbB4 | FGF1 | TRKB, C | EphA2, A3, A4, A7, B1, B2, B3, B5 | TRK1 |
| LLS | | | | | Amphlregulin |
| LLR | | | TRKA | | EphA4 |
| LRV | EGFR, ErbB2, ErbB4 | FGF3 | TRKA, B, C | EphA2, A3, A7 | FGF-12b, Eph-B3 |
| LRS | ErbB3 | | | | MEGF4, MEGF5, MEGFS, NRG-3, NGF-beta |
| RVS | EGFR, ErbB2, ErbB4 | FGF1, 2 | TRKB | EphA7 | MEGF10, amphiregulin |
| RSS | | FGF3 | TRKA | EphAS | EGF-TM7, FGF-S, NRG-3 |
| AGS | EGFR | | TRKA | | MEGF6, brain NGF |
| AGR | | | | | MEGF2, MEGF4, FGF6, NTF-5, NTF-6 |
| AGL | EGFR, ErbB2, ErbB3 | FGF1, 3 | | EphAS, A6, A8 | MEGF12 |
| AGG | | | | EphA5 | HB-EGF, Ephr-B3 |
| GVR | EGFR, ErbB2, ErbB4 | FGF1, 2 | TRKB | EphA7 | MEGF4, MEGF6 MEGF8, FGF-5, bFGF, brain NGF |
| GVL | | FGF1, 2 | | EphA2, A3, A5, A6, B3 | NGF2, Ephrin-B3, |
| GAV | | | | | MEGFS, MEGF6, NGF-beta |
| GLV | ErbB4 | FGF4 | | EphA5 | ESF-TM7, betaceilulin, NTF 3, Eph-B3, |
| GLR | ErbB4 | | | | MEGF5, EGFL5, FGF-12b, FGF-16, NRG-3 |
| LVS | | FGF1, 4 | | EphA5, A6 | EGFL5. FGF23, GDNF, Eph-B3 |
| ARG | ErbB2 | FGF2, 4 | TRKA | EphAI | FGF-12b, FGF23, NGF-beta. GDNF. NTF 6 |
| ASL | | FGF1, 2 | TRKC | | EGF-TM7, FGFR1 |
| AAV | | | TRKB | EphA2, A3, A4, A7, B3, B5 | • |

TABLE 1-continued

| Candidate ligand-receptor interactions mimicked* | | | | | |
|---|---|---|---|---|---|
| AAS | | FGF1, 2 | TRKC | | • |
| GGS | | | | EphA5 | Eph-B3, Eph A4 |
| GGR | EGFR.ErbB2 | FGF2 | | | EGF-TM7, HB-EGF, FGF23, Ephrin-B3 |
| GLG | ErbB2, ErbB3 | FGF2, 3, 4 | | EphA1, A6 | heparin binding growth factor 8 |
| GGL | ErbB2 | | | | HB-EGF, MEGF5, EGFL5, NRG-3 |
| GSS | EGFR, ErbB2 | FGF3 | TRKA, C | EphA5 | MEGFS |
| GSG | EGFR | | | EphA5 | |
| GSV | EGFR, ErbB2, ErbB4 | FGF4 | TRKB | EphA7, B2 | MEGF5, NRG-3, Ephrin-B3 |
| GRV | EGFR | | | | MEGFS, EGF-TM7, FGF23, NTF5 |
| GRL | EGFR.ErbB2 | | | EphAS, B1, B2, B4 | betacellulin, EGFL5, NGF2, NTF5, EphB3, EphA4 |
| GPS | EGFR, ErbB2, ERB4 | FGF3 | TRKB | EpnA2, A3, A4, A7, B2, B5 | MEGFS, EGFL5, EGF-like EMR3, SPGF |
| GVS | EGFR | FGF4 | TRKA | | MEGF-1, MEGF5, NRG-3, NTF-6, NTF-5 |

*NOTE:
Candidate peptide motif receptors are the human cell surface proteins (identified by COMPARE) expressed in profiles correlating with the selectivity of the corresponding tripeptides. Candidate peptide-mimicked receptor ligands are human proteins (identified by automated BLAST) that contained the corresponding tripeptides. Tripeptides in the column are ordered as in FIG. 1. Receptors of the same family and their corresponding candidate biological ligands identified based on tripeptide similarity are coded by the same color [EGFR, blue; FGFR, green; TRK receptor (NGFR), purple; ephrin receptor, red]. Tripeptides that both have a selectivity correlating with EGFR family receptor expression and are found within EGFR ligands (boldface). Tripeptides that were confirmed to reside within EGFR-binding SKOV3-slected peptides (FIG. 2; blue).

Example 10

Molecular Fingerprinting of Cancer Cell Lines

Proteomics can be defined as the systematic analysis of the proteins in biological samples that aims to document the overall distribution of proteins in tumor cells or tumor-associated cells, identify and characterize individual proteins of interest and to elucidate their relationships and functional roles. Ultimately, high-throughput profiling of protein expression will lead to the “proteome”, a protein-based fingerprint, for each tissue in humans and other species. As technologies related to proteomics advance, new approaches for systematic molecular analysis of cancer at the protein level are surfacing. However, methods for systematic protein expression profiling may also easily overlook potential targets for intervention. These methods often do not take anatomical context into account. Therefore, for the generation of molecular map of accessible receptors that can be used for targeting therapeutics, information derived from conventional protein profiling approaches should be enhanced by integration with data from functional screenings ex vivo and in vivo. Studies by the inventors and others have advanced the concept of cancer proteomics: the molecular phenotyping of tumor cells and cells forming blood vessels at the protein-protein interaction level. Exploiting the molecular diversity of cell surface receptors expressed in cancer will eventually result in a ligand-receptor functional map for targeted delivery.

A major goal in drug development has long been to generate targeted therapies. This approach would improve drug therapeutic indexes by limiting the systemic exposure of other tissues to untoward or toxic effects. Thus, the promise for the identification of selectively expressed tumor-associated receptors and the ligands that home to these receptors is translation of this knowledge into the development of targeted therapeutics. Generally, coupling of homing peptides yields targeted compounds that are more effective and less toxic than the parental compound. So far, peptides selected by homing to tumor vasculature have been used as carriers to guide the delivery of cytotoxic drugs, pro-apoptotic peptides, metalloprotease inhibitors, cytokines, fluorofores, and genes in transgenic and xenograft mouse models of human disease.

Recognition of molecular diversity in human cancer is essential for the development of targeted therapies. The methods developed have two main applications. First, they may identify ligands targeting human cancer. Second, the determination of molecular profiles of biomarkers in specific types of tumors may enable identification of differentially expressed cancer markers. Thus, the approach may lead to construction of a molecular profile of human tumors. Early identification of targets, optimized regimens tailored to molecular profile of individual cancer patients, combined with the identification of new vascular addresses may result in revisiting or salvaging of drug candidates that are ineffective or too toxic. Ultimately, it may be possible to guide imaging or therapeutic compounds to tumor targets in cancer patients.

By fingerprinting lung cancer cells the inventors have confirmed the expression of a previously characterized molecular target, EGFR, in multiple cancer origins, which demonstrates the power of the approach. Recently, the inventors used this approach to identify a new cancer origin-selective molecular target, Ephrin A5 receptor, which the inventors have preliminary validated in the context of human lung cancer cell lines and tissues.

Example 11

Motifs Targeting NCI-60 Cells in Correlation with EGFR Expression Pattern are Found within Peptides Similar to Domains of Biological EGFR Ligands and Bind to EGFR To show that the approach taken can lead to actual targetable tumor cell surface proteins, the inventors chose to test if the EGF receptor (EGFR) is bound by any of the tripeptide motifs distributed in the panel in a profile correlating with EGFR expression. Consistently, 24 out of 38 tripeptides surveyed displayed NCI-60 cell line association pattern consistent with that of EGFR expression (Kolonin et al., 2001). Of these, tripeptides, 22 were isolated in the screens on ovarian cancer cell lines SKOV3 and OVCAR4 (data not shown). Since EGFR is well known to be associated with ovarian cancer (Vogelstein, 2004; Maihle and Lafky, 2002), the inventors deemed these cell lines to be likely expressers of targetable EGFR, which would account for the selection of EGFR ligand-mimicking motifs. To validate EGFR binding by the selected motifs, the SKOV3-binding phage sub-library (pooled clones recovered in rounds 2 and 3) were screened against immobilized human EGFR. After 2 rounds of selection, phage displaying the EGFR-binding peptides were analyzed: the majority were comprised by different seven-mer peptides (FIG. 3A) that contained 17 out of 22 SKOV3-selected tripeptide motifs distributed in the panel in a profile correlating with EGFR expression.

Phage displaying these peptides had specific affinity to EGFR, as determined by subjecting the same sub-library to immobilized bovine serum albumin (BSA) control binding (FIG. 2B). Remarkably, computer-assisted analysis of sequences (FIG. 2A) revealed that 12 of the seven-mer EGFR-binding peptides contained amino acid motifs similar to those present in some of the biological EGFR ligands. These peptides, containing eight of the candidate tripeptides (RVS, AGS, AGL, GVR, GGR, GGL, GSV, and GVS) were found highly similar to fragments of EGF, Amphiregulin, heparin-binding EGF-like growth factor, and Epiregulin (FIG. 2A). Similarity search using the same algorithm on the same 12 seven-mers did not reveal any matches to two other EGFR ligands, TGF-α and betacellulin, or randomly chosen control ligands of tyrosine kinase receptors from the three other candidate families listed in Table 2 (Kolonin et al. 2001): Ephrin A, NGF-β, and FGF6. Taken together, these data suggest that at least some of the peptides selected on the NCI-60 cells target EGFR, while others may bind to different tyrosine kinases, possibly including those from TRK, Ephrin, or FGF receptor families.

A phage-displayed combinatorial library was systematically screened for peptides capable of targeting the cell lines in the NCI-60 panel. By statistical analysis of peptide motif sequences, each NCI-60 cell line was assigned a unique set of peptide motifs that were isolated during the selection for cell surface binders. It was shown that tumor cells can be grouped by profiles of their phage display-derived peptide ligands directed to differentially expressed cell surface receptors.

An approach for peptide-targeted receptor identification was designed. Profiles of peptide motif preference for specific lines of the NCI-60 were correlated with expression profiles of known breast cancer-related targets. Some of the peptide motifs were found within proteins known to bind the receptors that had NCI-60 expression profiles matching cell line recognition profiles of the peptides, and that are implicated in cancer.

Candidate targeted cell surface molecules were identified, which included a number of tyrosine kinase receptors. As a proof of principle, EGFR, a receptor known to be upregulated in various cancers, was validated as a target of tripeptides RVS, AGS, AGL, GVR, GGR, GGL, GSV, and GVS, which were The results described uncover a previously overlooked phenomenon. The data support the notion that many tumor cell surface-exposed receptors are expressed irrespective of tumor origin, thus suggesting they could be explored as broad tumor targets.

Example 12

Ephrin A5 Receptor as a Lung Cancer Cell Surface Marker

The peptide distribution-correlating tyrosine kinase receptors, belonging to EGFR, FGFR, NGFR and Ephrin receptor families are often up-regulated in many types of cancer. On the other hand, some of the receptors, such as EphA5 presumably targeted by GGS tripeptide and its derivatives predominantly selective for lung tumor-derived cell lines appear to be at least partially specific for the progenitor cancer type. Since this approach clearly allowed identification of cell surface receptors ubiquitously upregulated in various cancers, the inventors took a step further to attempt identification of cancer type-specific receptors.

Having chosen lung cancer for the initial procedure establishment, the inventors identified a distinct cluster of five tripeptides associated with lung tumor-derived cell lines. The inventors compared tripeptide frequencies for the 11 cell lines within this cluster with their frequencies for the rest of NCI-60 lines by using statistical tests (Fisher exact, Wilcoxon rank-sum, and t-test). Consistently, the inventors observed that motif GGS was isolated for the clustered lines significantly ($P<0.05$) more frequently than for the other NCI-60 cell lines (Table 2).

TABLE 2

Association of specific tripeptides with lung cancer-derived cell lines:

| Motif | Mean motif count (±SEM) inside vs. outside cluster | P value t-test, 1-sided | P value Wilcoxon rank-sum test, 1-sided | P value Fisher exact test, 1-sided |
|---|---|---|---|---|
| GGS | 2.2 (±0.5) vs. 1.2 (±0.2) | 0.0422 | 0.0407 | 0.0043 |
| GGR | 1.3 (±0.3) vs. 1.5 (±0.2) | 0.6991 | 0.6466 | 0.6739 |
| GLG | 0.7 (±0.4) vs. 0.7 (±0.2) | 0.5375 | 0.6888 | 0.5150 |
| GGL | 1.2 (±0.2) vs. 1.3 (±0.2) | 0.6457 | 0.4174 | 0.5485 |
| GSS | 2.2 (±0.4) vs. 1.1 (±0.2) | 0.0422 | 0.0026 | 0.0008 |

To determine statistical significance of association or dissociation between exemplary tripeptides and cell lines, normalized frequencies of five tripeptides predominantly associated (GGS, GGR, GLG, and GGL) or dissociated (GSS) with the cluster containing the majority of lung tumor-derived cell lines (FIG. 1, boxed) were compared for cell lines inside the cluster and outside the cluster. Selective association of tripeptide GGS with the clustered cell lines was found significant according to t-test, Fisher exact test and Wilcoxon rank-sum test (all tests one-tailed).

Based on the automated BLAST analysis (Table 2) the inventors identified proteins of the ephrin family candidate prototypes of the GGS-containing peptides: ephrins –B3 and A4 contain the GGS, consistent with a functional mimickry. Ephrins (A and B) and their receptors (EphA and EphB) represent a large class of cell-cell communication molecules with well-defined developmental functions. Their role in healthy adult tissues and in human disease is still largely unknown, although diverse roles in carcinogenesis have been postulated and a number of Eph receptors have been found overexpressed by various cancers (Hafner et al., 2004). Based on the COMPARE analysis of GGS distribution within NCI-60 (Kolonin et al., 2001, Table 2), the receptor expressed in the corresponding pattern is EphA5. The EphA5 expression (FIG. 4 has been explored using cDNA microarray analysis and is reported at the DTP server (dtp.nci.nih.gov/mtweb/servlet/moltidsearch?moltid=MT894), however, no studies of EphA5 function in cancer have been published. Intriguingly EphA5 is not expressed in normal lung and normally is only thought to have brain-specific functions.

Example 13

Validation of Ephrin-Mimic Peptides in Lung Cancer

Figure 3A:
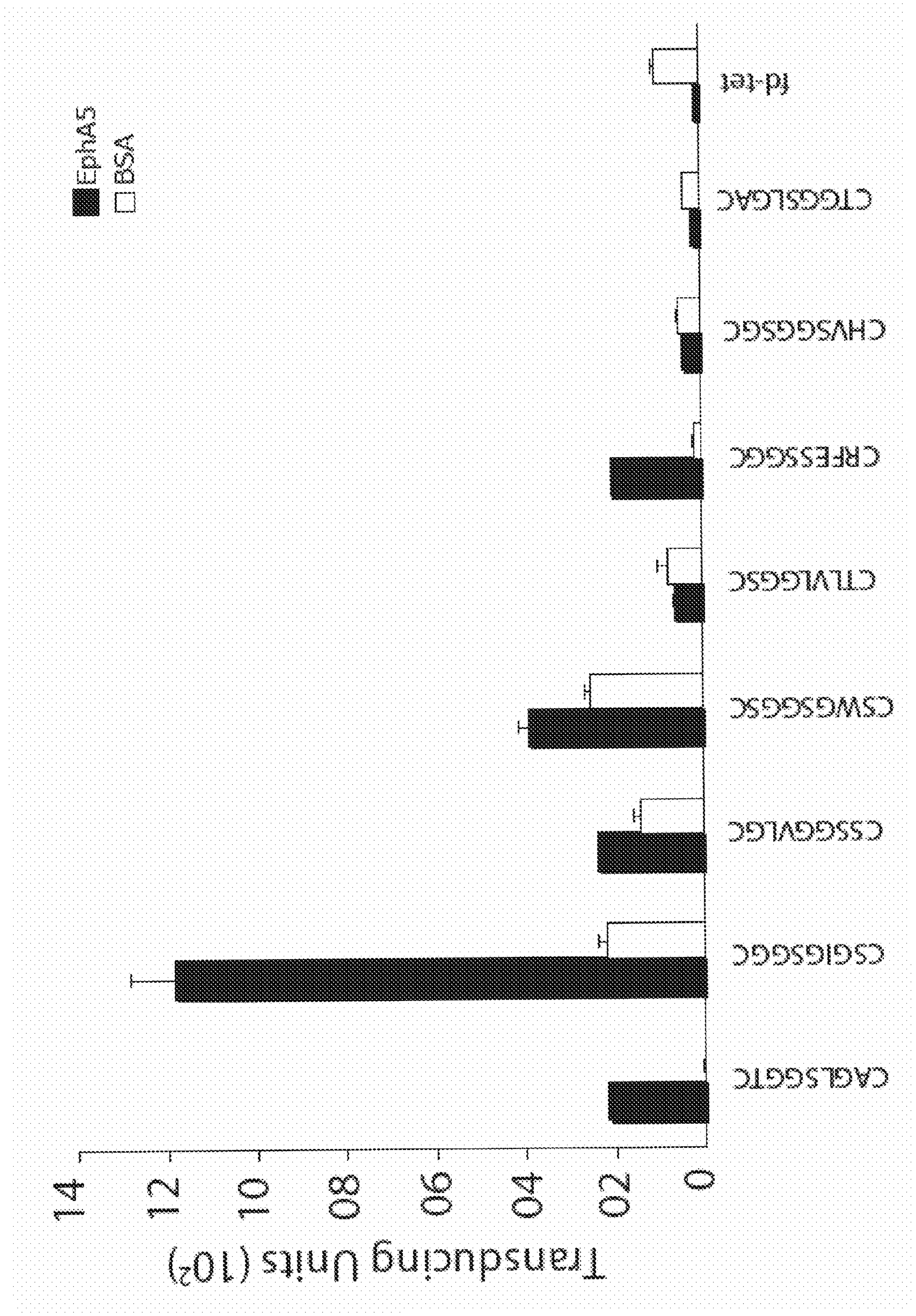
FIGS. 3A-3B: Phage selection on immobilized EphA5 receptor.
Figure 3B:
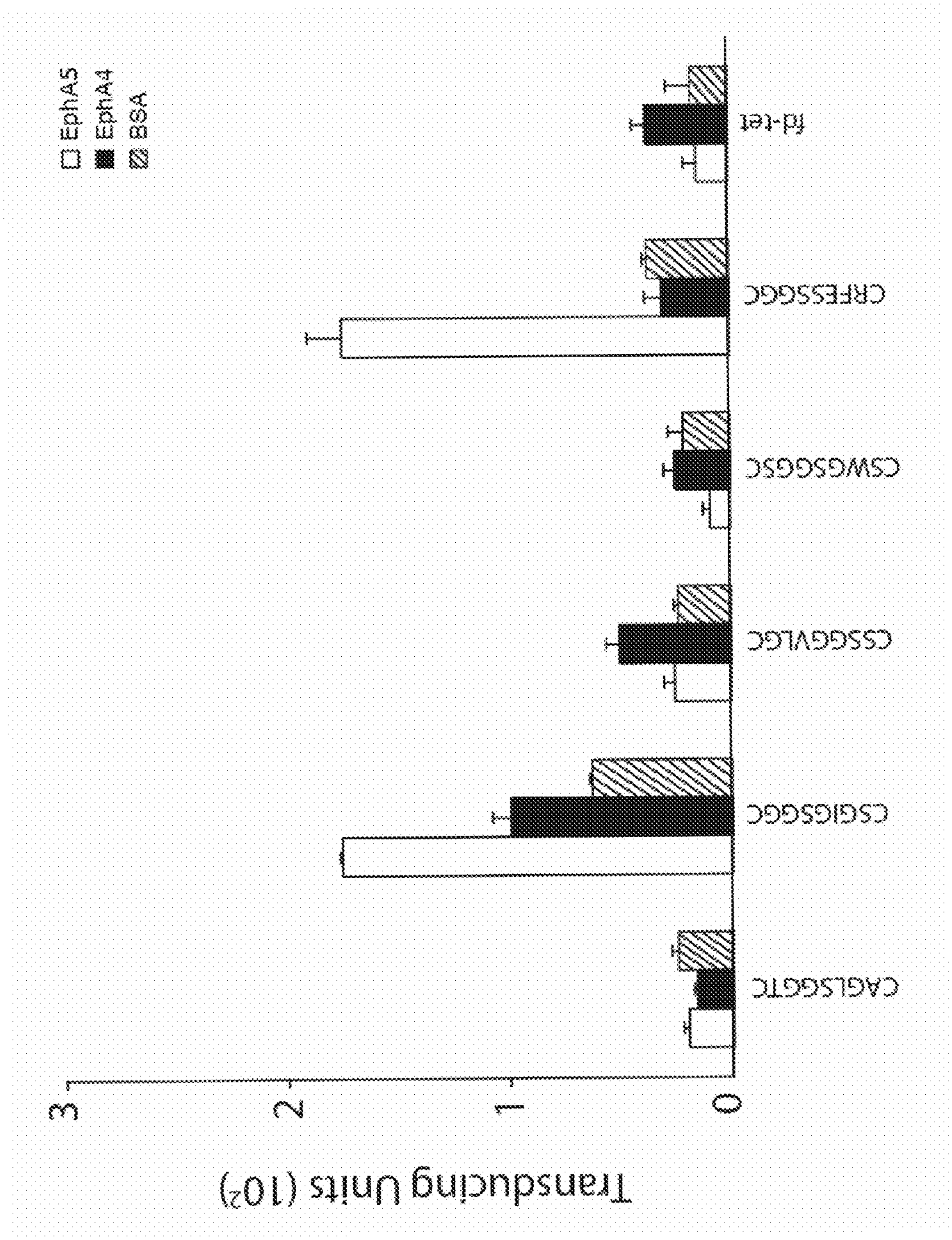
Figure 5:
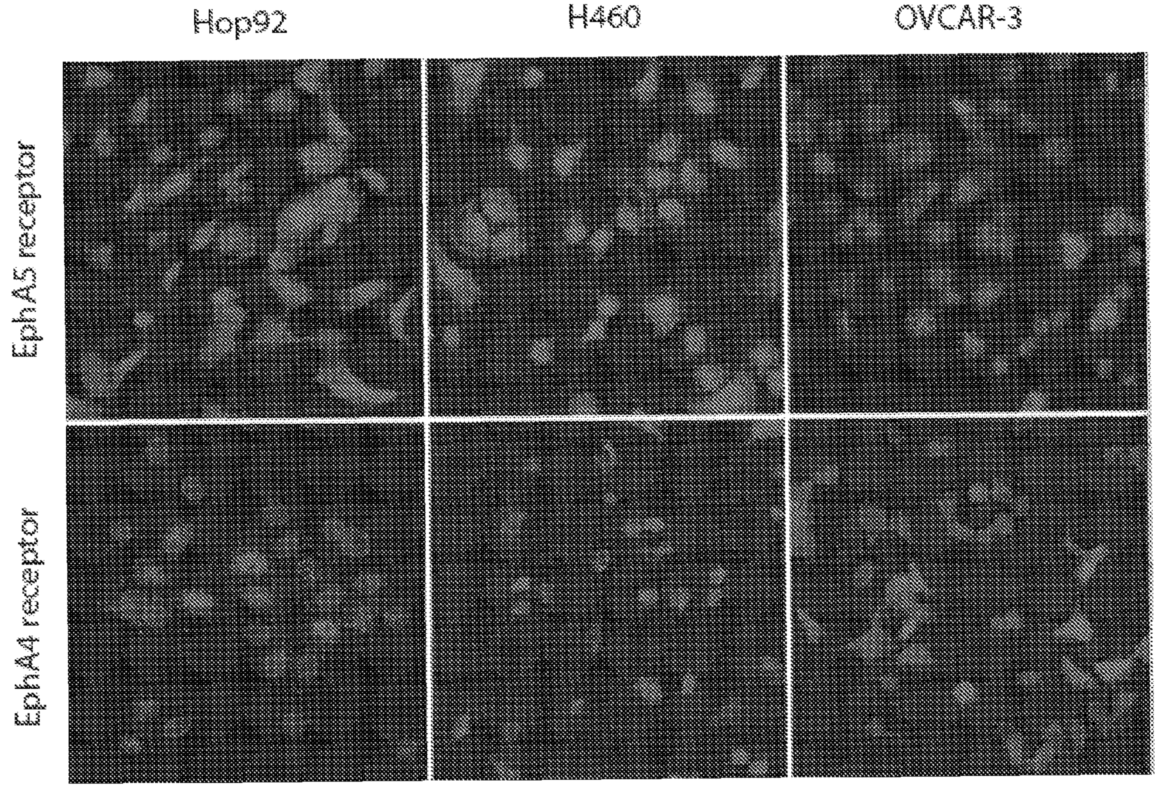
FIG. 5: EphA5 and EphA4 receptor expression by the lung cancer cell lines Hop92 and H460. The OVCAR3 cell line was used as negative control. 10× magnification.

To validate phage containing the motif GGS as a ligand of Eph receptors, the inventors tested phage binding to the EphA5 immobilized receptor. The inventors started testing eight peptides (CAGLSGGTC (SEQ ID NO:2133), CSGIGSGGC (SEQ ID NO:2134), CSSGGVLGC (SEQ ID NO:2135), CSWGSGGSC (SEQ ID NO:2136), CTLVLGGSC (SEQ ID NO:2137), CRFESSGGC (SEQ ID NO:2138), CHVSGGSGC (SEQ ID NO:2139), CTGGSLGAC (SEQ ID NO:2140)) containing the enriched motif GGS, all of them displayed by phage clones obtained from the screening on different cell lines known to express the EphA5 receptor (FIG. 3A). From this first round of selection, 5 clones (CAGLSGGTC (SEQ ID NO:2133), CSGIGSGGC (SEQ ID NO:2134), CSSGGVLGC (SEQ ID NO:2135), CRFESSGGC (SEQ ID NO:2138) and CSWGSGGSC (SEQ ID NO:2136) showed good binding to the receptor relative to the control (BSA) and were further analyzed by their ability to specifically bind to EphA5 but not to the control EphA4 receptor (FIG. 3B). Phage displaying the peptide sequences CSGIGSGGC (SEQ ID NO:2134) and CRFESSGGC (SEQ ID NO:2138) showed binding specificity and were chosen for characterization. The inventors investigated the binding of the selected phage to the lung cancer cells Hop92 and H460. These cells are known to express EphA5 receptor on its surface, as confirmed by immunofluorescence analysis (FIG. 5). The ovarian cancer cell line OVCAR-3, negative for EphA5 expression, was used as control.

Figure 6:
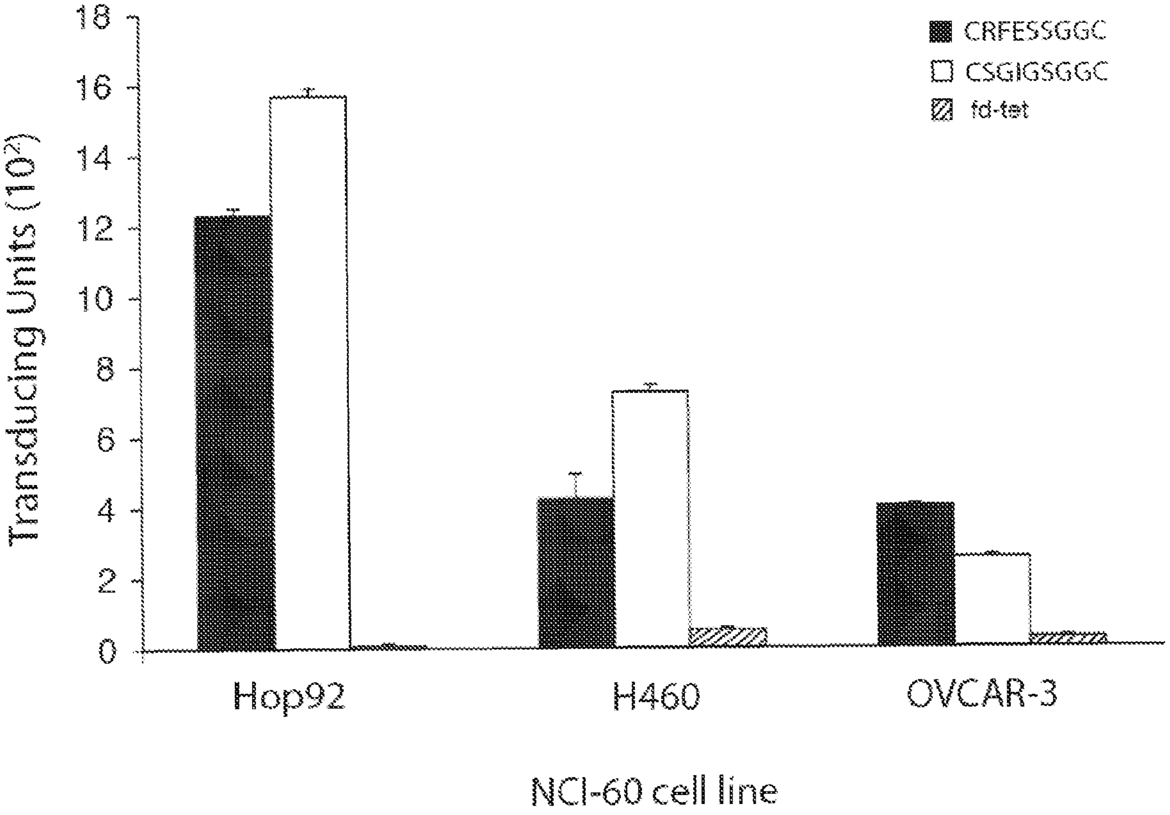
FIG. 6: Specific binding of the CSGIGSGGC (SEQ ID NO:2) and CRFESSGGC (SEQ ID NO:3)-phage to lung cancer cells Hop92 and H460 but not to the ovarian cancer cell line OVCAR-3. Insertless phage (fd-tet) was used as negative control.
Figure 7A:
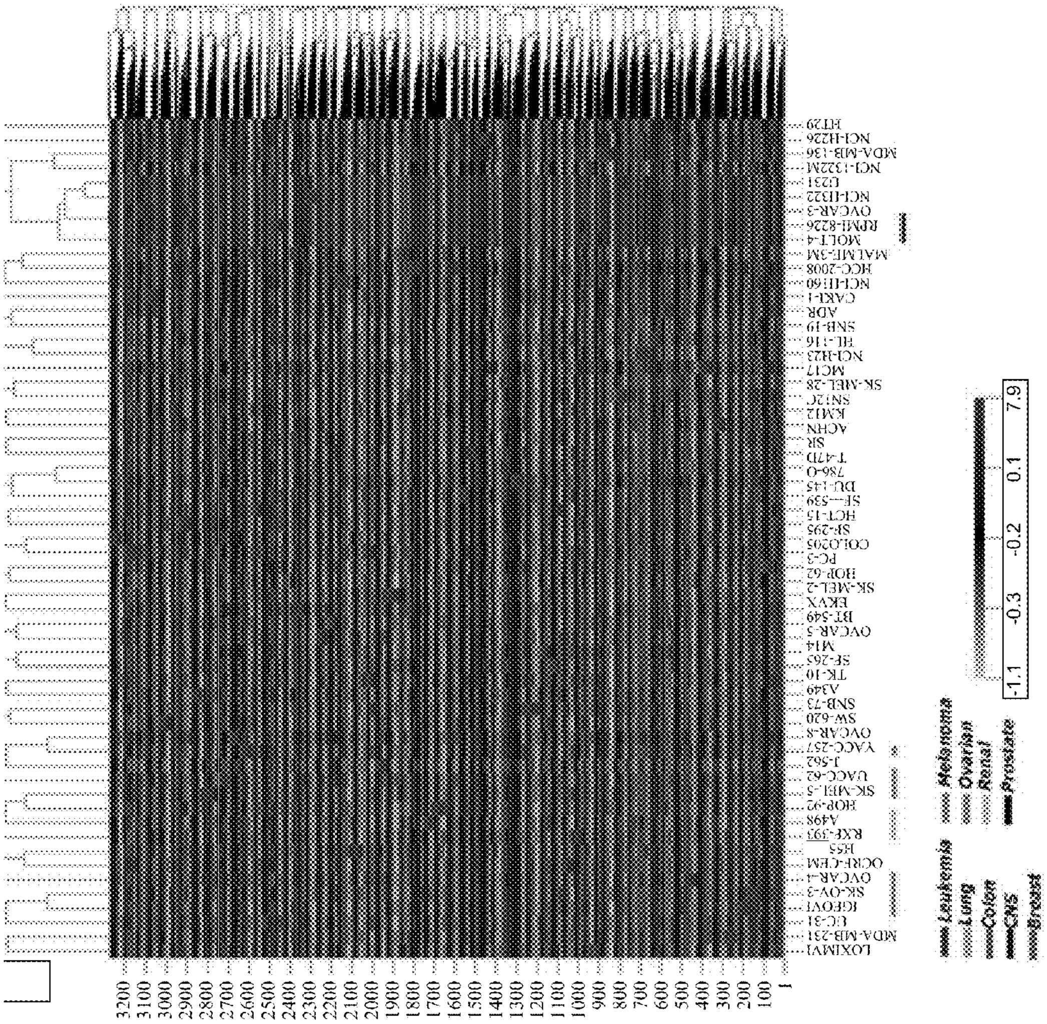
FIGS. 7A-B: A. Clustered image map relating all isolated NCI-60-binding tripeptides to NCI-60 cell lines.
Figure 7B:
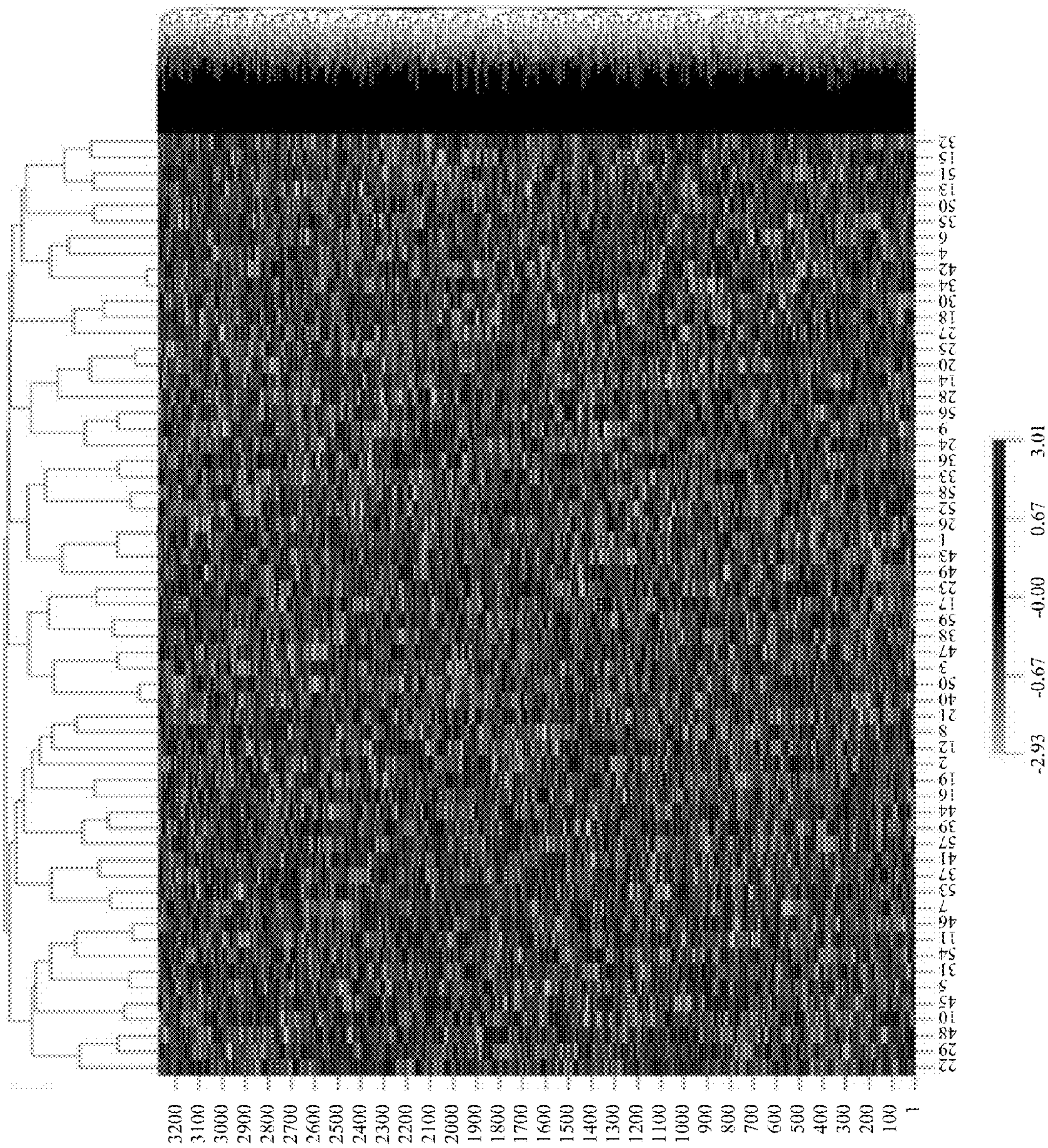

Next, the inventors used the BRASIL method (biopanning and rapid analysis of selective interactive ligands) to analyze binding of selected phage to lung cancer cells. The inventors observed specific binding of phage displaying the sequences CSGIGSGGC and CRFESSGGC to Hop92 and H460, confirming the data obtained from the screening on the immobilized EphA5 receptor (FIG. 6).

Finally, by using banked sections or patient tissues from the MD Anderson Cancer Center, the inventors showed that EphA5 protein is overexpressed by human lung adenocarcinoma epithelium.

Immunohistochemistry (polyclonal anti-prohibitin antibody) on formalin-fixed paraffin sections of human non-small cell lung cancer (NSLC) or normal prostate with EphA5 or EphA4-specific antibodies. Immunostaining demonstrates selective EphA5 upregulation of EphA5 protein expression in NSLC lung adenocarcinoma epithelium, but not stroma, as compared with the control prostate tissue.

Taken together, these data suggest that the two selected phage displaying the motif GGS are ligands of EphA5 receptor. Upregulation of EphA5 in gliomas has been reported, without any functional connections, and, up to date, there has been no reports of investigation of this tyrosine kinase receptor in lung cancer. Therefore, EphA5 protein overexpression in lung cancer cells (FIG. 4) in light of candidate ephrin mimics (GGS peptides) targeting these cells provides an original evidence for EphA5 being a lung cancer marker and has potential functional implications.

It is contemplated by the inventors that the cancer-associated motifs identified here can be used for the development of approaches for targeted imaging or therapy of breast tumors in patients. Their receptors, including EGFR, EphA5, and other cell surface molecules, can be further explored for their oncogenic properties and the potential to serve as universal or origin/grade-selective targets of cancer.

Example 14

Cell Internalization of Ephrin-Mimic Peptides

Figure 8:
FIG. 8: Targeted peptides mediate ligand-receptor cell internalization. CSGIGSGGC (SEQ ID NO:2) and CRFESSGGC (SEQ ID NO:3)-phage were permeabilized into A549 cells. No internalization was observed when cells were incubated with insertless phage

The ability of ephrin-mimic peptides to mediate cell internalization was assessed. The A549 cell line was used as a representative human lung cancer-derived cells expressing the EphA5 receptor on the cell surface. Each phage clone or control insertless phage was incubated with cells for 4 h at 37° C. Both CSGIGSGGC (SEQ ID NO:2) and CRFESSGGC (SEQ ID NO:3)-phage were internalized into A549 cells while only background fluorescence was obtained when non-targeted control phage was used (see FIG. 8).

Example 15

Activation of Cells by Ephrin-Mimic Peptide

Figure 9A:
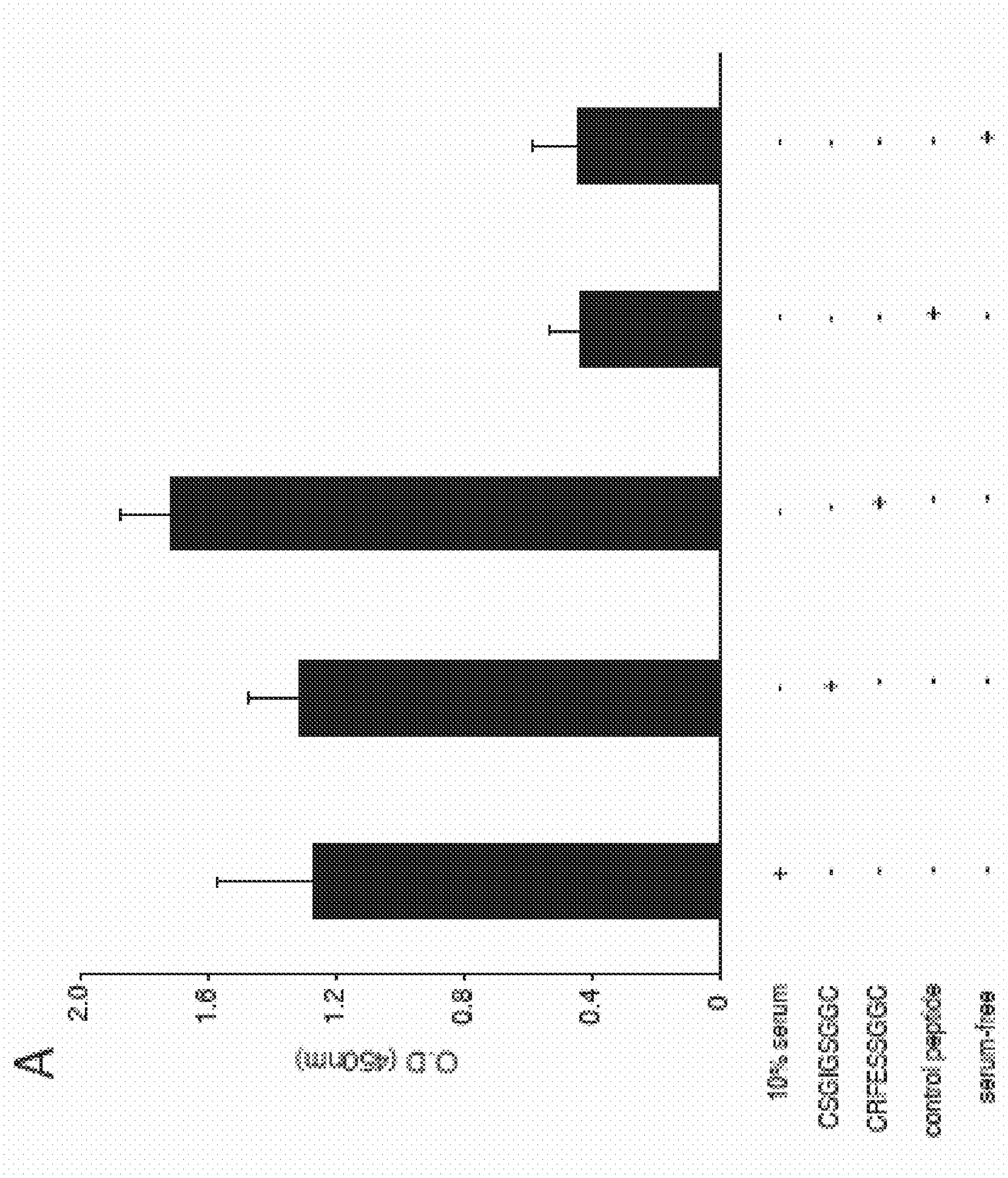
FIG. 9A-B: Biological effects of the peptides CSGIGSGGC (SEQ ID NO:2) and CRFESSGGC (SEQ ID NO:3 on lung cancer cells. Promotion of cell survival and proliferative response of starved lung cancer cells to the ephrin mimic peptides, control peptide and complete culture medium (A549 (FIG. 9A), H460 cells (FIG. 9B)). Concentrations of peptide were optimized. Values in the Y-axis correspond to the number of viable cells under each experimental condition evaluated after a 72 h incubation period. Data bars represent the mean and corresponding standard error of the mean.
Figure 9B:
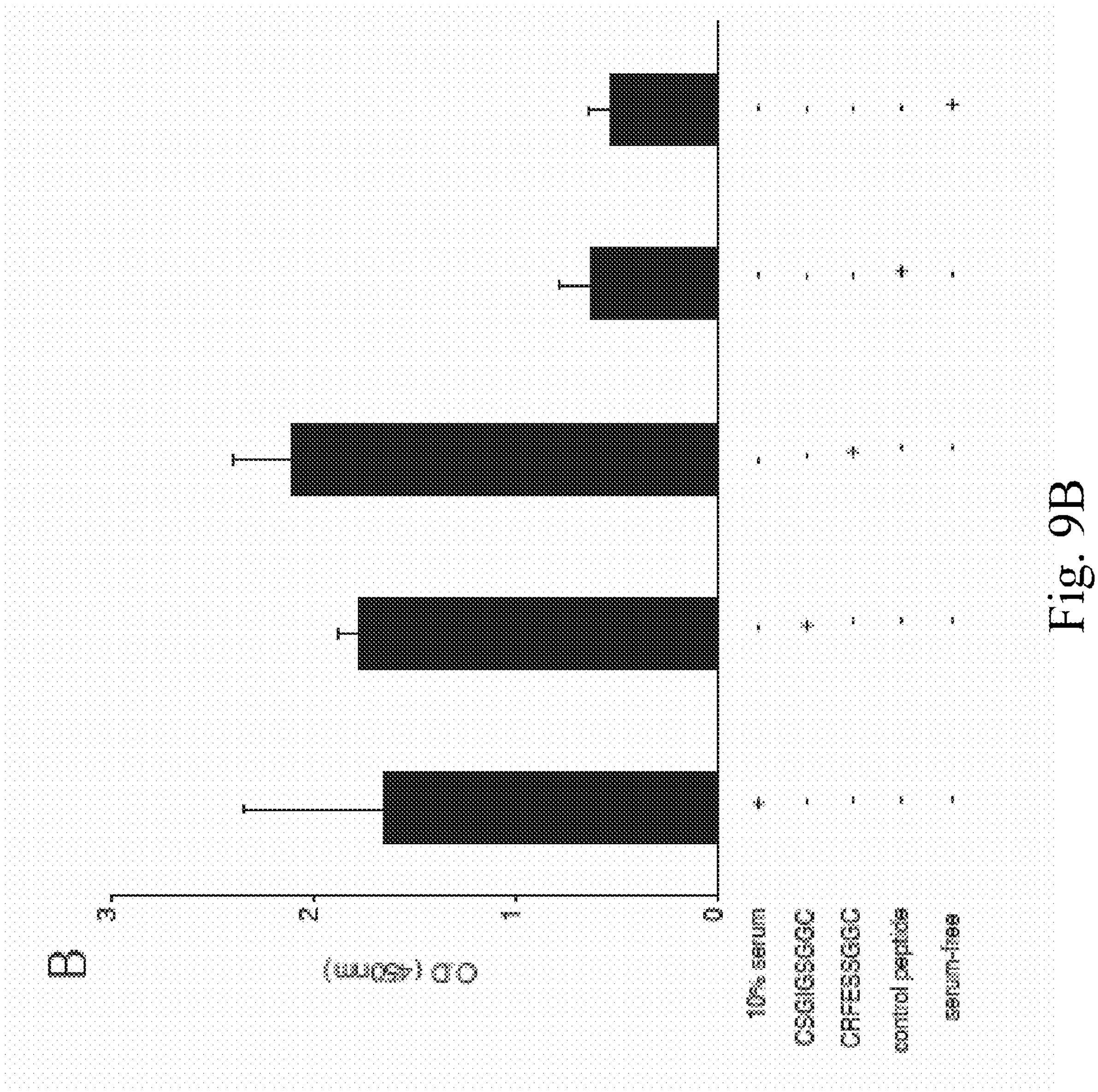

Activation of the EphA5 receptor by the peptides CSGIGSGGC (SEQ ID NO: 2) and CRFESSGGC (SEQ ID NO:3) lead to proliferation and/or survival of lung cancer cells. In the absence of sera, this peptides increased lung cancer cells proliferation by 4-fold (FIG. 9A-B). This effect was confirmed in two different human cell lines, which express the EphA5 receptor.

TABLE 3

Peptides and Motifs Associated with NCI-60 cell lines.

| Motif | Peptide w/ Seq ID:No. | Cell Line |
|---|---|---|
| RLS | LRLSSIP (6) | CCRF-CEM Leukemia |
| RGV | ARGVLLM (7) | CCRF-CEM Leukemia |
| RGS | RGSHLVP (8) | CCRF-CEM Leukemia |
| | DVETRGS (9) | CCRF-CEM Leukemia |
| RAV | SRAVIDM (10) | CCRF-CEM Leukemia |
| RAS | | CCRF-CEM Leukemia |
| GAG | | CCRF-CEM Leukemia |
| AVS | | CCRF-CEM Leukemia |
| LLS | GLLSLXL (11) | CCRF-CEM Leukemia |
| | TSLLSFR (12) | CCRF-CEM Leukemia |
| LLR | | CCRF-CEM Leukemia |
| LRV | | CCRF-CEM Leukemia |
| LRS | | CCRF-CEM Leukemia |
| RVS | RRVSLVA (13) | CCRF-CEM Leukemia |
| | SRFRVSI (14) | CCRF-CEM Leukemia |
| RSS | | CCRF-CEM Leukemia |
| AGS | AGSLSVF (15) | CCRF-CEM Leukemia |
| AGR | AGRICEG (16) | CCRF-CEM Leukemia |
| | QVAGRER (17) | CCRF-CEM Leukemia |
| | VEYAAGR (18) | CCRF-CEM Leukemia |
| AGL | YNRSAGL (19) | CCRF-CEM Leukemia |

TABLE 3-continued

Peptides and Motifs Associated with NCI-60 cell lines.

| Motif | Peptide w/ Seq ID:No. | Cell Line |
|---|---|---|
| AGG | AVLVAGG (20) | CCRF-CEM Leukemia |
| | LAGGVPG (21) | CCRF-CEM Leukemia |
| GVR | DWWAGVR (22) | CCRF-CEM Leukemia |
| | EPDGVRS (23) | CCRF-CEM Leukemia |
| | EQLSGVR (24) | CCRF-CEM Leukemia |
| GVL | GVLARVT (25) | CCRF-CEM Leukemia |
| | ARGVLLM (26) | CCRF-CEM Leukemia |
| GAV | GGAVLVA (27) | CCRF-CEM Leukemia |
| | RERGAVQ (28) | CCRF-CEM Leukemia |
| GLV | RALGLVS (29) | CCRF-CEM Leukemia |
| GLR | SLGLRNQ (30) | CCRF-CEM Leukemia |
| LVS | RALGLVS (31) | CCRF-CEM Leukemia |
| | GAYRLVS (32) | CCRF-CEM Leukemia |
| ARG | FDARGGL (33) | CCRF-CEM Leukemia |
| | MFARGWE (34) | CCRF-CEM Leukemia |
| | ARGVLLM (35) | CCRF-CEM Leukemia |
| ASL | | CCRF-CEM Leukemia |
| AAV | | CCRF-CEM Leukemia |
| AAS | | CCRF-CEM Leukemia |
| GGS | GGGSDGV (36) | CCRF-CEM Leukemia |
| GGR | LGGRADF (37) | CCRF-CEM Leukemia |
| | | CCRF-CEM Leukemia |
| GLG | | CCRF-CEM Leukemia |
| GGL | EVGGGLT (38) | CCRF-CEM Leukemia |
| | FDARGGL (39) | CCRF-CEM Leukemia |
| GSS | | CCRF-CEM Leukemia |
| GSG | | CCRF-CEM Leukemia |
| GSV | | CCRF-CEM Leukemia |
| GRV | TGRVVRR (40) | CCRF-CEM Leukemia |
| GRL | | CCRF-CEM Leukemia |
| GPS | MGMSGPS (41) | CCRF-CEM Leukemia |
| GVS | | CCRF-CEM Leukemia |
| RLS | | HL-60-Leukemia |
| RGV | AVRGVAR (42) | HL-60-Leukemia |
| | DRGVPGL (43) | HL-60-Leukemia |
| RGS | LSFSRGS (44) | HL-60-Leukemia |
| | RGSVRVL (45) | HL-60-Leukemia |

TABLE 3-continued

Peptides and Motifs Associated with NCI-60 cell lines.

| Motif | Peptide w/ Seq ID:No. | Cell Line |
|---|---|---|
| | PVRGSVD (46) | HL-60-Leukemia |
| | QVMMRGS (47) | HL-60-Leukemia |
| | NGRGSGW (48) | HL-60-Leukemia |
| RAV | RAVGRVA (49) | HL-60-Leukemia |
| RAS | RASCALT (50) | HL-60-Leukemia |
| GAG | ADIGAGG (51) | HL-60-Leukemia |
| | FMGAGFA (52) | HL-60-Leukemia |
| AVS | AGVFAVS (53) | HL-60-Leukemia |
| LLS | | HL-60-Leukemia |
| LLR | VMLLRPE (54) | HL-60-Leukemia |
| | LLRGLEL (55) | HL-60-Leukemia |
| | LPLLRGI (56) | HL-60-Leukemia |
| LRV | DPRGLRV (57) | HL-60-Leukemia |
| LRS | | HL-60-Leukemia |
| RVS | LVRVSGR (58) | HL-60-Leukemia |
| | SGSRVSL (59) | HL-60-Leukemia |
| RSS | | HL-60-Leukemia |
| AGS | AGSIALR (60) | HL-60-Leukemia |
| AGR | MLASAGR (61) | HL-60-Leukemia |
| AGL | | HL-60-Leukemia |
| AGG | ADIGAGG (62) | HL-60-Leukemia |
| | FAGGSTD (63) | HL-60-Leukemia |
| GVR | | HL-60-Leukemia |
| GVL | | HL-60-Leukemia |
| GAV | TGFGAVG (64) | HL-60-Leukemia |
| | | HL-60-Leukemia |
| GLV | | HL-60-Leukemia |
| GLR | FGLRNSR (65) | HL-60-Leukemia |
| | DPRGLRV (66) | HL-60-Leukemia |
| LVS | LVSSGSK (67) | HL-60-Leukemia |
| | LVSSSEP (68) | HL-60-Leukemia |
| ARG | | HL-60-Leukemia |
| ASL | | HL-60-Leukemia |
| AAV | AAVWAAD (69) | HL-60-Leukemia |
| AAS | | HL-60-Leukemia |
| GGS | FAGGSTD (70) | HL-60-Leukemia |

TABLE 3-continued

Peptides and Motifs Associated with NCI-60 cell lines.

| Motif | Peptide w/ Seq ID:No. | Cell Line |
|---|---|---|
| GGR | | HL-60-Leukemia |
| GLG | | HL-60-Leukemia |
| GGL | TFGKGGL (71) | HL-60-Leukemia |
| GSS | KSGSSVL (72) | HL-60-Leukemia |
| | | HL-60-Leukemia |
| GSG | WGSGRGN (73) | HL-60-Leukemia |
| GSV | RGSVRVL (74) | HL-60-Leukemia |
| | PVRGSVD (75) | HL-60-Leukemia |
| | TEGSVTV (76) | HL-60-Leukemia |
| GRV | RAVGRVA (77) | HL-60-Leukemia |
| | DVSGRVP (78) | HL-60-Leukemia |
| | LGQCGRV (79) | HL-60-Leukemia |
| GRL | GRLRLTD (80) | HL-60-Leukemia |
| | LELGRLL (81) | HL-60-Leukemia |
| | IGRLLPL (82) | HL-60-Leukemia |
| | SDENGRL (83) | HL-60-Leukemia |
| GPS | | HL-60-Leukemia |
| GVS | | HL-60-Leukemia |
| RLS | | K-562-Leukemia |
| RGV | ELHPRGV (84) | K-562-Leukemia |
| | FDRGVEA (85) | K-562-Leukemia |
| RGS | EAVSRGS (86) | K-562-Leukemia |
| | WTKRGSV (87) | K-562-Leukemia |
| RAV | | K-562-Leukemia |
| RAS | ERASQTA (88) | K-562-Leukemia |
| GAG | | K-562-Leukemia |
| AVS | EAVSRGS (89) | K-562-Leukemia |
| LLS | AATLLSF (90) | K-562-Leukemia |
| | LLSASLV (91) | K-562-Leukemia |
| | RRHGLLS (92) | K-562-Leukemia |
| LLR | RYSTLLR (93) | K-562-Leukemia |
| LRV | FTLRVDK (94) | K-562-Leukemia |
| LRS | | K-562-Leukemia |
| RVS | SHRVSDS (95) | K-562-Leukemia |
| | | K-562-Leukemia |
| RSS | NRSSAKF (96) | K-562-Leukemia |
| | LRRSSFS (97) | K-562-Leukemia |
| AGS | AIRAGSD (98) | K-562-Leukemia |
| | VLFSAGS (99) | K-562-Leukemia |
| AGR | | K-562-Leukemia |
| AGL | | K-562-Leukemia |
| AGG | | K-562-Leukemia |
| GVR | | K-562-Leukemia |
| GVL | GVLHSIA (100) | K-562-Leukemia |
| GAV | RQTTGAV (101) | K-562-Leukemia |
| GLV | CQGLVLQ (102) | K-562-Leukemia |
| GLR | PPPWGLR (103) | K-562-Leukemia |
| LVS | | K-562-Leukemia |
| ARG | SNARGPR (104) | K-562-Leukemia |
| ASL | LLSASLV (105) | K-562-Leukemia |
| AAV | AAVFVRS (106) | K-562-Leukemia |
| AAS | | K-562-Leukemia |
| GGS | FFGGSRA (107) | K-562-Leukemia |
| | GGSQCDT (108) | K-562-Leukemia |
| | VWGVGGS (109) | K-562-Leukemia |
| GGR | FAWGGRG (110) | K-562-Leukemia |
| GLG | GLGIMGP (111) | K-562-Leukemia |
| GGL | | K-562-Leukemia |
| GSS | SSGSSNG (112) | K-562-Leukemia |
| GSG | | K-562-Leukemia |
| GSV | WTKRGSV (113) | K-562-Leukemia |
| GRV | | K-562-Leukemia |
| GRL | | K-562-Leukemia |
| GPS | | K-562-Leukemia |
| GVS | GVSTGFT (114) | K-562-Leukemia |
| RLS | | Molt-4-Leukemia |
| RGV | CHARGVT (115) | Molt-4-Leukemia |
| RGS | WGRGSVA (116) | Molt-4-Leukemia |
| RAV | | Molt-4-Leukemia |
| RAS | | Molt-4-Leukemia |
| GAG | LRSGAGS (117) | Molt-4-Leukemia |
| AVS | RAAVSAI (118) | Molt-4-Leukemia |
| | AVSGRGW (119) | Molt-4-Leukemia |

TABLE 3-continued

Peptides and Motifs Associated with NCI-60 cell lines.

| Motif | Peptide w/ Seq ID:No. | Cell Line |
|---|---|---|
| LLS | LLSFLGR (120) | Molt-4-Leukemia |
| LLR | | Molt-4-Leukemia |
| LRV | | Molt-4-Leukemia |
| LRS | GFYWLRS (121) | Molt-4-Leukemia |
| RVS | RGARVSA (122) | Molt-4-Leukemia |
| RSS | GGRSSHP (123) | Molt-4-Leukemia |
| | RSSIAPS (124) | Molt-4-Leukemia |
| AGS | LAGSGSH (125) | Molt-4-Leukemia |
| | LRSGAGS (126) | Molt-4-Leukemia |
| AGR | ASVRAGR (127) | Molt-4-Leukemia |
| AGL | | Molt-4-Leukemia |
| AGG | | Molt-4-Leukemia |
| GVR | IGVRGFF (128) | Molt-4-Leukemia |
| GVL | ANGVLEL (129) | Molt-4-Leukemia |
| | | Molt-4-Leukemia |
| GAV | WFGAVGL (130) | Molt-4-Leukemia |
| GLV | GLVRGTA (131) | Molt-4-Leukemia |
| | GLVRGTA | Molt-4-Leukemia |
| | EGLVSVV (132) | Molt-4-Leukemia |
| GLR | DLGLRPV (133) | Molt-4-Leukemia |
| LVS | ALVSRRG (134) | Molt-4-Leukemia |
| | EVLVSGD (135) | Molt-4-Leukemia |
| | EGLVSVV (136) | Molt-4-Leukemia |
| ARG | CHARGVT (137) | Molt-4-Leukemia |
| ASL | | Molt-4-Leukemia |
| AAV | RAAVSAI (138) | Molt-4-Leukemia |
| AAS | | Molt-4-Leukemia |
| GGS | HRGGSQS (139) | Molt-4-Leukemia |
| GGR | GGRSSHP (140) | Molt-4-Leukemia |
| | SQSGGRH (141) | Molt-4-Leukemia |
| GLG | ARAIGLG (142) | Molt-4-Leukemia |
| GGL | STEGGGL (143) | Molt-4-Leukemia |
| GSS | | Molt-4-Leukemia |
| GSG | LAGSGSH (144) | Molt-4-Leukemia |
| GSV | DGSVLVE (145) | Molt-4-Leukemia |
| | WGRGSVA (146) | Molt-4-Leukemia |

TABLE 3-continued

Peptides and Motifs Associated with NCI-60 cell lines.

| Motif | Peptide w/ Seq ID:No. | Cell Line |
|---|---|---|
| GRV | ATGRVLG (147) | Molt-4-Leukemia |
| | ATGRVLG (148) | Molt-4-Leukemia |
| | FFGRVGI (149) | Molt-4-Leukemia |
| | RIGRVWA (150) | Molt-4-Leukemia |
| GRL | RGRLEVP (151) | Molt-4-Leukemia |
| GPS | | Molt-4-Leukemia |
| GVS | | Molt-4-Leukemia |
| RLS | RRLSYRD (152) | RPMI-8226-Leukemia |
| | SRLSYRG (153) | RPMI-8226-Leukemia |
| RGV | FSSKRGV (154) | RPMI-8226-Leukemia |
| RGS | RGSAQNF (155) | RPMI-8226-Leukemia |
| | LRSGRGS (156) | RPMI-8226-Leukemia |
| | LRSGRGS | RPMI-8226-Leukemia |
| | LRSGRGS | RPMI-8226-Leukemia |
| | YRGSSGK (157) | RPMI-8226-Leukemia |
| RAV | | RPMI-8226-Leukemia |
| RAS | FWISRAS (158) | RPMI-8226-Leukemia |
| GAG | GAGSISD (159) | RPMI-8226-Leukemia |
| | RAMGGAG (160) | RPMI-8226-Leukemia |
| AVS | | RPMI-8226-Leukemia |
| LLS | LLSTSIR (161) | RPMI-8226-Leukemia |
| LLR | LLLRSGG (162) | RPMI-8226-Leukemia |
| | LLRSAAP (163) | RPMI-8226-Leukemia |
| LRV | | RPMI-8226-Leukemia |
| LRS | LLLRSGG (164) | RPMI-8226-Leukemia |
| | GRYSLRS (165) | RPMI-8226-Leukemia |
| | LRSGRGS (166) | RPMI-8226-Leukemia |
| | LRYDLRS (167) | RPMI-8226-Leukemia |
| | LRYNLRS (168) | RPMI-8226-Leukemia |
| | LLRSAAP (169) | RPMI-8226-Leukemia |
| | SKYRLRS (170) | RPMI-8226-Leukemia |
| RVS | VHRVSGG (171) | RPMI-8226-Leukemia |
| RSS | | RPMI-8226-Leukemia |
| AGS | GAGSISD (172) | RPMI-8226-Leukemia |
| AGR | FAGRVPS (173) | RPMI-8226-Leukemia |
| AGL | AGLSGSQ (174) | RPMI-8226-Leukemia |
| | TDLAGLH (175) | RPMI-8226-Leukemia |

TABLE 3-continued

Peptides and Motifs Associated with NCI-60 cell lines.

| Motif | Peptide w/ Seq ID:No. | Cell Line |
|---|---|---|
| AGG | LAAGGEL (176) | RPMI-8226-Leukemia |
| | GAGGMAR (177) | RPMI-8226-Leukemia |
| | RAAGGSR (178) | RPMI-8226-Leukemia |
| GVR | LYGVRYG (179) | RPMI-8226-Leukemia |
| | PRYGVRA (180) | RPMI-8226-Leukemia |
| GVL | | RPMI-8226-Leukemia |
| GAV | GAVDGSR (181) | RPMI-8226-Leukemia |
| GLV | ADFFGLV (182) | RPMI-8226-Leukemia |
| GLR | KYYGLRR (183) | RPMI-8226-Leukemia |
| | SRYGLRR (184) | RPMI-8226-Leukemia |
| LVS | | RPMI-8226-Leukemia |
| ARG | | RPMI-8226-Leukemia |
| ASL | | RPMI-8226-Leukemia |
| AAV | | RPMI-8226-Leukemia |
| AAS | PAASRLL (185) | RPMI-8226-Leukemia |
| | RLRAASY (186) | RPMI-8226-Leukemia |
| | | RPMI-8226-Leukemia |
| GGS | GGSRLLL (187) | RPMI-8226-Leukemia |
| | RAAGGSR (188) | RPMI-8226-Leukemia |
| | GGSVRHV (189) | RPMI-8226-Leukemia |
| GGR | GGRSWVN (190) | RPMI-8226-Leukemia |
| GLG | GLGNRPT (191) | RPMI-8226-Leukemia |
| | HGLGSGT (192) | RPMI-8226-Leukemia |
| GGL | | RPMI-8226-Leukemia |
| GSS | GSSLHLL (193) | RPMI-8226-Leukemia |
| | YRGSSGK (194) | RPMI-8226-Leukemia |
| GSG | EGSGVDC (195) | RPMI-8226-Leukemia |
| | HGLGSGT (196) | RPMI-8226-Leukemia |
| GSV | SGSVNRG (197) | RPMI-8226-Leukemia |
| | GGSVRHV (198) | RPMI-8226-Leukemia |
| GRV | FAGRVPS (199) | RPMI-8226-Leukemia |
| GRL | AMRPGRL (200) | RPMI-8226-Leukemia |
| | GRLYYYR (201) | RPMI-8226-Leukemia |
| GPS | PAFGPSR (202) | RPMI-8226-Leukemia |
| GVS | HSGVSHG (203) | RPMI-8226-Leukemia |
| RLS | VYYRLSA (204) | SR Leukemia |

TABLE 3-continued

Peptides and Motifs Associated with NCI-60 cell lines.

| Motif | Peptide w/ Seq ID:No. | Cell Line |
|---|---|---|
| RGV | | SR Leukemia |
| RGS | GRGSFES (205) | SR Leukemia |
| | RRGSSRN (206) | SR Leukemia |
| RAV | HSRAVAP (207) | SR Leukemia |
| RAS | RASFRAG (208) | SR Leukemia |
| | LMGRASG (209) | SR Leukemia |
| | WRASAFT (210) | SR Leukemia |
| GAG | GAGRTVM (211) | SR Leukemia |
| AVS | PLAVSMV (212) | SR Leukemia |
| LLS | | SR Leukemia |
| LLR | FLLRSSF (213) | SR Leukemia |
| | WRLLRRQ (214) | SR Leukemia |
| LRV | | SR Leukemia |
| LRS | FLLRSSF (215) | SR Leukemia |
| | LRSRLGF (216) | SR Leukemia |
| RVS | GRRVSLV (217) | SR Leukemia |
| RSS | FLLRSSF (218) | SR Leukemia |
| | NRSSGRR (219) | SR Leukemia |
| | VLGMRSS (220) | SR Leukemia |
| | THRNRSS (221) | SR Leukemia |
| AGS | LAGSTRR (222) | SR Leukemia |
| AGR | AGRTGVG (223) | SR Leukemia |
| | EFAVAGR (224) | SR Leukemia |
| | GAGRTVM (225) | SR Leukemia |
| | REEFAGR (226) | SR Leukemia |
| AGL | | SR Leukemia |
| AGG | AGGPTKY (227) | SR Leukemia |
| | FHVAGGS (228) | SR Leukemia |
| | WSAGGPH (229) | SR Leukemia |
| GVR | | SR Leukemia |
| GVL | | SR Leukemia |
| GAV | RGAVAFE (230) | SR Leukemia |
| | SGGAVHF (231) | SR Leukemia |
| | GAVRARL (232) | SR Leukemia |
| GLV | GLVRGFP (233) | SR Leukemia |
| | GAHGLVR (234) | SR Leukemia |
| | SSRMGLV (235) | SR Leukemia |

TABLE 3-continued

Peptides and Motifs Associated with NCI-60 cell lines.

| Motif | Peptide w/ Seq ID:No. | Cell Line |
|---|---|---|
|  | YVGLVVS (236) | SR Leukemia |
| GLR | GLRKAGF (237) | SR Leukemia |
|  | AVDGLRL (238) | SR Leukemia |
|  | FGLRSRL (239) | SR Leukemia |
| LVS |  | SR Leukemia |
| ARG |  | SR Leukemia |
|  | ERARGYP (240) | SR Leukemia |
|  | GSARGML (241) | SR Leukemia |
| ASL | ASLRYYV (242) | SR Leukemia |
|  | NAASLPS (243) | SR Leukemia |
|  | WLDASLM (244) | SR Leukemia |
| AAV |  | SR Leukemia |
| AAS | NAASLPS (245) | SR Leukemia |
| GGS | FHVAGGS (246) | SR Leukemia |
|  | GEHLGGS (247) | SR Leukemia |
| GGR |  | SR Leukemia |
| GLG |  | SR Leukemia |
| GGL | SGGLHEG (248) | SR Leukemia |
| RLS | SRLSYRS (249) | A549-Lung |
| RGV | GGLRGVR (250) | A549-Lung |
|  | VAWRGVS (251) | A549-Lung |
|  | SVEGRGV (252) | A549-Lung |
| RGS | FWRGSVP (253) | A549-Lung |
| RAV |  | A549-Lung |
| RAS | EFTRRAS (254) | A549-Lung |
|  | WGWRASS (255) | A549-Lung |
| GAG |  | A549-Lung |
| AVS |  | A549-Lung |
| LLS |  | A549-Lung |
| LLR |  | A549-Lung |
| LRV |  | A549-Lung |
| LRS | RFYHLRS (256) | A549-Lung |
|  | SRYSLRS (257) | A549-Lung |
| RVS |  | A549-Lung |
| RSS | RRSSKQA (258) | A549-Lung |
|  | DWGRSSF (259) | A549-Lung |
|  | RFTRSSG (260) | A549-Lung |
|  | VFQRSSG (261) | A549-Lung |
| AGS | AGSQSWE (262) | A549-Lung |
| AGR |  | A549-Lung |
| AGL |  | A549-Lung |
| AGG | EHPAGGM (263) | A549-Lung |
| GVR | GVRTAGP (264) | A549-Lung |
|  | GGLRGVR (265) | A549-Lung |
|  | LYGGVRY (266) | A549-Lung |
| GVL | PVGGVLL (267) | A549-Lung |
| GAV | GAVVKPI (268) | A549-Lung |
|  | SVGAVGG (269) | A549-Lung |
| GLV | GLVSVEA (270) | A549-Lung |
| GLR | GGLRGVR (271) | A549-Lung |
| LVS | DIALVSP (272) | A549-Lung |
|  | GLVSVEA (273) | A549-Lung |
| ARG |  | A549-Lung |
| ASL |  | A549-Lung |
| AAV |  | A549-Lung |
| AAS | ARNAASP (274) | A549-Lung |
| GGS | AEGGSGH (275) | A549-Lung |
|  | GGSFSGL (276) | A549-Lung |
| GGR | VTGGRVD (277) | A549-Lung |
| GLG |  | A549-Lung |
| GGL | GGLRGVR (278) | A549-Lung |
|  |  | A549-Lung |
| GSS | GSSWVVD (279) | A549-Lung |
|  | GSSRTFR (280) | A549-Lung |
|  | GSSRQFV (281) | A549-Lung |
|  | WVGSSKF (282) | A549-Lung |
| GSG | AEGGSGH (283) | A549-Lung |
|  | EVIGSGI (284) | A549-Lung |
| GSV | FWRGSVP (285) | A549-Lung |
|  | VGSVSVN (286) | A549-Lung |
| GRV | VTGGRVD (287) | A549-Lung |
|  | GRVTVAV (288) | A549-Lung |
| GRL | RVGRLGG (289) | A549-Lung |

TABLE 3-continued

Peptides and Motifs Associated with NCI-60 cell lines.

| Motif | Peptide w/ Seq ID:No. | Cell Line |
|---|---|---|
| GPS | NYMGPSA (290) | A549-Lung |
| | GWHGPSH (291) | A549-Lung |
| GVS | GGVSPVD (292) | A549-Lung |
| | GVSKVRA (293) | A549-Lung |
| | GGVAGVS (294) | A549-Lung |
| | VAWRGVS (295) | A549-Lung |
| RLS | VIGSRLS (296) | EKVX-Lung |
| RGV | HLRGRGV (297) | EKVX-Lung |
| RGS | EVRSRGS (298) | EKVX-Lung |
| | RGSRLPA (299) | EKVX-Lung |
| RAV | DVRAVSS (300) | EKVX-Lung |
| RAS | | EKVX-Lung |
| GAG | | EKVX-Lung |
| AVS | DVRAVSS (301) | EKVX-Lung |
| LLS | | EKVX-Lung |
| LLR | | EKVX-Lung |
| LRV | | EKVX-Lung |
| LRS | APLRSGR (302) | EKVX-Lung |
| | SLRSGIV (303) | EKVX-Lung |
| RVS | | EKVX-Lung |
| RSS | DGGRRSS (304) | EKVX-Lung |
| AGS | QAGSFLR (305) | EKVX-Lung |
| | DAGSDRR (306) | EKVX-Lung |
| AGR | AGRRFGG (307) | EKVX-Lung |
| AGL | AGLSGGT (308) | EKVX-Lung |
| AGG | AGGGPPA (309) | EKVX-Lung |
| | AGGGPPA (310) | EKVX-Lung |
| | FFPAGGP (311) | EKVX-Lung |
| | PRAGGRW (312) | EKVX-Lung |
| GVR | DVPGVRF (313) | EKVX-Lung |
| GVL | FGVLFRS (314) | EKVX-Lung |
| | SRYGVLV (315) | EKVX-Lung |
| GAV | | EKVX-Lung |
| GLV | LRGGLVS (316) | EKVX-Lung |
| GLR | KSGLRPA (317) | EKVX-Lung |
| LVS | ALVSFSV (318) | EKVX-Lung |
| | LRGGLVS (319) | EKVX-Lung |

TABLE 3-continued

Peptides and Motifs Associated with NCI-60 cell lines.

| Motif | Peptide w/ Seq ID:No. | Cell Line |
|---|---|---|
| ARG | HKLARGR (320) | EKVX-Lung |
| ASL | ASLPPRA (321) | EKVX-Lung |
| AAV | | EKVX-Lung |
| AAS | | EKVX-Lung |
| GGS | TGGSLGA (322) | EKVX-Lung |
| | GGGSWLI (323) | EKVX-Lung |
| GGR | DGGRRSS (324) | EKVX-Lung |
| | SVLGGRL (325) | EKVX-Lung |
| | PRAGGRW (326) | EKVX-Lung |
| GLG | YWFIGLG (327) | EKVX-Lung |
| GGL | GGLSVDL (328) | EKVX-Lung |
| | LRGGLVS (329) | EKVX-Lung |
| GSS | SGVGSSL (330) | EKVX-Lung |
| GSG | GSGILDL (331) | EKVX-Lung |
| GSV | SLGSVGS (332) | EKVX-Lung |
| GRV | | EKVX-Lung |
| GRL | VGRGRLH (333) | EKVX-Lung |
| | SVLGGRL (334) | EKVX-Lung |
| | MSAFGRL (335) | EKVX-Lung |
| GPS | | EKVX-Lung |
| GVS | SGVSGLS (336) | EKVX-Lung |
| RLS | | Hop-62-Lung |
| RGV | GDSRRGV (337) | Hop-62-Lung |
| | GKALRGV (338) | Hop-62-Lung |
| RGS | PKAGRGS (339) | Hop-62-Lung |
| RAV | FDRAVAN (340) | Hop-62-Lung |
| | LLRRAVF (341) | Hop-62-Lung |
| RAS | FRASSEV (342) | Hop-62-Lung |
| | PDRASDG (343) | Hop-62-Lung |
| | FRASLQY (344) | Hop-62-Lung |
| GAG | | Hop-62-Lung |
| AVS | | Hop-62-Lung |
| LLS | | Hop-62-Lung |
| LLR | HVGLLRA (345) | Hop-62-Lung |
| | QVLLRSF (346) | Hop-62-Lung |
| | LLRRAVF (347) | Hop-62-Lung |

TABLE 3-continued

Peptides and Motifs Associated with NCI-60 cell lines.

| Motif | Peptide w/ Seq ID:No. | Cell Line |
|---|---|---|
| LRV | FLRVGEL (348) | Hop-62-Lung |
| LRS | QVLLRSF (349) | Hop-62-Lung |
| RVS | RRVSCDL (350) | Hop-62-Lung |
| RSS | RSSGLGF (351) | Hop-62-Lung |
| | SSGPRSS (352) | Hop-62-Lung |
| | YSQRSSL (353) | Hop-62-Lung |
| | | Hop-62-Lung |
| AGS | | Hop-62-Lung |
| AGR | DAGRTID (354) | Hop-62-Lung |
| | AAGREFR (355) | Hop-62-Lung |
| | PKAGRGS (356) | Hop-62-Lung |
| | VRAAGRV (357) | Hop-62-Lung |
| | | Hop-62-Lung |
| AGL | | Hop-62-Lung |
| AGG | HGYRAGG (358) | Hop-62-Lung |
| | WGATAGG (359) | Hop-62-Lung |
| | YYAGGLK (360) | Hop-62-Lung |
| GVR | LEGVRLF (361) | Hop-62-Lung |
| | GVRPFPR (362) | Hop-62-Lung |
| GVL | GTFGVLG (363) | Hop-62-Lung |
| | VWAGVLL (364) | Hop-62-Lung |
| GAV | GAVLFRV (365) | Hop-62-Lung |
| GLV | GLVGFTG (366) | Hop-62-Lung |
| | GLVSAFY (367) | Hop-62-Lung |
| GLR | ARAMGLR (368) | Hop-62-Lung |
| LVS | GLVSAFY (369) | Hop-62-Lung |
| | SWRPLVS (370) | Hop-62-Lung |
| ARG | | Hop-62-Lung |
| ASL | FRASLQY (371) | Hop-62-Lung |
| AAV | HSESAAV (372) | Hop-62-Lung |
| | LFAVAAV (373) | Hop-62-Lung |
| AAS | VAASESH (374) | Hop-62-Lung |
| GGS | | Hop-62-Lung |
| GGR | HPSMGGR (375) | Hop-62-Lung |
| GLG | GLGVSGV (376) | Hop-62-Lung |
| | KRESGLG (377) | Hop-62-Lung |
| | RSSGLGF (378) | Hop-62-Lung |

TABLE 3-continued

Peptides and Motifs Associated with NCI-60 cell lines.

| Motif | Peptide w/ Seq ID:No. | Cell Line |
|---|---|---|
| | VGLGHWP (379) | Hop-62-Lung |
| GGL | YYAGGLK (380) | Hop-62-Lung |
| GSS | NYGSSFH (381) | Hop-62-Lung |
| | FGLGSSR (382) | Hop-62-Lung |
| | SSRPGSS (383) | Hop-62-Lung |
| GSG | | Hop-62-Lung |
| GSV | VGSVGLG (384) | Hop-62-Lung |
| GRV | VRAAGRV (385) | Hop-62-Lung |
| GRL | HNGRLEV (386) | Hop-62-Lung |
| | VGRLAKG (387) | Hop-62-Lung |
| GPS | VMGGPSL (388) | Hop-62-Lung |
| GVS | GLGVSGV (389) | Hop-62-Lung |
| | SGVSVEG (390) | Hop-62-Lung |
| RLS | GESGRLS (391) | Hop-92-Lung |
| RGV | GSGRGVA (392) | Hop-92-Lung |
| | RGVVSAK (393) | Hop-92-Lung |
| | RGVVSGV (394) | Hop-92-Lung |
| RGS | AVGRGSG (395) | Hop-92-Lung |
| | SLRGSEG (396) | Hop-92-Lung |
| | PATRGSV (397) | Hop-92-Lung |
| RAV | SLTRAVR (398) | Hop-92-Lung |
| | VARAVPC (399) | Hop-92-Lung |
| RAS | EGARASD (400) | Hop-92-Lung |
| GAG | | Hop-92-Lung |
| AVS | MGSAVSL (401) | Hop-92-Lung |
| LLS | | Hop-92-Lung |
| LLR | GGALLRG (402) | Hop-92-Lung |
| LRV | | Hop-92-Lung |
| LRS | | Hop-92-Lung |
| RVS | PNRRVSA (403) | Hop-92-Lung |
| | QDRVSRS (404) | Hop-92-Lung |
| RSS | SERSSLG (405) | Hop-92-Lung |
| | LVRSSGL (406) | Hop-92-Lung |
| AGS | | Hop-92-Lung |
| AGR | | Hop-92-Lung |
| AGL | INWAGLS (407) | Hop-92-Lung |

TABLE 3-continued

Peptides and Motifs Associated with NCI-60 cell lines.

| Motif | Peptide w/ Seq ID:No. | Cell Line |
|---|---|---|
| | WAGLSPS (408) | Hop-92-Lung |
| AGG | GRLLAGG (409) | Hop-92-Lung |
| GVR | | Hop-92-Lung |
| GVL | | Hop-92-Lung |
| GAV | | Hop-92-Lung |
| GLV | SYGLVLP (410) | Hop-92-Lung |
| | SGGLVLT (411) | Hop-92-Lung |
| | HAAHGLV (412) | Hop-92-Lung |
| GLR | GLRTRQV (413) | Hop-92-Lung |
| LVS | LVSGYNG (414) | Hop-92-Lung |
| ARG | AGIARGG (415) | Hop-92-Lung |
| ASL | | Hop-92-Lung |
| AAV | | Hop-92-Lung |
| AAS | | Hop-92-Lung |
| GGS | HVSGGSG (416) | Hop-92-Lung |
| | GGSSEFR (417) | Hop-92-Lung |
| | GGSGIGS (418) | Hop-92-Lung |
| | SWGSGGS (419) | Hop-92-Lung |
| | TLVLGGS (420) | Hop-92-Lung |
| GGR | AVRGGRP (421) | Hop-92-Lung |
| | GGRAIGA (422) | Hop-92-Lung |
| GLG | | Hop-92-Lung |
| GGL | SGGLVLT (423) | Hop-92-Lung |
| GSS | RTGSSDL (424) | Hop-92-Lung |
| | LGSSRVL (425) | Hop-92-Lung |
| | GGSSEFR (426) | Hop-92-Lung |
| GSG | AVGRGSG (427) | Hop-92-Lung |
| | HVSGGSG (428) | Hop-92-Lung |
| | SGIGSGG (429) | Hop-92-Lung |
| | SWGSGGS (430) | Hop-92-Lung |
| | WVGSGSP (431) | Hop-92-Lung |
| GSV | GSGGSVH (432) | Hop-92-Lung |
| | GNYGSVL (433) | Hop-92-Lung |
| | VGSVVGR (434) | Hop-92-Lung |
| | PATRGSV (435) | Hop-92-Lung |
| GRV | PRGGRVA (436) | Hop-92-Lung |
| | GRVHLMP (437) | Hop-92-Lung |

TABLE 3-continued

Peptides and Motifs Associated with NCI-60 cell lines.

| Motif | Peptide w/ Seq ID:No. | Cell Line |
|---|---|---|
| GRL | GESGRLS (438) | Hop-92-Lung |
| | GRLLAGG (439) | Hop-92-Lung |
| | GRLWWHT (440) | Hop-92-Lung |
| | GRLWSRV (441) | Hop-92-Lung |
| GPS | AGPSAWL (442) | Hop-92-Lung |
| GVS | SGVSRGQ (443) | Hop-92-Lung |
| RLS | | H226-Lung |
| RGV | RGVSLKG (444) | H226-Lung |
| RGS | | H226-Lung |
| RAV | QMQGRAV (445) | H226-Lung |
| RAS | | H226-Lung |
| GAG | | H226-Lung |
| AVS | | H226-Lung |
| LLS | | H226-Lung |
| LLR | | H226-Lung |
| LRV | | H226-Lung |
| LRS | RGLRSVN (446) | H226-Lung |
| RVS | | H226-Lung |
| RSS | RSSLGLP (447) | H226-Lung |
| AGS | LEAGSQL (448) | H226-Lung |
| AGR | | H226-Lung |
| AGL | | H226-Lung |
| AGG | AGGQSER (449) | H226-Lung |
| GVR | | H226-Lung |
| GVL | GGVLYLE (450) | H226-Lung |
| GAV | | H226-Lung |
| GLV | | H226-Lung |
| GLR | RGLRSVN (451) | H226-Lung |
| LVS | | H226-Lung |
| ARG | VARGQMQ (452) | H226-Lung |
| ASL | | H226-Lung |
| AAV | | H226-Lung |
| AAS | | H226-Lung |
| GGS | GGSRNRW (453) | H226-Lung |
| GGR | GGGRSGV (454) | H226-Lung |
| GLG | GLGGWVA (455) | H226-Lung |

TABLE 3-continued

Peptides and Motifs Associated with NCI-60 cell lines.

| Motif | Peptide w/ Seq ID:No. | Cell Line |
|---|---|---|
| GGL | AVWGGLG (456) | H226-Lung |
| | GGLSECV (457) | H226-Lung |
| GSS | | H226-Lung |
| GSG | | H226-Lung |
| GSV | AKLGSVY (458) | H226-Lung |
| GRV | QGRVNVK (459) | H226-Lung |
| GRL | GRLWGFW (460) | H226-Lung |
| GPS | | H226-Lung |
| GVS | RGVSLKG (461) | H226-Lung |
| | GSLGVSL (462) | H226-Lung |
| RLS | LLRLSLA (463) | H23-Lung |
| RGV | | H23-Lung |
| RGS | RRGSGGL (464) | H23-Lung |
| | VRGSVRA (465) | H23-Lung |
| RAV | | H23-Lung |
| RAS | | H23-Lung |
| GAG | | H23-Lung |
| AVS | | H23-Lung |
| LLS | | H23-Lung |
| LLR | LLRLSLA (466) | H23-Lung |
| LRV | PLRVDNL (467) | H23-Lung |
| | LRVGIGY (468) | H23-Lung |
| | QGYALRV (469) | H23-Lung |
| LRS | PLRSFDS (470) | H23-Lung |
| RVS | ARVSGRV (471) | H23-Lung |
| RSS | PFPARSS (472) | H23-Lung |
| AGS | AGSPLAK (473) | H23-Lung |
| | FVDIAGS (474) | H23-Lung |
| AGR | SYFRAGR (475) | H23-Lung |
| AGL | AGLGHEG (476) | H23-Lung |
| AGG | AGGSLGS (477) | H23-Lung |
| GVR | YGIGVRL (478) | H23-Lung |
| GVL | RANGVLV (479) | H23-Lung |
| GAV | | H23-Lung |
| GLV | | H23-Lung |
| GLR | | H23-Lung |
| LVS | | H23-Lung |
| ARG | | H23-Lung |
| ASL | LASLGVG (480) | H23-Lung |
| AAV | RAAVGAR (481) | H23-Lung |
| AAS | | H23-Lung |
| GGS | GCDGGSA (482) | H23-Lung |
| | GGSGELG (483) | H23-Lung |
| | LGGSGRR (484) | H23-Lung |
| | AGGSLGS (485) | H23-Lung |
| GGR | IGGREIT (486) | H23-Lung |
| GLG | GEHGLGA (487) | H23-Lung |
| GGL | RRGSGGL (488) | H23-Lung |
| GSS | RSGSSVY (489) | H23-Lung |
| GSG | GLEGSGG (490) | H23-Lung |
| | LGGSGRR (491) | H23-Lung |
| GSV | TTGSVIV (492) | H23-Lung |
| | VRGSVRA (493) | H23-Lung |
| GRV | HGRVHRL (494) | H23-Lung |
| | ARVSGRV (495) | H23-Lung |
| GRL | | H23-Lung |
| GPS | | H23-Lung |
| GVS | SGHGVSA (496) | H23-Lung |
| RLS | AVWRLSH (497) | H322-Lung |
| RGV | RGVFYGK (498) | H322-Lung |
| | RGVGWAK (499) | H322-Lung |
| RGS | SRGSTAG (500) | H322-Lung |
| RAV | | H322-Lung |
| RAS | | H322-Lung |
| GAG | SEDEGAG (501) | H322-Lung |
| | STSLGAG (502) | H322-Lung |
| AVS | | H322-Lung |
| LLS | | H322-Lung |
| LLR | DLLRYLA (503) | H322-Lung |
| LRV | LRVRYAV (504) | H322-Lung |
| LRS | LRSSGAT (505) | H322-Lung |
| | LSMLRSA (506) | H322-Lung |
| RVS | REAERVS (507) | H322-Lung |

TABLE 3-continued

Peptides and Motifs Associated with NCI-60 cell lines.

| Motif | Peptide w/ Seq ID:No. | Cell Line |
|---|---|---|
| RSS | LRSSGAT (508) | H322-Lung |
| AGS | TAGSSRL (509) | H322-Lung |
| AGR | AAGRAGC (510) | H322-Lung |
| AGL | GAGLSTS (511) | H322-Lung |
| AGG | | H322-Lung |
| GVR | PSVGVRA (512) | H322-Lung |
| GVL | | H322-Lung |
| GAV | VGAVYFL (513) | H322-Lung |
| GLV | | H322-Lung |
| GLR | LGLRAFV (514) | H322-Lung |
| LVS | TELVSWS (515) | H322-Lung |
| ARG | CGARGAA (516) | H322-Lung |
| ASL | | H322-Lung |
| AAV | | H322-Lung |
| AAS | | H322-Lung |
| GGS | GGSRAAE (517) | H322-Lung |
| | VNLGGSW (518) | H322-Lung |
| GGR | LIGPGGR (519) | H322-Lung |
| GLG | | H322-Lung |
| GGL | LGGLSPH (520) | H322-Lung |
| | WSGGLNV (521) | H322-Lung |
| GSS | TAGSSRL (522) | H322-Lung |
| | SDVSGSS (523) | H322-Lung |
| | WGSSTVR (524) | H322-Lung |
| GSG | | H322-Lung |
| GSV | NLADGSV (525) | H322-Lung |
| | SSGSVDS (526) | H322-Lung |
| GRV | GRVPGFE (527) | H322-Lung |
| | GRVVGEA (528) | H322-Lung |
| GRL | | H322-Lung |
| GPS | SRFGPSV (529) | H322-Lung |
| GVS | ARVGVSP (530) | H322-Lung |
| RLS | | H460-Lung |
| RGV | PGKRGVQ (531) | H460-Lung |
| | RGVASRS (532) | H460-Lung |
| RGS | ERGSPSR (533) | H460-Lung |
| RAV | LIRAVSA (534) | H460-Lung |

TABLE 3-continued

Peptides and Motifs Associated with NCI-60 cell lines.

| Motif | Peptide w/ Seq ID:No. | Cell Line |
|---|---|---|
| | RAVEMGT (535) | H460-Lung |
| RAS | | H460-Lung |
| GAG | WGAGFWM (536) | H460-Lung |
| AVS | LIRAVSA (537) | H460-Lung |
| LLS | | H460-Lung |
| LLR | | H460-Lung |
| LRV | | H460-Lung |
| LRS | DRYMLRS (538) | H460-Lung |
| RVS | | H460-Lung |
| RSS | PRSSYNE (539) | H460-Lung |
| | PRSSLVV (540) | H460-Lung |
| AGS | | H460-Lung |
| AGR | | H460-Lung |
| AGL | RRFWAGL (541) | H460-Lung |
| AGG | PVHSAGG (542) | H460-Lung |
| GVR | | H460-Lung |
| GVL | FGGSGVL (543) | H460-Lung |
| | SSGGVLG (544) | H460-Lung |
| GAV | | H460-Lung |
| GLV | GLVGGSS (545) | H460-Lung |
| | LSSGLVS (546) | H460-Lung |
| GLR | | H460-Lung |
| LVS | LSSGLVS (547) | H460-Lung |
| | WFSWLVS (548) | H460-Lung |
| ARG | | H460-Lung |
| ASL | GASLTGD (549) | H460-Lung |
| | WSSTASL (550) | H460-Lung |
| AAV | | H460-Lung |
| AAS | | H460-Lung |
| GGS | FGGSGVL (551) | H460-Lung |
| | GLVGGSS (552) | H460-Lung |
| GGR | | H460-Lung |
| GLG | | H460-Lung |
| GGL | GGLSPHR (553) | H460-Lung |
| GSS | GLVGGSS (554) | H460-Lung |
| | SVLGSSL (555) | H460-Lung |

TABLE 3-continued

Peptides and Motifs Associated with NCI-60 cell lines.

| Motif | Peptide w/ Seq ID:No. | Cell Line |
|---|---|---|
| GSG | FGGSGVL (556) | H460-Lung |
| GSV | | H460-Lung |
| GRV | DVRGRVW (557) | H460-Lung |
| | AEPRGRV (558) | H460-Lung |
| GRL | | H460-Lung |
| GPS | SIGPSTN (559) | H460-Lung |
| GVS | GVSIRQL (560) | H460-Lung |
| RLS | | H522-Lung |
| RGV | | H522-Lung |
| RGS | | H522-Lung |
| RAV | | H522-Lung |
| RAS | | H522-Lung |
| GAG | | H522-Lung |
| AVS | AVSKRLP (561) | H522-Lung |
| | RLAVSGY (562) | H522-Lung |
| | | H522-Lung |
| LLS | | H522-Lung |
| LLR | | H522-Lung |
| LRV | | H522-Lung |
| LRS | RREGLRS (563) | H522-Lung |
| | SRYWLRS (564) | H522-Lung |
| | | H522-Lung |
| RVS | | H522-Lung |
| RSS | | H522-Lung |
| AGS | | H522-Lung |
| AGR | AVYRAGR (565) | H522-Lung |
| | | H522-Lung |
| AGL | | H522-Lung |
| AGG | | H522-Lung |
| GVR | | H522-Lung |
| GVL | | H522-Lung |
| GAV | | H522-Lung |
| GLV | | H522-Lung |
| GLR | RHFGLRE (566) | H522-Lung |
| | RREGLRS (567) | H522-Lung |
| | | H522-Lung |
| LVS | | H522-Lung |

TABLE 3-continued

Peptides and Motifs Associated with NCI-60 cell lines.

| Motif | Peptide w/ Seq ID:No. | Cell Line |
|---|---|---|
| ARG | | H522-Lung |
| ASL | GQGAASL (568) | H522-Lung |
| AAV | | H522-Lung |
| AAS | GQGAASL (569) | H522-Lung |
| | | H522-Lung |
| GGS | | H522-Lung |
| GGR | | H522-Lung |
| GLG | | H522-Lung |
| GGL | | H522-Lung |
| GSS | | H522-Lung |
| GSG | | H522-Lung |
| GSV | YGSVALR (570) | H522-Lung |
| | | H522-Lung |
| GRV | | H522-Lung |
| GRL | | H522-Lung |
| GPS | | H522-Lung |
| GVS | | H522-Lung |
| RLS | | COLO-205-Colon |
| RGV | ARRGVLG (571) | COLO-205-Colon |
| | LRIARGV (572) | COLO-205-Colon |
| RGS | YRGSMVG (573) | COLO-205-Colon |
| | GLRGSVW (574) | COLO-205-Colon |
| RAV | GPFRAVP (575) | COLO-205-Colon |
| RAS | | COLO-205-Colon |
| GAG | | COLO-205-Colon |
| AVS | | COLO-205-Colon |
| LLS | | COLO-205-Colon |
| LLR | | COLO-205-Colon |
| LRV | | COLO-205-Colon |
| LRS | AHYTLRS (576) | COLO-205-Colon |
| | SELRSIR (577) | COLO-205-Colon |
| | SVYALRS (578) | COLO-205-Colon |
| RVS | | COLO-205-Colon |
| RSS | | COLO-205-Colon |
| AGS | | COLO-205-Colon |
| AGR | | COLO-205-Colon |

TABLE 3-continued

Peptides and Motifs Associated with NCI-60 cell lines.

| Motif | Peptide w/ Seq ID:No. | Cell Line |
|---|---|---|
| AGL | | COLO-205-Colon |
| AGG | | COLO-205-Colon |
| GVR | | COLO-205-Colon |
| GVL | ARRGVLG (579) | COLO-205-Colon |
| GAV | PGAVLTV (580) | COLO-205-Colon |
| GLV | GLVGRRA (581) | COLO-205-Colon |
| | GLVRCVL (582) | COLO-205-Colon |
| | YDGLVSG (583) | COLO-205-Colon |
| | GLVTAPL (584) | COLO-205-Colon |
| | RGLVRVV (585) | COLO-205-Colon |
| GLR | GLRGSVW (586) | COLO-205-Colon |
| | NSFGLRY (587) | COLO-205-Colon |
| LVS | YDGLVSG (588) | COLO-205-Colon |
| ARG | AARGLEA (589) | COLO-205-Colon |
| | DNDGARG (590) | COLO-205-Colon |
| | LRIARGV (591) | COLO-205-Colon |
| ASL | | COLO-205-Colon |
| AAV | MSNLAAV (592) | COLO-205-Colon |
| AAS | | COLO-205-Colon |
| GGS | | COLO-205-Colon |
| GGR | | COLO-205-Colon |
| GLG | | COLO-205-Colon |
| GGL | | COLO-205-Colon |
| GSS | YSGSSDF (593) | COLO-205-Colon |
| GSG | | COLO-205-Colon |
| GSV | GSVLGDY (594) | COLO-205-Colon |
| | GLRGSVW (595) | COLO-205-Colon |
| GRV | DLDGRVV (596) | COLO-205-Colon |
| GRL | WVSGRLG (597) | COLO-205-Colon |
| GPS | GPSSMTF (598) | COLO-205-Colon |
| GVS | DGVSSDY (599) | COLO-205-Colon |
| | FTSGVSW (600) | COLO-205-Colon |
| RLS | | HCC-2998-Colon |
| RGV | | HCC-2998-Colon |
| RGS | | HCC-2998-Colon |
| RAV | | HCC-2998-Colon |
| RAS | VLTRAST (601) | HCC-2998-Colon |

TABLE 3-continued

Peptides and Motifs Associated with NCI-60 cell lines.

| Motif | Peptide w/ Seq ID:No. | Cell Line |
|---|---|---|
| | LRASLLW (602) | HCC-2998-Colon |
| GAG | | HCC-2998-Colon |
| AVS | | HCC-2998-Colon |
| LLS | WLLSARL (603) | HCC-2998-Colon |
| LLR | LLRPGTV (604) | HCC-2998-Colon |
| LRV | | HCC-2998-Colon |
| LRS | | HCC-2998-Colon |
| RVS | | HCC-2998-Colon |
| RSS | | HCC-2998-Colon |
| AGS | | HCC-2998-Colon |
| AGR | | HCC-2998-Colon |
| AGL | | HCC-2998-Colon |
| AGG | AAGGLLV (605) | HCC-2998-Colon |
| GVR | | HCC-2998-Colon |
| GVL | | HCC-2998-Colon |
| GAV | | HCC-2998-Colon |
| GLV | | HCC-2998-Colon |
| GLR | | HCC-2998-Colon |
| LVS | | HCC-2998-Colon |
| ARG | | HCC-2998-Colon |
| ASL | LRASLLW (606) | HCC-2998-Colon |
| AAV | | HCC-2998-Colon |
| AAS | | HCC-2998-Colon |
| GGS | | HCC-2998-Colon |
| GGR | | HCC-2998-Colon |
| GLG | LWGLGWL (607) | HCC-2998-Colon |
| | RRSGLGD (608) | HCC-2998-Colon |
| | WWGLGWL (609) | HCC-2998-Colon |
| GGL | AAGGLLV (610) | HCC-2998-Colon |
| GSS | | HCC-2998-Colon |
| GSG | | HCC-2998-Colon |
| GSV | | HCC-2998-Colon |
| GRV | | HCC-2998-Colon |
| GRL | | HCC-2998-Colon |
| GPS | | HCC-2998-Colon |
| GVS | | HCC-2998-Colon |

TABLE 3-continued

Peptides and Motifs Associated with NCI-60 cell lines.

| Motif | Peptide w/ Seq ID:No. | Cell Line |
|---|---|---|
| RLS | | HCT-116 Colon |
| RGV | GLRGVVK (611) | HCT-116 Colon |
| RGS | AVEGRGS (612) | HCT-116 Colon |
| | NAVRGSA (613) | HCT-116 Colon |
| RAV | | HCT-116 Colon |
| RAS | | HCT-116 Colon |
| GAG | | HCT-116 Colon |
| AVS | | HCT-116 Colon |
| LLS | | HCT-116 Colon |
| LLR | LLRSSLG (614) | HCT-116 Colon |
| | MYLRLLR (615) | HCT-116 Colon |
| LRV | | HCT-116 Colon |
| LRS | LLRSSLG (616) | HCT-116 Colon |
| | DEGLRSR (617) | HCT-116 Colon |
| RVS | YWQHRVS (618) | HCT-116 Colon |
| RSS | ARSSHRA (619) | HCT-116 Colon |
| | LLRSSLG (620) | HCT-116 Colon |
| AGS | | HCT-116 Colon |
| AGR | AGRSCNL (621) | HCT-116 Colon |
| | AGRPRAT (622) | HCT-116 Colon |
| AGL | | HCT-116 Colon |
| AGG | | HCT-116 Colon |
| GVR | GGVRIAA (623) | HCT-116 Colon |
| | GVRYLRT (624) | HCT-116 Colon |
| GVL | | HCT-116 Colon |
| GAV | | HCT-116 Colon |
| GLV | PLAVGLV (625) | HCT-116 Colon |
| GLR | GLRGVVK (626) | HCT-116 Colon |
| | DEGLRSR (627) | HCT-116 Colon |
| LVS | QLVSGSL (628) | HCT-116 Colon |
| ARG | | HCT-116 Colon |
| ASL | GWSASLG (629) | HCT-116 Colon |
| AAV | IAAVWRS (630) | HCT-116 Colon |
| AAS | | HCT-116 Colon |
| GGS | GGSSLDA (631) | HCT-116 Colon |
| | LGGSRDL (632) | HCT-116 Colon |
| GGR | LIGGRNA (633) | HCT-116 Colon |

TABLE 3-continued

Peptides and Motifs Associated with NCI-60 cell lines.

| Motif | Peptide w/ Seq ID:No. | Cell Line |
|---|---|---|
| GLG | | HCT-116 Colon |
| GGL | LDRSGGL (634) | HCT-116 Colon |
| GSS | GGSSLDA (635) | HCT-116 Colon |
| | GSSYSGP (636) | HCT-116 Colon |
| GSG | TVGSGCL (637) | HCT-116 Colon |
| GSV | LSGSVLQ (638) | HCT-116 Colon |
| GRV | ASGRVAN (639) | HCT-116 Colon |
| GRL | KVVGRLG (640) | HCT-116 Colon |
| | GRLVWGL (641) | HCT-116 Colon |
| | NEFLGRL (642) | HCT-116 Colon |
| GPS | LCDAGPS (643) | HCT-116 Colon |
| GVS | FRAGVSH (644) | HCT-116 Colon |
| RLS | AGDSRLS (645) | HCT-15 Colon |
| RGV | | HCT-15 Colon |
| RGS | | HCT-15 Colon |
| RAV | DWRRRAV (646) | HCT-15 Colon |
| RAS | WTERASA (647) | HCT-15 Colon |
| GAG | | HCT-15 Colon |
| AVS | | HCT-15 Colon |
| LLS | RLLSAFG (648) | HCT-15 Colon |
| LLR | GFASLLR (649) | HCT-15 Colon |
| LRV | GALRVPW (650) | HCT-15 Colon |
| | GALRVPW | HCT-15 Colon |
| | GALRVPW | HCT-15 Colon |
| LRS | SLRSDGA (651) | HCT-15 Colon |
| | DTLRSQW (652) | HCT-15 Colon |
| | LRSVGSW (653) | HCT-15 Colon |
| RVS | | HCT-15 Colon |
| RSS | ISPRSSG (654) | HCT-15 Colon |
| | WRVRSSG (655) | HCT-15 Colon |
| AGS | | HCT-15 Colon |
| AGR | AAGRIRP (656) | HCT-15 Colon |
| | RAAGRVG (657) | HCT-15 Colon |
| AGL | AGLQHAV (658) | HCT-15 Colon |
| AGG | AGGWWVG (659) | HCT-15 Colon |
| GVR | GVRGAAR (660) | HCT-15 Colon |

TABLE 3-continued

Peptides and Motifs Associated with NCI-60 cell lines.

| Motif | Peptide w/ Seq ID:No. | Cell Line |
|---|---|---|
| GVL | GVLPVVT (661) | HCT-15 Colon |
| | GVLPVVT | HCT-15 Colon |
| GAV | | HCT-15 Colon |
| GLV | GLVSSLP (662) | HCT-15 Colon |
| | SRHGLVR (663) | HCT-15 Colon |
| | SDRGLVV (664) | HCT-15 Colon |
| | SDRGLVV (665) | HCT-15 Colon |
| GLR | | HCT-15 Colon |
| LVS | GLVSSLP (666) | HCT-15 Colon |
| | LVSVWSR (667) | HCT-15 Colon |
| ARG | GSWARGY (668) | HCT-15 Colon |
| ASL | GFASLLR (669) | HCT-15 Colon |
| AAV | HAAVMSL (670) | HCT-15 Colon |
| AAS | | HCT-15 Colon |
| GGS | | HCT-15 Colon |
| GGR | DGGRRTD (671) | HCT-15 Colon |
| | GRPLGGR (672) | HCT-15 Colon |
| | GRVTGGR (673) | HCT-15 Colon |
| GLG | | HCT-15 Colon |
| GGL | RGGLPRG (674) | HCT-15 Colon |
| | YGQYGGL (675) | HCT-15 Colon |
| GSS | GSSRPSI (676) | HCT-15 Colon |
| | PGSSFVG (677) | HCT-15 Colon |
| | GSSRVRW (678) | HCT-15 Colon |
| GSG | | HCT-15 Colon |
| GSV | | HCT-15 Colon |
| GRV | RAAGRVG (679) | HCT-15 Colon |
| | GRVTGGR (680) | HCT-15 Colon |
| | YVRIGRV (681) | HCT-15 Colon |
| GRL | MITRGRL (682) | HCT-15 Colon |
| GPS | | HCT-15 Colon |
| GVS | SVVGVST (683) | HCT-15 Colon |
| | WSGVSRL (684) | HCT-15 Colon |
| RLS | RRLSYFH (685) | HT-29 Colon |
| | PRLSWVL (686) | HT-29 Colon |
| | RLSALTD (687) | HT-29 Colon |
| RGV | GRGVGTD (688) | HT-29 Colon |

TABLE 3-continued

Peptides and Motifs Associated with NCI-60 cell lines.

| Motif | Peptide w/ Seq ID:No. | Cell Line |
|---|---|---|
| | LKVRGVL (689) | HT-29 Colon |
| | SSTRGVY (690) | HT-29 Colon |
| | QVRRGVV (691) | HT-29 Colon |
| | GRGVTIW (692) | HT-29 Colon |
| RGS | RGSVASA (693) | HT-29 Colon |
| | HFIRGSV (694) | HT-29 Colon |
| | RGSWAGV (695) | HT-29 Colon |
| | VRGSRWR (696) | HT-29 Colon |
| RAV | LERAVRT (697) | HT-29 Colon |
| RAS | GYSRASD (698) | HT-29 Colon |
| | SRASGHG (699) | HT-29 Colon |
| | GHYRASV (700) | HT-29 Colon |
| | DWVCRAS (701) | HT-29 Colon |
| GAG | GAGRGTP (702) | HT-29 Colon |
| | LSLAGAG (703) | HT-29 Colon |
| AVS | ASAVSGR (704) | HT-29 Colon |
| | FSGDAVS (705) | HT-29 Colon |
| LLS | LKLLSVP (706) | HT-29 Colon |
| LLR | | HT-29 Colon |
| LRV | GTLRVGS (707) | HT-29 Colon |
| LRS | EHYRLRS (708) | HT-29 Colon |
| | LRSWLLF (709) | HT-29 Colon |
| | RRPGLRS (710) | HT-29 Colon |
| | SKYNLRS (711) | HT-29 Colon |
| | WQVALRS (712) | HT-29 Colon |
| | LRSDPRS (713) | HT-29 Colon |
| | VPLRSSA (714) | HT-29 Colon |
| RVS | | HT-29 Colon |
| RSS | GRSSGME (715) | HT-29 Colon |
| | VPLRSSA (716) | HT-29 Colon |
| AGS | AGSGFPF (717) | HT-29 Colon |
| AGR | GAGRGTP (718) | HT-29 Colon |
| | AGRIASK (719) | HT-29 Colon |
| AGL | WGVAGLG (720) | HT-29 Colon |
| | LAGLVSG (721) | HT-29 Colon |
| AGG | DAGGMDL (722) | HT-29 Colon |

TABLE 3-continued

Peptides and Motifs Associated with NCI-60 cell lines.

| Motif | Peptide w/ Seq ID:No. | Cell Line |
|---|---|---|
| | AGGRWNL (723) | HT-29 Colon |
| GVR | GCGGVRD (724) | HT-29 Colon |
| | SGVRLTG (725) | HT-29 Colon |
| GVL | LKVRGVL (726) | HT-29 Colon |
| GAV | GLGAVGW (727) | HT-29 Colon |
| | PGAVPGA (728) | HT-29 Colon |
| | RIGAVWY (729) | HT-29 Colon |
| GLV | FSGLVVA (730) | HT-29 Colon |
| | PGGLVPG (731) | HT-29 Colon |
| | LAGLVSG (732) | HT-29 Colon |
| | LGLVSTT (733) | HT-29 Colon |
| GLR | GLRLGVT (734) | HT-29 Colon |
| | RRPGLRS (735) | HT-29 Colon |
| LVS | LAGLVSG (736) | HT-29 Colon |
| | LGLVSTT (737) | HT-29 Colon |
| | RQLVSPA (738) | HT-29 Colon |
| ARG | LRARGGH (739) | HT-29 Colon |
| ASL | ELWASLG (740) | HT-29 Colon |
| | DTLASLR (741) | HT-29 Colon |
| | VVASLPH (742) | HT-29 Colon |
| AAV | | HT-29 Colon |
| AAS | VLRAASR (743) | HT-29 Colon |
| | AASGSYY (744) | HT-29 Colon |
| GGS | GGSALFG (745) | HT-29 Colon |
| | GRGGSGY (746) | HT-29 Colon |
| GGR | YGSGGRG (747) | HT-29 Colon |
| | GTLGGRV (748) | HT-29 Colon |
| | AGGRWNL (749) | HT-29 Colon |
| | HGGRARL (750) | HT-29 Colon |
| | RGGRSPS (751) | HT-29 Colon |
| | RKPGGGR (752) | HT-29 Colon |
| | EGGRTHW (753) | HT-29 Colon |
| GLG | GEVGLGV (754) | HT-29 Colon |
| | GLGAVGW (755) | HT-29 Colon |
| GGL | PGGLVPG (756) | HT-29 Colon |
| | VRGGLTG (757) | HT-29 Colon |
| | RQKCGGL (758) | HT-29 Colon |

TABLE 3-continued

Peptides and Motifs Associated with NCI-60 cell lines.

| Motif | Peptide w/ Seq ID:No. | Cell Line |
|---|---|---|
| | RYGVGGL (759) | HT-29 Colon |
| GSS | EMGSSRG (760) | HT-29 Colon |
| GSG | AGSGFPF (761) | HT-29 Colon |
| | GRGGSGY (762) | HT-29 Colon |
| GSV | GSVSAGA (763) | HT-29 Colon |
| | RGSVASA (764) | HT-29 Colon |
| | DLGSVQH (765) | HT-29 Colon |
| | HFIRGSV (766) | HT-29 Colon |
| | GSVLGAL (767) | HT-29 Colon |
| GRV | GTLGGRV (768) | HT-29 Colon |
| | LGRVHVW (769) | HT-29 Colon |
| | LVGRVKL (770) | HT-29 Colon |
| | RWRSGRV (771) | HT-29 Colon |
| GRL | RNPGRLA (772) | HT-29 Colon |
| | PRGRLFD (773) | HT-29 Colon |
| | GRLAVVA (774) | HT-29 Colon |
| | LAQGRLA (775) | HT-29 Colon |
| | GGMNGRL (776) | HT-29 Colon |
| GPS | RSTLGPS (777) | HT-29 Colon |
| GVS | GVSALSL (778) | HT-29 Colon |
| RLS | SRLSYYA (779) | KM-12C Colon |
| | SRLSYYA | KM-12C Colon |
| RGV | ARGVSAP (780) | KM-12C Colon |
| | GRGVLAF (781) | KM-12C Colon |
| RGS | MRGSGRN (782) | KM-12C Colon |
| RAV | RDGRAVR (783) | KM-12C Colon |
| | GRAVWMV (784) | KM-12C Colon |
| RAS | | KM-12C Colon |
| GAG | | KM-12C Colon |
| AVS | | KM-12C Colon |
| LLS | | KM-12C Colon |
| LLR | | KM-12C Colon |
| LRV | LRVPGGP (785) | KM-12C Colon |
| LRS | AYYSLRS (786) | KM-12C Colon |
| | AYYSLRS | KM-12C Colon |
| | VLRSALQ (787) | KM-12C Colon |
| | VYYALRS (788) | KM-12C Colon |

TABLE 3-continued

| Peptides and Motifs Associated with NCI-60 cell lines. | | |
|---|---|---|
| Motif | Peptide w/ Seq ID:No. | Cell Line |
| | VYYALRS | KM-12C Colon |
| | VYYALRS | KM-12C Colon |
| | VYYALRS | KM-12C Colon |
| | VYYALRS | KM-12C Colon |
| | VYYALRS | KM-12C Colon |
| | VYYALRS | KM-12C Colon |
| RVS | RYRVSVY (789) | KM-12C Colon |
| RSS | | KM-12C Colon |
| AGS | | KM-12C Colon |
| AGR | | KM-12C Colon |
| AGL | | KM-12C Colon |
| AGG | AGGIWIR (790) | KM-12C Colon |
| GVR | WQVSGVR (791) | KM-12C Colon |
| GVL | GRGVLAF (792) | KM-12C Colon |
| GAV | | KM-12C Colon |
| GLV | | KM-12C Colon |
| GLR | | KM-12C Colon |
| LVS | HAELVSL (793) | KM-12C Colon |
| ARG | ARGVSAP (794) | KM-12C Colon |
| | RVARGDR (795) | KM-12C Colon |
| | VMWVARG (796) | KM-12C Colon |
| ASL | | KM-12C Colon |
| AAV | AAVTVVR (797) | KM-12C Colon |
| AAS | | KM-12C Colon |
| GGS | | KM-12C Colon |
| GGR | | KM-12C Colon |
| GLG | | KM-12C Colon |
| GGL | TREGGLD (798) | KM-12C Colon |
| | LGGGGLL (799) | KM-12C Colon |
| GSS | | KM-12C Colon |
| GSG | GSGHSFA (800) | KM-12C Colon |
| | MRGSGRN (801) | KM-12C Colon |
| GSV | RVGSVQW (802) | KM-12C Colon |
| | EGTSGSV (803) | KM-12C Colon |
| GRV | GRVPTVV (804) | KM-12C Colon |
| | | KM-12C Colon |

TABLE 3-continued

| Peptides and Motifs Associated with NCI-60 cell lines. | | |
|---|---|---|
| Motif | Peptide w/ Seq ID:No. | Cell Line |
| GRL | ADGRLRY (805) | KM-12C Colon |
| GPS | | KM-12C Colon |
| GVS | ARGVSAP (806) | KM-12C Colon |
| RLS | | SW620-Colon |
| RGV | RGVKLGD (807) | SW620-Colon |
| RGS | LRGSYVL (808) | SW620-Colon |
| | RRGSLMF (809) | SW620-Colon |
| | RGSVGPS (810) | SW620-Colon |
| RAV | | SW620-Colon |
| RAS | SRASDVT (811) | SW620-Colon |
| GAG | | SW620-Colon |
| AVS | | SW620-Colon |
| LLS | AAKTLLS (812) | SW620-Colon |
| LLR | | SW620-Colon |
| LRV | | SW620-Colon |
| LRS | RSYPLRS (813) | SW620-Colon |
| RVS | YLGRRVS (814) | SW620-Colon |
| RSS | RSSPVWT (815) | SW620-Colon |
| AGS | DLRRAGS (816) | SW620-Colon |
| AGR | | SW620-Colon |
| AGL | GVAGLRW (817) | SW620-Colon |
| AGG | RIDAGGG (818) | SW620-Colon |
| | GVAGGAT (819) | SW620-Colon |
| GVR | | SW620-Colon |
| GVL | | SW620-Colon |
| GAV | TAGGAVG (820) | SW620-Colon |
| | WRLGAVG (821) | SW620-Colon |
| GLV | SGLVAMV (822) | SW620-Colon |
| GLR | VGLRDWG (823) | SW620-Colon |
| | GVAGLRW (824) | SW620-Colon |
| LVS | | SW620-Colon |
| ARG | ARGIVRV (825) | SW620-Colon |
| ASL | ASLHHRR (826) | SW620-Colon |
| AAV | | SW620-Colon |
| AAS | GAAASGY (827) | SW620-Colon |
| GGS | | SW620-Colon |
| GGR | | SW620-Colon |

TABLE 3-continued

Peptides and Motifs Associated with NCI-60 cell lines.

| Motif | Peptide w/ Seq ID:No. | Cell Line |
|---|---|---|
| GLG | LAIRGLG (828) | SW620-Colon |
| GGL | GGLSNVV (829) | SW620-Colon |
| | PPGGLKW (830) | SW620-Colon |
| GSS | | SW620-Colon |
| GSG | | SW620-Colon |
| GSV | EGSVDAH (831) | SW620-Colon |
| | RGSVGPS (832) | SW620-Colon |
| GRV | | SW620-Colon |
| GRL | LVYSGRL (833) | SW620-Colon |
| | VEEGRLR (834) | SW620-Colon |
| GPS | RGSVGPS (835) | SW620-Colon |
| GVS | SPGVSGR (836) | SW620-Colon |
| RGV | RVGRGVL (837) | SF-268 CNS |
| RGS | | SF-268 CNS |
| RAV | WIWRAVS (838) | SF-268 CNS |
| RAS | | SF-268 CNS |
| GAG | VTDGAGQ (839) | SF-268 CNS |
| AVS | LGTAVSS (840) | SF-268 CNS |
| | WIWRAVS (841) | SF-268 CNS |
| | DTPSAVS (842) | SF-268 CNS |
| LLS | GLLSAGI (843) | SF-268 CNS |
| LLR | YLLRALG (844) | SF-268 CNS |
| LRV | | SF-268 CNS |
| LRS | LRSGSLG (845) | SF-268 CNS |
| | PLRSVWS (846) | SF-268 CNS |
| RVS | | SF-268 CNS |
| RSS | ARSSIVR (847) | SF-268 CNS |
| AGS | | SF-268 CNS |
| AGR | | SF-268 CNS |
| AGL | | SF-268 CNS |
| AGG | AGGRLGL (848) | SF-268 CNS |
| | AGGWRGR (849) | SF-268 CNS |
| GVR | LVGRGVR (850) | SF-268 CNS |
| GVL | DVVGVLK (851) | SF-268 CNS |
| | RVGRGVL (852) | SF-268 CNS |
| GAV | GAVTGYP (853) | SF-268 CNS |

TABLE 3-continued

Peptides and Motifs Associated with NCI-60 cell lines.

| Motif | Peptide w/ Seq ID:No. | Cell Line |
|---|---|---|
| GLV | WGLVRHA (854) | SF-268 CNS |
| GLR | LGLRGGA (855) | SF-268 CNS |
| LVS | | SF-268 CNS |
| ARG | | SF-268 CNS |
| ASL | IGASLLG (856) | SF-268 CNS |
| AAV | AAVETGV (857) | SF-268 CNS |
| AAS | | SF-268 CNS |
| GGS | GLGGGGS (858) | SF-268 CNS |
| GGR | EVLWGGR (859) | SF-268 CNS |
| | AGGRLGL (860) | SF-268 CNS |
| | GGRSKKV (861) | SF-268 CNS |
| GLG | GLGGGGS (862) | SF-268 CNS |
| GGL | SGGGGLG (863) | SF-268 CNS |
| | GAYGGLL (864) | SF-268 CNS |
| | GGLSRSN (865) | SF-268 CNS |
| GSS | FGSSNRS (866) | SF-268 CNS |
| GSG | | SF-268 CNS |
| GSV | GSVSDRF (867) | SF-268 CNS |
| GRV | | SF-268 CNS |
| GRL | AGGRLGL (868) | SF-268 CNS |
| GPS | WFKGPSV (869) | SF-268 CNS |
| GVS | | SF-268 CNS |
| RLS | | SF-295 CNS |
| RGV | LSERRGV (870) | SF-295 CNS |
| | ARGVAEY (871) | SF-295 CNS |
| | | SF-295 CNS |
| RGS | FDRGSLT (872) | SF-295 CNS |
| | | SF-295 CNS |
| RAV | | SF-295 CNS |
| RAS | GRLRASL (873) | SF-295 CNS |
| | | SF-295 CNS |
| GAG | RDGRGAG (874) | SF-295 CNS |
| | | SF-295 CNS |
| AVS | GAVSVLA (875) | SF-295 CNS |
| | TRGDAVS (876) | SF-295 CNS |
| | | SF-295 CNS |
| LLS | LLSPRGT (877) | SF-295 CNS |

TABLE 3-continued

Peptides and Motifs Associated with NCI-60 cell lines.

| Motif | Peptide w/ Seq ID:No. | Cell Line |
|---|---|---|
| | | SF-295 CNS |
| LLR | LLRSHGV (878) | SF-295 CNS |
| | | SF-295 CNS |
| LRV | PLRVLKR (879) | SF-295 CNS |
| | GRLRLRV (880) | SF-295 CNS |
| | | SF-295 CNS |
| LRS | LLRSHGV (881) | SF-295 CNS |
| | VLRSGEL (882) | SF-295 CNS |
| | VLRSIPS (883) | SF-295 CNS |
| | VLRSIPS | SF-295 CNS |
| | | SF-295 CNS |
| RVS | GSMHRVS (884) | SF-295 CNS |
| | YSIMRVS (885) | SF-295 CNS |
| | | SF-295 CNS |
| RSS | | SF-295 CNS |
| AGS | RAGSRVQ (886) | SF-295 CNS |
| | | SF-295 CNS |
| AGR | RRDAGRM (887) | SF-295 CNS |
| | GAGRGDR (888) | SF-295 CNS |
| | | SF-295 CNS |
| AGL | RWAGLVA (889) | SF-295 CNS |
| | | SF-295 CNS |
| AGG | QTLSAGG (890) | SF-295 CNS |
| | LAGGWGS (891) | SF-295 CNS |
| | | SF-295 CNS |
| GVR | RHGVRSK (892) | SF-295 CNS |
| | | SF-295 CNS |
| GVL | | SF-295 CNS |
| GAV | GAVSVLA (893) | SF-295 CNS |
| | | SF-295 CNS |
| GLV | RWAGLVA (894) | SF-295 CNS |
| | | SF-295 CNS |
| GLR | GRGLRTD (895) | SF-295 CNS |
| | TLGGLRT (896) | SF-295 CNS |
| | | SF-295 CNS |
| LVS | ALVSVAG (897) | SF-295 CNS |

TABLE 3-continued

Peptides and Motifs Associated with NCI-60 cell lines.

| Motif | Peptide w/ Seq ID:No. | Cell Line |
|---|---|---|
| | | SF-295 CNS |
| ARG | ARGVAEY (898) | SF-295 CNS |
| | | SF-295 CNS |
| ASL | GGASLTQ (899) | SF-295 CNS |
| | GRLRASL (900) | SF-295 CNS |
| | SNHTASL (901) | SF-295 CNS |
| | | SF-295 CNS |
| AAV | YADGAAV (902) | SF-295 CNS |
| | | SF-295 CNS |
| AAS | | SF-295 CNS |
| GGS | | SF-295 CNS |
| GGR | | SF-295 CNS |
| GLG | LGGLGIH (903) | SF-295 CNS |
| | | SF-295 CNS |
| GGL | GGFTGGL (904) | SF-295 CNS |
| | HIGLGGL (905) | SF-295 CNS |
| | TRLGGLT (906) | SF-295 CNS |
| | | SF-295 CNS |
| GSS | | SF-295 CNS |
| GSG | | SF-295 CNS |
| GSV | VMPGSVV (907) | SF-295 CNS |
| | | SF-295 CNS |
| GRV | | SF-295 CNS |
| GRL | GRLRASL (908) | SF-295 CNS |
| | GRLYLGI (909) | SF-295 CNS |
| | GRLRLRV (910) | SF-295 CNS |
| | | SF-295 CNS |
| | | SF-295 CNS |
| GPS | SHCGPSN (911) | SF-295 CNS |
| | SHCGPSN | SF-295 CNS |
| | | SF-295 CNS |
| GVS | | SF-295 CNS |
| RLS | VRLSGRA (912) | SNB-19 CNS |
| | RLSTFAG (913) | SNB-19 CNS |
| RGV | | SNB-19 CNS |
| RGS | ARGSLRV (914) | SNB-19 CNS |
| | FSPRGSV (915) | SNB-19 CNS |

TABLE 3-continued

Peptides and Motifs Associated with NCI-60 cell lines.

| Motif | Peptide w/ Seq ID:No. | Cell Line |
|---|---|---|
| RAV | GGRLRAV (916) | SNB-19 CNS |
| RAS | | SNB-19 CNS |
| GAG | | SNB-19 CNS |
| AVS | VLSAVSS (917) | SNB-19 CNS |
| LLS | | SNB-19 CNS |
| LLR | | SNB-19 CNS |
| LRV | ARGSLRV (918) | SNB-19 CNS |
| LRS | LRSYAWS (919) | SNB-19 CNS |
| RVS | KGRVSAG (920) | SNB-19 CNS |
| RSS | | SNB-19 CNS |
| AGS | | SNB-19 CNS |
| AGR | | SNB-19 CNS |
| AGL | AGLTIGI (921) | SNB-19 CNS |
| AGG | AWRHAGG (922) | SNB-19 CNS |
| | WARAGGF (923) | SNB-19 CNS |
| GVR | | SNB-19 CNS |
| GVL | MGVLTAE (924) | SNB-19 CNS |
| | FAGYGVL (925) | SNB-19 CNS |
| GAV | RIFHGAV (926) | SNB-19 CNS |
| GLV | EGLVVFE (927) | SNB-19 CNS |
| GLR | REVPGLR (928) | SNB-19 CNS |
| LVS | LVSVNGA (929) | SNB-19 CNS |
| | HSLVSQP (930) | SNB-19 CNS |
| ARG | ARGSLRV (931) | SNB-19 CNS |
| ASL | SSVASLV (932) | SNB-19 CNS |
| AAV | AAVWQMK (933) | SNB-19 CNS |
| | QRAAVIV (934) | SNB-19 CNS |
| AAS | | SNB-19 CNS |
| GGS | PGGSDAA (935) | SNB-19 CNS |
| GGR | GGRLRAV (936) | SNB-19 CNS |
| GLG | | SNB-19 CNS |
| GGL | LPCGGLA (937) | SNB-19 CNS |
| GSS | GSSHDAL (938) | SNB-19 CNS |
| | TQYYGSS (939) | SNB-19 CNS |
| GSG | | SNB-19 CNS |
| GSV | FSPRGSV (940) | SNB-19 CNS |

TABLE 3-continued

Peptides and Motifs Associated with NCI-60 cell lines.

| Motif | Peptide w/ Seq ID:No. | Cell Line |
|---|---|---|
| GRV | KGRVSAG (941) | SNB-19 CNS |
| | QGRVNVK (942) | SNB-19 CNS |
| GRL | GGRLRAV (943) | SNB-19 CNS |
| | YDGRLAR (944) | SNB-19 CNS |
| GPS | | SNB-19 CNS |
| GVS | | SNB-19 CNS |
| RLS | | SNB-75 CNS |
| RGV | PQGRGVK (945) | SNB-75 CNS |
| RGS | MVLRGSY (946) | SNB-75 CNS |
| RAV | GGWARAV (947) | SNB-75 CNS |
| | VRAVCLM (948) | SNB-75 CNS |
| RAS | TRASRRG (949) | SNB-75 CNS |
| GAG | LGAGEGD (950) | SNB-75 CNS |
| AVS | IGAVSGW (951) | SNB-75 CNS |
| LLS | LLSRRVG (952) | SNB-75 CNS |
| | LELLSVV (953) | SNB-75 CNS |
| | RLLSEGY (954) | SNB-75 CNS |
| LLR | QLPGLLR (955) | SNB-75 CNS |
| | YGESLLR (956) | SNB-75 CNS |
| LRV | LRVYGEG (957) | SNB-75 CNS |
| LRS | | SNB-75 CNS |
| RVS | YRVSSGS (958) | SNB-75 CNS |
| RSS | RSSSSTR (959) | SNB-75 CNS |
| AGS | WAGSNYS (960) | SNB-75 CNS |
| AGR | CAGRARR (961) | SNB-75 CNS |
| AGL | IAGLAVV (962) | SNB-75 CNS |
| | DGEGAGL (963) | SNB-75 CNS |
| AGG | ALAGGGL (964) | SNB-75 CNS |
| GVR | GVRRSLL (965) | SNB-75 CNS |
| GVL | ADWGVLE (966) | SNB-75 CNS |
| GAV | IGAVSGW (967) | SNB-75 CNS |
| GLV | ASGLVVT (968) | SNB-75 CNS |
| GLR | IGLRGEN (969) | SNB-75 CNS |
| LVS | | SNB-75 CNS |
| ARG | RRARGAC (970) | SNB-75 CNS |
| ASL | YAASLMG (971) | SNB-75 CNS |
| AAV | LTAAVMV (972) | SNB-75 CNS |

TABLE 3-continued

Peptides and Motifs Associated with NCI-60 cell lines.

| Motif | Peptide w/ Seq ID:No. | Cell Line |
|---|---|---|
| AAS | YAASLMG (973) | SNB-75 CNS |
| GGS | RARTGGS (974) | SNB-75 CNS |
| | VSGDGGS (975) | SNB-75 CNS |
| GGR | FGGRSLS (976) | SNB-75 CNS |
| | SLGGRTF (977) | SNB-75 CNS |
| GLG | ARRGLGL (978) | SNB-75 CNS |
| GGL | ALAGGGL (979) | SNB-75 CNS |
| | FRALGGL (980) | SNB-75 CNS |
| | FTRGGLS (981) | SNB-75 CNS |
| GSS | SGSSVRY (982) | SNB-75 CNS |
| GSG | | SNB-75 CNS |
| GSV | WGSVAGI (983) | SNB-75 CNS |
| | SGGDGSV (984) | SNB-75 CNS |
| GRV | | SNB-75 CNS |
| GRL | NEGRLGI (985) | SNB-75 CNS |
| | YSGRLVM (986) | SNB-75 CNS |
| GPS | DGPSGCS (987) | SNB-75 CNS |
| GVS | | SNB-75 CNS |
| RLS | | U251 CNS |
| RGV | | U251 CNS |
| RGS | RGSRTGP (988) | U251 CNS |
| RAV | | U251 CNS |
| RAS | | U251 CNS |
| GAG | | U251 CNS |
| AVS | | U251 CNS |
| LLS | | U251 CNS |
| LLR | | U251 CNS |
| LRV | | U251 CNS |
| LRS | | U251 CNS |
| RVS | | U251 CNS |
| RSS | | U251 CNS |
| AGS | | U251 CNS |
| AGR | | U251 CNS |
| AGL | | U251 CNS |
| AGG | | U251 CNS |
| GVR | | U251 CNS |

TABLE 3-continued

Peptides and Motifs Associated with NCI-60 cell lines.

| Motif | Peptide w/ Seq ID:No. | Cell Line |
|---|---|---|
| GVL | | U251 CNS |
| GAV | | U251 CNS |
| GLV | | U251 CNS |
| GLR | | U251 CNS |
| LVS | | U251 CNS |
| ARG | | U251 CNS |
| ASL | | U251 CNS |
| AAV | | U251 CNS |
| AAS | | U251 CNS |
| GGS | | U251 CNS |
| GGR | | U251 CNS |
| GLG | | U251 CNS |
| GGL | | U251 CNS |
| GSS | GSSACGA (989) | U251 CNS |
| GSG | | U251 CNS |
| GSV | | U251 CNS |
| GRV | | U251 CNS |
| GRL | | U251 CNS |
| GPS | | U251 CNS |
| GVS | | U251 CNS |
| RLS | VRLSGRA (990) | SF-539 CNS |
| | RLSTFAG (991) | SF-539 CNS |
| RGV | | SF-539 CNS |
| RGS | ARGSLRV (992) | SF-539 CNS |
| | FSPRGSV (993) | SF-539 CNS |
| RAV | GGRLRAV (994) | SF-539 CNS |
| RAS | | SF-539 CNS |
| GAG | | SF-539 CNS |
| AVS | VLSAVSS (995) | SF-539 CNS |
| LLS | | SF-539 CNS |
| LLR | | SF-539 CNS |
| LRV | ARGSLRV (996) | SF-539 CNS |
| LRS | LRSYAWS (997) | SF-539 CNS |
| RVS | KGRVSAG (998) | SF-539 CNS |
| RSS | | SF-539 CNS |
| AGS | | SF-539 CNS |
| AGR | | SF-539 CNS |

TABLE 3-continued

Peptides and Motifs Associated with NCI-60 cell lines.

| Motif | Peptide w/ Seq ID:No. | Cell Line |
|---|---|---|
| AGL | AGLTIGI (999) | SF-539 CNS |
| AGG | AWRHAGG (1000) | SF-539 CNS |
| | WARAGGF (1001) | SF-539 CNS |
| GVR | | SF-539 CNS |
| GVL | MGVLTAE (1002) | SF-539 CNS |
| | FAGYGVL (1003) | SF-539 CNS |
| GAV | RIFHGAV (1004) | SF-539 CNS |
| GLV | EGLVVFE (1005) | SF-539 CNS |
| GLR | REVPGLR (1006) | SF-539 CNS |
| LVS | LVSVNGA (1007) | SF-539 CNS |
| | HSLVSQP (1008) | SF-539 CNS |
| ARG | ARGSLRV (1009) | SF-539 CNS |
| ASL | SSVASLV (1010) | SF-539 CNS |
| AAV | AAVWQMK (1011) | SF-539 CNS |
| | QRAAVIV (1012) | SF-539 CNS |
| AAS | | SF-539 CNS |
| GGS | | SF-539 CNS |
| GGR | GGRLRAV (1013) | SF-539 CNS |
| GLG | | SF-539 CNS |
| GGL | LPCGGLA (1014) | SF-539 CNS |
| GSS | GSSHDAL (1015) | SF-539 CNS |
| | TQYYGSS (1016) | SF-539 CNS |
| GSG | | SF-539 CNS |
| GSV | FSPRGSV (1017) | SF-539 CNS |
| GRV | KGRVSAG (1018) | SF-539 CNS |
| | QGRVNVK (1019) | SF-539 CNS |
| GRL | GGRLRAV (1020) | SF-539 CNS |
| | YDGRLAR (1021) | SF-539 CNS |
| GPS | | SF-539 CNS |
| GVS | | SF-539 CNS |
| RLS | SRLSYWQ (1022) | LOX-IMVI Melanoma |
| RGV | FVGSRGV (1023) | LOX-IMVI Melanoma |
| | SVDRGVI (1024) | LOX-IMVI Melanoma |
| RGS | GRGSGGF (1025) | LOX-IMVI Melanoma |
| RAV | | LOX-IMVI Melanoma |
| RAS | | LOX-IMVI Melanoma |

TABLE 3-continued

Peptides and Motifs Associated with NCI-60 cell lines.

| Motif | Peptide w/ Seq ID:No. | Cell Line |
|---|---|---|
| GAG | IFGAGLR (1026) | LOX-IMVI Melanoma |
| AVS | GWVAVSC (1027) | LOX-IMVI Melanoma |
| LLS | LLSGVIL (1028) | LOX-IMVI Melanoma |
| | GSTLLSR (1029) | LOX-IMVI Melanoma |
| LLR | | LOX-IMVI Melanoma |
| LRV | | LOX-IMVI Melanoma |
| LRS | QWYSLRS (1030) | LOX-IMVI Melanoma |
| RVS | TWIGRVS (1031) | LOX-IMVI Melanoma |
| RSS | | LOX-IMVI Melanoma |
| AGS | SVVLAGS (1032) | LOX-IMVI Melanoma |
| AGR | | LOX-IMVI Melanoma |
| AGL | IFGAGLR (1033) | LOX-IMVI Melanoma |
| AGG | SAGGWCA (1034) | LOX-IMVI Melanoma |
| GVR | RDGVRVG (1035) | LOX-IMVI Melanoma |
| | VSRIGVR (1036) | LOX-IMVI Melanoma |
| | GVRSMPV (1037) | LOX-IMVI Melanoma |
| GVL | GGVLGSD (1038) | LOX-IMVI Melanoma |
| | WGVLQLE (1039) | LOX-IMVI Melanoma |
| GAV | HGGPGAV (1040) | LOX-IMVI Melanoma |
| GLV | DSGLVGG (1041) | LOX-IMVI Melanoma |
| GLR | IFGAGLR (1042) | LOX-IMVI Melanoma |
| | RMGFGLR (1043) | LOX-IMVI Melanoma |
| LVS | | LOX-IMVI Melanoma |
| ARG | | LOX-IMVI Melanoma |
| ASL | | LOX-IMVI Melanoma |
| AAV | WLDAAVK (1044) | LOX-IMVI Melanoma |
| AAS | IAASYRG (1045) | LOX-IMVI Melanoma |
| GGS | ATIPGGS (1046) | LOX-IMVI Melanoma |
| | DGGSLVV (1047) | LOX-IMVI Melanoma |
| | FGGSGRG (1048) | LOX-IMVI Melanoma |
| GGR | SPTGGRR (1049) | LOX-IMVI Melanoma |
| | TWSTGGR (1050) | LOX-IMVI Melanoma |
| GLG | | LOX-IMVI Melanoma |
| GGL | SRSCGGL (1051) | LOX-IMVI Melanoma |
| GSS | | LOX-IMVI Melanoma |
| GSG | CPGSGII (1052) | LOX-IMVI Melanoma |
| | FGGSGRG (1053) | LOX-IMVI Melanoma |

TABLE 3-continued

Peptides and Motifs Associated with NCI-60 cell lines.

| Motif | Peptide w/ Seq ID:No. | Cell Line |
|---|---|---|
| GSV | SGSVVQR (1054) | LOX-IMVI Melanoma |
| GRV | TWIGRVS (1055) | LOX-IMVI Melanoma |
| GRL | | LOX-IMVI Melanoma |
| GPS | GPSWATV (1056) | LOX-IMVI Melanoma |
| GVS | | LOX-IMVI Melanoma |
| RLS | | MALME-3M Melanoma |
| RGV | | MALME-3M Melanoma |
| RGS | ARRGSGL (1057) | MALME-3M Melanoma |
| RAV | RAVGYNA (1058) | MALME-3M Melanoma |
| | LRAVEFL (1059) | MALME-3M Melanoma |
| RAS | | MALME-3M Melanoma |
| GAG | | MALME-3M Melanoma |
| AVS | | MALME-3M Melanoma |
| LLS | FEDLLSL (1060) | MALME-3M Melanoma |
| | RWLSLLS (1061) | MALME-3M Melanoma |
| LLR | | MALME-3M Melanoma |
| LRV | HAPGLRV (1062) | MALME-3M Melanoma |
| LRS | LRSSMML (1063) | MALME-3M Melanoma |
| | RPKLRSV (1064) | MALME-3M Melanoma |
| RVS | SRVSFHE (1065) | MALME-3M Melanoma |
| RSS | LRSSMML (1066) | MALME-3M Melanoma |
| | SSGGRSS (1067) | MALME-3M Melanoma |
| AGS | | MALME-3M Melanoma |
| AGR | VAGRVGI (1068) | MALME-3M Melanoma |
| AGL | AGLALTV (1069) | MALME-3M Melanoma |
| AGG | | MALME-3M Melanoma |
| GVR | IGVRGAV (1070) | MALME-3M Melanoma |
| GVL | LVRDGVL (1071) | MALME-3M Melanoma |
| GAV | IGVRGAV (1072) | MALME-3M Melanoma |
| GLV | HGLVTHN (1073) | MALME-3M Melanoma |
| GLR | HAPGLRV (1074) | MALME-3M Melanoma |
| LVS | | MALME-3M Melanoma |
| ARG | VSSTARG (1075) | MALME-3M Melanoma |
| ASL | | MALME-3M Melanoma |
| AAV | RAAVIHT (1076) | MALME-3M Melanoma |
| AAS | AASTRSL (1077) | MALME-3M Melanoma |

TABLE 3-continued

Peptides and Motifs Associated with NCI-60 cell lines.

| Motif | Peptide w/ Seq ID:No. | Cell Line |
|---|---|---|
| GGS | GWGGGSA (1078) | MALME-3M Melanoma |
| | SSRGGSS (1079) | MALME-3M Melanoma |
| GGR | SSGGRSS (1080) | MALME-3M Melanoma |
| GLG | | MALME-3M Melanoma |
| GGL | | MALME-3M Melanoma |
| GSS | SSRGGSS (1081) | MALME-3M Melanoma |
| GSG | ARRGSGL (1082) | MALME-3M Melanoma |
| GSV | | MALME-3M Melanoma |
| GRV | VAGRVGI (1083) | MALME-3M Melanoma |
| GRL | EGRLMLA (1084) | MALME-3M Melanoma |
| GPS | | MALME-3M Melanoma |
| GVS | | MALME-3M Melanoma |
| RLS | RLSSAPS (1085) | M14 Melanoma |
| | RRLSYHS (1086) | M14 Melanoma |
| | FLHMRLS (1087) | M14 Melanoma |
| RGV | LARGVPP (1088) | M14 Melanoma |
| RGS | LSRGSVA (1089) | M14 Melanoma |
| | VWLRGST (1090) | M14 Melanoma |
| RAV | | M14 Melanoma |
| RAS | RGGQRAS (1091) | M14 Melanoma |
| GAG | | M14 Melanoma |
| AVS | AVSGRSL (1092) | M14 Melanoma |
| LLS | GLLSSFS (1093) | M14 Melanoma |
| LLR | RMGLLRQ (1094) | M14 Melanoma |
| LRV | | M14 Melanoma |
| LRS | RLHYLRS (1095) | M14 Melanoma |
| | GGYWLRS (1096) | M14 Melanoma |
| RVS | | M14 Melanoma |
| RSS | NRSSHCG (1097) | M14 Melanoma |
| | QRSSDLT (1098) | M14 Melanoma |
| AGS | | M14 Melanoma |
| AGR | AAGRSRI (1099) | M14 Melanoma |
| AGL | | M14 Melanoma |
| AGG | GRAGGNG (1100) | M14 Melanoma |
| GVR | ANASGVR (1101) | M14 Melanoma |
| GVL | WAHGVLS (1102) | M14 Melanoma |
| GAV | | M14 Melanoma |

TABLE 3-continued

Peptides and Motifs Associated with NCI-60 cell lines.

| Motif | Peptide w/ Seq ID:No. | Cell Line |
|---|---|---|
| GLV | | M14 Melanoma |
| GLR | SLYGLRW (1103) | M14 Melanoma |
| LVS | | M14 Melanoma |
| ARG | GNGGARG (1104) | M14 Melanoma |
| | LARGVPP (1105) | M14 Melanoma |
| | NWDARGR (1106) | M14 Melanoma |
| ASL | ASLPVLD (1107) | M14 Melanoma |
| | PPGASLY (1108) | M14 Melanoma |
| AAV | AAVGGRV (1109) | M14 Melanoma |
| AAS | AASSWAV (1110) | M14 Melanoma |
| GGS | AFKTGGS (1111) | M14 Melanoma |
| GGR | FEGGRSG (1112) | M14 Melanoma |
| | RTWGGRM (1113) | M14 Melanoma |
| | SARQGGR (1114) | M14 Melanoma |
| | AAVGGRV (1115) | M14 Melanoma |
| GLG | | M14 Melanoma |
| GGL | | M14 Melanoma |
| GSS | ARHGSSV (1116) | M14 Melanoma |
| | SNFYGSS (1117) | M14 Melanoma |
| GSG | GSGQLIP (1118) | M14 Melanoma |
| GSV | LSRGSVA (1119) | M14 Melanoma |
| GRV | AEYGRVL (1120) | M14 Melanoma |
| | RGRVLLP (1121) | M14 Melanoma |
| | AAVGGRV (1122) | M14 Melanoma |
| GRL | RGRLALL (1123) | M14 Melanoma |
| | SGPGRLP (1124) | M14 Melanoma |
| | TSGRLWV (1125) | M14 Melanoma |
| GPS | | M14 Melanoma |
| GVS | MVYSGVS (1126) | M14 Melanoma |
| RLS | WRLSREG (1127) | SK-MEL-2 Melanoma |
| | LLRRLSW (1128) | SK-MEL-2 Melanoma |
| RGV | AARGVMV (1129) | SK-MEL-2 Melanoma |
| RGS | ALARGSG (1130) | SK-MEL-2 Melanoma |
| | NLRGSRS (1131) | SK-MEL-2 Melanoma |
| RAV | RAVWRAS (1132) | SK-MEL-2 Melanoma |
| RAS | RAVWRAS | SK-MEL-2 Melanoma |

TABLE 3-continued

Peptides and Motifs Associated with NCI-60 cell lines.

| Motif | Peptide w/ Seq ID:No. | Cell Line |
|---|---|---|
| GAG | GAGSFSS (1133) | SK-MEL-2 Melanoma |
| AVS | | SK-MEL-2 Melanoma |
| LLS | LLSSRRC (1134) | SK-MEL-2 Melanoma |
| | LLSLDPG (1135) | SK-MEL-2 Melanoma |
| | SSLLSSL (1136) | SK-MEL-2 Melanoma |
| LLR | LLRPAHG (1137) | SK-MEL-2 Melanoma |
| | LLRRLSW (1138) | SK-MEL-2 Melanoma |
| LRV | | SK-MEL-2 Melanoma |
| LRS | CMLRSAT (1139) | SK-MEL-2 Melanoma |
| | SKAVLRS (1140) | SK-MEL-2 Melanoma |
| RVS | SRVSNPS (1141) | SK-MEL-2 Melanoma |
| RSS | CRRSSLL (1142) | SK-MEL-2 Melanoma |
| AGS | GAGSFSS (1143) | SK-MEL-2 Melanoma |
| AGR | SAAGRTF (1144) | SK-MEL-2 Melanoma |
| | PAGRMLS (1145) | SK-MEL-2 Melanoma |
| AGL | IAMAGLR (1146) | SK-MEL-2 Melanoma |
| AGG | AGGFRFI (1147) | SK-MEL-2 Melanoma |
| GVR | SGVRPVI (1148) | SK-MEL-2 Melanoma |
| GVL | GVLSDRS (1149) | SK-MEL-2 Melanoma |
| GAV | GAVTSAD (1150) | SK-MEL-2 Melanoma |
| | GAVTSAD (1151) | SK-MEL-2 Melanoma |
| | GAVNTPA (1152) | SK-MEL-2 Melanoma |
| GLV | GGLVKRL (1153) | SK-MEL-2 Melanoma |
| | EVASGLV (1154) | SK-MEL-2 Melanoma |
| GLR | IAMAGLR (1155) | SK-MEL-2 Melanoma |
| | GTHSGLR (1156) | SK-MEL-2 Melanoma |
| LVS | LVSTSNR (1157) | SK-MEL-2 Melanoma |
| | FSLVSFV (1158) | SK-MEL-2 Melanoma |
| | ALVSSHV (1159) | SK-MEL-2 Melanoma |
| ARG | AARGVMV (1160) | SK-MEL-2 Melanoma |
| | ALARGSG (1161) | SK-MEL-2 Melanoma |
| ASL | | SK-MEL-2 Melanoma |
| AAV | LRYWAAV (1162) | SK-MEL-2 Melanoma |
| AAS | FTRGAAS (1163) | SK-MEL-2 Melanoma |
| | EWHAASG (1164) | SK-MEL-2 Melanoma |
| GGS | FGGSMAP (1165) | SK-MEL-2 Melanoma |
| | GGSLKWV (1166) | SK-MEL-2 Melanoma |

TABLE 3-continued

Peptides and Motifs Associated with NCI-60 cell lines.

| Motif | Peptide w/ Seq ID:No. | Cell Line |
|---|---|---|
| GGR | RGLQGGR (1167) | SK-MEL-2 Melanoma |
| | TCGGRSY (1168) | SK-MEL-2 Melanoma |
| GLG | GEALGLG (1169) | SK-MEL-2 Melanoma |
| | PRGLGVG (1170) | SK-MEL-2 Melanoma |
| | VGLGNSA (1171) | SK-MEL-2 Melanoma |
| GGL | GGLVKRL (1172) | SK-MEL-2 Melanoma |
| GSS | | SK-MEL-2 Melanoma |
| GSG | GSGRALA (1173) | SK-MEL-2 Melanoma |
| GSV | | SK-MEL-2 Melanoma |
| GRV | | SK-MEL-2 Melanoma |
| GRL | SRSGRLN (1174) | SK-MEL-2 Melanoma |
| GPS | | SK-MEL-2 Melanoma |
| GVS | SAGVSDS (1175) | SK-MEL-2 Melanoma |
| RLS | PRLSDKS (1176) | SK-MEL-28 Melanoma |
| RGV | GRGDRGV (1177) | SK-MEL-28 Melanoma |
| | RGVSGRL (1178) | SK-MEL-28 Melanoma |
| RGS | INRGSRE (1179) | SK-MEL-28 Melanoma |
| | LRGSRQF (1180) | SK-MEL-28 Melanoma |
| | LRGSVGR (1181) | SK-MEL-28 Melanoma |
| RAV | GLWYRAV (1182) | SK-MEL-28 Melanoma |
| | RVRAVLG (1183) | SK-MEL-28 Melanoma |
| | RAVLELW (1184) | SK-MEL-28 Melanoma |
| RAS | LVRASNG (1185) | SK-MEL-28 Melanoma |
| GAG | | SK-MEL-28 Melanoma |
| AVS | | SK-MEL-28 Melanoma |
| LLS | | SK-MEL-28 Melanoma |
| LLR | ASGTLLR (1186) | SK-MEL-28 Melanoma |
| LRV | | SK-MEL-28 Melanoma |
| LRS | | SK-MEL-28 Melanoma |
| RVS | GSGVRVS (1187) | SK-MEL-28 Melanoma |
| RSS | VGSTRSS (1188) | SK-MEL-28 Melanoma |
| AGS | RAGSRYI (1189) | SK-MEL-28 Melanoma |
| AGR | | SK-MEL-28 Melanoma |
| AGL | | SK-MEL-28 Melanoma |
| AGG | | SK-MEL-28 Melanoma |
| GVR | VGVRFSR (1190) | SK-MEL-28 Melanoma |

TABLE 3-continued

Peptides and Motifs Associated with NCI-60 cell lines.

| Motif | Peptide w/ Seq ID:No. | Cell Line |
|---|---|---|
| | GSGVRVS (1191) | SK-MEL-28 Melanoma |
| GVL | IGVLASA (1192) | SK-MEL-28 Melanoma |
| GAV | | SK-MEL-28 Melanoma |
| GLV | GLVARVR (1193) | SK-MEL-28 Melanoma |
| GLR | | SK-MEL-28 Melanoma |
| LVS | | SK-MEL-28 Melanoma |
| ARG | | SK-MEL-28 Melanoma |
| ASL | | SK-MEL-28 Melanoma |
| AAV | | SK-MEL-28 Melanoma |
| AAS | | SK-MEL-28 Melanoma |
| GGS | LLGIGGS (1194) | SK-MEL-28 Melanoma |
| | QLGGSFR (1195) | SK-MEL-28 Melanoma |
| GGR | LFRWGGR (1196) | SK-MEL-28 Melanoma |
| GLG | | SK-MEL-28 Melanoma |
| GGL | RFSGGLQ (1197) | SK-MEL-28 Melanoma |
| GSS | VGSSHGL (1198) | SK-MEL-28 Melanoma |
| GSG | SVRVGSG (1199) | SK-MEL-28 Melanoma |
| GSV | GVNGSVS (1200) | SK-MEL-28 Melanoma |
| | LRGSVGR (1201) | SK-MEL-28 Melanoma |
| GRV | HVKNGRV (1202) | SK-MEL-28 Melanoma |
| GRL | FQRSGRL (1203) | SK-MEL-28 Melanoma |
| | HGRLAFG (1204) | SK-MEL-28 Melanoma |
| | RGVSGRL (1205) | SK-MEL-28 Melanoma |
| GPS | | SK-MEL-28 Melanoma |
| GVS | RGVSGRL (1206) | SK-MEL-28 Melanoma |
| RLS | | SK-MEL-5 Melanoma |
| RGV | FGIGRGV (1207) | SK-MEL-5 Melanoma |
| RGS | | SK-MEL-5 Melanoma |
| RAV | | SK-MEL-5 Melanoma |
| RAS | | SK-MEL-5 Melanoma |
| GAG | | SK-MEL-5 Melanoma |
| AVS | GVVQAVS (1208) | SK-MEL-5 Melanoma |
| | LSAVSVK (1209) | SK-MEL-5 Melanoma |
| LLS | LYLLSSA (1210) | SK-MEL-5 Melanoma |
| | LIGGLLS (1211) | SK-MEL-5 Melanoma |
| LLR | LLRRGIG (1212) | SK-MEL-5 Melanoma |
| LRV | | SK-MEL-5 Melanoma |

TABLE 3-continued

Peptides and Motifs Associated with NCI-60 cell lines.

| Motif | Peptide w/ Seq ID:No. | Cell Line |
|---|---|---|
| LRS | FLRSLSL (1213) | SK-MEL-5 Melanoma |
| RVS | VRVSGLT (1214) | SK-MEL-5 Melanoma |
| RSS | | SK-MEL-5 Melanoma |
| AGS | AGSVDLV (1215) | SK-MEL-5 Melanoma |
| AGR | GFVAGRT (1216) | SK-MEL-5 Melanoma |
| AGL | | SK-MEL-5 Melanoma |
| AGG | | SK-MEL-5 Melanoma |
| GVR | | SK-MEL-5 Melanoma |
| GVL | | SK-MEL-5 Melanoma |
| GAV | TRGAVFG (1217) | SK-MEL-5 Melanoma |
| GLV | IYGGLVI (1218) | SK-MEL-5 Melanoma |
| GLR | PTGEGLR (1219) | SK-MEL-5 Melanoma |
| LVS | | SK-MEL-5 Melanoma |
| ARG | | SK-MEL-5 Melanoma |
| ASL | KVSVASL (1220) | SK-MEL-5 Melanoma |
| | RYSMASL (1221) | SK-MEL-5 Melanoma |
| AAV | | SK-MEL-5 Melanoma |
| AAS | ANAASSP (1222) | SK-MEL-5 Melanoma |
| GGS | PGGSRHA (1223) | SK-MEL-5 Melanoma |
| | GGSPGVW (1224) | SK-MEL-5 Melanoma |
| GGR | | SK-MEL-5 Melanoma |
| GLG | | SK-MEL-5 Melanoma |
| GGL | IYGGLVI (1225) | SK-MEL-5 Melanoma |
| | LIGGLLS (1226) | SK-MEL-5 Melanoma |
| GSS | | SK-MEL-5 Melanoma |
| GSG | ACGSGLD (1227) | SK-MEL-5 Melanoma |
| GSV | AGSVDLV (1228) | SK-MEL-5 Melanoma |
| | TLGSVRV (1229) | SK-MEL-5 Melanoma |
| GRV | HVRGRVA (1230) | SK-MEL-5 Melanoma |
| | IDLGRVN (1231) | SK-MEL-5 Melanoma |
| GRL | GRLDAFG (1232) | SK-MEL-5 Melanoma |
| GPS | WVGPSGG (1233) | SK-MEL-5 Melanoma |
| GVS | | SK-MEL-5 Melanoma |
| RLS | DLRLSFP (1234) | UACC 257 Melanoma |
| | SARLSHV (1235) | UACC 257 Melanoma |
| RGV | VMDRGVA (1236) | UACC 257 Melanoma |

TABLE 3-continued

Peptides and Motifs Associated with NCI-60 cell lines.

| Motif | Peptide w/ Seq ID:No. | Cell Line |
|---|---|---|
| RGS | RGSLLWA (1237) | UACC 257 Melanoma |
| | RGSPLTK (1238) | UACC 257 Melanoma |
| RAV | | UACC 257 Melanoma |
| RAS | RASIGIE (1239) | UACC 257 Melanoma |
| | VHSLRAS (1240) | UACC 257 Melanoma |
| GAG | | UACC 257 Melanoma |
| AVS | | UACC 257 Melanoma |
| LLS | AWLLSGR (1241) | UACC 257 Melanoma |
| LLR | | UACC 257 Melanoma |
| LRV | | UACC 257 Melanoma |
| LRS | LWLRSRE (1242) | UACC 257 Melanoma |
| RVS | VTRIRVS (1243) | UACC 257 Melanoma |
| RSS | NSQRSSV (1244) | UACC 257 Melanoma |
| AGS | AATRAGS (1245) | UACC 257 Melanoma |
| AGR | | UACC 257 Melanoma |
| AGL | | UACC 257 Melanoma |
| AGG | | UACC 257 Melanoma |
| GVR | TDGVRAF (1246) | UACC 257 Melanoma |
| GVL | FAASGVL (1247) | UACC 257 Melanoma |
| | GVLEGRR (1248) | UACC 257 Melanoma |
| GAV | EADPGAV (1249) | UACC 257 Melanoma |
| | DGAVILH (1250) | UACC 257 Melanoma |
| | RDGAVNL (1251) | UACC 257 Melanoma |
| GLV | | UACC 257 Melanoma |
| GLR | GLRPHGA (1252) | UACC 257 Melanoma |
| | TSRGLRL (1253) | UACC 257 Melanoma |
| LVS | RMLVSSF (1254) | UACC 257 Melanoma |
| ARG | DVIARGW (1255) | UACC 257 Melanoma |
| | | UACC 257 Melanoma |
| ASL | | UACC 257 Melanoma |
| AAV | TLTAAVF (1256) | UACC 257 Melanoma |
| | GWLNAAV (1257) | UACC 257 Melanoma |
| AAS | FAASGVL (1258) | UACC 257 Melanoma |
| GGS | GGSKGSA (1259) | UACC 257 Melanoma |
| | AVALGGS (1260) | UACC 257 Melanoma |
| GGR | HGGRYRH (1261) | UACC 257 Melanoma |
| | SGVGGRY (1262) | UACC 257 Melanoma |

TABLE 3-continued

Peptides and Motifs Associated with NCI-60 cell lines.

| Motif | Peptide w/ Seq ID:No. | Cell Line |
|---|---|---|
| GLG | | UACC 257 Melanoma |
| GGL | SGGLAVA (1263) | UACC 257 Melanoma |
| GSS | | UACC 257 Melanoma |
| GSG | | UACC 257 Melanoma |
| GSV | | UACC 257 Melanoma |
| GRV | | UACC 257 Melanoma |
| GRL | GRLAKSI (1264) | UACC 257 Melanoma |
| GPS | AGPSRGP (1265) | UACC 257 Melanoma |
| | | UACC 257 Melanoma |
| GVS | | UACC 257 Melanoma |
| RLS | GLMRLSH (1266) | UACC62 Melanoma |
| | VRVGRLS (1267) | UACC62 Melanoma |
| | TGRLSAA (1268) | UACC62 Melanoma |
| RGV | SLRGVRV (1269) | UACC62 Melanoma |
| | DNCERGV (1270) | UACC62 Melanoma |
| | TTQLRGV (1271) | UACC62 Melanoma |
| RGS | GVIGRGS (1272) | UACC62 Melanoma |
| | LAGMRGS (1273) | UACC62 Melanoma |
| RAV | VRPRAVL (1274) | UACC62 Melanoma |
| | PPRAVTN (1275) | UACC62 Melanoma |
| RAS | WRARASP (1276) | UACC62 Melanoma |
| GAG | | UACC62 Melanoma |
| AVS | | UACC62 Melanoma |
| LLS | FGRLLSP (1277) | UACC62 Melanoma |
| LLR | PSLLRGF (1278) | UACC62 Melanoma |
| LRV | RDLRVHL (1279) | UACC62 Melanoma |
| | LRVSNPR (1280) | UACC62 Melanoma |
| | LRVDQLY (1281) | UACC62 Melanoma |
| LRS | HRLRSMS (1282) | UACC62 Melanoma |
| RVS | LRVSNPR (1283) | UACC62 Melanoma |
| RSS | | UACC62 Melanoma |
| AGS | PGFMAGS (1284) | UACC62 Melanoma |
| AGR | AGRGISQ (1285) | UACC62 Melanoma |
| | RAGRDAP (1286) | UACC62 Melanoma |
| | RAGRGFE (1287) | UACC62 Melanoma |
| AGL | | UACC62 Melanoma |

TABLE 3-continued

Peptides and Motifs Associated with NCI-60 cell lines.

| Motif | Peptide w/ Seq ID:No. | Cell Line |
|---|---|---|
| AGG | HQAGGVT (1288) | UACC62 Melanoma |
| GVR | SLRGVRV (1289) | UACC62 Melanoma |
| GVL | DWVGVLM (1290) | UACC62 Melanoma |
| | GTLGVLS (1291) | UACC62 Melanoma |
| | GVLLWRP (1292) | UACC62 Melanoma |
| GAV | | UACC62 Melanoma |
| GLV | | UACC62 Melanoma |
| GLR | GLREAHV (1293) | UACC62 Melanoma |
| LVS | | UACC62 Melanoma |
| ARG | AARGELR (1294) | UACC62 Melanoma |
| ASL | AASLRGT (1295) | UACC62 Melanoma |
| AAV | PVGAAVA (1296) | UACC62 Melanoma |
| AAS | AASLRGT (1297) | UACC62 Melanoma |
| GGS | | UACC62 Melanoma |
| GGR | | UACC62 Melanoma |
| GLG | | UACC62 Melanoma |
| GGL | | UACC62 Melanoma |
| GSS | | UACC62 Melanoma |
| GSG | SNPGSGS (1298) | UACC62 Melanoma |
| GSV | | UACC62 Melanoma |
| GRV | GRVRETP (1299) | UACC62 Melanoma |
| | | UACC62 Melanoma |
| GRL | FGRLLSP (1300) | UACC62 Melanoma |
| | VRVGRLS (1301) | UACC62 Melanoma |
| | TGRLSAA (1302) | UACC62 Melanoma |
| | VGRLQTT (1303) | UACC62 Melanoma |
| GPS | DGPSCVI (1304) | UACC62 Melanoma |
| | | UACC62 Melanoma |
| GVS | | UACC62 Melanoma |
| RLS | | IGROV1 Ovarian |
| RGV | | IGROV1 Ovarian |
| RGS | | IGROV1 Ovarian |
| RAV | RFSSRAV (1305) | IGROV1 Ovarian |
| RAS | HAGSRAS (1306) | IGROV1 Ovarian |
| GAG | GAGLGVS (1307) | IGROV1 Ovarian |
| | LLGAGTP (1308) | IGROV1 Ovarian |
| AVS | | IGROV1 Ovarian |

TABLE 3-continued

Peptides and Motifs Associated with NCI-60 cell lines.

| Motif | Peptide w/ Seq ID:No. | Cell Line |
|---|---|---|
| LLS | LLSILKA (1309) | IGROV1 Ovarian |
| | GLLSGGT (1310) | IGROV1 Ovarian |
| LLR | | IGROV1 Ovarian |
| LRV | LSVLRVL (1311) | IGROV1 Ovarian |
| LRS | SRYTLRS (1312) | IGROV1 Ovarian |
| RVS | | IGROV1 Ovarian |
| RSS | LFHTRSS (1313) | IGROV1 Ovarian |
| | VARSSFR (1314) | IGROV1 Ovarian |
| AGS | CTAGSVS (1315) | IGROV1 Ovarian |
| | RAAGSAG (1316) | IGROV1 Ovarian |
| | HAGSRAS (1317) | IGROV1 Ovarian |
| AGR | | IGROV1 Ovarian |
| AGL | GAGLGVS (1318) | IGROV1 Ovarian |
| | PTGAGLL (1319) | IGROV1 Ovarian |
| | ASYAGLV (2) (1320) | IGROV1 Ovarian |
| AGG | AGGFGVL (1321) | IGROV1 Ovarian |
| | NMAGGQE (1322) | IGROV1 Ovarian |
| | LRAGGSY (1323) | IGROV1 Ovarian |
| | YLAGGKA (1324) | IGROV1 Ovarian |
| GVR | PYYNGVR (1325) | IGROV1 Ovarian |
| GVL | AGGFGVL (1326) | IGROV1 Ovarian |
| | LIGGVLH (1327) | IGROV1 Ovarian |
| GAV | | IGROV1 Ovarian |
| GLV | DGLVPVA (1328) | IGROV1 Ovarian |
| | GLVASMP (1329) | IGROV1 Ovarian |
| | ASYAGLV (2) (1330) | IGROV1 Ovarian |
| GLR | | IGROV1 Ovarian |
| LVS | LVRLVSL (1331) | IGROV1 Ovarian |
| ARG | | IGROV1 Ovarian |
| ASL | VLASLSG (1332) | IGROV1 Ovarian |
| AAV | | IGROV1 Ovarian |
| AAS | | IGROV1 Ovarian |
| GGS | GSITGGS (1333) | IGROV1 Ovarian |
| | LRAGGSY (1334) | IGROV1 Ovarian |
| | TGGSLLG (1335) | IGROV1 Ovarian |

TABLE 3-continued

Peptides and Motifs Associated with NCI-60 cell lines.

| Motif | Peptide w/ Seq ID:No. | Cell Line |
|---|---|---|
| | DEGGSRW (1336) | IGROV1 Ovarian |
| GGR | | IGROV1 Ovarian |
| GLG | GAGLGVS (1337) | IGROV1 Ovarian |
| GGL | | IGROV1 Ovarian |
| GSS | WGSSAVK (1338) | IGROV1 Ovarian |
| | QGSSNSV (1339) | IGROV1 Ovarian |
| GSG | | IGROV1 Ovarian |
| GSV | CTAGSVS (1340) | IGROV1 Ovarian |
| | SVTGSVG (1341) | IGROV1 Ovarian |
| GRV | SPGRVAD (1342) | IGROV1 Ovarian |
| GRL | | IGROV1 Ovarian |
| GPS | DAVRGPS (1343) | IGROV1 Ovarian |
| GVS | GAGLGVS (1344) | IGROV1 Ovarian |
| | GVSGTVS (1345) | IGROV1 Ovarian |
| | SGVSISC (1346) | IGROV1 Ovarian |
| RLS | RRLSYHS (65) (1347) | OVCAR-3 Ovarian |
| RGV | | OVCAR-3 Ovarian |
| RGS | | OVCAR-3 Ovarian |
| RAV | | OVCAR-3 Ovarian |
| RAS | | OVCAR-3 Ovarian |
| GAG | | OVCAR-3 Ovarian |
| AVS | | OVCAR-3 Ovarian |
| LLS | | OVCAR-3 Ovarian |
| LLR | | OVCAR-3 Ovarian |
| LRV | | OVCAR-3 Ovarian |
| LRS | RREGLRS (10) (1348) | OVCAR-3 Ovarian |
| RVS | ERVSAAV (1349) | OVCAR-3 Ovarian |
| RSS | | OVCAR-3 Ovarian |
| AGS | AGSMMEF (1350) | OVCAR-3 Ovarian |
| AGR | | OVCAR-3 Ovarian |
| AGL | | OVCAR-3 Ovarian |
| AGG | | OVCAR-3 Ovarian |
| GVR | | OVCAR-3 Ovarian |
| GVL | RHGPGVL (1351) | OVCAR-3 Ovarian |
| GAV | | OVCAR-3 Ovarian |
| GLV | | OVCAR-3 Ovarian |

TABLE 3-continued

Peptides and Motifs Associated with NCI-60 cell lines.

| Motif | Peptide w/ Seq ID:No. | Cell Line |
|---|---|---|
| GLR | GLRRDNG (1352) | OVCAR-3 Ovarian |
| | RREGLRS (10) (1353) | OVCAR-3 Ovarian |
| LVS | | OVCAR-3 Ovarian |
| ARG | | OVCAR-3 Ovarian |
| ASL | | OVCAR-3 Ovarian |
| AAV | ERVSAAV (1354) | OVCAR-3 Ovarian |
| AAS | VAASVRE (1355) | OVCAR-3 Ovarian |
| GGS | | OVCAR-3 Ovarian |
| GGR | | OVCAR-3 Ovarian |
| GLG | | OVCAR-3 Ovarian |
| GGL | | OVCAR-3 Ovarian |
| GSS | | OVCAR-3 Ovarian |
| GSG | | OVCAR-3 Ovarian |
| GSV | PWYDGSV (1356) | OVCAR-3 Ovarian |
| GRV | GRVTLES (1357) | OVCAR-3 Ovarian |
| GRL | | OVCAR-3 Ovarian |
| GPS | | OVCAR-3 Ovarian |
| GVS | | OVCAR-3 Ovarian |
| RLS | GRLSRAP (1358) | OVCAR-4 Ovarian |
| | SRLSYCN (1359) | OVCAR-4 Ovarian |
| RGV | | OVCAR-4 Ovarian |
| RGS | QARGSWL (1360) | OVCAR-4 Ovarian |
| | FVPRGSY (1361) | OVCAR-4 Ovarian |
| RAV | AALLRAV (1362) | OVCAR-4 Ovarian |
| RAS | LAGRASE (1363) | OVCAR-4 Ovarian |
| GAG | AAGAGWR (1364) | OVCAR-4 Ovarian |
| | ADLGAGW (1365) | OVCAR-4 Ovarian |
| | ADLGAGW (1366) | OVCAR-4 Ovarian |
| | GGAGRGA (1367) | OVCAR-4 Ovarian |
| AVS | DVWVAVS (1368) | OVCAR-4 Ovarian |
| LLS | | OVCAR-4 Ovarian |
| LLR | AALLRAV (1369) | OVCAR-4 Ovarian |
| LRV | NLRVGAE (1370) | OVCAR-4 Ovarian |
| LRS | NCYSLRS (1371) | OVCAR-4 Ovarian |
| RVS | LAGSRVS (1372) | OVCAR-4 Ovarian |
| RSS | | OVCAR-4 Ovarian |

TABLE 3-continued

Peptides and Motifs Associated with NCI-60 cell lines.

| Motif | Peptide w/ Seq ID:No. | Cell Line |
|---|---|---|
| AGS | SGPAGSF (1373) | OVCAR-4 Ovarian |
| | LAGSRVS (1374) | OVCAR-4 Ovarian |
| AGR | GGAGRGA (1375) | OVCAR-4 Ovarian |
| | LAGRASE (1376) | OVCAR-4 Ovarian |
| | VAGRLQM (1377) | OVCAR-4 Ovarian |
| AGL | WGAGLDA (1378) | OVCAR-4 Ovarian |
| | WGAGLDA (1379) | OVCAR-4 Ovarian |
| AGG | AGRGAGG (1380) | OVCAR-4 Ovarian |
| GVR | EAGVRLN (1381) | OVCAR-4 Ovarian |
| GVL | | OVCAR-4 Ovarian |
| GAV | MQLRGAV (1382) | OVCAR-4 Ovarian |
| GLV | GGPGLVM (1383) | OVCAR-4 Ovarian |
| | QGLVRGG (1384) | OVCAR-4 Ovarian |
| GLR | PGLRGPA (1385) | OVCAR-4 Ovarian |
| | PGLRGPA (1386) | OVCAR-4 Ovarian |
| LVS | GRMLVSG (1387) | OVCAR-4 Ovarian |
| ARG | ESARGAL (1388) | OVCAR-4 Ovarian |
| | QARGSWL (1389) | OVCAR-4 Ovarian |
| ASL | | OVCAR-4 Ovarian |
| AAV | | OVCAR-4 Ovarian |
| AAS | | OVCAR-4 Ovarian |
| GGS | GGGSGGG (1390) | OVCAR-4 Ovarian |
| | NNVGGSS (1391) | OVCAR-4 Ovarian |
| GGR | GGRVLGQ (1392) | OVCAR-4 Ovarian |
| | GGRVRGG (1393) | OVCAR-4 Ovarian |
| | GGRVRGG (1394) | OVCAR-4 Ovarian |
| | WYGGRGN (1395) | OVCAR-4 Ovarian |
| GLG | CVGLGCH (1396) | OVCAR-4 Ovarian |
| GGL | | OVCAR-4 Ovarian |
| GSS | NNVGGSS (1397) | OVCAR-4 Ovarian |
| GSG | FMTYGSG (1398) | OVCAR-4 Ovarian |
| | GGGSGGG (1399) | OVCAR-4 Ovarian |
| | WDQGSGY (1400) | OVCAR-4 Ovarian |
| GSV | GSVLMRG (1401) | OVCAR-4 Ovarian |
| GRV | GGRVLGQ (1402) | OVCAR-4 Ovarian |
| | GGRVRGG (1403) | OVCAR-4 Ovarian |

TABLE 3-continued

Peptides and Motifs Associated with NCI-60 cell lines.

| Motif | Peptide w/ Seq ID:No. | Cell Line |
|---|---|---|
| | GGRVRGG (1404) | OVCAR-4 Ovarian |
| | YMYHGRV (1405) | OVCAR-4 Ovarian |
| GRL | GRLSRAP (1406) | OVCAR-4 Ovarian |
| | VAGRLQM (1407) | OVCAR-4 Ovarian |
| | APGRLGP (1408) | OVCAR-4 Ovarian |
| | APGRLGP (1409) | OVCAR-4 Ovarian |
| GPS | RDLAGPS (1410) | OVCAR-4 Ovarian |
| GVS | | OVCAR-4 Ovarian |
| RLS | RLSGAGD (1411) | OVCAR-5 Ovarian |
| RGV | LQRGVAR (1412) | OVCAR-5 Ovarian |
| RGS | | OVCAR-5 Ovarian |
| RAV | RAVGRQL (1413) | OVCAR-5 Ovarian |
| | SRAVIRL (1414) | OVCAR-5 Ovarian |
| RAS | VRASSKR (1415) | OVCAR-5 Ovarian |
| GAG | DGAGSLR (1416) | OVCAR-5 Ovarian |
| | SVSGAGS (1417) | OVCAR-5 Ovarian |
| AVS | | OVCAR-5 Ovarian |
| LLS | TTLLSRQ (1418) | OVCAR-5 Ovarian |
| | VAELLSM (1419) | OVCAR-5 Ovarian |
| LLR | | OVCAR-5 Ovarian |
| LRV | LPGRLRV (1420) | OVCAR-5 Ovarian |
| LRS | LKAGLRS (1421) | OVCAR-5 Ovarian |
| RVS | HRVSESV (1422) | OVCAR-5 Ovarian |
| RSS | YYGERSS (1423) | OVCAR-5 Ovarian |
| AGS | DGAGSLR (1424) | OVCAR-5 Ovarian |
| | SVSGAGS (1425) | OVCAR-5 Ovarian |
| | AGSVYSV (1426) | OVCAR-5 Ovarian |
| AGR | | OVCAR-5 Ovarian |
| AGL | SAGLLPS (1427) | OVCAR-5 Ovarian |
| | LKAGLRS (1428) | OVCAR-5 Ovarian |
| AGG | RRAGGSV (1429) | OVCAR-5 Ovarian |
| GVR | SWAGVRF (1430) | OVCAR-5 Ovarian |
| GVL | | OVCAR-5 Ovarian |
| GAV | IYPGAVL (1431) | OVCAR-5 Ovarian |
| GLV | | OVCAR-5 Ovarian |
| GLR | LKAGLRS (1432) | OVCAR-5 Ovarian |
| LVS | SLVSPRT (1433) | OVCAR-5 Ovarian |

TABLE 3-continued

Peptides and Motifs Associated with NCI-60 cell lines.

| Motif | Peptide w/ Seq ID:No. | Cell Line |
|---|---|---|
| ARG | | OVCAR-5 Ovarian |
| ASL | | OVCAR-5 Ovarian |
| AAV | HAAVEPS (1434) | OVCAR-5 Ovarian |
| | TAAAVLL (1435) | OVCAR-5 Ovarian |
| AAS | | OVCAR-5 Ovarian |
| GGS | FHFGGSG (1436) | OVCAR-5 Ovarian |
| | GEGGSGG (1437) | OVCAR-5 Ovarian |
| | RRAGGSV (1438) | OVCAR-5 Ovarian |
| GGR | ALPGGGR (1439) | OVCAR-5 Ovarian |
| | YVGGRLR (1440) | OVCAR-5 Ovarian |
| GLG | GKGMGLG (1441) | OVCAR-5 Ovarian |
| | SLGLGGL (1442) | OVCAR-5 Ovarian |
| GGL | DGGLNDC (1443) | OVCAR-5 Ovarian |
| | LGGLGLS (1444) | OVCAR-5 Ovarian |
| GSS | | OVCAR-5 Ovarian |
| GSG | FHFGGSG (1445) | OVCAR-5 Ovarian |
| | GEGGSGG (1446) | OVCAR-5 Ovarian |
| GSV | RRAGGSV (1447) | OVCAR-5 Ovarian |
| | SGAGSVS (1448) | OVCAR-5 Ovarian |
| | AGSVYSV (1449) | OVCAR-5 Ovarian |
| GRV | GRVTWRS (1450) | OVCAR-5 Ovarian |
| GRL | LPGRLRV (1451) | OVCAR-5 Ovarian |
| | YVGGRLR (1452) | OVCAR-5 Ovarian |
| GPS | GPSSAVE (1453) | OVCAR-5 Ovarian |
| GVS | | OVCAR-5 Ovarian |
| RLS | RRLSYRE (28) (1454) | OVCAR-8 Ovarian |
| RGV | | OVCAR-8 Ovarian |
| RGS | | OVCAR-8 Ovarian |
| RAV | HTRAVSE (1455) | OVCAR-8 Ovarian |
| | NVSRAVG (1456) | OVCAR-8 Ovarian |
| RAS | PRHRASQ (1457) | OVCAR-8 Ovarian |
| GAG | LGAGMIA (1458) | OVCAR-8 Ovarian |
| AVS | AVSLVVL (1459) | OVCAR-8 Ovarian |
| | HTRAVSE (1460) | OVCAR-8 Ovarian |
| LLS | | OVCAR-8 Ovarian |
| LLR | | OVCAR-8 Ovarian |

TABLE 3-continued

Peptides and Motifs Associated with NCI-60 cell lines.

| Motif | Peptide w/ Seq ID:No. | Cell Line |
|---|---|---|
| LRV | ELGLRVP (1461) | OVCAR-8 Ovarian |
| LRS | | OVCAR-8 Ovarian |
| RVS | | OVCAR-8 Ovarian |
| RSS | GRSSVSD (1462) | OVCAR-8 Ovarian |
| AGS | YAGSGQL (2) (1463) | OVCAR-8 Ovarian |
| AGR | AGRFGAR (1464) | OVCAR-8 Ovarian |
| AGL | AIMGAGL (1465) | OVCAR-8 Ovarian |
| AGG | | OVCAR-8 Ovarian |
| GVR | THVGGVR (1466) | OVCAR-8 Ovarian |
| GVL | GVLTRGN (1467) | OVCAR-8 Ovarian |
| GAV | | OVCAR-8 Ovarian |
| GLV | | OVCAR-8 Ovarian |
| GLR | ELGLRVP (1468) | OVCAR-8 Ovarian |
| | GLGLRLG (1469) | OVCAR-8 Ovarian |
| LVS | IDLVSPG (1470) | OVCAR-8 Ovarian |
| ARG | | OVCAR-8 Ovarian |
| ASL | | OVCAR-8 Ovarian |
| AAV | | OVCAR-8 Ovarian |
| AAS | | OVCAR-8 Ovarian |
| GGS | GGSTVPQ (1471) | OVCAR-8 Ovarian |
| GGR | | OVCAR-8 Ovarian |
| GLG | GLGLRLG (1472) | OVCAR-8 Ovarian |
| GGL | TATGGLL (1473) | OVCAR-8 Ovarian |
| GSS | GSNGSSH (3) (1474) | OVCAR-8 Ovarian |
| GSG | LQGSGAY (2) (1475) | OVCAR-8 Ovarian |
| | LQHLGSG (1476) | OVCAR-8 Ovarian |
| GSV | | OVCAR-8 Ovarian |
| GRV | | OVCAR-8 Ovarian |
| GRL | | OVCAR-8 Ovarian |
| GPS | GPSVLDI (1477) | OVCAR-8 Ovarian |
| GVS | GATGVSS (1478) | OVCAR-8 Ovarian |
| RLS | TRLSFRH (1479) | SK-OV-3-3 Ovarian |
| RGV | FLRGVEL (1480) | SK-OV-3-3 Ovarian |
| RGS | NSVRGSR (1481) | SK-OV-3-3 Ovarian |
| RAV | NRAVLSA (1482) | SK-OV-3-3 Ovarian |
| RAS | LIGRASM (1483) | SK-OV-3-3 Ovarian |
| GAG | RVGAGAF (1484) | SK-OV-3-3 Ovarian |
| AVS | WISAVSK (1485) | SK-OV-3-3 Ovarian |
| | SAVSESP (1486) | SK-OV-3-3 Ovarian |
| LLS | | SK-OV-3-3 Ovarian |
| LLR | | SK-OV-3-3 Ovarian |
| LRV | RVGTLRV (4) (1487) | SK-OV-3-3 Ovarian |
| LRS | | SK-OV-3-3 Ovarian |
| RVS | RVSGDGK (1488) | SK-OV-3-3 Ovarian |
| | RSGRVSN (1489) | SK-OV-3-3 Ovarian |
| | RVSNEAL (1490) | SK-OV-3-3 Ovarian |
| | RVSSDPI (1491) | SK-OV-3-3 Ovarian |
| RSS | VRSSGVL (1492) | SK-OV-3-3 Ovarian |
| AGS | SGWFAGS (1493) | SK-OV-3-3 Ovarian |
| AGR | | SK-OV-3-3 Ovarian |
| AGL | AGLGLLD (1494) | SK-OV-3-3 Ovarian |
| | SAAGLAR (1495) | SK-OV-3-3 Ovarian |
| AGG | | SK-OV-3-3 Ovarian |
| GVR | FAGAGVR (1496) | SK-OV-3-3 Ovarian |
| | VRLTGVR (4) (1497) | SK-OV-3-3 Ovarian |
| GVL | VRSSGVL (1498) | SK-OV-3-3 Ovarian |
| GAV | RPWGAVA (1499) | SK-OV-3-3 Ovarian |
| GLV | PVSDGLV (1500) | SK-OV-3-3 Ovarian |
| GLR | NKGGLRQ (1501) | SK-OV-3-3 Ovarian |
| LVS | GGFLLVS (1502) | SK-OV-3-3 Ovarian |
| | LVPLVSG (1503) | SK-OV-3-3 Ovarian |
| ARG | ARGGESA (1504) | SK-OV-3-3 Ovarian |
| | MSARGIL (1505) | SK-OV-3-3 Ovarian |
| ASL | ASLVARN (1506) | SK-OV-3-3 Ovarian |
| AAV | RVEAAVP (1507) | SK-OV-3-3 Ovarian |
| AAS | RALGAAS (1508) | SK-OV-3-3 Ovarian |
| GGS | | SK-OV-3-3 Ovarian |
| GGR | ASEGGRA (1509) | SK-OV-3-3 Ovarian |
| | IGGRWVV (1510) | SK-OV-3-3 Ovarian |
| GLG | AGLGLLD (1511) | SK-OV-3-3 Ovarian |

TABLE 3-continued

Peptides and Motifs Associated with NCI-60 cell lines.

| Motif | Peptide w/ Seq ID:No. | Cell Line |
|---|---|---|
| GGL | LGGLSER (1512) | SK-OV-3-3 Ovarian |
| | NKGGLRQ (1513) | SK-OV-3-3 Ovarian |
| GSS | LVGSSRV (1514) | SK-OV-3-3 Ovarian |
| | YTGSSPS (1515) | SK-OV-3-3 Ovarian |
| GSG | | SK-OV-3-3 Ovarian |
| GSV | GSVLPVL (1516) | SK-OV-3-3 Ovarian |
| | KGDGSVR (1517) | SK-OV-3-3 Ovarian |
| | GSVSHRR (1518) | SK-OV-3-3 Ovarian |
| | RLWGSVV (1519) | SK-OV-3-3 Ovarian |
| GRV | MQGRVIV (1520) | SK-OV-3-3 Ovarian |
| | RSGRVSN (1521) | SK-OV-3-3 Ovarian |
| GRL | LEVGRLF (1522) | SK-OV-3-3 Ovarian |
| GPS | SQFGPSF (3) (1523) | SK-OV-3-3 Ovarian |
| GVS | ATLDGVS (1524) | SK-OV-3-3 Ovarian |
| RLS | RLSWTVL (1525) | PC3 Prostate |
| RGV | LRFRRGV (1526) | PC3 Prostate |
| RGS | ARGRGSQ (1527) | PC3 Prostate |
| | VLRGSTP (1528) | PC3 Prostate |
| RAV | | PC3 Prostate |
| RAS | ARLRASR (1529) | PC3 Prostate |
| GAG | RIGAGHR (1530) | PC3 Prostate |
| AVS | | PC3 Prostate |
| LLS | WLLSSEI (1531) | PC3 Prostate |
| LLR | | PC3 Prostate |
| LRV | GGLRVGG (1532) | PC3 Prostate |
| | GLRVYEP (1533) | PC3 Prostate |
| LRS | YLRSAGM (1534) | PC3 Prostate |
| RVS | RVSRAGG (1535) | PC3 Prostate |
| RSS | | PC3 Prostate |
| AGS | | PC3 Prostate |
| AGR | AGRPGGY (1536) | PC3 Prostate |
| AGL | YGALAGL (1537) | PC3 Prostate |
| AGG | RVSRAGG (1538) | PC3 Prostate |
| | SHTAGGG (1539) | PC3 Prostate |
| | AGGVRDL (1540) | PC3 Prostate |
| | RPAGGRT (1541) | PC3 Prostate |

TABLE 3-continued

Peptides and Motifs Associated with NCI-60 cell lines.

| Motif | Peptide w/ Seq ID:No. | Cell Line |
|---|---|---|
| GVR | GGVRLGG (1542) | PC3 Prostate |
| | AGGVRDL (1543) | PC3 Prostate |
| GVL | GVLGCDG (1544) | PC3 Prostate |
| GAV | CGAVAEW (1545) | PC3 Prostate |
| GLV | GDCGLVG (1546) | PC3 Prostate |
| GLR | GGLRVGG (1547) | PC3 Prostate |
| | GLRVYEP (1548) | PC3 Prostate |
| LVS | | PC3 Prostate |
| ARG | ARGRGSQ (1549) | PC3 Prostate |
| ASL | | PC3 Prostate |
| AAV | | PC3 Prostate |
| AAS | | PC3 Prostate |
| GGS | | PC3 Prostate |
| GGR | GGRELKA (1550) | PC3 Prostate |
| | GGGRRAL (1551) | PC3 Prostate |
| | RPAGGRT (1552) | PC3 Prostate |
| GLG | | PC3 Prostate |
| GGL | GGLKVWR (1553) | PC3 Prostate |
| | GGLRVGG (1554) | PC3 Prostate |
| | GGLPVQM (1555) | PC3 Prostate |
| | RQDGGLY (1556) | PC3 Prostate |
| GSS | YATLGSS (1557) | PC3 Prostate |
| GSG | SGSGCVF (1558) | PC3 Prostate |
| | VSGSGTA (1559) | PC3 Prostate |
| GSV | VGSVKAS (1560) | PC3 Prostate |
| | ATGSGSV (1561) | PC3 Prostate |
| GRV | | PC3 Prostate |
| GRL | PTSGRLV (1562) | PC3 Prostate |
| GPS | LACRGPS (1563) | PC3 Prostate |
| | RGPSQVL (1564) | PC3 Prostate |
| GVS | | PC3 Prostate |
| RLS | TLGRLSS (1565) | DU-145 Prostate |
| RGV | AGDRGVA (1566) | DU-145 Prostate |
| RGS | | DU-145 Prostate |
| RAV | LPRRAVF (1567) | DU-145 Prostate |
| RAS | RASCVWR (6) (1568) | DU-145 Prostate |

TABLE 3-continued

Peptides and Motifs Associated with NCI-60 cell lines.

| Motif | Peptide w/ Seq ID:No. | Cell Line |
|---|---|---|
| | FSKMRAS (1569) | DU-145 Prostate |
| GAG | DYVGAGT (1570) | DU-145 Prostate |
| AVS | | DU-145 Prostate |
| LLS | | DU-145 Prostate |
| LLR | ARLLRGG (1571) | DU-145 Prostate |
| | LLRSVGY (1572) | DU-145 Prostate |
| LRV | | DU-145 Prostate |
| LRS | HLRSGFS (1573) | DU-145 Prostate |
| | LLRSVGY (1574) | DU-145 Prostate |
| RVS | | DU-145 Prostate |
| RSS | | DU-145 Prostate |
| AGS | | DU-145 Prostate |
| AGR | AGRPDGV (1575) | DU-145 Prostate |
| AGL | DENRAGL (1576) | DU-145 Prostate |
| AGG | AWAGGDM (1577) | DU-145 Prostate |
| | LNAGGSG (1578) | DU-145 Prostate |
| GVR | | DU-145 Prostate |
| GVL | | DU-145 Prostate |
| GAV | NMGAVGS (1579) | DU-145 Prostate |
| | PIGAVMN (1580) | DU-145 Prostate |
| GLV | LTGGLVF (1581) | DU-145 Prostate |
| | CGEGLVV (1582) | DU-145 Prostate |
| GLR | SDLGLRR (1583) | DU-145 Prostate |
| LVS | HADVLVS (1584) | DU-145 Prostate |
| ARG | FSNARGY (1585) | DU-145 Prostate |
| ASL | | DU-145 Prostate |
| AAV | AAVWWAA (1586) | DU-145 Prostate |
| AAS | | DU-145 Prostate |
| GGS | LNAGGSG (1587) | DU-145 Prostate |
| | GGSAWWG (1588) | DU-145 Prostate |
| | VYGWGGS (1589) | DU-145 Prostate |
| GGR | GGRLLRA (1590) | DU-145 Prostate |
| | LGGRTIS (1591) | DU-145 Prostate |
| GLG | YLGLGGL (1592) | DU-145 Prostate |
| GGL | SITRGGL (1593) | DU-145 Prostate |
| | LTGGLVF (1594) | DU-145 Prostate |
| | LGGLGLY (1595) | DU-145 Prostate |

TABLE 3-continued

Peptides and Motifs Associated with NCI-60 cell lines.

| Motif | Peptide w/ Seq ID:No. | Cell Line |
|---|---|---|
| GSS | GSSELSR (1596) | DU-145 Prostate |
| GSG | GSGGANL (1597) | DU-145 Prostate |
| | VDGSGDD (1598) | DU-145 Prostate |
| GSV | RSLGSVG (1599) | DU-145 Prostate |
| GRV | GRVKPGA (1600) | DU-145 Prostate |
| GRL | GGRLLRA (1601) | DU-145 Prostate |
| | GRLWYVA (1602) | DU-145 Prostate |
| | TLGRLSS (1603) | DU-145 Prostate |
| GPS | | DU-145 Prostate |
| GVS | GVSGLSR (1604) | DU-145 Prostate |
| | YGVSRLL (1605) | DU-145 Prostate |
| RLS | SRLSYRA (1606) | 786-0 Renal |
| RGV | IHRGVWG (1607) | 786-0 Renal |
| RGS | YFRARGS (1608) | 786-0 Renal |
| RAV | | 786-0 Renal |
| RAS | | 786-0 Renal |
| GAG | GAGRFPH (1609) | 786-0 Renal |
| | SGAGAAF (1610) | 786-0 Renal |
| | VDVGGAG (1611) | 786-0 Renal |
| AVS | ASAGAVS (1612) | 786-0 Renal |
| LLS | | 786-0 Renal |
| LLR | | 786-0 Renal |
| LRV | | 786-0 Renal |
| LRS | ARYSLRS (1613) | 786-0 Renal |
| | RLRSYVA (1614) | 786-0 Renal |
| | SRKGLRS (1615) | 786-0 Renal |
| RVS | SVTGRVS (1616) | 786-0 Renal |
| RSS | | 786-0 Renal |
| AGS | AGSAFWA (1617) | 786-0 Renal |
| | DQQEAGS (1618) | 786-0 Renal |
| | FAAGAGS (1619) | 786-0 Renal |
| AGR | GAGRFPH (1620) | 786-0 Renal |
| AGL | | 786-0 Renal |
| AGG | GAGGVDV (1621) | 786-0 Renal |
| GVR | | 786-0 Renal |
| GVL | | 786-0 Renal |

TABLE 3-continued

Peptides and Motifs Associated with NCI-60 cell lines.

| Motif | Peptide w/ Seq ID:No. | Cell Line |
|---|---|---|
| GAV | ASAGAVS (1622) | 786-0 Renal |
| GLV | RRDGLVE (1623) | 786-0 Renal |
| GLR | SRKGLRS (1624) | 786-0 Renal |
| LVS | GDATLVS (1625) | 786-0 Renal |
| | GDATLVS (1626) | 786-0 Renal |
| ARG | YFRARGS (1627) | 786-0 Renal |
| ASL | | 786-0 Renal |
| AAV | | 786-0 Renal |
| AAS | | 786-0 Renal |
| GGS | | 786-0 Renal |
| GGR | | 786-0 Renal |
| GLG | DRGLGMS (1628) | 786-0 Renal |
| GGL | | 786-0 Renal |
| GSS | | 786-0 Renal |
| GSG | GSGYFIT (1629) | 786-0 Renal |
| GSV | | 786-0 Renal |
| GRV | SVTGRVS (1630) | 786-0 Renal |
| GRL | | 786-0 Renal |
| GPS | VGPSVHL (1631) | 786-0 Renal |
| GVS | | 786-0 Renal |
| RLS | | A498 Renal |
| RGV | EGVRGVF (1632) | A498 Renal |
| | GDRGVRG (1633) | A498 Renal |
| | MRGVARK (1634) | A498 Renal |
| RGS | | A498 Renal |
| RAV | KRAVGRM (1635) | A498 Renal |
| RAS | DRASSWA (1636) | A498 Renal |
| GAG | LQGAGIH (1637) | A498 Renal |
| AVS | | A498 Renal |
| LLS | | A498 Renal |
| LLR | WLLRGFG (1638) | A498 Renal |
| LRV | | A498 Renal |
| LRS | ASPPLRS (1639) | A498 Renal |
| RVS | RVSSETF (1640) | A498 Renal |
| RSS | | A498 Renal |
| AGS | ARAGSTF (1641) | A498 Renal |
| AGR | TFAGRSL (1642) | A498 Renal |

TABLE 3-continued

Peptides and Motifs Associated with NCI-60 cell lines.

| Motif | Peptide w/ Seq ID:No. | Cell Line |
|---|---|---|
| AGL | | A498 Renal |
| AGG | YAAGGST (1643) | A498 Renal |
| GVR | EGVRGVF (1644) | A498 Renal |
| | GDRGVRG (1645) | A498 Renal |
| GVL | PGVLREP (1646) | A498 Renal |
| GAV | | A498 Renal |
| GLV | | A498 Renal |
| GLR | GLRDGVE (1647) | A498 Renal |
| LVS | | A498 Renal |
| ARG | FPARGED (1648) | A498 Renal |
| ASL | MLGSASL (1649) | A498 Renal |
| AAV | | A498 Renal |
| AAS | | A498 Renal |
| GGS | HGGSNDR (1650) | A498 Renal |
| | YAAGGST (1651) | A498 Renal |
| GGR | QGGRSGV (1652) | A498 Renal |
| | WTVGGRV (1653) | A498 Renal |
| GLG | | A498 Renal |
| GGL | | A498 Renal |
| GSS | VKGSSMR (1654) | A498 Renal |
| GSG | | A498 Renal |
| GSV | | A498 Renal |
| GRV | FVGRVGE (1655) | A498 Renal |
| | GRVGRDG (1656) | A498 Renal |
| | SVSRGRV (1657) | A498 Renal |
| | WTVGGRV (1658) | A498 Renal |
| GRL | GFGRLLW (1659) | A498 Renal |
| GPS | AAYWGPS (1660) | A498 Renal |
| GVS | MDGVSTE (1661) | A498 Renal |
| | VYWWGVS (1662) | A498 Renal |
| RLS | RLSMASR (1663) | ACHN Renal |
| | GRLSFGV (1664) | ACHN Renal |
| RGV | GLSRGVL (1665) | ACHN Renal |
| RGS | LRGSHVA (1666) | ACHN Renal |
| | NMGRGSL (1667) | ACHN Renal |
| | SVVRRGS (1668) | ACHN Renal |

TABLE 3-continued

Peptides and Motifs Associated with NCI-60 cell lines.

| Motif | Peptide w/ Seq ID:No. | Cell Line |
|---|---|---|
| RAV | | ACHN Renal |
| RAS | | ACHN Renal |
| GAG | VMGAGVQ (1669) | ACHN Renal |
| AVS | | ACHN Renal |
| LLS | | ACHN Renal |
| LLR | PLLRQQL (1670) | ACHN Renal |
| LRV | SNGLRVV (1671) | ACHN Renal |
| LRS | LRSMAVM (1672) | ACHN Renal |
| | VDLRSAF (1673) | ACHN Renal |
| RVS | FRVSLGY (1674) | ACHN Renal |
| RSS | RSSYAPP (1675) | ACHN Renal |
| AGS | FPGSAGS (1676) | ACHN Renal |
| AGR | FAGRAPR (1677) | ACHN Renal |
| AGL | | ACHN Renal |
| AGG | FIAGGVG (1678) | ACHN Renal |
| | LIHAGGQ (1679) | ACHN Renal |
| | RAGGGAP (1680) | ACHN Renal |
| | TWHAGGI (1681) | ACHN Renal |
| GVR | GVRSITL (1682) | ACHN Renal |
| GVL | GLSRGVL (1683) | ACHN Renal |
| GAV | RVVGAVL (1684) | ACHN Renal |
| GLV | | ACHN Renal |
| GLR | FGLRMSN (1685) | ACHN Renal |
| | LGLRGWT (1686) | ACHN Renal |
| | AFFMGLR (1687) | ACHN Renal |
| | SNGLRVV (1688) | ACHN Renal |
| LVS | | ACHN Renal |
| ARG | ARGTMTG (1689) | ACHN Renal |
| | RPARGAF (1690) | ACHN Renal |
| ASL | ASLPMLH (1691) | ACHN Renal |
| AAV | | ACHN Renal |
| AAS | | ACHN Renal |
| GGS | GGSVEGQ (1692) | ACHN Renal |
| GGR | LGGRQES (1693) | ACHN Renal |
| | NGGRVLS (1694) | ACHN Renal |
| GLG | | ACHN Renal |
| GGL | PIGGLFG (1695) | ACHN Renal |

TABLE 3-continued

Peptides and Motifs Associated with NCI-60 cell lines.

| Motif | Peptide w/ Seq ID:No. | Cell Line |
|---|---|---|
| | AECCGGL (1696) | ACHN Renal |
| | SEQRGGL (1697) | ACHN Renal |
| GSS | DRFGSSA (1698) | ACHN Renal |
| GSG | GHGSGSR (1699) | ACHN Renal |
| GSV | GGSVEGQ (1700) | ACHN Renal |
| | GSVVSSW (1701) | ACHN Renal |
| GRV | NGGRVLS (1702) | ACHN Renal |
| GRL | GRLMPGG (1703) | ACHN Renal |
| | TWGRLGL (1704) | ACHN Renal |
| | AVHSGRL (1705) | ACHN Renal |
| | GRLSFGV (1706) | ACHN Renal |
| GPS | PQGPSSV (1707) | ACHN Renal |
| GVS | | ACHN Renal |
| RLS | AGWRLSQ (1708) | CAIK-1 Renal |
| RGV | | CAIK-1 Renal |
| RGS | RVDRGSL (1709) | CAIK-1 Renal |
| RAV | RAVCEWD (1710) | CAIK-1 Renal |
| | RAVERVA (1711) | CAIK-1 Renal |
| RAS | AVFRASR (1712) | CAIK-1 Renal |
| GAG | GAGSSVW (1713) | CAIK-1 Renal |
| | GAGSSVW (1714) | CAIK-1 Renal |
| AVS | | CAIK-1 Renal |
| LLS | | CAIK-1 Renal |
| LLR | WLLRSWS (1715) | CAIK-1 Renal |
| LRV | RKEALRV (1716) | CAIK-1 Renal |
| | RLRVSVR (1717) | CAIK-1 Renal |
| LRS | LRPGLRS (1718) | CAIK-1 Renal |
| | QRYHLRS (13) (1719) | CAIK-1 Renal |
| | WLLRSWS (1720) | CAIK-1 Renal |
| RVS | GRERVSH (2) (1721) | CAIK-1 Renal |
| | RVSVRLR (1722) | CAIK-1 Renal |
| RSS | | CAIK-1 Renal |
| AGS | GAGSSVW (1723) | CAIK-1 Renal |
| | GAGSSVW (1724) | CAIK-1 Renal |
| AGR | | CAIK-1 Renal |

TABLE 3-continued

Peptides and Motifs Associated with NCI-60 cell lines.

| Motif | Peptide w/ Seq ID:No. | Cell Line |
|---|---|---|
| AGL | AGLWPWN (1725) | CAIK-1 Renal |
| AGG | | CAIK-1 Renal |
| GVR | GVRGGGD (1726) | CAIK-1 Renal |
| GVL | | CAIK-1 Renal |
| GAV | | CAIK-1 Renal |
| GLV | GLVRRVV (1727) | CAIK-1 Renal |
| GLR | LRPGLRS (1728) | CAIK-1 Renal |
| LVS | | CAIK-1 Renal |
| ARG | | CAIK-1 Renal |
| ASL | | CAIK-1 Renal |
| AAV | | CAIK-1 Renal |
| AAS | WAHAASY (1729) | CAIK-1 Renal |
| GGS | | CAIK-1 Renal |
| GGR | DGGGRVG (1730) | CAIK-1 Renal |
| | VGVMGGR (1731) | CAIK-1 Renal |
| | VYGGRSE (1732) | CAIK-1 Renal |
| GLG | TICLGLG (1733) | CAIK-1 Renal |
| GGL | | CAIK-1 Renal |
| GSS | GAGSSVW (1734) | CAIK-1 Renal |
| | GAGSSVW (1735) | CAIK-1 Renal |
| GSG | | CAIK-1 Renal |
| GSV | DHVSGSV (1736) | CAIK-1 Renal |
| GRV | DGGGRVG (1737) | CAIK-1 Renal |
| GRL | GEGRLCG (1738) | CAIK-1 Renal |
| | GVAIGRL (1739) | CAIK-1 Renal |
| GPS | | CAIK-1 Renal |
| GVS | FGVSQVH (1740) | CAIK-1 Renal |
| | GGVSRMR (1741) | CAIK-1 Renal |
| RLS | GRIRLSF (1742) | RXF393 Renal |
| RGV | RGVNYRS (1743) | RXF393 Renal |
| | TEGTRGV (1744) | RXF393 Renal |
| RGS | GYARGSG (1745) | RXF393 Renal |
| | GVWLRGS (1746) | RXF393 Renal |
| RAV | AARAVWG (1747) | RXF393 Renal |
| RAS | RASYYGV (1748) | RXF393 Renal |
| GAG | GAGVEYF (1749) | RXF393 Renal |
| AVS | | RXF393 Renal |

TABLE 3-continued

Peptides and Motifs Associated with NCI-60 cell lines.

| Motif | Peptide w/ Seq ID:No. | Cell Line |
|---|---|---|
| LLS | LLLLSGS (1750) | RXF393 Renal |
| | VLLSAGL (1751) | RXF393 Renal |
| LLR | TGLLRLY (1752) | RXF393 Renal |
| LRV | | RXF393 Renal |
| LRS | LRSSLVS (1753) | RXF393 Renal |
| RVS | | RXF393 Renal |
| RSS | LRSSLVS (1754) | RXF393 Renal |
| | PRSSGPM (1755) | RXF393 Renal |
| AGS | | RXF393 Renal |
| AGR | TAGRLEV (1756) | RXF393 Renal |
| AGL | AGLEDLG (1757) | RXF393 Renal |
| | MPAGLGV (1758) | RXF393 Renal |
| | VLLSAGL (1759) | RXF393 Renal |
| AGG | | RXF393 Renal |
| GVR | GVRWNWS (1760) | RXF393 Renal |
| | TRDGVRW (1761) | RXF393 Renal |
| GVL | | RXF393 Renal |
| GAV | | RXF393 Renal |
| GLV | RAHGLVC (1762) | RXF393 Renal |
| GLR | LGSSGLR (1763) | RXF393 Renal |
| LVS | LLVSLSS (1764) | RXF393 Renal |
| | LRSSLVS (1765) | RXF393 Renal |
| | LVSTRWA (1766) | RXF393 Renal |
| | LVSYSAV (1767) | RXF393 Renal |
| ARG | GYARGSG (1768) | RXF393 Renal |
| ASL | LGASLLV (1769) | RXF393 Renal |
| AAV | GTGAAVF (1770) | RXF393 Renal |
| | AAVGTAL (1771) | RXF393 Renal |
| AAS | VSAASSV (1772) | RXF393 Renal |
| GGS | RGGSPPV (1773) | RXF393 Renal |
| GGR | VPPSGGR (1774) | RXF393 Renal |
| GLG | GLGSCAP (1775) | RXF393 Renal |
| | MPAGLGV (1776) | RXF393 Renal |
| GGL | | RXF393 Renal |
| GSS | MPGSSRP (1777) | RXF393 Renal |
| | GSSLSRP (1778) | RXF393 Renal |

TABLE 3-continued

Peptides and Motifs Associated with NCI-60 cell lines.

| Motif | Peptide w/ Seq ID:No. | Cell Line |
|---|---|---|
| | RLGSSGL (1779) | RXF393 Renal |
| GSG | GYARGSG (1780) | RXF393 Renal |
| GSV | | RXF393 Renal |
| GRV | | RXF393 Renal |
| GRL | SGRLWVG (1781) | RXF393 Renal |
| | TAGRLEV (1782) | RXF393 Renal |
| GPS | GPSFDAK (1783) | RXF393 Renal |
| GVS | ACTGVSR (1784) | RXF393 Renal |
| RLS | | SN12C Renal |
| RGV | LGMGRGV (1785) | SN12C Renal |
| RGS | MLGRGSV (1786) | SN12C Renal |
| RAV | | SN12C Renal |
| RAS | PRASSTG (1787) | SN12C Renal |
| | RASCFWD (1788) | SN12C Renal |
| | RASCFWD (1789) | SN12C Renal |
| GAG | | SN12C Renal |
| AVS | | SN12C Renal |
| LLS | FLLLSHR (1790) | SN12C Renal |
| | LLSVTSX (1791) | SN12C Renal |
| LLR | PLLREVG (1792) | SN12C Renal |
| LRV | LRVGHAG (1793) | SN12C Renal |
| | NELRVCR (1794) | SN12C Renal |
| LRS | MRYELRS (1795) | SN12C Renal |
| RVS | RVSVWWA (1796) | SN12C Renal |
| | FAQRRVS (1797) | SN12C Renal |
| RSS | SHHRSSI (1798) | SN12C Renal |
| AGS | CMAGSQD (1799) | SN12C Renal |
| | RYGTAGS (1800) | SN12C Renal |
| | SAGSHPA (1801) | SN12C Renal |
| | PNSAGSV (1802) | SN12C Renal |
| AGR | KMRIAGR (1803) | SN12C Renal |
| | MERVAGR (1804) | SN12C Renal |
| AGL | WAGLSRP (1805) | SN12C Renal |
| AGG | | SN12C Renal |
| GVR | GAHGVRL (1806) | SN12C Renal |
| | RVPTGVR (1807) | SN12C Renal |
| GVL | | SN12C Renal |

TABLE 3-continued

Peptides and Motifs Associated with NCI-60 cell lines.

| Motif | Peptide w/ Seq ID:No. | Cell Line |
|---|---|---|
| GAV | RGAVREM (1808) | SN12C Renal |
| GLV | | SN12C Renal |
| GLR | FDPGGLR (1809) | SN12C Renal |
| LVS | ILSDLVS (1810) | SN12C Renal |
| ARG | LLNPARG (1811) | SN12C Renal |
| ASL | | SN12C Renal |
| AAV | WWAAVPG (1812) | SN12C Renal |
| AAS | KAASTED (1813) | SN12C Renal |
| | SYMGAAS (1814) | SN12C Renal |
| GGS | GGSIDCC (1815) | SN12C Renal |
| | GPGGSKR (1816) | SN12C Renal |
| | AFGGGSM (1817) | SN12C Renal |
| GGR | PEGGRRP (1818) | SN12C Renal |
| GLG | | SN12C Renal |
| GGL | GGLEQDG (1819) | SN12C Renal |
| | FDPGGLR (1820) | SN12C Renal |
| GSS | LFGSSVS (1821) | SN12C Renal |
| | WDGSSVS (1822) | SN12C Renal |
| GSG | | SN12C Renal |
| GSV | PNSAGSV (1823) | SN12C Renal |
| | MLGRGSV (1824) | SN12C Renal |
| GRV | | SN12C Renal |
| GRL | TRRGRLD (1825) | SN12C Renal |
| GPS | | SN12C Renal |
| GVS | GVSISDG (1826) | SN12C Renal |
| | GVSIYDL (1827) | SN12C Renal |
| RLS | ARLSLEL (1828) | TK-10 Renal |
| | RLRLSSW (1829) | TK-10 Renal |
| | RRLSSIA (1830) | TK-10 Renal |
| | SRLSYRT (1831) | TK-10 Renal |
| RGV | | TK-10 Renal |
| RGS | ARGSWRE (1832) | TK-10 Renal |
| RAV | VRLRAVF (1833) | TK-10 Renal |
| RAS | RASRIGL (1834) | TK-10 Renal |
| GAG | GAGTSEG (1835) | TK-10 Renal |
| AVS | | TK-10 Renal |

TABLE 3-continued

Peptides and Motifs Associated with NCI-60 cell lines.

| Motif | Peptide w/ Seq ID:No. | Cell Line |
|---|---|---|
| LLS | LLSTVWV (1836) | TK-10 Renal |
| | ELRRLLS (1837) | TK-10 Renal |
| LLR | LLRGLRP (1838) | TK-10 Renal |
| | SLLRRLE (1839) | TK-10 Renal |
| LRV | LRVSRGL (1840) | TK-10 Renal |
| | TLGLRVP (1841) | TK-10 Renal |
| | FVARLRV (1842) | TK-10 Renal |
| LRS | GVYWLRS (1843) | TK-10 Renal |
| | SFWWLRS (1844) | TK-10 Renal |
| | TRYSLRS (1845) | TK-10 Renal |
| RVS | LRVSRGL (1846) | TK-10 Renal |
| RSS | RSSSGSG (1847) | TK-10 Renal |
| | TRSSLTH (1848) | TK-10 Renal |
| | TGRSSFW (1849) | TK-10 Renal |
| AGS | | TK-10 Renal |
| AGR | NAGRGAS (1850) | TK-10 Renal |
| AGL | HAGLLVV (1851) | TK-10 Renal |
| AGG | | TK-10 Renal |
| GVR | HTYGVRF (1852) | TK-10 Renal |
| GVL | | TK-10 Renal |
| GAV | GAVRSVM (1853) | TK-10 Renal |
| | VLVEGAV (1854) | TK-10 Renal |
| GLV | | TK-10 Renal |
| GLR | LLRGLRP (1855) | TK-10 Renal |
| | TLGLRVP (1856) | TK-10 Renal |
| LVS | | TK-10 Renal |
| ARG | ARGSWRE (1857) | TK-10 Renal |
| ASL | | TK-10 Renal |
| AAV | GLWAAVL (1858) | TK-10 Renal |
| AAS | GWTMAAS (1859) | TK-10 Renal |
| GGS | LYMGGSH (1860) | TK-10 Renal |
| GGR | GVGGRQS (1861) | TK-10 Renal |
| GLG | RRGLGDA (1862) | TK-10 Renal |
| GGL | TGGLHWY (1863) | TK-10 Renal |
| GSS | GSGSSSR (1864) | TK-10 Renal |
| | GSSTLQW (1865) | TK-10 Renal |
| GSG | RSSSGSG (1866) | TK-10 Renal |

TABLE 3-continued

Peptides and Motifs Associated with NCI-60 cell lines.

| Motif | Peptide w/ Seq ID:No. | Cell Line |
|---|---|---|
| GSV | DELGSVQ (1867) | TK-10 Renal |
| GRV | | TK-10 Renal |
| GRL | GRLRPFS (1868) | TK-10 Renal |
| | PRLGRLL (1869) | TK-10 Renal |
| GPS | | TK-10 Renal |
| GVS | VGVSQEW (1870) | TK-10 Renal |
| | DGVSPLW (1871) | TK-10 Renal |
| RLS | | UO31 Renal |
| RGV | | UO31 Renal |
| RGS | PRGSLFA (1872) | UO31 Renal |
| | VIVRGSL (1873) | UO31 Renal |
| RAV | GDRAVGL (1874) | UO31 Renal |
| | VHKRAVL (1875) | UO31 Renal |
| RAS | | UO31 Renal |
| GAG | GGAGSRR (1876) | UO31 Renal |
| AVS | | UO31 Renal |
| LLS | RLETLLS (1877) | UO31 Renal |
| LLR | LLRAGVR (1878) | UO31 Renal |
| LRV | PAILRVR (1879) | UO31 Renal |
| | GDLRVSV (1880) | UO31 Renal |
| LRS | | UO31 Renal |
| RVS | GDLRVSV (1881) | UO31 Renal |
| RSS | | UO31 Renal |
| AGS | GGAGSRR (1882) | UO31 Renal |
| | AGSVTEQ (1883) | UO31 Renal |
| | SSSLAGS (1884) | UO31 Renal |
| AGR | RSWNAGR (1885) | UO31 Renal |
| AGL | AGLPHRF (1886) | UO31 Renal |
| | RNSRAGL (1887) | UO31 Renal |
| AGG | RRSGAGG (1888) | UO31 Renal |
| | AGGPSSY (1889) | UO31 Renal |
| GVR | TGVRNSP (1890) | UO31 Renal |
| | LLRAGVR (1891) | UO31 Renal |
| GVL | | UO31 Renal |
| GAV | | UO31 Renal |
| GLV | | UO31 Renal |

TABLE 3-continued

Peptides and Motifs Associated with NCI-60 cell lines.

| Motif | Peptide w/ Seq ID:No. | Cell Line |
|---|---|---|
| GLR | | UO31 Renal |
| LVS | ALVSTIL (1892) | UO31 Renal |
| ARG | ARGRDEG (1893) | UO31 Renal |
| ASL | ASLSVVI (1894) | UO31 Renal |
| AAV | | UO31 Renal |
| AAS | | UO31 Renal |
| GGS | GGSRGYR (1895) | UO31 Renal |
| | YWGGSVP (1896) | UO31 Renal |
| GGR | GGRPVER (1897) | UO31 Renal |
| | GGRSQEG (1898) | UO31 Renal |
| | PGGGRGR (1899) | UO31 Renal |
| GLG | | UO31 Renal |
| GGL | | UO31 Renal |
| GSS | FSLGSSP (1900) | UO31 Renal |
| GSG | | UO31 Renal |
| GSV | GSVFGTP (1901) | UO31 Renal |
| | AGSVTEQ (1902) | UO31 Renal |
| | YWGGSVP (1903) | UO31 Renal |
| GRV | LSGRVIV (1904) | UO31 Renal |
| | LSTPGRV (1905) | UO31 Renal |
| GRL | | UO31 Renal |
| GPS | AGGPSSY (1906) | UO31 Renal |
| | | UO31 Renal |
| GVS | | UO31 Renal |
| RLS | | MCF-7 Breast |
| RGV | | MCF-7 Breast |
| RGS | RVMRGSL (1907) | MCF-7 Breast |
| RAV | | MCF-7 Breast |
| RAS | RASCVWA (1908) | MCF-7 Breast |
| GAG | | MCF-7 Breast |
| AVS | | MCF-7 Breast |
| LLS | QLLSQVY (1909) | MCF-7 Breast |
| LLR | | MCF-7 Breast |
| LRV | | MCF-7 Breast |
| LRS | ERYYLRS (1910) | MCF-7 Breast |
| | GLVKLRS (1911) | MCF-7 Breast |
| RVS | | MCF-7 Breast |

TABLE 3-continued

Peptides and Motifs Associated with NCI-60 cell lines.

| Motif | Peptide w/ Seq ID:No. | Cell Line |
|---|---|---|
| RSS | | MCF-7 Breast |
| AGS | GRLAAGS (1912) | MCF-7 Breast |
| AGR | | MCF-7 Breast |
| AGL | | MCF-7 Breast |
| AGG | | MCF-7 Breast |
| GVR | | MCF-7 Breast |
| GVL | | MCF-7 Breast |
| GAV | | MCF-7 Breast |
| GLV | GLVKLRS (1913) | MCF-7 Breast |
| GLR | | MCF-7 Breast |
| LVS | LWFELVS (1914) | MCF-7 Breast |
| ARG | | MCF-7 Breast |
| ASL | | MCF-7 Breast |
| AAV | | MCF-7 Breast |
| AAS | IGAASWF (1915) | MCF-7 Breast |
| GGS | | MCF-7 Breast |
| GGR | GGRRGTS (1916) | MCF-7 Breast |
| | RDLGGRW (1917) | MCF-7 Breast |
| GLG | | MCF-7 Breast |
| GGL | WRGGLDR (1918) | MCF-7 Breast |
| GSS | GRWTGSS (1919) | MCF-7 Breast |
| | SYWVGSS (1920) | MCF-7 Breast |
| GSG | | MCF-7 Breast |
| GSV | | MCF-7 Breast |
| GRV | | MCF-7 Breast |
| GRL | GRLAAGS (1921) | MCF-7 Breast |
| GPS | | MCF-7 Breast |
| GVS | AKAGVSR (1922) | MCF-7 Breast |
| RLS | LRLSGHD (1923) | NCI/ADR-RES Breast |
| RGV | RGVGAKA (1924) | NCI/ADR-RES Breast |
| | LRGVYVA (1925) | NCI/ADR-RES Breast |
| RGS | | NCI/ADR-RES Breast |
| RAV | | NCI/ADR-RES Breast |
| RAS | | NCI/ADR-RES Breast |
| GAG | | NCI/ADR-RES Breast |
| AVS | GTPAVSY (1926) | NCI/ADR-RES Breast |

TABLE 3-continued

Peptides and Motifs Associated with NCI-60 cell lines.

| Motif | Peptide w/ Seq ID:No. | Cell Line |
|---|---|---|
| LLS | FLLSRSA (1927) | NCI/ADR-RES Breast |
| | AGLLSDV (1928) | NCI/ADR-RES Breast |
| LLR | | NCI/ADR-RES Breast |
| LRV | LRVGXPG (1929) | NCI/ADR-RES Breast |
| LRS | | NCI/ADR-RES Breast |
| RVS | RVSGSPV (1930) | NCI/ADR-RES Breast |
| RSS | RSSIDVG (1931) | NCI/ADR-RES Breast |
| AGS | | NCI/ADR-RES Breast |
| AGR | AGRRLRD (1932) | NCI/ADR-RES Breast |
| AGL | WRLAGLG (1933) | NCI/ADR-RES Breast |
| | PTVSAGL (1934) | NCI/ADR-RES Breast |
| | AGLLSDV (1935) | NCI/ADR-RES Breast |
| AGG | | NCI/ADR-RES Breast |
| GVR | | NCI/ADR-RES Breast |
| GVL | TLGVLVT (1936) | NCI/ADR-RES Breast |
| GAV | | NCI/ADR-RES Breast |
| GLV | | NCI/ADR-RES Breast |
| GLR | | NCI/ADR-RES Breast |
| LVS | GDRRLVS (1937) | NCI/ADR-RES Breast |
| | LMLVSGK (1938) | NCI/ADR-RES Breast |
| ARG | DVHARGD (1939) | NCI/ADR-RES Breast |
| ASL | | NCI/ADR-RES Breast |
| AAV | | NCI/ADR-RES Breast |
| AAS | | NCI/ADR-RES Breast |
| GGS | REGGSDT (1940) | NCI/ADR-RES Breast |
| GGR | GGRRVVV (1941) | NCI/ADR-RES Breast |
| | NVGGGRF (1942) | NCI/ADR-RES Breast |
| GLG | GLGALRW (1943) | NCI/ADR-RES Breast |
| | LGLSGLG (1944) | NCI/ADR-RES Breast |
| | RGLGRPV (1945) | NCI/ADR-RES Breast |
| GGL | | NCI/ADR-RES Breast |
| GSS | GSSGLLA (1946) | NCI/ADR-RES Breast |
| | LGSSSHI (1947) | NCI/ADR-RES Breast |
| GSG | IGSGVGV (1948) | NCI/ADR-RES Breast |
| GSV | KGSVLML (1949) | NCI/ADR-RES Breast |
| | VPSGSVR (1950) | NCI/ADR-RES Breast |
| GRV | | NCI/ADR-RES Breast |

TABLE 3-continued

Peptides and Motifs Associated with NCI-60 cell lines.

| Motif | Peptide w/ Seq ID:No. | Cell Line |
|---|---|---|
| GRL | GYLGRLP (1951) | NCI/ADR-RES Breast |
| | AVYVGRL (1952) | NCI/ADR-RES Breast |
| GPS | | NCI/ADR-RES Breast |
| GVS | | NCI/ADR-RES Breast |
| RLS | LGGRLSL (1953) | MDA-MB-231 Breast |
| RGV | RGVGKTK (1954) | MDA-MB-231 Breast |
| | LGGARGV (1955) | MDA-MB-231 Breast |
| | HAWDRGV (1956) | MDA-MB-231 Breast |
| | DWGSRGV (1957) | MDA-MB-231 Breast |
| RGS | PYRRGSC (1958) | MDA-MB-231 Breast |
| | ALNRGSR (3) (1959) | MDA-MB-231 Breast |
| RAV | | MDA-MB-231 Breast |
| RAS | | MDA-MB-231 Breast |
| GAG | TFRGAGV (1960) | MDA-MB-231 Breast |
| AVS | | MDA-MB-231 Breast |
| LLS | LLSAARF (1961) | MDA-MB-231 Breast |
| LLR | | MDA-MB-231 Breast |
| LRV | | MDA-MB-231 Breast |
| LRS | MRPGLRS (1962) | MDA-MB-231 Breast |
| RVS | PRVSALV (1963) | MDA-MB-231 Breast |
| | VRVSLNS (1964) | MDA-MB-231 Breast |
| RSS | GRSSAGP (1965) | MDA-MB-231 Breast |
| AGS | LHAGSSV (1966) | MDA-MB-231 Breast |
| | VVMIAGS (1967) | MDA-MB-231 Breast |
| AGR | DTPAGRL (1968) | MDA-MB-231 Breast |
| | VGAGRFT (1969) | MDA-MB-231 Breast |
| AGL | | MDA-MB-231 Breast |
| AGG | AGGTDRT (1970) | MDA-MB-231 Breast |
| | FISAGGW (1971) | MDA-MB-231 Breast |
| | TIPAGGG (1972) | MDA-MB-231 Breast |
| | VGRAGGL (1973) | MDA-MB-231 Breast |
| GVR | | MDA-MB-231 Breast |
| GVL | | MDA-MB-231 Breast |
| GAV | | MDA-MB-231 Breast |
| GLV | NPGLVWN (1974) | MDA-MB-231 Breast |
| | LGLVHWV (1975) | MDA-MB-231 Breast |

TABLE 3-continued

Peptides and Motifs Associated with NCI-60 cell lines.

| Motif | Peptide w/ Seq ID:No. | Cell Line |
|---|---|---|
| GLR | MRPGLRS (1976) | MDA-MB-231 Breast |
| LVS | | MDA-MB-231 Breast |
| ARG | ARGNVRF (1977) | MDA-MB-231 Breast |
| | LGGARGV (1978) | MDA-MB-231 Breast |
| ASL | FRAASLL (1979) | MDA-MB-231 Breast |
| AAV | | MDA-MB-231 Breast |
| AAS | AASVGVA (1980) | MDA-MB-231 Breast |
| | FRAASLL (1981) | MDA-MB-231 Breast |
| GGS | PVFRGGS (1982) | MDA-MB-231 Breast |
| | SGGSVGF (1983) | MDA-MB-231 Breast |
| | VRANGGS (1984) | MDA-MB-231 Breast |
| GGR | FHIWGGR (1985) | MDA-MB-231 Breast |
| | LGGRLSL (1986) | MDA-MB-231 Breast |
| | SGGRFVP (1987) | MDA-MB-231 Breast |
| GLG | | MDA-MB-231 Breast |
| GGL | GGGLPVD (1988) | MDA-MB-231 Breast |
| | LSLRGGL (1989) | MDA-MB-231 Breast |
| | VGRAGGL (1990) | MDA-MB-231 Breast |
| GSS | ANGSSKK (1991) | MDA-MB-231 Breast |
| | DFTLGSS (1992) | MDA-MB-231 Breast |
| | LHAGSSV (1993) | MDA-MB-231 Breast |
| GSG | | MDA-MB-231 Breast |
| GSV | NSGSVVS (1994) | MDA-MB-231 Breast |
| | SGGSVGF (1995) | MDA-MB-231 Breast |
| | WSISGSV (1996) | MDA-MB-231 Breast |
| GRV | | MDA-MB-231 Breast |
| GRL | DTPAGRL (1997) | MDA-MB-231 Breast |
| | LGGRLSL (1998) | MDA-MB-231 Breast |
| GPS | | MDA-MB-231 Breast |
| GVS | AVGVSAA (1999) | MDA-MB-231 Breast |
| | SGVSNPG (2000) | MDA-MB-231 Breast |
| | FGVSGGS (2001) | MDA-MB-231 Breast |
| | ESATGVS (2002) | MDA-MB-231 Breast |
| | AAIVGVS (2003) | MDA-MB-231 Breast |
| RLS | | MDA-MB-435-Breast |
| RGV | | MDA-MB-435-Breast |

TABLE 3-continued

Peptides and Motifs Associated with NCI-60 cell lines.

| Motif | Peptide w/ Seq ID:No. | Cell Line |
|---|---|---|
| RGS | LRSGRGS (2004) | MDA-MB-435-Breast |
| | LRSGRGS (2005) | MDA-MB-435-Breast |
| | RGRGSTL (2006) | MDA-MB-435-Breast |
| | RGSPAAA (2007) | MDA-MB-435-Breast |
| | SRGSYGS (2008) | MDA-MB-435-Breast |
| | | MDA-MB-435-Breast |
| RAV | | MDA-MB-435-Breast |
| RAS | | MDA-MB-435-Breast |
| GAG | GVGGGAG (2009) | MDA-MB-435-Breast |
| | | MDA-MB-435-Breast |
| AVS | | MDA-MB-435-Breast |
| LLS | | MDA-MB-435-Breast |
| LLR | | MDA-MB-435-Breast |
| LRV | | MDA-MB-435-Breast |
| LRS | LRSGRGS (49) (2010) | MDA-MB-435-Breast |
| RVS | | MDA-MB-435-Breast |
| RSS | | MDA-MB-435-Breast |
| AGS | | MDA-MB-435-Breast |
| AGR | | MDA-MB-435-Breast |
| AGL | | MDA-MB-435-Breast |
| AGG | AGGGGYH (2011) | MDA-MB-435-Breast |
| | GAGGGVG (2012) | MDA-MB-435-Breast |
| | YRALAGG (2) (2013) | MDA-MB-435-Breast |
| | | MDA-MB-435-Breast |
| GVR | | MDA-MB-435-Breast |
| GVL | | MDA-MB-435-Breast |
| GAV | | MDA-MB-435-Breast |
| GLV | | MDA-MB-435-Breast |
| GLR | | MDA-MB-435-Breast |
| LVS | | MDA-MB-435-Breast |
| ARG | | MDA-MB-435-Breast |
| ASL | LYVDASL (2014) | MDA-MB-435-Breast |
| AAV | | MDA-MB-435-Breast |
| AAS | | MDA-MB-435-Breast |
| GGS | | MDA-MB-435-Breast |
| GGR | | MDA-MB-435-Breast |

TABLE 3-continued

Peptides and Motifs Associated with NCI-60 cell lines.

| Motif | Peptide w/ Seq ID:No. | Cell Line |
|---|---|---|
| GLG | | MDA-MB-435-Breast |
| GGL | | MDA-MB-435-Breast |
| GSS | | MDA-MB-435-Breast |
| GSG | GEGSGSA (2015) | MDA-MB-435-Breast |
| GSV | | MDA-MB-435-Breast |
| GRV | | MDA-MB-435-Breast |
| GRL | | MDA-MB-435-Breast |
| GPS | | MDA-MB-435-Breast |
| GVS | | MDA-MB-435-Breast |
| RLS | | BT-549 Breast |
| RGV | RVRGVLD (2016) | BT-549 Breast |
| | SMRGVLS (2017) | BT-549 Breast |
| | EAGPRGV (2018) | BT-549 Breast |
| RGS | CRGSIGA (2019) | BT-549 Breast |
| | PLQRGSG (2020) | BT-549 Breast |
| | RGSRWSS (2021) | BT-549 Breast |
| | RGSYVER (2022) | BT-549 Breast |
| RAV | TYCDRAV (2023) | BT-549 Breast |
| RAS | LGVRASP (2024) | BT-549 Breast |
| | WRASPGM (2025) | BT-549 Breast |
| | PRASDIL (2026) | BT-549 Breast |
| GAG | RVGAGWP (2027) | BT-549 Breast |
| AVS | | BT-549 Breast |
| LLS | LLSRAQA (2028) | BT-549 Breast |
| LLR | | BT-549 Breast |
| LRV | SALRVGL (2029) | BT-549 Breast |
| | VGLRVRF (2030) | BT-549 Breast |
| LRS | YGLRSLV (2031) | BT-549 Breast |
| RVS | TRVSGSG (2032) | BT-549 Breast |
| RSS | VRRSSKF (2033) | BT-549 Breast |
| AGS | | BT-549 Breast |
| AGR | | BT-549 Breast |
| AGL | TFAGLAQ (2034) | BT-549 Breast |
| AGG | | BT-549 Breast |
| GVR | LGVRASP (2035) | BT-549 Breast |
| | LGVRLAS (2036) | BT-549 Breast |

TABLE 3-continued

Peptides and Motifs Associated with NCI-60 cell lines.

| Motif | Peptide w/ Seq ID:No. | Cell Line |
|---|---|---|
| | PWGAGVR (2037) | BT-549 Breast |
| GVL | GVLTIGA (2038) | BT-549 Breast |
| | RVRGVLD (2039) | BT-549 Breast |
| | IGWGVLG (2040) | BT-549 Breast |
| | SMRGVLS (2041) | BT-549 Breast |
| GAV | GAVLTSC (2042) | BT-549 Breast |
| GLV | GLVSTLI (2043) | BT-549 Breast |
| | GLVGWGI (2044) | BT-549 Breast |
| GLR | VGLRCSV (2045) | BT-549 Breast |
| | VGLRVRF (2046) | BT-549 Breast |
| | YGLRSLV (2047) | BT-549 Breast |
| LVS | GLVSTLI (2048) | BT-549 Breast |
| ARG | PRGMARG (2049) | BT-549 Breast |
| ASL | | BT-549 Breast |
| AAV | | BT-549 Breast |
| AAS | | BT-549 Breast |
| GGS | RGGSDEA (2050) | BT-549 Breast |
| GGR | AEDSGGR (2051) | BT-549 Breast |
| | GGRCGAE (2052) | BT-549 Breast |
| GLG | | BT-549 Breast |
| GGL | GGLMPRY (2053) | BT-549 Breast |
| GSS | GSSVSLG (2054) | BT-549 Breast |
| GSG | GSGRQLP (2055) | BT-549 Breast |
| | RKGSGTA (2056) | BT-549 Breast |
| | TRVSGSG (2057) | BT-549 Breast |
| GSV | GSGSVRT (2058) | BT-549 Breast |
| GRV | DDGRVHR (2059) | BT-549 Breast |
| | DLVGRVR (2060) | BT-549 Breast |
| GRL | WGRLEST (2061) | BT-549 Breast |
| GPS | MGPSARW (2062) | BT-549 Breast |
| GVS | ISGVSDD (2063) | BT-549 Breast |
| RLS | GHSERLS (2064) | T-47D Breast |
| RGV | ERGVFVY (2065) | T-47D Breast |
| | TRGVIGG (2066) | T-47D Breast |
| RGS | RGSFGLG (2067) | T-47D Breast |
| RAV | PFHRRAV (2068) | T-47D Breast |
| RAS | | T-47D Breast |

TABLE 3-continued

Peptides and Motifs Associated with NCI-60 cell lines.

| Motif | Peptide w/ Seq ID:No. | Cell Line |
|---|---|---|
| GAG | VGIGAGG (2) (2069) | T-47D Breast |
| AVS | AVSLAWQ (2070) | T-47D Breast |
| | FPAVSTE (2071) | T-47D Breast |
| LLS | | T-47D Breast |
| LLR | | T-47D Breast |
| LRV | | T-47D Breast |
| LRS | SGARLRS (2072) | T-47D Breast |
| RVS | | T-47D Breast |
| RSS | SHRSSTG (2073) | T-47D Breast |
| AGS | SRLRAGS (2074) | T-47D Breast |
| AGR | SFAGRIL (2075) | T-47D Breast |
| AGL | | T-47D Breast |
| AGG | RVAAGGL (2076) | T-47D Breast |
| | VGIGAGG (2077) | T-47D Breast |
| | VGIGAGG (2078) | T-47D Breast |
| GVR | | T-47D Breast |
| GVL | | T-47D Breast |
| GAV | QKPGAVG (2079) | T-47D Breast |
| | LGYYGAV (2080) | T-47D Breast |
| GLV | LPLGLVS (2081) | T-47D Breast |
| | LGLVFTR (2082) | T-47D Breast |
| GLR | | T-47D Breast |
| LVS | LPLGLVS (2083) | T-47D Breast |
| | NSKPLVS (2084) | T-47D Breast |
| ARG | TNRFARG (2085) | T-47D Breast |
| ASL | LASLARP (2086) | T-47D Breast |
| AAV | LGGAAVR (2087) | T-47D Breast |
| AAS | AASPHPG (2088) | T-47D Breast |
| GGS | LSKGGSE (2089) | T-47D Breast |
| GGR | | T-47D Breast |
| GLG | GLGRSVN (2090) | T-47D Breast |
| | PGLGYAL (2091) | T-47D Breast |
| | RGSFGLG (2092) | T-47D Breast |
| GGL | GRDWGGL (2093) | T-47D Breast |
| | RVAAGGL (2094) | T-47D Breast |
| GSS | TVGSSLG (2095) | T-47D Breast |

TABLE 3-continued

Peptides and Motifs Associated with NCI-60 cell lines.

| Motif | Peptide w/ Seq ID:No. | Cell Line |
|---|---|---|
| GSG | | T-47D Breast |
| GSV | | T-47D Breast |
| GRV | GRVDPVD (2096) | T-47D Breast |
| GRL | SLYRGRL (2097) | T-47D Breast |
| GPS | | T-47D Breast |
| GVS | VALGVSS (2098) | T-47D Breast |
| RLS | VSVTRLS (2099) | HS 578 T Breast |
| RGV | | HS 578 T Breast |
| RGS | AGATRGS (2100) | HS 578 T Breast |
| | RRGSVAE (2101) | HS 578 T Breast |
| | FRFVRGS (2102) | HS 578 T Breast |
| | TRGSGAG (2103) | HS 578 T Breast |
| RAV | GARAVAP (2104) | HS 578 T Breast |
| RAS | | HS 578 T Breast |
| GAG | TRGSGAG (2105) | HS 578 T Breast |
| AVS | EAVSGRR (2106) | HS 578 T Breast |
| LLS | | HS 578 T Breast |
| LLR | | HS 578 T Breast |
| LRV | | HS 578 T Breast |
| LRS | | HS 578 T Breast |
| RVS | PVRRVSS (2107) | HS 578 T Breast |
| | IRVSAVV (2108) | HS 578 T Breast |
| RSS | HVRSSYA (2109) | HS 578 T Breast |
| | RVRSSLA (2110) | HS 578 T Breast |
| AGS | TAAGSSF (2111) | HS 578 T Breast |
| | GAGSGRT (2112) | HS 578 T Breast |
| | PAVAGST (2113) | HS 578 T Breast |
| AGR | AGRHLDA (2114) | HS 578 T Breast |
| | DRQLAGR (2115) | HS 578 T Breast |
| AGL | | HS 578 T Breast |
| AGG | | HS 578 T Breast |
| GVR | LGVREVG (2116) | HS 578 T Breast |
| | VAVGVRS (2117) | HS 578 T Breast |
| GVL | SFGVLSG (2118) | HS 578 T Breast |
| GAV | TSGAVAP (2119) | HS 578 T Breast |
| GLV | | HS 578 T Breast |

TABLE 3-continued

Peptides and Motifs Associated with NCI-60 cell lines.

| Motif | Peptide w/ Seq ID:No. | Cell Line |
|---|---|---|
| GLR | GLREVQD (2120) | HS 578 T Breast |
| LVS | SLVSERA (2121) | HS 578 T Breast |
|  | SVHLVSG (2122) | HS 578 T Breast |
| ARG | TQVEARG (2123) | HS 578 T Breast |
| ASL |  | HS 578 T Breast |
| AAV |  | HS 578 T Breast |
| AAS |  | HS 578 T Breast |
| GGS |  | HS 578 T Breast |
| GGR | GGRPTVT (2124) | HS 578 T Breast |
|  | VVGGRRT (2125) | HS 578 T Breast |
| GLG |  | HS 578 T Breast |
| GGL | GVGGLSS (2126) | HS 578 T Breast |
| GSS | TAAGSSF (2127) | HS 578 T Breast |
| GSG | TRGSGAG (2128) | HS 578 T Breast |
| GSV | RRGSVAE (2129) | HS 578 T Breast |
|  | GSVLHVS (2130) | HS 578 T Breast |
| GRV | SGRVFRF (2131) | HS 578 T Breast |
| GRL |  | HS 578 T Breast |
| GPS |  | HS 578 T Breast |
| GVS | WSATGVS (2132) | HS 578 T Breast |

REFERENCES

The following references, to the extent that they provide exemplary procedural or other details supplementary to those set forth herein, are specifically incorporated herein by reference.

Arap et al., *Nature Med.* 8, 121-127, 2002.
Arap et al., *Science,* 279:377-80, 1998.
Blower et al., *Pharmacogenomics J.,* 2:259-271, 2002.
Brown, *Oncol. Res.,* 1997; 9:213-5, 1997.
Giordano et al., *Nat. Med.,* 7:1249-1253, 2001.
Hafner et al., *Clin. Chem.,* 50:490-499, 2004.
Holbeck, *Eur. J. Cancer,* 40:785-793, 2004.
Kolonin et al., *Cancer Res.,* 66(1):1-7, 2006.
Kolonin et al., *Curr. Opin. Chem. Biol.,* 5:308-13, 2001.
Kolonin et al., *Nat. Med.,* 6:625-632, 2004.
Kolonin et al., *Proc. Natl. Acad. Sci. USA,* 99:13055-13060, 2002.
Maihle and Lafky, *Trends Cell Biol.,* 12:160-161, 2002.
Monks et al., *J. Natl. Cancer Inst.,* 1991; 83:757-66, 1991.
Myers et al, *Electrophoresis,* 18:647-653, 1997.
Nishizuka et al., *Proc. Natl. Acad. Sci. USA,* 100:14229-14234, 2003.
Pasqualini and Ruoslahti, *Nature,* 380:364-366, 1996.
Pasqualini et al, *Cancer Res.,* 60:722-727, 2000.
Pasqualini et al., In: *Phage Display*, A Laboratory Manual, Barbas et al. (Eds.), NY, Cold Spring Harbor Laboratory Press, 22:1-24, 2001.
Rabow et al, *J. Med. Chem.,* 45:818-40, 2002.
Scherf et al., *Nat. Genet.,* 24:236-244, 2000.
Szakacs et al., *Cancer Cell,* 6:129-37, 2004.
Vogelstein and Kinzler, *Nat. Med.,* 10:789-799, 2004.
Walloyist et al., *Bioinformatics,* 19:2212-24, 2003.
Wallqvist et al., *Mol. Cancer. Ther.,* 1:311-20, 2002.
Weinstein et al., *Science,* 275:343-349, 1997.
Zaharevitz et al., *J. Mol. Graph. Model,* 30:297-303, 2002.
Zurita et al., *Cancer Res.,* 2004:64:435-9, 2004.

What is claimed is:

1. An isolated EphA5 receptor targeting fusion protein comprising:

a) an EphA5 receptor targeting peptide comprising CSGIGSGGC (SEQ ID NO:2) or CRFESSGGC (SEQ ID NO:3); and b) a therapeutic polypeptide, wherein the EphA5 receptor targeting peptide and the therapeutic polypeptide comprise a fusion protein that binds to an EphA5 receptor on a cell.

2. An isolated EphA5 receptor targeting fusion protein comprising:

a) an EphA5 receptor targeting peptide comprising RFESSGG (SEQ ID NO:5), and b) a therapeutic polypeptide, wherein the EphA5 receptor targeting peptide and the therapeutic polypeptide comprise a fusion protein that binds to an EphA5 receptor on a cell.

3. The fusion protein of claim 2, wherein the therapeutic polypeptide is a toxin or other cytotoxic molecule capable of inducing cell death in Eph5A receptor expressing cells.

4. A method for treating an Eph5A receptor positive cell comprising administering to the cell an Eph5A targeting fusion protein of claim 2.

5. A method for treating a subject comprising an Eph5A receptor positive cell by administering an effective amount of an Eph5A targeting fusion protein of claim 2 to the subject.

6. The method of claim 5, wherein the subject is a patient that has a cancer.

7. The method of claim 6, wherein the cancer is a lung cancer or a neuronal cancer.

8. A method for treating a subject with an Eph5A receptor positive cancer by administering an Eph5A targeting fusion protein of claim 2, wherein the therapeutic comprises a cytotoxic agent or an anticancer agent.

9. The fusion protein of claim 3, wherein the therapeutic polypeptide is a cytotoxic polypeptide.

10. The fusion protein of claim 3, wherein the therapeutic polypeptide is a toxin.

11. The fusion protein of claim 10, wherein the toxin is alpha toxin.

12. The fusion protein of claim 10, wherein the toxin is ricin.

13. The fusion protein of claim 10, wherein the toxin is abrin.

14. The fusion protein of claim 10, wherein the toxin is *Pseudomonas* exotoxin A.

15. The fusion protein of claim 10, wherein the toxin is diphtheria toxin.

16. The fusion protein of claim 10, wherein the toxin is saporin.

17. The fusion protein of claim 10, wherein the toxin is momordin.

18. The fusion protein of claim 10, wherein the toxin is gelonin.

19. The fusion protein of claim 10, wherein the toxin is pokeweed antiviral protein.

20. The fusion protein of claim 10, wherein the toxin is alpha-sarcin.

21. The fusion protein of claim 10, wherein the toxin is cholera toxin.

22. The fusion protein of claim 1, wherein the therapeutic polypeptide is a toxin or other cytotoxic molecule capable of inducing cell death in Eph5A receptor expressing cells.

23. The fusion protein of claim 22, wherein the therapeutic polypeptide is a cytotoxic polypeptide.

24. The fusion protein of claim 22, wherein the therapeutic polypeptide is a toxin.

25. The fusion protein of claim 24, wherein the toxin is alpha toxin.

26. The fusion protein of claim 24, wherein the toxin is ricin.

27. The fusion protein of claim 24, wherein the toxin is abrin.

28. The fusion protein of claim 24, wherein the toxin is *Pseudomonas* exotoxin A.

29. The fusion protein of claim 24, wherein the toxin is diphtheria toxin.

30. The fusion protein of claim 10, wherein the toxin is saporin.

31. The fusion protein of claim 10, wherein the toxin is momordin.

32. The fusion protein of claim 10, wherein the toxin is gelonin.

33. The fusion protein of claim 10, wherein the toxin is pokeweed antiviral protein.

34. The fusion protein of claim 10, wherein the toxin is alpha-sarcin.

35. The fusion protein of claim 10, wherein the toxin is cholera toxin.

* * * * *

UNITED STATES PATENT AND TRADEMARK OFFICE

CERTIFICATE OF CORRECTION

PATENT NO. : 7,781,565 B2
APPLICATION NO. : 11/684379
DATED : August 24, 2010
INVENTOR(S) : Renata Pasqualini et al.

It is certified that error appears in the above-identified patent and that said Letters Patent is hereby corrected as shown below:

In column 1, delete lines 7-10 and insert
--This invention was made with government support under grant number DAMD17-03-1-0638 awarded by the Department of Defense and grant number CA103056 awarded by the National Institutes of Health. The government has certain rights in the invention.-- therefor.

Signed and Sealed this

Second Day of November, 2010

David J. Kappos
*Director of the United States Patent and Trademark Office*

SEQUENCE LISTING

```
<160> NUMBER OF SEQ ID NOS: 2140

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(8)
<223> OTHER INFORMATION: Xaa can be any naturally occurring amino acid

<400> SEQUENCE: 1

Cys Xaa Xaa Xaa Xaa Xaa Xaa Xaa Cys
1               5

<210> SEQ ID NO 2
<211> LENGTH: 9
<212> TYPE: PRT
<213> ORGANISM: Artificial Sequence
<220> FEATURE:
```

-continued

<223> OTHER INFORMATION: Synthetic peptide

<400> SEQUENCE: 2

Cys Ser Gly Ile Gly Ser Gly Gly Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Cys Arg Phe Glu Ser Ser Gly Gly Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Ser Gly Ile Gly Ser Gly Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Arg Phe Glu Ser Ser Gly Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Leu Arg Leu Ser Ser Ile Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ala Arg Gly Val Leu Leu Met
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 8

Arg Gly Ser His Leu Val Pro
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Asp Val Glu Thr Arg Gly Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Ser Arg Ala Val Ile Asp Met
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 11

Gly Leu Leu Ser Leu Xaa Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Thr Ser Leu Leu Ser Phe Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Arg Arg Val Ser Leu Val Ala
1               5

<210> SEQ ID NO 14
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 14

Ser Arg Phe Arg Val Ser Ile
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Ala Gly Ser Leu Ser Val Phe
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Ala Gly Arg Ile Cys Glu Gly
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Gln Val Ala Gly Arg Glu Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Val Glu Tyr Ala Ala Gly Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Tyr Asn Arg Ser Ala Gly Leu
1               5

<210> SEQ ID NO 20
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 20

Ala Val Leu Val Ala Gly Gly
1 5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Leu Ala Gly Gly Val Pro Gly
1 5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Asp Trp Trp Ala Gly Val Arg
1 5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Glu Pro Asp Gly Val Arg Ser
1 5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Glu Gln Leu Ser Gly Val Arg
1 5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Gly Val Leu Ala Arg Val Thr
1 5

<210> SEQ ID NO 26
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 26

Ala Arg Gly Val Leu Leu Met
1 5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Gly Gly Ala Val Leu Val Ala
1 5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Arg Glu Arg Gly Ala Val Gln
1 5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

Arg Ala Leu Gly Leu Val Ser
1 5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Ser Leu Gly Leu Arg Asn Gln
1 5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Arg Ala Leu Gly Leu Val Ser
1 5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 32

Gly Ala Tyr Arg Leu Val Ser
1 5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Phe Asp Ala Arg Gly Gly Leu
1 5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Met Phe Ala Arg Gly Trp Glu
1 5

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide

<400> SEQUENCE: 35

Ala Arg Gly Val Leu Leu Met
1 5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Gly Gly Gly Ser Asp Gly Val
1 5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

Leu Gly Gly Arg Ala Asp Phe
1 5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 38

Glu Val Gly Gly Gly Leu Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Phe Asp Ala Arg Gly Gly Leu
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Thr Gly Arg Val Val Arg Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Met Gly Met Ser Gly Pro Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Ala Val Arg Gly Val Ala Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide

<400> SEQUENCE: 43

Asp Arg Gly Val Pro Gly Leu
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

-continued

Leu Ser Phe Ser Arg Gly Ser
1 5

<210> SEQ ID NO 45
<211> LENGTH: 7
<212> TYPE: PRT
<213> ORGANISM: Artificial Sequence
<220> FEATURE:
<223> OTHER INFORMATION: Synthetic peptide

<400> SEQUENCE: 45

Arg Gly Ser Val Arg Val Leu
1 5

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide

<400> SEQUENCE: 46

Pro Val Arg Gly Ser Val Asp
1 5

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Gln Val Met Met Arg Gly Ser
1 5

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Asn Gly Arg Gly Ser Gly Trp
1 5

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Arg Ala Val Gly Arg Val Ala
1 5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

-continued

Arg Ala Ser Cys Ala Leu Thr
1 5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide

<400> SEQUENCE: 51

Ala Asp Ile Gly Ala Gly Gly
1 5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Phe Met Gly Ala Gly Phe Ala
1 5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Ala Gly Val Phe Ala Val Ser
1 5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide

<400> SEQUENCE: 54

Val Met Leu Leu Arg Pro Glu
1 5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Leu Leu Arg Gly Leu Glu Leu
1 5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Leu Pro Leu Leu Arg Gly Ile

-continued 1 5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Asp Pro Arg Gly Leu Arg Val
1 5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Leu Val Arg Val Ser Gly Arg
1 5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Ser Gly Ser Arg Val Ser Leu
1 5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Ala Gly Ser Ile Ala Leu Arg
1 5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Met Leu Ala Ser Ala Gly Arg
1 5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Ala Asp Ile Gly Ala Gly Gly
1 5

-continued

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Phe Ala Gly Gly Ser Thr Asp
1 5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Thr Gly Phe Gly Ala Val Gly
1 5

<210> SEQ ID NO 65
<211> LENGTH: 7
<212> TYPE: PRT
<213> ORGANISM: Artificial Sequence
<220> FEATURE:
<223> OTHER INFORMATION: Synthetic peptide

<400> SEQUENCE: 65

Phe Gly Leu Arg Asn Ser Arg
1 5

<210> SEQ ID NO 66
<211> LENGTH: 7
<212> TYPE: PRT
<213> ORGANISM: Artificial Sequence
<220> FEATURE:
<223> OTHER INFORMATION: Synthetic peptide

<400> SEQUENCE: 66

Asp Pro Arg Gly Leu Arg Val
1 5

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide

<400> SEQUENCE: 67

Leu Val Ser Ser Gly Ser Lys
1 5

<210> SEQ ID NO 68
<211> LENGTH: 7
<212> TYPE: PRT
<213> ORGANISM: Artificial Sequence
<220> FEATURE:
<223> OTHER INFORMATION: Synthetic peptide

<400> SEQUENCE: 68

Leu Val Ser Ser Ser Glu Pro
1 5

-continued

<210> SEQ ID NO 69
<211> LENGTH: 7
<212> TYPE: PRT
<213> ORGANISM: Artificial Sequence
<220> FEATURE:
<223> OTHER INFORMATION: Synthetic peptide

<400> SEQUENCE: 69

Ala Ala Val Trp Ala Ala Asp
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide

<400> SEQUENCE: 70

Phe Ala Gly Gly Ser Thr Asp
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic peptide

<400> SEQUENCE: 71

Thr Phe Gly Lys Gly Gly Leu
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic peptide

<400> SEQUENCE: 72

Lys Ser Gly Ser Ser Val Leu
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic peptide

<400> SEQUENCE: 73

Trp Gly Ser Gly Arg Gly Asn
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide

<400> SEQUENCE: 74

Arg Gly Ser Val Arg Val Leu
1               5

-continued

<210> SEQ ID NO 75
<211> LENGTH: 7
<212> TYPE: PRT
<213> ORGANISM: Artificial Sequence
<220> FEATURE:
<223> OTHER INFORMATION: Synthetic peptide

<400> SEQUENCE: 75

Pro Val Arg Gly Ser Val Asp
1 5

<210> SEQ ID NO 76
<211> LENGTH: 7
<212> TYPE: PRT
<213> ORGANISM: Artificial Sequence
<220> FEATURE:
<223> OTHER INFORMATION: Synthetic peptide

<400> SEQUENCE: 76

Thr Glu Gly Ser Val Thr Val
1 5

<210> SEQ ID NO 77
<211> LENGTH: 7
<212> TYPE: PRT
<213> ORGANISM: Artificial Sequence
<220> FEATURE:
<223> OTHER INFORMATION: Synthetic peptide

<400> SEQUENCE: 77

Arg Ala Val Gly Arg Val Ala
1 5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Asp Val Ser Gly Arg Val Pro
1 5

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide

<400> SEQUENCE: 79

Leu Gly Gln Cys Gly Arg Val
1 5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Gly Arg Leu Arg Leu Thr Asp
1 5

<210> SEQ ID NO 81

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 81

Leu Glu Leu Gly Arg Leu Leu
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide

<400> SEQUENCE: 82

Ile Gly Arg Leu Leu Pro Leu
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide

<400> SEQUENCE: 83

Ser Asp Glu Asn Gly Arg Leu
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide

<400> SEQUENCE: 84

Glu Leu His Pro Arg Gly Val
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide

<400> SEQUENCE: 85

Phe Asp Arg Gly Val Glu Ala
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide

<400> SEQUENCE: 86

Glu Ala Val Ser Arg Gly Ser
1               5

<210> SEQ ID NO 87
<211> LENGTH: 7

<212> TYPE: PRT
<213> ORGANISM: Artificial Sequence
<220> FEATURE:
<223> OTHER INFORMATION: Synthetic peptide

<400> SEQUENCE: 87

Trp Thr Lys Arg Gly Ser Val
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide

<400> SEQUENCE: 88

Glu Arg Ala Ser Gln Thr Ala
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide

<400> SEQUENCE: 89

Glu Ala Val Ser Arg Gly Ser
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide

<400> SEQUENCE: 90

Ala Ala Thr Leu Leu Ser Phe
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide

<400> SEQUENCE: 91

Leu Leu Ser Ala Ser Leu Val
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Arg Arg His Gly Leu Leu Ser
1               5

<210> SEQ ID NO 93
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 93

Arg Tyr Ser Thr Leu Leu Arg
1 5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide

<400> SEQUENCE: 94

Phe Thr Leu Arg Val Asp Lys
1 5

<210> SEQ ID NO 95
<211> LENGTH: 7
<212> TYPE: PRT
<213> ORGANISM: Artificial Sequence
<220> FEATURE:
<223> OTHER INFORMATION: Synthetic peptide

<400> SEQUENCE: 95

Ser His Arg Val Ser Asp Ser
1 5

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide

<400> SEQUENCE: 96

Asn Arg Ser Ser Ala Lys Phe
1 5

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide

<400> SEQUENCE: 97

Leu Arg Arg Ser Ser Phe Ser
1 5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide

<400> SEQUENCE: 98

Ala Ile Arg Ala Gly Ser Asp
1 5

<210> SEQ ID NO 99
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 99

Val Leu Phe Ser Ala Gly Ser
1 5

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide

<400> SEQUENCE: 100

Gly Val Leu His Ser Ile Ala
1 5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide

<400> SEQUENCE: 101

Arg Gln Thr Thr Gly Ala Val
1 5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 102

Cys Gln Gly Leu Val Leu Gln
1 5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide

<400> SEQUENCE: 103

Pro Pro Pro Trp Gly Leu Arg
1 5

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide

<400> SEQUENCE: 104

Ser Asn Ala Arg Gly Pro Arg
1 5

<210> SEQ ID NO 105
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 105

Leu Leu Ser Ala Ser Leu Val
1 5

<210> SEQ ID NO 106
<211> LENGTH: 7
<212> TYPE: PRT
<213> ORGANISM: Artificial Sequence
<220> FEATURE:
<223> OTHER INFORMATION: Synthetic peptide

<400> SEQUENCE: 106

Ala Ala Val Phe Val Arg Ser
1 5

<210> SEQ ID NO 107
<211> LENGTH: 7
<212> TYPE: PRT
<213> ORGANISM: Artificial Sequence
<220> FEATURE:
<223> OTHER INFORMATION: Synthetic peptide

<400> SEQUENCE: 107

Phe Phe Gly Gly Ser Arg Ala
1 5

<210> SEQ ID NO 108
<211> LENGTH: 7
<212> TYPE: PRT
<213> ORGANISM: Artificial Sequence
<220> FEATURE:
<223> OTHER INFORMATION: Synthetic peptide

<400> SEQUENCE: 108

Gly Gly Ser Gln Cys Asp Thr
1 5

<210> SEQ ID NO 109
<211> LENGTH: 7
<212> TYPE: PRT
<213> ORGANISM: Artificial Sequence
<220> FEATURE:
<223> OTHER INFORMATION: Synthetic peptide

<400> SEQUENCE: 109

Val Trp Gly Val Gly Gly Ser
1 5

<210> SEQ ID NO 110
<211> LENGTH: 7
<212> TYPE: PRT
<213> ORGANISM: Artificial Sequence
<220> FEATURE:
<223> OTHER INFORMATION: Synthetic peptide

<400> SEQUENCE: 110

Phe Ala Trp Gly Gly Arg Gly
1 5

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 111

Gly Leu Gly Ile Met Gly Pro
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic peptide

<400> SEQUENCE: 112

Ser Ser Gly Ser Ser Asn Gly
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic peptide

<400> SEQUENCE: 113

Trp Thr Lys Arg Gly Ser Val
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic peptide

<400> SEQUENCE: 114

Gly Val Ser Thr Gly Phe Thr
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic peptide

<400> SEQUENCE: 115

Cys His Ala Arg Gly Val Thr
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide

<400> SEQUENCE: 116

Trp Gly Arg Gly Ser Val Ala
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 117

Leu Arg Ser Gly Ala Gly Ser
1 5

<210> SEQ ID NO 118
<211> LENGTH: 7
<212> TYPE: PRT
<213> ORGANISM: Artificial Sequence
<220> FEATURE:
<223> OTHER INFORMATION: Synthetic peptide

<400> SEQUENCE: 118

Arg Ala Ala Val Ser Ala Ile
1 5

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide

<400> SEQUENCE: 119

Ala Val Ser Gly Arg Gly Trp
1 5

<210> SEQ ID NO 120
<211> LENGTH: 7
<212> TYPE: PRT
<213> ORGANISM: Artificial Sequence
<220> FEATURE:
<223> OTHER INFORMATION: Synthetic peptide

<400> SEQUENCE: 120

Leu Leu Ser Phe Leu Gly Arg
1 5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide

<400> SEQUENCE: 121

Gly Phe Tyr Trp Leu Arg Ser
1 5

<210> SEQ ID NO 122
<211> LENGTH: 7
<212> TYPE: PRT
<213> ORGANISM: Artificial Sequence
<220> FEATURE:
<223> OTHER INFORMATION: Synthetic peptide

<400> SEQUENCE: 122

Arg Gly Ala Arg Val Ser Ala
1 5

<210> SEQ ID NO 123
<211> LENGTH: 7
<212> TYPE: PRT
<213> ORGANISM: Artificial Sequence
<220> FEATURE:
<223> OTHER INFORMATION: Synthetic peptide

<400> SEQUENCE: 123

Gly Gly Arg Ser Ser His Pro
1 5

<210> SEQ ID NO 124
<211> LENGTH: 7
<212> TYPE: PRT
<213> ORGANISM: Artificial Sequence
<220> FEATURE:
<223> OTHER INFORMATION: Synthetic peptide

<400> SEQUENCE: 124

Arg Ser Ser Ile Ala Pro Ser
1 5

<210> SEQ ID NO 125
<211> LENGTH: 7
<212> TYPE: PRT
<213> ORGANISM: Artificial Sequence
<220> FEATURE:
<223> OTHER INFORMATION: Synthetic peptide

<400> SEQUENCE: 125

Leu Ala Gly Ser Gly Ser His
1 5

<210> SEQ ID NO 126
<211> LENGTH: 7
<212> TYPE: PRT
<213> ORGANISM: Artificial Sequence
<220> FEATURE:
<223> OTHER INFORMATION: Synthetic peptide

<400> SEQUENCE: 126

Leu Arg Ser Gly Ala Gly Ser
1 5

<210> SEQ ID NO 127
<211> LENGTH: 7
<212> TYPE: PRT
<213> ORGANISM: Artificial Sequence
<220> FEATURE:
<223> OTHER INFORMATION: Synthetic peptide

<400> SEQUENCE: 127

Ala Ser Val Arg Ala Gly Arg
1 5

<210> SEQ ID NO 128
<211> LENGTH: 7
<212> TYPE: PRT
<213> ORGANISM: Artificial Sequence
<220> FEATURE:
<223> OTHER INFORMATION: Synthetic peptide

<400> SEQUENCE: 128

Ile Gly Val Arg Gly Phe Phe
1 5

<210> SEQ ID NO 129
<211> LENGTH: 7
<212> TYPE: PRT
<213> ORGANISM: Artificial Sequence
<220> FEATURE:
<223> OTHER INFORMATION: Synthetic peptide

<400> SEQUENCE: 129

-continued

Ala Asn Gly Val Leu Glu Leu
1 5

<210> SEQ ID NO 130
<211> LENGTH: 7
<212> TYPE: PRT
<213> ORGANISM: Artificial Sequence
<220> FEATURE:
<223> OTHER INFORMATION: Synthetic peptide

<400> SEQUENCE: 130

Trp Phe Gly Ala Val Gly Leu
1 5

<210> SEQ ID NO 131
<211> LENGTH: 7
<212> TYPE: PRT
<213> ORGANISM: Artificial Sequence
<220> FEATURE:
<223> OTHER INFORMATION: Synthetic peptide

<400> SEQUENCE: 131

Gly Leu Val Arg Gly Thr Ala
1 5

<210> SEQ ID NO 132
<211> LENGTH: 7
<212> TYPE: PRT
<213> ORGANISM: Artificial Sequence
<220> FEATURE:
<223> OTHER INFORMATION: Synthetic peptide

<400> SEQUENCE: 132

Glu Gly Leu Val Ser Val Val
1 5

<210> SEQ ID NO 133
<211> LENGTH: 7
<212> TYPE: PRT
<213> ORGANISM: Artificial Sequence
<220> FEATURE:
<223> OTHER INFORMATION: Synthetic peptide

<400> SEQUENCE: 133

Asp Leu Gly Leu Arg Pro Val
1 5

<210> SEQ ID NO 134
<211> LENGTH: 7
<212> TYPE: PRT
<213> ORGANISM: Artificial Sequence
<220> FEATURE:
<223> OTHER INFORMATION: Synthetic peptide

<400> SEQUENCE: 134

Ala Leu Val Ser Arg Arg Gly
1 5

<210> SEQ ID NO 135
<211> LENGTH: 7
<212> TYPE: PRT
<213> ORGANISM: Artificial Sequence
<220> FEATURE:
<223> OTHER INFORMATION: Synthetic peptide

<400> SEQUENCE: 135

Glu Val Leu Val Ser Gly Asp

-continued

```
1               5


<210> SEQ ID NO 136
<211> LENGTH: 7
<212> TYPE: PRT
<213> ORGANISM: Artificial Sequence
<220> FEATURE:
<223> OTHER INFORMATION: Synthetic peptide

<400> SEQUENCE: 136

Glu Gly Leu Val Ser Val Val
1               5


<210> SEQ ID NO 137
<211> LENGTH: 7
<212> TYPE: PRT
<213> ORGANISM: Artificial Sequence
<220> FEATURE:
<223> OTHER INFORMATION: Synthetic peptide

<400> SEQUENCE: 137

Cys His Ala Arg Gly Val Thr
1               5


<210> SEQ ID NO 138
<211> LENGTH: 7
<212> TYPE: PRT
<213> ORGANISM: Artificial Sequence
<220> FEATURE:
<223> OTHER INFORMATION: Synthetic peptide

<400> SEQUENCE: 138

Arg Ala Ala Val Ser Ala Ile
1               5


<210> SEQ ID NO 139
<211> LENGTH: 7
<212> TYPE: PRT
<213> ORGANISM: Artificial Sequence
<220> FEATURE:
<223> OTHER INFORMATION: Synthetic peptide

<400> SEQUENCE: 139

His Arg Gly Gly Ser Gln Ser
1               5


<210> SEQ ID NO 140
<211> LENGTH: 7
<212> TYPE: PRT
<213> ORGANISM: Artificial Sequence
<220> FEATURE:
<223> OTHER INFORMATION: Synthetic peptide

<400> SEQUENCE: 140

Gly Gly Arg Ser Ser His Pro
1               5


<210> SEQ ID NO 141
<211> LENGTH: 7
<212> TYPE: PRT
<213> ORGANISM: Artificial Sequence
<220> FEATURE:
<223> OTHER INFORMATION: Synthetic peptide

<400> SEQUENCE: 141

Ser Gln Ser Gly Gly Arg His
1               5
```

-continued

<210> SEQ ID NO 142
<211> LENGTH: 7
<212> TYPE: PRT
<213> ORGANISM: Artificial Sequence
<220> FEATURE:
<223> OTHER INFORMATION: Synthetic peptide

<400> SEQUENCE: 142

Ala Arg Ala Ile Gly Leu Gly
1 5

<210> SEQ ID NO 143
<211> LENGTH: 7
<212> TYPE: PRT
<213> ORGANISM: Artificial Sequence
<220> FEATURE:
<223> OTHER INFORMATION: Synthetic peptide

<400> SEQUENCE: 143

Ser Thr Glu Gly Gly Gly Leu
1 5

<210> SEQ ID NO 144
<211> LENGTH: 7
<212> TYPE: PRT
<213> ORGANISM: Artificial Sequence
<220> FEATURE:
<223> OTHER INFORMATION: Synthetic peptide

<400> SEQUENCE: 144

Leu Ala Gly Ser Gly Ser His
1 5

<210> SEQ ID NO 145
<211> LENGTH: 7
<212> TYPE: PRT
<213> ORGANISM: Artificial Sequence
<220> FEATURE:
<223> OTHER INFORMATION: Synthetic peptide

<400> SEQUENCE: 145

Asp Gly Ser Val Leu Val Glu
1 5

<210> SEQ ID NO 146
<211> LENGTH: 7
<212> TYPE: PRT
<213> ORGANISM: Artificial Sequence
<220> FEATURE:
<223> OTHER INFORMATION: Synthetic peptide

<400> SEQUENCE: 146

Trp Gly Arg Gly Ser Val Ala
1 5

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide

<400> SEQUENCE: 147

Ala Thr Gly Arg Val Leu Gly
1 5

-continued

<210> SEQ ID NO 148
<211> LENGTH: 7
<212> TYPE: PRT
<213> ORGANISM: Artificial Sequence
<220> FEATURE:
<223> OTHER INFORMATION: Synthetic peptide

<400> SEQUENCE: 148

Ala Thr Gly Arg Val Leu Gly
1 5

<210> SEQ ID NO 149
<211> LENGTH: 7
<212> TYPE: PRT
<213> ORGANISM: Artificial Sequence
<220> FEATURE:
<223> OTHER INFORMATION: Synthetic peptide

<400> SEQUENCE: 149

Phe Phe Gly Arg Val Gly Ile
1 5

<210> SEQ ID NO 150
<211> LENGTH: 7
<212> TYPE: PRT
<213> ORGANISM: Artificial Sequence
<220> FEATURE:
<223> OTHER INFORMATION: Synthetic peptide

<400> SEQUENCE: 150

Arg Ile Gly Arg Val Trp Ala
1 5

<210> SEQ ID NO 151
<211> LENGTH: 7
<212> TYPE: PRT
<213> ORGANISM: Artificial Sequence
<220> FEATURE:
<223> OTHER INFORMATION: Synthetic peptide

<400> SEQUENCE: 151

Arg Gly Arg Leu Glu Val Pro
1 5

<210> SEQ ID NO 152
<211> LENGTH: 7
<212> TYPE: PRT
<213> ORGANISM: Artificial Sequence
<220> FEATURE:
<223> OTHER INFORMATION: Synthetic peptide

<400> SEQUENCE: 152

Arg Arg Leu Ser Tyr Arg Asp
1 5

<210> SEQ ID NO 153
<211> LENGTH: 7
<212> TYPE: PRT
<213> ORGANISM: Artificial Sequence
<220> FEATURE:
<223> OTHER INFORMATION: Synthetic peptide

<400> SEQUENCE: 153

Ser Arg Leu Ser Tyr Arg Gly
1 5

-continued

<210> SEQ ID NO 154
<211> LENGTH: 7
<212> TYPE: PRT
<213> ORGANISM: Artificial Sequence
<220> FEATURE:
<223> OTHER INFORMATION: Synthetic peptide

<400> SEQUENCE: 154

Phe Ser Ser Lys Arg Gly Val
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic peptide

<400> SEQUENCE: 155

Arg Gly Ser Ala Gln Asn Phe
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic peptide

<400> SEQUENCE: 156

Leu Arg Ser Gly Arg Gly Ser
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic peptide

<400> SEQUENCE: 157

Tyr Arg Gly Ser Ser Gly Lys
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic peptide

<400> SEQUENCE: 158

Phe Trp Ile Ser Arg Ala Ser
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic peptide

<400> SEQUENCE: 159

Gly Ala Gly Ser Ile Ser Asp
1               5

<210> SEQ ID NO 160

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 160

Arg Ala Met Gly Gly Ala Gly
1 5

<210> SEQ ID NO 161
<211> LENGTH: 7
<212> TYPE: PRT
<213> ORGANISM: Artificial Sequence
<220> FEATURE:
<223> OTHER INFORMATION: Synthetic peptide

<400> SEQUENCE: 161

Leu Leu Ser Thr Ser Ile Arg
1 5

<210> SEQ ID NO 162
<211> LENGTH: 7
<212> TYPE: PRT
<213> ORGANISM: Artificial Sequence
<220> FEATURE:
<223> OTHER INFORMATION: Synthetic peptide

<400> SEQUENCE: 162

Leu Leu Leu Arg Ser Gly Gly
1 5

<210> SEQ ID NO 163
<211> LENGTH: 7
<212> TYPE: PRT
<213> ORGANISM: Artificial Sequence
<220> FEATURE:
<223> OTHER INFORMATION: Synthetic peptide

<400> SEQUENCE: 163

Leu Leu Arg Ser Ala Ala Pro
1 5

<210> SEQ ID NO 164
<211> LENGTH: 7
<212> TYPE: PRT
<213> ORGANISM: Artificial Sequence
<220> FEATURE:
<223> OTHER INFORMATION: Synthetic peptide

<400> SEQUENCE: 164

Leu Leu Leu Arg Ser Gly Gly
1 5

<210> SEQ ID NO 165
<211> LENGTH: 7
<212> TYPE: PRT
<213> ORGANISM: Artificial Sequence
<220> FEATURE:
<223> OTHER INFORMATION: Synthetic peptide

<400> SEQUENCE: 165

Gly Arg Tyr Ser Leu Arg Ser
1 5

<210> SEQ ID NO 166
<211> LENGTH: 7

-continued

```
<212> TYPE: PRT
<213> ORGANISM: Artificial Sequence
<220> FEATURE:
<223> OTHER INFORMATION: Synthetic peptide

<400> SEQUENCE: 166

Leu Arg Ser Gly Arg Gly Ser
1               5


<210> SEQ ID NO 167
<211> LENGTH: 7
<212> TYPE: PRT
<213> ORGANISM: Artificial Sequence
<220> FEATURE:
<223> OTHER INFORMATION: Synthetic peptide

<400> SEQUENCE: 167

Leu Arg Tyr Asp Leu Arg Ser
1               5


<210> SEQ ID NO 168
<211> LENGTH: 7
<212> TYPE: PRT
<213> ORGANISM: Artificial Sequence
<220> FEATURE:
<223> OTHER INFORMATION: Synthetic peptide

<400> SEQUENCE: 168

Leu Arg Tyr Asn Leu Arg Ser
1               5


<210> SEQ ID NO 169
<211> LENGTH: 7
<212> TYPE: PRT
<213> ORGANISM: Artificial Sequence
<220> FEATURE:
<223> OTHER INFORMATION: Synthetic peptide

<400> SEQUENCE: 169

Leu Leu Arg Ser Ala Ala Pro
1               5


<210> SEQ ID NO 170
<211> LENGTH: 7
<212> TYPE: PRT
<213> ORGANISM: Artificial Sequence
<220> FEATURE:
<223> OTHER INFORMATION: Synthetic peptide

<400> SEQUENCE: 170

Ser Lys Tyr Arg Leu Arg Ser
1               5


<210> SEQ ID NO 171
<211> LENGTH: 7
<212> TYPE: PRT
<213> ORGANISM: Artificial Sequence
<220> FEATURE:
<223> OTHER INFORMATION: Synthetic peptide

<400> SEQUENCE: 171

Val His Arg Val Ser Gly Gly
1               5


<210> SEQ ID NO 172
<211> LENGTH: 7
<212> TYPE: PRT
```

-continued

<213> ORGANISM: Artificial Sequence
<220> FEATURE:
<223> OTHER INFORMATION: Synthetic peptide

<400> SEQUENCE: 172

Gly Ala Gly Ser Ile Ser Asp
1 5

<210> SEQ ID NO 173
<211> LENGTH: 7
<212> TYPE: PRT
<213> ORGANISM: Artificial Sequence
<220> FEATURE:
<223> OTHER INFORMATION: Synthetic peptide

<400> SEQUENCE: 173

Phe Ala Gly Arg Val Pro Ser
1 5

<210> SEQ ID NO 174
<211> LENGTH: 7
<212> TYPE: PRT
<213> ORGANISM: Artificial Sequence
<220> FEATURE:
<223> OTHER INFORMATION: Synthetic peptide

<400> SEQUENCE: 174

Ala Gly Leu Ser Gly Ser Gln
1 5

<210> SEQ ID NO 175
<211> LENGTH: 7
<212> TYPE: PRT
<213> ORGANISM: Artificial Sequence
<220> FEATURE:
<223> OTHER INFORMATION: Synthetic peptide

<400> SEQUENCE: 175

Thr Asp Leu Ala Gly Leu His
1 5

<210> SEQ ID NO 176
<211> LENGTH: 7
<212> TYPE: PRT
<213> ORGANISM: Artificial Sequence
<220> FEATURE:
<223> OTHER INFORMATION: Synthetic peptide

<400> SEQUENCE: 176

Leu Ala Ala Gly Gly Glu Leu
1 5

<210> SEQ ID NO 177
<211> LENGTH: 7
<212> TYPE: PRT
<213> ORGANISM: Artificial Sequence
<220> FEATURE:
<223> OTHER INFORMATION: Synthetic peptide

<400> SEQUENCE: 177

Gly Ala Gly Gly Met Ala Arg
1 5

<210> SEQ ID NO 178
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 178

Arg Ala Ala Gly Gly Ser Arg
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic peptide

<400> SEQUENCE: 179

Leu Tyr Gly Val Arg Tyr Gly
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic peptide

<400> SEQUENCE: 180

Pro Arg Tyr Gly Val Arg Ala
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic peptide

<400> SEQUENCE: 181

Gly Ala Val Asp Gly Ser Arg
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic peptide

<400> SEQUENCE: 182

Ala Asp Phe Phe Gly Leu Val
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic peptide

<400> SEQUENCE: 183

Lys Tyr Tyr Gly Leu Arg Arg
1               5

<210> SEQ ID NO 184
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 184

Ser Arg Tyr Gly Leu Arg Arg
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic peptide

<400> SEQUENCE: 185

Pro Ala Ala Ser Arg Leu Leu
1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic peptide

<400> SEQUENCE: 186

Arg Leu Arg Ala Ala Ser Tyr
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic peptide

<400> SEQUENCE: 187

Gly Gly Ser Arg Leu Leu Leu
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic peptide

<400> SEQUENCE: 188

Arg Ala Ala Gly Gly Ser Arg
1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic peptide

<400> SEQUENCE: 189

Gly Gly Ser Val Arg His Val
1               5

<210> SEQ ID NO 190
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 190

Gly Gly Arg Ser Trp Val Asn
1 5

<210> SEQ ID NO 191
<211> LENGTH: 7
<212> TYPE: PRT
<213> ORGANISM: Artificial Sequence
<220> FEATURE:
<223> OTHER INFORMATION: Synthetic peptide

<400> SEQUENCE: 191

Gly Leu Gly Asn Arg Pro Thr
1 5

<210> SEQ ID NO 192
<211> LENGTH: 7
<212> TYPE: PRT
<213> ORGANISM: Artificial Sequence
<220> FEATURE:
<223> OTHER INFORMATION: Synthetic peptide

<400> SEQUENCE: 192

His Gly Leu Gly Ser Gly Thr
1 5

<210> SEQ ID NO 193
<211> LENGTH: 7
<212> TYPE: PRT
<213> ORGANISM: Artificial Sequence
<220> FEATURE:
<223> OTHER INFORMATION: Synthetic peptide

<400> SEQUENCE: 193

Gly Ser Ser Leu His Leu Leu
1 5

<210> SEQ ID NO 194
<211> LENGTH: 7
<212> TYPE: PRT
<213> ORGANISM: Artificial Sequence
<220> FEATURE:
<223> OTHER INFORMATION: Synthetic peptide

<400> SEQUENCE: 194

Tyr Arg Gly Ser Ser Gly Lys
1 5

<210> SEQ ID NO 195
<211> LENGTH: 7
<212> TYPE: PRT
<213> ORGANISM: Artificial Sequence
<220> FEATURE:
<223> OTHER INFORMATION: Synthetic peptide

<400> SEQUENCE: 195

Glu Gly Ser Gly Val Asp Cys
1 5

<210> SEQ ID NO 196
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 196

His Gly Leu Gly Ser Gly Thr
1 5

<210> SEQ ID NO 197
<211> LENGTH: 7
<212> TYPE: PRT
<213> ORGANISM: Artificial Sequence
<220> FEATURE:
<223> OTHER INFORMATION: Synthetic peptide

<400> SEQUENCE: 197

Ser Gly Ser Val Asn Arg Gly
1 5

<210> SEQ ID NO 198
<211> LENGTH: 7
<212> TYPE: PRT
<213> ORGANISM: Artificial Sequence
<220> FEATURE:
<223> OTHER INFORMATION: Synthetic peptide

<400> SEQUENCE: 198

Gly Gly Ser Val Arg His Val
1 5

<210> SEQ ID NO 199
<211> LENGTH: 7
<212> TYPE: PRT
<213> ORGANISM: Artificial Sequence
<220> FEATURE:
<223> OTHER INFORMATION: Synthetic peptide

<400> SEQUENCE: 199

Phe Ala Gly Arg Val Pro Ser
1 5

<210> SEQ ID NO 200
<211> LENGTH: 7
<212> TYPE: PRT
<213> ORGANISM: Artificial Sequence
<220> FEATURE:
<223> OTHER INFORMATION: Synthetic peptide

<400> SEQUENCE: 200

Ala Met Arg Pro Gly Arg Leu
1 5

<210> SEQ ID NO 201
<211> LENGTH: 7
<212> TYPE: PRT
<213> ORGANISM: Artificial Sequence
<220> FEATURE:
<223> OTHER INFORMATION: Synthetic peptide

<400> SEQUENCE: 201

Gly Arg Leu Tyr Tyr Tyr Arg
1 5

<210> SEQ ID NO 202
<211> LENGTH: 7
<212> TYPE: PRT
<213> ORGANISM: Artificial Sequence
<220> FEATURE:
<223> OTHER INFORMATION: Synthetic peptide

<400> SEQUENCE: 202

-continued

Pro Ala Phe Gly Pro Ser Arg
1 5

<210> SEQ ID NO 203
<211> LENGTH: 7
<212> TYPE: PRT
<213> ORGANISM: Artificial Sequence
<220> FEATURE:
<223> OTHER INFORMATION: Synthetic peptide

<400> SEQUENCE: 203

His Ser Gly Val Ser His Gly
1 5

<210> SEQ ID NO 204
<211> LENGTH: 7
<212> TYPE: PRT
<213> ORGANISM: Artificial Sequence
<220> FEATURE:
<223> OTHER INFORMATION: Synthetic peptide

<400> SEQUENCE: 204

Val Tyr Tyr Arg Leu Ser Ala
1 5

<210> SEQ ID NO 205
<211> LENGTH: 7
<212> TYPE: PRT
<213> ORGANISM: Artificial Sequence
<220> FEATURE:
<223> OTHER INFORMATION: Synthetic peptide

<400> SEQUENCE: 205

Gly Arg Gly Ser Phe Glu Ser
1 5

<210> SEQ ID NO 206
<211> LENGTH: 7
<212> TYPE: PRT
<213> ORGANISM: Artificial Sequence
<220> FEATURE:
<223> OTHER INFORMATION: Synthetic peptide

<400> SEQUENCE: 206

Arg Arg Gly Ser Ser Arg Asn
1 5

<210> SEQ ID NO 207
<211> LENGTH: 7
<212> TYPE: PRT
<213> ORGANISM: Artificial Sequence
<220> FEATURE:
<223> OTHER INFORMATION: Synthetic peptide

<400> SEQUENCE: 207

His Ser Arg Ala Val Ala Pro
1 5

<210> SEQ ID NO 208
<211> LENGTH: 7
<212> TYPE: PRT
<213> ORGANISM: Artificial Sequence
<220> FEATURE:
<223> OTHER INFORMATION: Synthetic peptide

<400> SEQUENCE: 208

-continued

```
Arg Ala Ser Phe Arg Ala Gly
1               5


<210> SEQ ID NO 209
<211> LENGTH: 7
<212> TYPE: PRT
<213> ORGANISM: Artificial Sequence
<220> FEATURE:
<223> OTHER INFORMATION: Synthetic peptide

<400> SEQUENCE: 209

Leu Met Gly Arg Ala Ser Gly
1               5


<210> SEQ ID NO 210
<211> LENGTH: 7
<212> TYPE: PRT
<213> ORGANISM: Artificial Sequence
<220> FEATURE:
<223> OTHER INFORMATION: Synthetic peptide

<400> SEQUENCE: 210

Trp Arg Ala Ser Ala Phe Thr
1               5


<210> SEQ ID NO 211
<211> LENGTH: 7
<212> TYPE: PRT
<213> ORGANISM: Artificial Sequence
<220> FEATURE:
<223> OTHER INFORMATION: Synthetic peptide

<400> SEQUENCE: 211

Gly Ala Gly Arg Thr Val Met
1               5


<210> SEQ ID NO 212
<211> LENGTH: 7
<212> TYPE: PRT
<213> ORGANISM: Artificial Sequence
<220> FEATURE:
<223> OTHER INFORMATION: Synthetic peptide

<400> SEQUENCE: 212

Pro Leu Ala Val Ser Met Val
1               5


<210> SEQ ID NO 213
<211> LENGTH: 7
<212> TYPE: PRT
<213> ORGANISM: Artificial Sequence
<220> FEATURE:
<223> OTHER INFORMATION: Synthetic peptide

<400> SEQUENCE: 213

Phe Leu Leu Arg Ser Ser Phe
1               5


<210> SEQ ID NO 214
<211> LENGTH: 7
<212> TYPE: PRT
<213> ORGANISM: Artificial Sequence
<220> FEATURE:
<223> OTHER INFORMATION: Synthetic peptide

<400> SEQUENCE: 214

Trp Arg Leu Leu Arg Arg Gln
```

-continued 1 5

<210> SEQ ID NO 215
<211> LENGTH: 7
<212> TYPE: PRT
<213> ORGANISM: Artificial Sequence
<220> FEATURE:
<223> OTHER INFORMATION: Synthetic peptide

<400> SEQUENCE: 215

Phe Leu Leu Arg Ser Ser Phe
1 5

<210> SEQ ID NO 216
<211> LENGTH: 7
<212> TYPE: PRT
<213> ORGANISM: Artificial Sequence
<220> FEATURE:
<223> OTHER INFORMATION: Synthetic peptide

<400> SEQUENCE: 216

Leu Arg Ser Arg Leu Gly Phe
1 5

<210> SEQ ID NO 217
<211> LENGTH: 7
<212> TYPE: PRT
<213> ORGANISM: Artificial Sequence
<220> FEATURE:
<223> OTHER INFORMATION: Synthetic peptide

<400> SEQUENCE: 217

Gly Arg Arg Val Ser Leu Val
1 5

<210> SEQ ID NO 218
<211> LENGTH: 7
<212> TYPE: PRT
<213> ORGANISM: Artificial Sequence
<220> FEATURE:
<223> OTHER INFORMATION: Synthetic peptide

<400> SEQUENCE: 218

Phe Leu Leu Arg Ser Ser Phe
1 5

<210> SEQ ID NO 219
<211> LENGTH: 7
<212> TYPE: PRT
<213> ORGANISM: Artificial Sequence
<220> FEATURE:
<223> OTHER INFORMATION: Synthetic peptide

<400> SEQUENCE: 219

Asn Arg Ser Ser Gly Arg Arg
1 5

<210> SEQ ID NO 220
<211> LENGTH: 7
<212> TYPE: PRT
<213> ORGANISM: Artificial Sequence
<220> FEATURE:
<223> OTHER INFORMATION: Synthetic peptide

<400> SEQUENCE: 220

Val Leu Gly Met Arg Ser Ser
1 5

-continued

<210> SEQ ID NO 221
<211> LENGTH: 7
<212> TYPE: PRT
<213> ORGANISM: Artificial Sequence
<220> FEATURE:
<223> OTHER INFORMATION: Synthetic peptide

<400> SEQUENCE: 221

Thr His Arg Asn Arg Ser Ser
1 5

<210> SEQ ID NO 222
<211> LENGTH: 7
<212> TYPE: PRT
<213> ORGANISM: Artificial Sequence
<220> FEATURE:
<223> OTHER INFORMATION: Synthetic peptide

<400> SEQUENCE: 222

Leu Ala Gly Ser Thr Arg Arg
1 5

<210> SEQ ID NO 223
<211> LENGTH: 7
<212> TYPE: PRT
<213> ORGANISM: Artificial Sequence
<220> FEATURE:
<223> OTHER INFORMATION: Synthetic peptide

<400> SEQUENCE: 223

Ala Gly Arg Thr Gly Val Gly
1 5

<210> SEQ ID NO 224
<211> LENGTH: 7
<212> TYPE: PRT
<213> ORGANISM: Artificial Sequence
<220> FEATURE:
<223> OTHER INFORMATION: Synthetic peptide

<400> SEQUENCE: 224

Glu Phe Ala Val Ala Gly Arg
1 5

<210> SEQ ID NO 225
<211> LENGTH: 7
<212> TYPE: PRT
<213> ORGANISM: Artificial Sequence
<220> FEATURE:
<223> OTHER INFORMATION: Synthetic peptide

<400> SEQUENCE: 225

Gly Ala Gly Arg Thr Val Met
1 5

<210> SEQ ID NO 226
<211> LENGTH: 7
<212> TYPE: PRT
<213> ORGANISM: Artificial Sequence
<220> FEATURE:
<223> OTHER INFORMATION: Synthetic peptide

<400> SEQUENCE: 226

Arg Glu Glu Phe Ala Gly Arg
1 5

-continued

<210> SEQ ID NO 227
<211> LENGTH: 7
<212> TYPE: PRT
<213> ORGANISM: Artificial Sequence
<220> FEATURE:
<223> OTHER INFORMATION: Synthetic peptide

<400> SEQUENCE: 227

Ala Gly Gly Pro Thr Lys Tyr
1               5

<210> SEQ ID NO 228
<211> LENGTH: 7
<212> TYPE: PRT
<213> ORGANISM: Artificial Sequence
<220> FEATURE:
<223> OTHER INFORMATION: Synthetic peptide

<400> SEQUENCE: 228

Phe His Val Ala Gly Gly Ser
1               5

<210> SEQ ID NO 229
<211> LENGTH: 7
<212> TYPE: PRT
<213> ORGANISM: Artificial Sequence
<220> FEATURE:
<223> OTHER INFORMATION: Synthetic peptide

<400> SEQUENCE: 229

Trp Ser Ala Gly Gly Pro His
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic peptide

<400> SEQUENCE: 230

Arg Gly Ala Val Ala Phe Glu
1               5

<210> SEQ ID NO 231
<211> LENGTH: 7
<212> TYPE: PRT
<213> ORGANISM: Artificial Sequence
<220> FEATURE:
<223> OTHER INFORMATION: Synthetic peptide

<400> SEQUENCE: 231

Ser Gly Gly Ala Val His Phe
1               5

<210> SEQ ID NO 232
<211> LENGTH: 7
<212> TYPE: PRT
<213> ORGANISM: Artificial Sequence
<220> FEATURE:
<223> OTHER INFORMATION: Synthetic peptide

<400> SEQUENCE: 232

Gly Ala Val Arg Ala Arg Leu
1               5

-continued

<210> SEQ ID NO 233
<211> LENGTH: 7
<212> TYPE: PRT
<213> ORGANISM: Artificial Sequence
<220> FEATURE:
<223> OTHER INFORMATION: Synthetic peptide

<400> SEQUENCE: 233

Gly Leu Val Arg Gly Phe Pro
1 5

<210> SEQ ID NO 234
<211> LENGTH: 7
<212> TYPE: PRT
<213> ORGANISM: Artificial Sequence
<220> FEATURE:
<223> OTHER INFORMATION: Synthetic peptide

<400> SEQUENCE: 234

Gly Ala His Gly Leu Val Arg
1 5

<210> SEQ ID NO 235
<211> LENGTH: 7
<212> TYPE: PRT
<213> ORGANISM: Artificial Sequence
<220> FEATURE:
<223> OTHER INFORMATION: Synthetic peptide

<400> SEQUENCE: 235

Ser Ser Arg Met Gly Leu Val
1 5

<210> SEQ ID NO 236
<211> LENGTH: 7
<212> TYPE: PRT
<213> ORGANISM: Artificial Sequence
<220> FEATURE:
<223> OTHER INFORMATION: Synthetic peptide

<400> SEQUENCE: 236

Tyr Val Gly Leu Val Val Ser
1 5

<210> SEQ ID NO 237
<211> LENGTH: 7
<212> TYPE: PRT
<213> ORGANISM: Artificial Sequence
<220> FEATURE:
<223> OTHER INFORMATION: Synthetic peptide

<400> SEQUENCE: 237

Gly Leu Arg Lys Ala Gly Phe
1 5

<210> SEQ ID NO 238
<211> LENGTH: 7
<212> TYPE: PRT
<213> ORGANISM: Artificial Sequence
<220> FEATURE:
<223> OTHER INFORMATION: Synthetic peptide

<400> SEQUENCE: 238

Ala Val Asp Gly Leu Arg Leu
1 5

<210> SEQ ID NO 239

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 239

Phe Gly Leu Arg Ser Arg Leu
1 5

<210> SEQ ID NO 240
<211> LENGTH: 7
<212> TYPE: PRT
<213> ORGANISM: Artificial Sequence
<220> FEATURE:
<223> OTHER INFORMATION: Synthetic peptide

<400> SEQUENCE: 240

Glu Arg Ala Arg Gly Tyr Pro
1 5

<210> SEQ ID NO 241
<211> LENGTH: 7
<212> TYPE: PRT
<213> ORGANISM: Artificial Sequence
<220> FEATURE:
<223> OTHER INFORMATION: Synthetic peptide

<400> SEQUENCE: 241

Gly Ser Ala Arg Gly Met Leu
1 5

<210> SEQ ID NO 242
<211> LENGTH: 7
<212> TYPE: PRT
<213> ORGANISM: Artificial Sequence
<220> FEATURE:
<223> OTHER INFORMATION: Synthetic peptide

<400> SEQUENCE: 242

Ala Ser Leu Arg Tyr Tyr Val
1 5

<210> SEQ ID NO 243
<211> LENGTH: 7
<212> TYPE: PRT
<213> ORGANISM: Artificial Sequence
<220> FEATURE:
<223> OTHER INFORMATION: Synthetic peptide

<400> SEQUENCE: 243

Asn Ala Ala Ser Leu Pro Ser
1 5

<210> SEQ ID NO 244
<211> LENGTH: 7
<212> TYPE: PRT
<213> ORGANISM: Artificial Sequence
<220> FEATURE:
<223> OTHER INFORMATION: Synthetic peptide

<400> SEQUENCE: 244

Trp Leu Asp Ala Ser Leu Met
1 5

<210> SEQ ID NO 245
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 245

Asn Ala Ala Ser Leu Pro Ser
1 5

<210> SEQ ID NO 246
<211> LENGTH: 7
<212> TYPE: PRT
<213> ORGANISM: Artificial Sequence
<220> FEATURE:
<223> OTHER INFORMATION: Synthetic peptide

<400> SEQUENCE: 246

Phe His Val Ala Gly Gly Ser
1 5

<210> SEQ ID NO 247
<211> LENGTH: 7
<212> TYPE: PRT
<213> ORGANISM: Artificial Sequence
<220> FEATURE:
<223> OTHER INFORMATION: Synthetic peptide

<400> SEQUENCE: 247

Gly Glu His Leu Gly Gly Ser
1 5

<210> SEQ ID NO 248
<211> LENGTH: 7
<212> TYPE: PRT
<213> ORGANISM: Artificial Sequence
<220> FEATURE:
<223> OTHER INFORMATION: Synthetic peptide

<400> SEQUENCE: 248

Ser Gly Gly Leu His Glu Gly
1 5

<210> SEQ ID NO 249
<211> LENGTH: 7
<212> TYPE: PRT
<213> ORGANISM: Artificial Sequence
<220> FEATURE:
<223> OTHER INFORMATION: Synthetic peptide

<400> SEQUENCE: 249

Ser Arg Leu Ser Tyr Arg Ser
1 5

<210> SEQ ID NO 250
<211> LENGTH: 7
<212> TYPE: PRT
<213> ORGANISM: Artificial Sequence
<220> FEATURE:
<223> OTHER INFORMATION: Synthetic peptide

<400> SEQUENCE: 250

Gly Gly Leu Arg Gly Val Arg
1 5

<210> SEQ ID NO 251
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 251

Val Ala Trp Arg Gly Val Ser
1               5

<210> SEQ ID NO 252
<211> LENGTH: 7
<212> TYPE: PRT
<213> ORGANISM: Artificial Sequence
<220> FEATURE:
<223> OTHER INFORMATION: Synthetic peptide

<400> SEQUENCE: 252

Ser Val Glu Gly Arg Gly Val
1               5

<210> SEQ ID NO 253
<211> LENGTH: 7
<212> TYPE: PRT
<213> ORGANISM: Artificial Sequence
<220> FEATURE:
<223> OTHER INFORMATION: Synthetic peptide

<400> SEQUENCE: 253

Phe Trp Arg Gly Ser Val Pro
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic peptide

<400> SEQUENCE: 254

Glu Phe Thr Arg Arg Ala Ser
1               5

<210> SEQ ID NO 255
<211> LENGTH: 7
<212> TYPE: PRT
<213> ORGANISM: Artificial Sequence
<220> FEATURE:
<223> OTHER INFORMATION: Synthetic peptide

<400> SEQUENCE: 255

Trp Gly Trp Arg Ala Ser Ser
1               5

<210> SEQ ID NO 256
<211> LENGTH: 7
<212> TYPE: PRT
<213> ORGANISM: Artificial Sequence
<220> FEATURE:
<223> OTHER INFORMATION: Synthetic peptide

<400> SEQUENCE: 256

Arg Phe Tyr His Leu Arg Ser
1               5

<210> SEQ ID NO 257
<211> LENGTH: 7
<212> TYPE: PRT
<213> ORGANISM: Artificial Sequence -continued

```
<220> FEATURE:
<223> OTHER INFORMATION: Synthetic peptide

<400> SEQUENCE: 257

Ser Arg Tyr Ser Leu Arg Ser
1               5


<210> SEQ ID NO 258
<211> LENGTH: 7
<212> TYPE: PRT
<213> ORGANISM: Artificial Sequence
<220> FEATURE:
<223> OTHER INFORMATION: Synthetic peptide

<400> SEQUENCE: 258

Arg Arg Ser Ser Lys Gln Ala
1               5


<210> SEQ ID NO 259
<211> LENGTH: 7
<212> TYPE: PRT
<213> ORGANISM: Artificial Sequence
<220> FEATURE:
<223> OTHER INFORMATION: Synthetic peptide

<400> SEQUENCE: 259

Asp Trp Gly Arg Ser Ser Phe
1               5


<210> SEQ ID NO 260
<211> LENGTH: 7
<212> TYPE: PRT
<213> ORGANISM: Artificial Sequence
<220> FEATURE:
<223> OTHER INFORMATION: Synthetic peptide

<400> SEQUENCE: 260

Arg Phe Thr Arg Ser Ser Gly
1               5


<210> SEQ ID NO 261
<211> LENGTH: 7
<212> TYPE: PRT
<213> ORGANISM: Artificial Sequence
<220> FEATURE:
<223> OTHER INFORMATION: Synthetic peptide

<400> SEQUENCE: 261

Val Phe Gln Arg Ser Ser Gly
1               5


<210> SEQ ID NO 262
<211> LENGTH: 7
<212> TYPE: PRT
<213> ORGANISM: Artificial Sequence
<220> FEATURE:
<223> OTHER INFORMATION: Synthetic peptide

<400> SEQUENCE: 262

Ala Gly Ser Gln Ser Trp Glu
1               5


<210> SEQ ID NO 263
<211> LENGTH: 7
<212> TYPE: PRT
<213> ORGANISM: Artificial Sequence
<220> FEATURE:
```

-continued

<223> OTHER INFORMATION: Synthetic peptide

<400> SEQUENCE: 263

Glu His Pro Ala Gly Gly Met
1               5

<210> SEQ ID NO 264
<211> LENGTH: 7
<212> TYPE: PRT
<213> ORGANISM: Artificial Sequence
<220> FEATURE:
<223> OTHER INFORMATION: Synthetic peptide

<400> SEQUENCE: 264

Gly Val Arg Thr Ala Gly Pro
1               5

<210> SEQ ID NO 265
<211> LENGTH: 7
<212> TYPE: PRT
<213> ORGANISM: Artificial Sequence
<220> FEATURE:
<223> OTHER INFORMATION: Synthetic peptide

<400> SEQUENCE: 265

Gly Gly Leu Arg Gly Val Arg
1               5

<210> SEQ ID NO 266
<211> LENGTH: 7
<212> TYPE: PRT
<213> ORGANISM: Artificial Sequence
<220> FEATURE:
<223> OTHER INFORMATION: Synthetic peptide

<400> SEQUENCE: 266

Leu Tyr Gly Gly Val Arg Tyr
1               5

<210> SEQ ID NO 267
<211> LENGTH: 7
<212> TYPE: PRT
<213> ORGANISM: Artificial Sequence
<220> FEATURE:
<223> OTHER INFORMATION: Synthetic peptide

<400> SEQUENCE: 267

Pro Val Gly Gly Val Leu Leu
1               5

<210> SEQ ID NO 268
<211> LENGTH: 7
<212> TYPE: PRT
<213> ORGANISM: Artificial Sequence
<220> FEATURE:
<223> OTHER INFORMATION: Synthetic peptide

<400> SEQUENCE: 268

Gly Ala Val Val Lys Pro Ile
1               5

<210> SEQ ID NO 269
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 269

Ser Val Gly Ala Val Gly Gly
1               5

<210> SEQ ID NO 270
<211> LENGTH: 7
<212> TYPE: PRT
<213> ORGANISM: Artificial Sequence
<220> FEATURE:
<223> OTHER INFORMATION: Synthetic peptide

<400> SEQUENCE: 270

Gly Leu Val Ser Val Glu Ala
1               5

<210> SEQ ID NO 271
<211> LENGTH: 7
<212> TYPE: PRT
<213> ORGANISM: Artificial Sequence
<220> FEATURE:
<223> OTHER INFORMATION: Synthetic peptide

<400> SEQUENCE: 271

Gly Gly Leu Arg Gly Val Arg
1               5

<210> SEQ ID NO 272
<211> LENGTH: 7
<212> TYPE: PRT
<213> ORGANISM: Artificial Sequence
<220> FEATURE:
<223> OTHER INFORMATION: Synthetic peptide

<400> SEQUENCE: 272

Asp Ile Ala Leu Val Ser Pro
1               5

<210> SEQ ID NO 273
<211> LENGTH: 7
<212> TYPE: PRT
<213> ORGANISM: Artificial Sequence
<220> FEATURE:
<223> OTHER INFORMATION: Synthetic peptide

<400> SEQUENCE: 273

Gly Leu Val Ser Val Glu Ala
1               5

<210> SEQ ID NO 274
<211> LENGTH: 7
<212> TYPE: PRT
<213> ORGANISM: Artificial Sequence
<220> FEATURE:
<223> OTHER INFORMATION: Synthetic peptide

<400> SEQUENCE: 274

Ala Arg Asn Ala Ala Ser Pro
1               5

<210> SEQ ID NO 275
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 275

Ala Glu Gly Gly Ser Gly His
1               5

<210> SEQ ID NO 276
<211> LENGTH: 7
<212> TYPE: PRT
<213> ORGANISM: Artificial Sequence
<220> FEATURE:
<223> OTHER INFORMATION: Synthetic peptide

<400> SEQUENCE: 276

Gly Gly Ser Phe Ser Gly Leu
1               5

<210> SEQ ID NO 277
<211> LENGTH: 7
<212> TYPE: PRT
<213> ORGANISM: Artificial Sequence
<220> FEATURE:
<223> OTHER INFORMATION: Synthetic peptide

<400> SEQUENCE: 277

Val Thr Gly Gly Arg Val Asp
1               5

<210> SEQ ID NO 278
<211> LENGTH: 7
<212> TYPE: PRT
<213> ORGANISM: Artificial Sequence
<220> FEATURE:
<223> OTHER INFORMATION: Synthetic peptide

<400> SEQUENCE: 278

Gly Gly Leu Arg Gly Val Arg
1               5

<210> SEQ ID NO 279
<211> LENGTH: 7
<212> TYPE: PRT
<213> ORGANISM: Artificial Sequence
<220> FEATURE:
<223> OTHER INFORMATION: Synthetic peptide

<400> SEQUENCE: 279

Gly Ser Ser Trp Val Val Asp
1               5

<210> SEQ ID NO 280
<211> LENGTH: 7
<212> TYPE: PRT
<213> ORGANISM: Artificial Sequence
<220> FEATURE:
<223> OTHER INFORMATION: Synthetic peptide

<400> SEQUENCE: 280

Gly Ser Ser Arg Thr Phe Arg
1               5

<210> SEQ ID NO 281
<211> LENGTH: 7
<212> TYPE: PRT
<213> ORGANISM: Artificial Sequence
<220> FEATURE:
<223> OTHER INFORMATION: Synthetic peptide

<400> SEQUENCE: 281

```
Gly Ser Ser Arg Gln Phe Val
1               5


<210> SEQ ID NO 282
<211> LENGTH: 7
<212> TYPE: PRT
<213> ORGANISM: Artificial Sequence
<220> FEATURE:
<223> OTHER INFORMATION: Synthetic peptide

<400> SEQUENCE: 282

Trp Val Gly Ser Ser Lys Phe
1               5


<210> SEQ ID NO 283
<211> LENGTH: 7
<212> TYPE: PRT
<213> ORGANISM: Artificial Sequence
<220> FEATURE:
<223> OTHER INFORMATION: Synthetic peptide

<400> SEQUENCE: 283

Ala Glu Gly Gly Ser Gly His
1               5


<210> SEQ ID NO 284
<211> LENGTH: 7
<212> TYPE: PRT
<213> ORGANISM: Artificial Sequence
<220> FEATURE:
<223> OTHER INFORMATION: Synthetic peptide

<400> SEQUENCE: 284

Glu Val Ile Gly Ser Gly Ile
1               5


<210> SEQ ID NO 285
<211> LENGTH: 7
<212> TYPE: PRT
<213> ORGANISM: Artificial Sequence
<220> FEATURE:
<223> OTHER INFORMATION: Synthetic peptide

<400> SEQUENCE: 285

Phe Trp Arg Gly Ser Val Pro
1               5


<210> SEQ ID NO 286
<211> LENGTH: 7
<212> TYPE: PRT
<213> ORGANISM: Artificial Sequence
<220> FEATURE:
<223> OTHER INFORMATION: Synthetic peptide

<400> SEQUENCE: 286

Val Gly Ser Val Ser Val Asn
1               5


<210> SEQ ID NO 287
<211> LENGTH: 7
<212> TYPE: PRT
<213> ORGANISM: Artificial Sequence
<220> FEATURE:
<223> OTHER INFORMATION: Synthetic peptide

<400> SEQUENCE: 287
```

-continued

Val Thr Gly Gly Arg Val Asp
1 5

<210> SEQ ID NO 288
<211> LENGTH: 7
<212> TYPE: PRT
<213> ORGANISM: Artificial Sequence
<220> FEATURE:
<223> OTHER INFORMATION: Synthetic peptide

<400> SEQUENCE: 288

Gly Arg Val Thr Val Ala Val
1 5

<210> SEQ ID NO 289
<211> LENGTH: 7
<212> TYPE: PRT
<213> ORGANISM: Artificial Sequence
<220> FEATURE:
<223> OTHER INFORMATION: Synthetic peptide

<400> SEQUENCE: 289

Arg Val Gly Arg Leu Gly Gly
1 5

<210> SEQ ID NO 290
<211> LENGTH: 7
<212> TYPE: PRT
<213> ORGANISM: Artificial Sequence
<220> FEATURE:
<223> OTHER INFORMATION: Synthetic peptide

<400> SEQUENCE: 290

Asn Tyr Met Gly Pro Ser Ala
1 5

<210> SEQ ID NO 291
<211> LENGTH: 7
<212> TYPE: PRT
<213> ORGANISM: Artificial Sequence
<220> FEATURE:
<223> OTHER INFORMATION: Synthetic peptide

<400> SEQUENCE: 291

Gly Trp His Gly Pro Ser His
1 5

<210> SEQ ID NO 292
<211> LENGTH: 7
<212> TYPE: PRT
<213> ORGANISM: Artificial Sequence
<220> FEATURE:
<223> OTHER INFORMATION: Synthetic peptide

<400> SEQUENCE: 292

Gly Gly Val Ser Pro Val Asp
1 5

<210> SEQ ID NO 293
<211> LENGTH: 7
<212> TYPE: PRT
<213> ORGANISM: Artificial Sequence
<220> FEATURE:
<223> OTHER INFORMATION: Synthetic peptide

<400> SEQUENCE: 293

Gly Val Ser Lys Val Arg Ala

-continued 1 5

<210> SEQ ID NO 294
<211> LENGTH: 7
<212> TYPE: PRT
<213> ORGANISM: Artificial Sequence
<220> FEATURE:
<223> OTHER INFORMATION: Synthetic peptide

<400> SEQUENCE: 294

Gly Gly Val Ala Gly Val Ser
1 5

<210> SEQ ID NO 295
<211> LENGTH: 7
<212> TYPE: PRT
<213> ORGANISM: Artificial Sequence
<220> FEATURE:
<223> OTHER INFORMATION: Synthetic peptide

<400> SEQUENCE: 295

Val Ala Trp Arg Gly Val Ser
1 5

<210> SEQ ID NO 296
<211> LENGTH: 7
<212> TYPE: PRT
<213> ORGANISM: Artificial Sequence
<220> FEATURE:
<223> OTHER INFORMATION: Synthetic peptide

<400> SEQUENCE: 296

Val Ile Gly Ser Arg Leu Ser
1 5

<210> SEQ ID NO 297
<211> LENGTH: 7
<212> TYPE: PRT
<213> ORGANISM: Artificial Sequence
<220> FEATURE:
<223> OTHER INFORMATION: Synthetic peptide

<400> SEQUENCE: 297

His Leu Arg Gly Arg Gly Val
1 5

<210> SEQ ID NO 298
<211> LENGTH: 7
<212> TYPE: PRT
<213> ORGANISM: Artificial Sequence
<220> FEATURE:
<223> OTHER INFORMATION: Synthetic peptide

<400> SEQUENCE: 298

Glu Val Arg Ser Arg Gly Ser
1 5

<210> SEQ ID NO 299
<211> LENGTH: 7
<212> TYPE: PRT
<213> ORGANISM: Artificial Sequence
<220> FEATURE:
<223> OTHER INFORMATION: Synthetic peptide

<400> SEQUENCE: 299

Arg Gly Ser Arg Leu Pro Ala
1 5

-continued

<210> SEQ ID NO 300
<211> LENGTH: 7
<212> TYPE: PRT
<213> ORGANISM: Artificial Sequence
<220> FEATURE:
<223> OTHER INFORMATION: Synthetic peptide

<400> SEQUENCE: 300

Asp Val Arg Ala Val Ser Ser
1 5

<210> SEQ ID NO 301
<211> LENGTH: 7
<212> TYPE: PRT
<213> ORGANISM: Artificial Sequence
<220> FEATURE:
<223> OTHER INFORMATION: Synthetic peptide

<400> SEQUENCE: 301

Asp Val Arg Ala Val Ser Ser
1 5

<210> SEQ ID NO 302
<211> LENGTH: 7
<212> TYPE: PRT
<213> ORGANISM: Artificial Sequence
<220> FEATURE:
<223> OTHER INFORMATION: Synthetic peptide

<400> SEQUENCE: 302

Ala Pro Leu Arg Ser Gly Arg
1 5

<210> SEQ ID NO 303
<211> LENGTH: 7
<212> TYPE: PRT
<213> ORGANISM: Artificial Sequence
<220> FEATURE:
<223> OTHER INFORMATION: Synthetic peptide

<400> SEQUENCE: 303

Ser Leu Arg Ser Gly Ile Val
1 5

<210> SEQ ID NO 304
<211> LENGTH: 7
<212> TYPE: PRT
<213> ORGANISM: Artificial Sequence
<220> FEATURE:
<223> OTHER INFORMATION: Synthetic peptide

<400> SEQUENCE: 304

Asp Gly Gly Arg Arg Ser Ser
1 5

<210> SEQ ID NO 305
<211> LENGTH: 7
<212> TYPE: PRT
<213> ORGANISM: Artificial Sequence
<220> FEATURE:
<223> OTHER INFORMATION: Synthetic peptide

<400> SEQUENCE: 305

Gln Ala Gly Ser Phe Leu Arg
1 5

-continued

<210> SEQ ID NO 306
<211> LENGTH: 7
<212> TYPE: PRT
<213> ORGANISM: Artificial Sequence
<220> FEATURE:
<223> OTHER INFORMATION: Synthetic peptide

<400> SEQUENCE: 306

Asp Ala Gly Ser Asp Arg Arg
1               5

<210> SEQ ID NO 307
<211> LENGTH: 7
<212> TYPE: PRT
<213> ORGANISM: Artificial Sequence
<220> FEATURE:
<223> OTHER INFORMATION: Synthetic peptide

<400> SEQUENCE: 307

Ala Gly Arg Arg Phe Gly Gly
1               5

<210> SEQ ID NO 308
<211> LENGTH: 7
<212> TYPE: PRT
<213> ORGANISM: Artificial Sequence
<220> FEATURE:
<223> OTHER INFORMATION: Synthetic peptide

<400> SEQUENCE: 308

Ala Gly Leu Ser Gly Gly Thr
1               5

<210> SEQ ID NO 309
<211> LENGTH: 7
<212> TYPE: PRT
<213> ORGANISM: Artificial Sequence
<220> FEATURE:
<223> OTHER INFORMATION: Synthetic peptide

<400> SEQUENCE: 309

Ala Gly Gly Gly Pro Pro Ala
1               5

<210> SEQ ID NO 310
<211> LENGTH: 7
<212> TYPE: PRT
<213> ORGANISM: Artificial Sequence
<220> FEATURE:
<223> OTHER INFORMATION: Synthetic peptide

<400> SEQUENCE: 310

Ala Gly Gly Gly Pro Pro Ala
1               5

<210> SEQ ID NO 311
<211> LENGTH: 7
<212> TYPE: PRT
<213> ORGANISM: Artificial Sequence
<220> FEATURE:
<223> OTHER INFORMATION: Synthetic peptide

<400> SEQUENCE: 311

Phe Phe Pro Ala Gly Gly Pro
1               5

-continued

<210> SEQ ID NO 312
<211> LENGTH: 7
<212> TYPE: PRT
<213> ORGANISM: Artificial Sequence
<220> FEATURE:
<223> OTHER INFORMATION: Synthetic peptide

<400> SEQUENCE: 312

Pro Arg Ala Gly Gly Arg Trp
1               5

<210> SEQ ID NO 313
<211> LENGTH: 7
<212> TYPE: PRT
<213> ORGANISM: Artificial Sequence
<220> FEATURE:
<223> OTHER INFORMATION: Synthetic peptide

<400> SEQUENCE: 313

Asp Val Pro Gly Val Arg Phe
1               5

<210> SEQ ID NO 314
<211> LENGTH: 7
<212> TYPE: PRT
<213> ORGANISM: Artificial Sequence
<220> FEATURE:
<223> OTHER INFORMATION: Synthetic peptide

<400> SEQUENCE: 314

Phe Gly Val Leu Phe Arg Ser
1               5

<210> SEQ ID NO 315
<211> LENGTH: 7
<212> TYPE: PRT
<213> ORGANISM: Artificial Sequence
<220> FEATURE:
<223> OTHER INFORMATION: Synthetic peptide

<400> SEQUENCE: 315

Ser Arg Tyr Gly Val Leu Val
1               5

<210> SEQ ID NO 316
<211> LENGTH: 7
<212> TYPE: PRT
<213> ORGANISM: Artificial Sequence
<220> FEATURE:
<223> OTHER INFORMATION: Synthetic peptide

<400> SEQUENCE: 316

Leu Arg Gly Gly Leu Val Ser
1               5

<210> SEQ ID NO 317
<211> LENGTH: 7
<212> TYPE: PRT
<213> ORGANISM: Artificial Sequence
<220> FEATURE:
<223> OTHER INFORMATION: Synthetic peptide

<400> SEQUENCE: 317

Lys Ser Gly Leu Arg Pro Ala
1               5

<210> SEQ ID NO 318

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 318

Ala Leu Val Ser Phe Ser Val
1               5

<210> SEQ ID NO 319
<211> LENGTH: 7
<212> TYPE: PRT
<213> ORGANISM: Artificial Sequence
<220> FEATURE:
<223> OTHER INFORMATION: Synthetic peptide

<400> SEQUENCE: 319

Leu Arg Gly Gly Leu Val Ser
1               5

<210> SEQ ID NO 320
<211> LENGTH: 7
<212> TYPE: PRT
<213> ORGANISM: Artificial Sequence
<220> FEATURE:
<223> OTHER INFORMATION: Synthetic peptide

<400> SEQUENCE: 320

His Lys Leu Ala Arg Gly Arg
1               5

<210> SEQ ID NO 321
<211> LENGTH: 7
<212> TYPE: PRT
<213> ORGANISM: Artificial Sequence
<220> FEATURE:
<223> OTHER INFORMATION: Synthetic peptide

<400> SEQUENCE: 321

Ala Ser Leu Pro Pro Arg Ala
1               5

<210> SEQ ID NO 322
<211> LENGTH: 7
<212> TYPE: PRT
<213> ORGANISM: Artificial Sequence
<220> FEATURE:
<223> OTHER INFORMATION: Synthetic peptide

<400> SEQUENCE: 322

Thr Gly Gly Ser Leu Gly Ala
1               5

<210> SEQ ID NO 323
<211> LENGTH: 7
<212> TYPE: PRT
<213> ORGANISM: Artificial Sequence
<220> FEATURE:
<223> OTHER INFORMATION: Synthetic peptide

<400> SEQUENCE: 323

Gly Gly Gly Ser Trp Leu Ile
1               5

<210> SEQ ID NO 324
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 324

Asp Gly Gly Arg Arg Ser Ser
1               5

<210> SEQ ID NO 325
<211> LENGTH: 7
<212> TYPE: PRT
<213> ORGANISM: Artificial Sequence
<220> FEATURE:
<223> OTHER INFORMATION: Synthetic peptide

<400> SEQUENCE: 325

Ser Val Leu Gly Gly Arg Leu
1               5

<210> SEQ ID NO 326
<211> LENGTH: 7
<212> TYPE: PRT
<213> ORGANISM: Artificial Sequence
<220> FEATURE:
<223> OTHER INFORMATION: Synthetic peptide

<400> SEQUENCE: 326

Pro Arg Ala Gly Gly Arg Trp
1               5

<210> SEQ ID NO 327
<211> LENGTH: 7
<212> TYPE: PRT
<213> ORGANISM: Artificial Sequence
<220> FEATURE:
<223> OTHER INFORMATION: Synthetic peptide

<400> SEQUENCE: 327

Tyr Trp Phe Ile Gly Leu Gly
1               5

<210> SEQ ID NO 328
<211> LENGTH: 7
<212> TYPE: PRT
<213> ORGANISM: Artificial Sequence
<220> FEATURE:
<223> OTHER INFORMATION: Synthetic peptide

<400> SEQUENCE: 328

Gly Gly Leu Ser Val Asp Leu
1               5

<210> SEQ ID NO 329
<211> LENGTH: 7
<212> TYPE: PRT
<213> ORGANISM: Artificial Sequence
<220> FEATURE:
<223> OTHER INFORMATION: Synthetic peptide

<400> SEQUENCE: 329

Leu Arg Gly Gly Leu Val Ser
1               5

<210> SEQ ID NO 330
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 330

Ser Gly Val Gly Ser Ser Leu
1 5

<210> SEQ ID NO 331
<211> LENGTH: 7
<212> TYPE: PRT
<213> ORGANISM: Artificial Sequence
<220> FEATURE:
<223> OTHER INFORMATION: Synthetic peptide

<400> SEQUENCE: 331

Gly Ser Gly Ile Leu Asp Leu
1 5

<210> SEQ ID NO 332
<211> LENGTH: 7
<212> TYPE: PRT
<213> ORGANISM: Artificial Sequence
<220> FEATURE:
<223> OTHER INFORMATION: Synthetic peptide

<400> SEQUENCE: 332

Ser Leu Gly Ser Val Gly Ser
1 5

<210> SEQ ID NO 333
<211> LENGTH: 7
<212> TYPE: PRT
<213> ORGANISM: Artificial Sequence
<220> FEATURE:
<223> OTHER INFORMATION: Synthetic peptide

<400> SEQUENCE: 333

Val Gly Arg Gly Arg Leu His
1 5

<210> SEQ ID NO 334
<211> LENGTH: 7
<212> TYPE: PRT
<213> ORGANISM: Artificial Sequence
<220> FEATURE:
<223> OTHER INFORMATION: Synthetic peptide

<400> SEQUENCE: 334

Ser Val Leu Gly Gly Arg Leu
1 5

<210> SEQ ID NO 335
<211> LENGTH: 7
<212> TYPE: PRT
<213> ORGANISM: Artificial Sequence
<220> FEATURE:
<223> OTHER INFORMATION: Synthetic peptide

<400> SEQUENCE: 335

Met Ser Ala Phe Gly Arg Leu
1 5

<210> SEQ ID NO 336
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 336

Ser Gly Val Ser Gly Leu Ser
1 5

<210> SEQ ID NO 337
<211> LENGTH: 7
<212> TYPE: PRT
<213> ORGANISM: Artificial Sequence
<220> FEATURE:
<223> OTHER INFORMATION: Synthetic peptide

<400> SEQUENCE: 337

Gly Asp Ser Arg Arg Gly Val
1 5

<210> SEQ ID NO 338
<211> LENGTH: 7
<212> TYPE: PRT
<213> ORGANISM: Artificial Sequence
<220> FEATURE:
<223> OTHER INFORMATION: Synthetic peptide

<400> SEQUENCE: 338

Gly Lys Ala Leu Arg Gly Val
1 5

<210> SEQ ID NO 339
<211> LENGTH: 7
<212> TYPE: PRT
<213> ORGANISM: Artificial Sequence
<220> FEATURE:
<223> OTHER INFORMATION: Synthetic peptide

<400> SEQUENCE: 339

Pro Lys Ala Gly Arg Gly Ser
1 5

<210> SEQ ID NO 340
<211> LENGTH: 7
<212> TYPE: PRT
<213> ORGANISM: Artificial Sequence
<220> FEATURE:
<223> OTHER INFORMATION: Synthetic peptide

<400> SEQUENCE: 340

Phe Asp Arg Ala Val Ala Asn
1 5

<210> SEQ ID NO 341
<211> LENGTH: 7
<212> TYPE: PRT
<213> ORGANISM: Artificial Sequence
<220> FEATURE:
<223> OTHER INFORMATION: Synthetic peptide

<400> SEQUENCE: 341

Leu Leu Arg Arg Ala Val Phe
1 5

<210> SEQ ID NO 342
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 342

Phe Arg Ala Ser Ser Glu Val
1               5

<210> SEQ ID NO 343
<211> LENGTH: 7
<212> TYPE: PRT
<213> ORGANISM: Artificial Sequence
<220> FEATURE:
<223> OTHER INFORMATION: Synthetic peptide

<400> SEQUENCE: 343

Pro Asp Arg Ala Ser Asp Gly
1               5

<210> SEQ ID NO 344
<211> LENGTH: 7
<212> TYPE: PRT
<213> ORGANISM: Artificial Sequence
<220> FEATURE:
<223> OTHER INFORMATION: Synthetic peptide

<400> SEQUENCE: 344

Phe Arg Ala Ser Leu Gln Tyr
1               5

<210> SEQ ID NO 345
<211> LENGTH: 7
<212> TYPE: PRT
<213> ORGANISM: Artificial Sequence
<220> FEATURE:
<223> OTHER INFORMATION: Synthetic peptide

<400> SEQUENCE: 345

His Val Gly Leu Leu Arg Ala
1               5

<210> SEQ ID NO 346
<211> LENGTH: 7
<212> TYPE: PRT
<213> ORGANISM: Artificial Sequence
<220> FEATURE:
<223> OTHER INFORMATION: Synthetic peptide

<400> SEQUENCE: 346

Gln Val Leu Leu Arg Ser Phe
1               5

<210> SEQ ID NO 347
<211> LENGTH: 7
<212> TYPE: PRT
<213> ORGANISM: Artificial Sequence
<220> FEATURE:
<223> OTHER INFORMATION: Synthetic peptide

<400> SEQUENCE: 347

Leu Leu Arg Arg Ala Val Phe
1               5

<210> SEQ ID NO 348
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 348

Phe Leu Arg Val Gly Glu Leu
1               5

<210> SEQ ID NO 349
<211> LENGTH: 7
<212> TYPE: PRT
<213> ORGANISM: Artificial Sequence
<220> FEATURE:
<223> OTHER INFORMATION: Synthetic peptide

<400> SEQUENCE: 349

Gln Val Leu Leu Arg Ser Phe
1               5

<210> SEQ ID NO 350
<211> LENGTH: 7
<212> TYPE: PRT
<213> ORGANISM: Artificial Sequence
<220> FEATURE:
<223> OTHER INFORMATION: Synthetic peptide

<400> SEQUENCE: 350

Arg Arg Val Ser Cys Asp Leu
1               5

<210> SEQ ID NO 351
<211> LENGTH: 7
<212> TYPE: PRT
<213> ORGANISM: Artificial Sequence
<220> FEATURE:
<223> OTHER INFORMATION: Synthetic peptide

<400> SEQUENCE: 351

Arg Ser Ser Gly Leu Gly Phe
1               5

<210> SEQ ID NO 352
<211> LENGTH: 7
<212> TYPE: PRT
<213> ORGANISM: Artificial Sequence
<220> FEATURE:
<223> OTHER INFORMATION: Synthetic peptide

<400> SEQUENCE: 352

Ser Ser Gly Pro Arg Ser Ser
1               5

<210> SEQ ID NO 353
<211> LENGTH: 7
<212> TYPE: PRT
<213> ORGANISM: Artificial Sequence
<220> FEATURE:
<223> OTHER INFORMATION: Synthetic peptide

<400> SEQUENCE: 353

Tyr Ser Gln Arg Ser Ser Leu
1               5

<210> SEQ ID NO 354
<211> LENGTH: 7
<212> TYPE: PRT
<213> ORGANISM: Artificial Sequence
<220> FEATURE:
<223> OTHER INFORMATION: Synthetic peptide

<400> SEQUENCE: 354

Asp Ala Gly Arg Thr Ile Asp
1 5

<210> SEQ ID NO 355
<211> LENGTH: 7
<212> TYPE: PRT
<213> ORGANISM: Artificial Sequence
<220> FEATURE:
<223> OTHER INFORMATION: Synthetic peptide

<400> SEQUENCE: 355

Ala Ala Gly Arg Glu Phe Arg
1 5

<210> SEQ ID NO 356
<211> LENGTH: 7
<212> TYPE: PRT
<213> ORGANISM: Artificial Sequence
<220> FEATURE:
<223> OTHER INFORMATION: Synthetic peptide

<400> SEQUENCE: 356

Pro Lys Ala Gly Arg Gly Ser
1 5

<210> SEQ ID NO 357
<211> LENGTH: 7
<212> TYPE: PRT
<213> ORGANISM: Artificial Sequence
<220> FEATURE:
<223> OTHER INFORMATION: Synthetic peptide

<400> SEQUENCE: 357

Val Arg Ala Ala Gly Arg Val
1 5

<210> SEQ ID NO 358
<211> LENGTH: 7
<212> TYPE: PRT
<213> ORGANISM: Artificial Sequence
<220> FEATURE:
<223> OTHER INFORMATION: Synthetic peptide

<400> SEQUENCE: 358

His Gly Tyr Arg Ala Gly Gly
1 5

<210> SEQ ID NO 359
<211> LENGTH: 7
<212> TYPE: PRT
<213> ORGANISM: Artificial Sequence
<220> FEATURE:
<223> OTHER INFORMATION: Synthetic peptide

<400> SEQUENCE: 359

Trp Gly Ala Thr Ala Gly Gly
1 5

<210> SEQ ID NO 360
<211> LENGTH: 7
<212> TYPE: PRT
<213> ORGANISM: Artificial Sequence
<220> FEATURE:
<223> OTHER INFORMATION: Synthetic peptide

<400> SEQUENCE: 360

-continued

```
Tyr Tyr Ala Gly Gly Leu Lys
1               5


<210> SEQ ID NO 361
<211> LENGTH: 7
<212> TYPE: PRT
<213> ORGANISM: Artificial Sequence
<220> FEATURE:
<223> OTHER INFORMATION: Synthetic peptide

<400> SEQUENCE: 361

Leu Glu Gly Val Arg Leu Phe
1               5


<210> SEQ ID NO 362
<211> LENGTH: 7
<212> TYPE: PRT
<213> ORGANISM: Artificial Sequence
<220> FEATURE:
<223> OTHER INFORMATION: Synthetic peptide

<400> SEQUENCE: 362

Gly Thr Phe Gly Val Leu Gly
1               5


<210> SEQ ID NO 363
<211> LENGTH: 7
<212> TYPE: PRT
<213> ORGANISM: Artificial Sequence
<220> FEATURE:
<223> OTHER INFORMATION: Synthetic peptide

<400> SEQUENCE: 363

Gly Thr Phe Gly Val Leu Gly
1               5


<210> SEQ ID NO 364
<211> LENGTH: 7
<212> TYPE: PRT
<213> ORGANISM: Artificial Sequence
<220> FEATURE:
<223> OTHER INFORMATION: Synthetic peptide

<400> SEQUENCE: 364

Val Trp Ala Gly Val Leu Leu
1               5


<210> SEQ ID NO 365
<211> LENGTH: 7
<212> TYPE: PRT
<213> ORGANISM: Artificial Sequence
<220> FEATURE:
<223> OTHER INFORMATION: Synthetic peptide

<400> SEQUENCE: 365

Gly Ala Val Leu Phe Arg Val
1               5


<210> SEQ ID NO 366
<211> LENGTH: 7
<212> TYPE: PRT
<213> ORGANISM: Artificial Sequence
<220> FEATURE:
<223> OTHER INFORMATION: Synthetic peptide

<400> SEQUENCE: 366
```

-continued

Gly Leu Val Gly Phe Thr Gly
1               5

<210> SEQ ID NO 367
<211> LENGTH: 7
<212> TYPE: PRT
<213> ORGANISM: Artificial Sequence
<220> FEATURE:
<223> OTHER INFORMATION: Synthetic peptide

<400> SEQUENCE: 367

Gly Leu Val Ser Ala Phe Tyr
1               5

<210> SEQ ID NO 368
<211> LENGTH: 7
<212> TYPE: PRT
<213> ORGANISM: Artificial Sequence
<220> FEATURE:
<223> OTHER INFORMATION: Synthetic peptide

<400> SEQUENCE: 368

Ala Arg Ala Met Gly Leu Arg
1               5

<210> SEQ ID NO 369
<211> LENGTH: 7
<212> TYPE: PRT
<213> ORGANISM: Artificial Sequence
<220> FEATURE:
<223> OTHER INFORMATION: Synthetic peptide

<400> SEQUENCE: 369

Gly Leu Val Ser Ala Phe Tyr
1               5

<210> SEQ ID NO 370
<211> LENGTH: 7
<212> TYPE: PRT
<213> ORGANISM: Artificial Sequence
<220> FEATURE:
<223> OTHER INFORMATION: Synthetic peptide

<400> SEQUENCE: 370

Ser Trp Arg Pro Leu Val Ser
1               5

<210> SEQ ID NO 371
<211> LENGTH: 7
<212> TYPE: PRT
<213> ORGANISM: Artificial Sequence
<220> FEATURE:
<223> OTHER INFORMATION: Synthetic peptide

<400> SEQUENCE: 371

Phe Arg Ala Ser Leu Gln Tyr
1               5

<210> SEQ ID NO 372
<211> LENGTH: 7
<212> TYPE: PRT
<213> ORGANISM: Artificial Sequence
<220> FEATURE:
<223> OTHER INFORMATION: Synthetic peptide

<400> SEQUENCE: 372

His Ser Glu Ser Ala Ala Val

-continued 1 5

<210> SEQ ID NO 373
<211> LENGTH: 7
<212> TYPE: PRT
<213> ORGANISM: Artificial Sequence
<220> FEATURE:
<223> OTHER INFORMATION: Synthetic peptide

<400> SEQUENCE: 373

Leu Phe Ala Val Ala Ala Val
1 5

<210> SEQ ID NO 374
<211> LENGTH: 7
<212> TYPE: PRT
<213> ORGANISM: Artificial Sequence
<220> FEATURE:
<223> OTHER INFORMATION: Synthetic peptide

<400> SEQUENCE: 374

Val Ala Ala Ser Glu Ser His
1 5

<210> SEQ ID NO 375
<211> LENGTH: 7
<212> TYPE: PRT
<213> ORGANISM: Artificial Sequence
<220> FEATURE:
<223> OTHER INFORMATION: Synthetic peptide

<400> SEQUENCE: 375

His Pro Ser Met Gly Gly Arg
1 5

<210> SEQ ID NO 376
<211> LENGTH: 7
<212> TYPE: PRT
<213> ORGANISM: Artificial Sequence
<220> FEATURE:
<223> OTHER INFORMATION: Synthetic peptide

<400> SEQUENCE: 376

Gly Leu Gly Val Ser Gly Val
1 5

<210> SEQ ID NO 377
<211> LENGTH: 7
<212> TYPE: PRT
<213> ORGANISM: Artificial Sequence
<220> FEATURE:
<223> OTHER INFORMATION: Synthetic peptide

<400> SEQUENCE: 377

Lys Arg Glu Ser Gly Leu Gly
1 5

<210> SEQ ID NO 378
<211> LENGTH: 7
<212> TYPE: PRT
<213> ORGANISM: Artificial Sequence
<220> FEATURE:
<223> OTHER INFORMATION: Synthetic peptide

<400> SEQUENCE: 378

Arg Ser Ser Gly Leu Gly Phe
1 5

-continued

<210> SEQ ID NO 379
<211> LENGTH: 7
<212> TYPE: PRT
<213> ORGANISM: Artificial Sequence
<220> FEATURE:
<223> OTHER INFORMATION: Synthetic peptide

<400> SEQUENCE: 379

Val Gly Leu Gly His Trp Pro
1               5

<210> SEQ ID NO 380
<211> LENGTH: 7
<212> TYPE: PRT
<213> ORGANISM: Artificial Sequence
<220> FEATURE:
<223> OTHER INFORMATION: Synthetic peptide

<400> SEQUENCE: 380

Tyr Tyr Ala Gly Gly Leu Lys
1               5

<210> SEQ ID NO 381
<211> LENGTH: 7
<212> TYPE: PRT
<213> ORGANISM: Artificial Sequence
<220> FEATURE:
<223> OTHER INFORMATION: Synthetic peptide

<400> SEQUENCE: 381

Asn Tyr Gly Ser Ser Phe His
1               5

<210> SEQ ID NO 382
<211> LENGTH: 7
<212> TYPE: PRT
<213> ORGANISM: Artificial Sequence
<220> FEATURE:
<223> OTHER INFORMATION: Synthetic peptide

<400> SEQUENCE: 382

Phe Gly Leu Gly Ser Ser Arg
1               5

<210> SEQ ID NO 383
<211> LENGTH: 7
<212> TYPE: PRT
<213> ORGANISM: Artificial Sequence
<220> FEATURE:
<223> OTHER INFORMATION: Synthetic peptide

<400> SEQUENCE: 383

Ser Ser Arg Pro Gly Ser Ser
1               5

<210> SEQ ID NO 384
<211> LENGTH: 7
<212> TYPE: PRT
<213> ORGANISM: Artificial Sequence
<220> FEATURE:
<223> OTHER INFORMATION: Synthetic peptide

<400> SEQUENCE: 384

Val Gly Ser Val Gly Leu Gly
1               5

-continued

<210> SEQ ID NO 385
<211> LENGTH: 7
<212> TYPE: PRT
<213> ORGANISM: Artificial Sequence
<220> FEATURE:
<223> OTHER INFORMATION: Synthetic peptide

<400> SEQUENCE: 385

Val Arg Ala Ala Gly Arg Val
1 5

<210> SEQ ID NO 386
<211> LENGTH: 7
<212> TYPE: PRT
<213> ORGANISM: Artificial Sequence
<220> FEATURE:
<223> OTHER INFORMATION: Synthetic peptide

<400> SEQUENCE: 386

His Asn Gly Arg Leu Glu Val
1 5

<210> SEQ ID NO 387
<211> LENGTH: 7
<212> TYPE: PRT
<213> ORGANISM: Artificial Sequence
<220> FEATURE:
<223> OTHER INFORMATION: Synthetic peptide

<400> SEQUENCE: 387

Val Gly Arg Leu Ala Lys Gly
1 5

<210> SEQ ID NO 388
<211> LENGTH: 7
<212> TYPE: PRT
<213> ORGANISM: Artificial Sequence
<220> FEATURE:
<223> OTHER INFORMATION: Synthetic peptide

<400> SEQUENCE: 388

Val Met Gly Gly Pro Ser Leu
1 5

<210> SEQ ID NO 389
<211> LENGTH: 7
<212> TYPE: PRT
<213> ORGANISM: Artificial Sequence
<220> FEATURE:
<223> OTHER INFORMATION: Synthetic peptide

<400> SEQUENCE: 389

Gly Leu Gly Val Ser Gly Val
1 5

<210> SEQ ID NO 390
<211> LENGTH: 7
<212> TYPE: PRT
<213> ORGANISM: Artificial Sequence
<220> FEATURE:
<223> OTHER INFORMATION: Synthetic peptide

<400> SEQUENCE: 390

Ser Gly Val Ser Val Glu Gly
1 5

-continued

<210> SEQ ID NO 391
<211> LENGTH: 7
<212> TYPE: PRT
<213> ORGANISM: Artificial Sequence
<220> FEATURE:
<223> OTHER INFORMATION: Synthetic peptide

<400> SEQUENCE: 391

Gly Glu Ser Gly Arg Leu Ser
1 5

<210> SEQ ID NO 392
<211> LENGTH: 7
<212> TYPE: PRT
<213> ORGANISM: Artificial Sequence
<220> FEATURE:
<223> OTHER INFORMATION: Synthetic peptide

<400> SEQUENCE: 392

Gly Ser Gly Arg Gly Val Ala
1 5

<210> SEQ ID NO 393
<211> LENGTH: 7
<212> TYPE: PRT
<213> ORGANISM: Artificial Sequence
<220> FEATURE:
<223> OTHER INFORMATION: Synthetic peptide

<400> SEQUENCE: 393

Arg Gly Val Val Ser Ala Lys
1 5

<210> SEQ ID NO 394
<211> LENGTH: 7
<212> TYPE: PRT
<213> ORGANISM: Artificial Sequence
<220> FEATURE:
<223> OTHER INFORMATION: Synthetic peptide

<400> SEQUENCE: 394

Arg Gly Val Val Ser Gly Val
1 5

<210> SEQ ID NO 395
<211> LENGTH: 7
<212> TYPE: PRT
<213> ORGANISM: Artificial Sequence
<220> FEATURE:
<223> OTHER INFORMATION: Synthetic peptide

<400> SEQUENCE: 395

Ala Val Gly Arg Gly Ser Gly
1 5

<210> SEQ ID NO 396
<211> LENGTH: 7
<212> TYPE: PRT
<213> ORGANISM: Artificial Sequence
<220> FEATURE:
<223> OTHER INFORMATION: Synthetic peptide

<400> SEQUENCE: 396

Ser Leu Arg Gly Ser Glu Gly
1 5

<210> SEQ ID NO 397

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 397

Pro Ala Thr Arg Gly Ser Val
1 5

<210> SEQ ID NO 398
<211> LENGTH: 7
<212> TYPE: PRT
<213> ORGANISM: Artificial Sequence
<220> FEATURE:
<223> OTHER INFORMATION: Synthetic peptide

<400> SEQUENCE: 398

Ser Leu Thr Arg Ala Val Arg
1 5

<210> SEQ ID NO 399
<211> LENGTH: 7
<212> TYPE: PRT
<213> ORGANISM: Artificial Sequence
<220> FEATURE:
<223> OTHER INFORMATION: Synthetic peptide

<400> SEQUENCE: 399

Val Ala Arg Ala Val Pro Cys
1 5

<210> SEQ ID NO 400
<211> LENGTH: 7
<212> TYPE: PRT
<213> ORGANISM: Artificial Sequence
<220> FEATURE:
<223> OTHER INFORMATION: Synthetic peptide

<400> SEQUENCE: 400

Glu Gly Ala Arg Ala Ser Asp
1 5

<210> SEQ ID NO 401
<211> LENGTH: 7
<212> TYPE: PRT
<213> ORGANISM: Artificial Sequence
<220> FEATURE:
<223> OTHER INFORMATION: Synthetic peptide

<400> SEQUENCE: 401

Met Gly Ser Ala Val Ser Leu
1 5

<210> SEQ ID NO 402
<211> LENGTH: 7
<212> TYPE: PRT
<213> ORGANISM: Artificial Sequence
<220> FEATURE:
<223> OTHER INFORMATION: Synthetic peptide

<400> SEQUENCE: 402

Gly Gly Ala Leu Leu Arg Gly
1 5

<210> SEQ ID NO 403
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 403

Pro Asn Arg Arg Val Ser Ala
1 5

<210> SEQ ID NO 404
<211> LENGTH: 7
<212> TYPE: PRT
<213> ORGANISM: Artificial Sequence
<220> FEATURE:
<223> OTHER INFORMATION: Synthetic peptide

<400> SEQUENCE: 404

Gln Asp Arg Val Ser Arg Ser
1 5

<210> SEQ ID NO 405
<211> LENGTH: 7
<212> TYPE: PRT
<213> ORGANISM: Artificial Sequence
<220> FEATURE:
<223> OTHER INFORMATION: Synthetic peptide

<400> SEQUENCE: 405

Ser Glu Arg Ser Ser Leu Gly
1 5

<210> SEQ ID NO 406
<211> LENGTH: 7
<212> TYPE: PRT
<213> ORGANISM: Artificial Sequence
<220> FEATURE:
<223> OTHER INFORMATION: Synthetic peptide

<400> SEQUENCE: 406

Leu Val Arg Ser Ser Gly Leu
1 5

<210> SEQ ID NO 407
<211> LENGTH: 7
<212> TYPE: PRT
<213> ORGANISM: Artificial Sequence
<220> FEATURE:
<223> OTHER INFORMATION: Synthetic peptide

<400> SEQUENCE: 407

Ile Asn Trp Ala Gly Leu Ser
1 5

<210> SEQ ID NO 408
<211> LENGTH: 7
<212> TYPE: PRT
<213> ORGANISM: Artificial Sequence
<220> FEATURE:
<223> OTHER INFORMATION: Synthetic peptide

<400> SEQUENCE: 408

Trp Ala Gly Leu Ser Pro Ser
1 5

<210> SEQ ID NO 409
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 409

Gly Arg Leu Leu Ala Gly Gly
1 5

<210> SEQ ID NO 410
<211> LENGTH: 7
<212> TYPE: PRT
<213> ORGANISM: Artificial Sequence
<220> FEATURE:
<223> OTHER INFORMATION: Synthetic peptide

<400> SEQUENCE: 410

Ser Tyr Gly Leu Val Leu Pro
1 5

<210> SEQ ID NO 411
<211> LENGTH: 7
<212> TYPE: PRT
<213> ORGANISM: Artificial Sequence
<220> FEATURE:
<223> OTHER INFORMATION: Synthetic peptide

<400> SEQUENCE: 411

Ser Gly Gly Leu Val Leu Thr
1 5

<210> SEQ ID NO 412
<211> LENGTH: 7
<212> TYPE: PRT
<213> ORGANISM: Artificial Sequence
<220> FEATURE:
<223> OTHER INFORMATION: Synthetic peptide

<400> SEQUENCE: 412

His Ala Ala His Gly Leu Val
1 5

<210> SEQ ID NO 413
<211> LENGTH: 7
<212> TYPE: PRT
<213> ORGANISM: Artificial Sequence
<220> FEATURE:
<223> OTHER INFORMATION: Synthetic peptide

<400> SEQUENCE: 413

Gly Leu Arg Thr Arg Gln Val
1 5

<210> SEQ ID NO 414
<211> LENGTH: 7
<212> TYPE: PRT
<213> ORGANISM: Artificial Sequence
<220> FEATURE:
<223> OTHER INFORMATION: Synthetic peptide

<400> SEQUENCE: 414

Leu Val Ser Gly Tyr Asn Gly
1 5

<210> SEQ ID NO 415
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 415

Ala Gly Ile Ala Arg Gly Gly
1               5

<210> SEQ ID NO 416
<211> LENGTH: 7
<212> TYPE: PRT
<213> ORGANISM: Artificial Sequence
<220> FEATURE:
<223> OTHER INFORMATION: Synthetic peptide

<400> SEQUENCE: 416

His Val Ser Gly Gly Ser Gly
1               5

<210> SEQ ID NO 417
<211> LENGTH: 7
<212> TYPE: PRT
<213> ORGANISM: Artificial Sequence
<220> FEATURE:
<223> OTHER INFORMATION: Synthetic peptide

<400> SEQUENCE: 417

Gly Gly Ser Ser Glu Phe Arg
1               5

<210> SEQ ID NO 418
<211> LENGTH: 7
<212> TYPE: PRT
<213> ORGANISM: Artificial Sequence
<220> FEATURE:
<223> OTHER INFORMATION: Synthetic peptide

<400> SEQUENCE: 418

Gly Gly Ser Gly Ile Gly Ser
1               5

<210> SEQ ID NO 419
<211> LENGTH: 7
<212> TYPE: PRT
<213> ORGANISM: Artificial Sequence
<220> FEATURE:
<223> OTHER INFORMATION: Synthetic peptide

<400> SEQUENCE: 419

Ser Trp Gly Ser Gly Gly Ser
1               5

<210> SEQ ID NO 420
<211> LENGTH: 7
<212> TYPE: PRT
<213> ORGANISM: Artificial Sequence
<220> FEATURE:
<223> OTHER INFORMATION: Synthetic peptide

<400> SEQUENCE: 420

Thr Leu Val Leu Gly Gly Ser
1               5

<210> SEQ ID NO 421
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 421

Ala Val Arg Gly Gly Arg Pro
1               5

<210> SEQ ID NO 422
<211> LENGTH: 7
<212> TYPE: PRT
<213> ORGANISM: Artificial Sequence
<220> FEATURE:
<223> OTHER INFORMATION: Synthetic peptide

<400> SEQUENCE: 422

Gly Gly Arg Ala Ile Gly Ala
1               5

<210> SEQ ID NO 423
<211> LENGTH: 7
<212> TYPE: PRT
<213> ORGANISM: Artificial Sequence
<220> FEATURE:
<223> OTHER INFORMATION: Synthetic peptide

<400> SEQUENCE: 423

Ser Gly Gly Leu Val Leu Thr
1               5

<210> SEQ ID NO 424
<211> LENGTH: 7
<212> TYPE: PRT
<213> ORGANISM: Artificial Sequence
<220> FEATURE:
<223> OTHER INFORMATION: Synthetic peptide

<400> SEQUENCE: 424

Arg Thr Gly Ser Ser Asp Leu
1               5

<210> SEQ ID NO 425
<211> LENGTH: 7
<212> TYPE: PRT
<213> ORGANISM: Artificial Sequence
<220> FEATURE:
<223> OTHER INFORMATION: Synthetic peptide

<400> SEQUENCE: 425

Leu Gly Ser Ser Arg Val Leu
1               5

<210> SEQ ID NO 426
<211> LENGTH: 7
<212> TYPE: PRT
<213> ORGANISM: Artificial Sequence
<220> FEATURE:
<223> OTHER INFORMATION: Synthetic peptide

<400> SEQUENCE: 426

Gly Gly Ser Ser Glu Phe Arg
1               5

<210> SEQ ID NO 427
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 427

Ala Val Gly Arg Gly Ser Gly
1 5

<210> SEQ ID NO 428
<211> LENGTH: 7
<212> TYPE: PRT
<213> ORGANISM: Artificial Sequence
<220> FEATURE:
<223> OTHER INFORMATION: Synthetic peptide

<400> SEQUENCE: 428

His Val Ser Gly Gly Ser Gly
1 5

<210> SEQ ID NO 429
<211> LENGTH: 7
<212> TYPE: PRT
<213> ORGANISM: Artificial Sequence
<220> FEATURE:
<223> OTHER INFORMATION: Synthetic peptide

<400> SEQUENCE: 429

Ser Gly Ile Gly Ser Gly Gly
1 5

<210> SEQ ID NO 430
<211> LENGTH: 7
<212> TYPE: PRT
<213> ORGANISM: Artificial Sequence
<220> FEATURE:
<223> OTHER INFORMATION: Synthetic peptide

<400> SEQUENCE: 430

Ser Trp Gly Ser Gly Gly Ser
1 5

<210> SEQ ID NO 431
<211> LENGTH: 7
<212> TYPE: PRT
<213> ORGANISM: Artificial Sequence
<220> FEATURE:
<223> OTHER INFORMATION: Synthetic peptide

<400> SEQUENCE: 431

Trp Val Gly Ser Gly Ser Pro
1 5

<210> SEQ ID NO 432
<211> LENGTH: 7
<212> TYPE: PRT
<213> ORGANISM: Artificial Sequence
<220> FEATURE:
<223> OTHER INFORMATION: Synthetic peptide

<400> SEQUENCE: 432

Gly Ser Gly Gly Ser Val His
1 5

<210> SEQ ID NO 433
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 433

Gly Asn Tyr Gly Ser Val Leu
1               5

<210> SEQ ID NO 434
<211> LENGTH: 7
<212> TYPE: PRT
<213> ORGANISM: Artificial Sequence
<220> FEATURE:
<223> OTHER INFORMATION: Synthetic peptide

<400> SEQUENCE: 434

Val Gly Ser Val Val Gly Arg
1               5

<210> SEQ ID NO 435
<211> LENGTH: 7
<212> TYPE: PRT
<213> ORGANISM: Artificial Sequence
<220> FEATURE:
<223> OTHER INFORMATION: Synthetic peptide

<400> SEQUENCE: 435

Pro Ala Thr Arg Gly Ser Val
1               5

<210> SEQ ID NO 436
<211> LENGTH: 7
<212> TYPE: PRT
<213> ORGANISM: Artificial Sequence
<220> FEATURE:
<223> OTHER INFORMATION: Synthetic peptide

<400> SEQUENCE: 436

Pro Arg Gly Gly Arg Val Ala
1               5

<210> SEQ ID NO 437
<211> LENGTH: 7
<212> TYPE: PRT
<213> ORGANISM: Artificial Sequence
<220> FEATURE:
<223> OTHER INFORMATION: Synthetic peptide

<400> SEQUENCE: 437

Gly Arg Val His Leu Met Pro
1               5

<210> SEQ ID NO 438
<211> LENGTH: 7
<212> TYPE: PRT
<213> ORGANISM: Artificial Sequence
<220> FEATURE:
<223> OTHER INFORMATION: Synthetic peptide

<400> SEQUENCE: 438

Gly Glu Ser Gly Arg Leu Ser
1               5

<210> SEQ ID NO 439
<211> LENGTH: 7
<212> TYPE: PRT
<213> ORGANISM: Artificial Sequence
<220> FEATURE:
<223> OTHER INFORMATION: Synthetic peptide

<400> SEQUENCE: 439

-continued

Gly Arg Leu Leu Ala Gly Gly
1 5

<210> SEQ ID NO 440
<211> LENGTH: 7
<212> TYPE: PRT
<213> ORGANISM: Artificial Sequence
<220> FEATURE:
<223> OTHER INFORMATION: Synthetic peptide

<400> SEQUENCE: 440

Gly Arg Leu Trp Trp His Thr
1 5

<210> SEQ ID NO 441
<211> LENGTH: 7
<212> TYPE: PRT
<213> ORGANISM: Artificial Sequence
<220> FEATURE:
<223> OTHER INFORMATION: Synthetic peptide

<400> SEQUENCE: 441

Gly Arg Leu Trp Ser Arg Val
1 5

<210> SEQ ID NO 442
<211> LENGTH: 7
<212> TYPE: PRT
<213> ORGANISM: Artificial Sequence
<220> FEATURE:
<223> OTHER INFORMATION: Synthetic peptide

<400> SEQUENCE: 442

Ala Gly Pro Ser Ala Trp Leu
1 5

<210> SEQ ID NO 443
<211> LENGTH: 7
<212> TYPE: PRT
<213> ORGANISM: Artificial Sequence
<220> FEATURE:
<223> OTHER INFORMATION: Synthetic peptide

<400> SEQUENCE: 443

Ser Gly Val Ser Arg Gly Gln
1 5

<210> SEQ ID NO 444
<211> LENGTH: 7
<212> TYPE: PRT
<213> ORGANISM: Artificial Sequence
<220> FEATURE:
<223> OTHER INFORMATION: Synthetic peptide

<400> SEQUENCE: 444

Arg Gly Val Ser Leu Lys Gly
1 5

<210> SEQ ID NO 445
<211> LENGTH: 7
<212> TYPE: PRT
<213> ORGANISM: Artificial Sequence
<220> FEATURE:
<223> OTHER INFORMATION: Synthetic peptide

<400> SEQUENCE: 445

-continued

Gln Met Gln Gly Arg Ala Val
1 5

<210> SEQ ID NO 446
<211> LENGTH: 7
<212> TYPE: PRT
<213> ORGANISM: Artificial Sequence
<220> FEATURE:
<223> OTHER INFORMATION: Synthetic peptide

<400> SEQUENCE: 446

Arg Gly Leu Arg Ser Val Asn
1 5

<210> SEQ ID NO 447
<211> LENGTH: 7
<212> TYPE: PRT
<213> ORGANISM: Artificial Sequence
<220> FEATURE:
<223> OTHER INFORMATION: Synthetic peptide

<400> SEQUENCE: 447

Arg Ser Ser Leu Gly Leu Pro
1 5

<210> SEQ ID NO 448
<211> LENGTH: 7
<212> TYPE: PRT
<213> ORGANISM: Artificial Sequence
<220> FEATURE:
<223> OTHER INFORMATION: Synthetic peptide

<400> SEQUENCE: 448

Leu Glu Ala Gly Ser Gln Leu
1 5

<210> SEQ ID NO 449
<211> LENGTH: 7
<212> TYPE: PRT
<213> ORGANISM: Artificial Sequence
<220> FEATURE:
<223> OTHER INFORMATION: Synthetic peptide

<400> SEQUENCE: 449

Ala Gly Gly Gln Ser Glu Arg
1 5

<210> SEQ ID NO 450
<211> LENGTH: 7
<212> TYPE: PRT
<213> ORGANISM: Artificial Sequence
<220> FEATURE:
<223> OTHER INFORMATION: Synthetic peptide

<400> SEQUENCE: 450

Gly Gly Val Leu Tyr Leu Glu
1 5

<210> SEQ ID NO 451
<211> LENGTH: 7
<212> TYPE: PRT
<213> ORGANISM: Artificial Sequence
<220> FEATURE:
<223> OTHER INFORMATION: Synthetic peptide

<400> SEQUENCE: 451

Arg Gly Leu Arg Ser Val Asn

-continued 1 5

<210> SEQ ID NO 452
<211> LENGTH: 7
<212> TYPE: PRT
<213> ORGANISM: Artificial Sequence
<220> FEATURE:
<223> OTHER INFORMATION: Synthetic peptide

<400> SEQUENCE: 452

Val Ala Arg Gly Gln Met Gln
1 5

<210> SEQ ID NO 453
<211> LENGTH: 7
<212> TYPE: PRT
<213> ORGANISM: Artificial Sequence
<220> FEATURE:
<223> OTHER INFORMATION: Synthetic peptide

<400> SEQUENCE: 453

Gly Gly Ser Arg Asn Arg Trp
1 5

<210> SEQ ID NO 454
<211> LENGTH: 7
<212> TYPE: PRT
<213> ORGANISM: Artificial Sequence
<220> FEATURE:
<223> OTHER INFORMATION: Synthetic peptide

<400> SEQUENCE: 454

Gly Gly Gly Arg Ser Gly Val
1 5

<210> SEQ ID NO 455
<211> LENGTH: 7
<212> TYPE: PRT
<213> ORGANISM: Artificial Sequence
<220> FEATURE:
<223> OTHER INFORMATION: Synthetic peptide

<400> SEQUENCE: 455

Gly Leu Gly Gly Trp Val Ala
1 5

<210> SEQ ID NO 456
<211> LENGTH: 7
<212> TYPE: PRT
<213> ORGANISM: Artificial Sequence
<220> FEATURE:
<223> OTHER INFORMATION: Synthetic peptide

<400> SEQUENCE: 456

Ala Val Trp Gly Gly Leu Gly
1 5

<210> SEQ ID NO 457
<211> LENGTH: 7
<212> TYPE: PRT
<213> ORGANISM: Artificial Sequence
<220> FEATURE:
<223> OTHER INFORMATION: Synthetic peptide

<400> SEQUENCE: 457

Gly Gly Leu Ser Glu Cys Val
1 5

<210> SEQ ID NO 458
<211> LENGTH: 7
<212> TYPE: PRT
<213> ORGANISM: Artificial Sequence
<220> FEATURE:
<223> OTHER INFORMATION: Synthetic peptide

<400> SEQUENCE: 458

Ala Lys Leu Gly Ser Val Tyr
1 5

<210> SEQ ID NO 459
<211> LENGTH: 7
<212> TYPE: PRT
<213> ORGANISM: Artificial Sequence
<220> FEATURE:
<223> OTHER INFORMATION: Synthetic peptide

<400> SEQUENCE: 459

Gln Gly Arg Val Asn Val Lys
1 5

<210> SEQ ID NO 460
<211> LENGTH: 7
<212> TYPE: PRT
<213> ORGANISM: Artificial Sequence
<220> FEATURE:
<223> OTHER INFORMATION: Synthetic peptide

<400> SEQUENCE: 460

Gly Arg Leu Trp Gly Phe Trp
1 5

<210> SEQ ID NO 461
<211> LENGTH: 7
<212> TYPE: PRT
<213> ORGANISM: Artificial Sequence
<220> FEATURE:
<223> OTHER INFORMATION: Synthetic peptide

<400> SEQUENCE: 461

Arg Gly Val Ser Leu Lys Gly
1 5

<210> SEQ ID NO 462
<211> LENGTH: 7
<212> TYPE: PRT
<213> ORGANISM: Artificial Sequence
<220> FEATURE:
<223> OTHER INFORMATION: Synthetic peptide

<400> SEQUENCE: 462

Gly Ser Leu Gly Val Ser Leu
1 5

<210> SEQ ID NO 463
<211> LENGTH: 7
<212> TYPE: PRT
<213> ORGANISM: Artificial Sequence
<220> FEATURE:
<223> OTHER INFORMATION: Synthetic peptide

<400> SEQUENCE: 463

Leu Leu Arg Leu Ser Leu Ala
1 5

-continued

<210> SEQ ID NO 464
<211> LENGTH: 7
<212> TYPE: PRT
<213> ORGANISM: Artificial Sequence
<220> FEATURE:
<223> OTHER INFORMATION: Synthetic peptide

<400> SEQUENCE: 464

Arg Arg Gly Ser Gly Gly Leu
1 5

<210> SEQ ID NO 465
<211> LENGTH: 7
<212> TYPE: PRT
<213> ORGANISM: Artificial Sequence
<220> FEATURE:
<223> OTHER INFORMATION: Synthetic peptide

<400> SEQUENCE: 465

Val Arg Gly Ser Val Arg Ala
1 5

<210> SEQ ID NO 466
<211> LENGTH: 7
<212> TYPE: PRT
<213> ORGANISM: Artificial Sequence
<220> FEATURE:
<223> OTHER INFORMATION: Synthetic peptide

<400> SEQUENCE: 466

Leu Leu Arg Leu Ser Leu Ala
1 5

<210> SEQ ID NO 467
<211> LENGTH: 7
<212> TYPE: PRT
<213> ORGANISM: Artificial Sequence
<220> FEATURE:
<223> OTHER INFORMATION: Synthetic peptide

<400> SEQUENCE: 467

Pro Leu Arg Val Asp Asn Leu
1 5

<210> SEQ ID NO 468
<211> LENGTH: 7
<212> TYPE: PRT
<213> ORGANISM: Artificial Sequence
<220> FEATURE:
<223> OTHER INFORMATION: Synthetic peptide

<400> SEQUENCE: 468

Leu Arg Val Gly Ile Gly Tyr
1 5

<210> SEQ ID NO 469
<211> LENGTH: 7
<212> TYPE: PRT
<213> ORGANISM: Artificial Sequence
<220> FEATURE:
<223> OTHER INFORMATION: Synthetic peptide

<400> SEQUENCE: 469

Gln Gly Tyr Ala Leu Arg Val
1 5

-continued

<210> SEQ ID NO 470
<211> LENGTH: 7
<212> TYPE: PRT
<213> ORGANISM: Artificial Sequence
<220> FEATURE:
<223> OTHER INFORMATION: Synthetic peptide

<400> SEQUENCE: 470

Pro Leu Arg Ser Phe Asp Ser
1 5

<210> SEQ ID NO 471
<211> LENGTH: 7
<212> TYPE: PRT
<213> ORGANISM: Artificial Sequence
<220> FEATURE:
<223> OTHER INFORMATION: Synthetic peptide

<400> SEQUENCE: 471

Ala Arg Val Ser Gly Arg Val
1 5

<210> SEQ ID NO 472
<211> LENGTH: 7
<212> TYPE: PRT
<213> ORGANISM: Artificial Sequence
<220> FEATURE:
<223> OTHER INFORMATION: Synthetic peptide

<400> SEQUENCE: 472

Pro Phe Pro Ala Arg Ser Ser
1 5

<210> SEQ ID NO 473
<211> LENGTH: 7
<212> TYPE: PRT
<213> ORGANISM: Artificial Sequence
<220> FEATURE:
<223> OTHER INFORMATION: Synthetic peptide

<400> SEQUENCE: 473

Ala Gly Ser Pro Leu Ala Lys
1 5

<210> SEQ ID NO 474
<211> LENGTH: 7
<212> TYPE: PRT
<213> ORGANISM: Artificial Sequence
<220> FEATURE:
<223> OTHER INFORMATION: Synthetic peptide

<400> SEQUENCE: 474

Phe Val Asp Ile Ala Gly Ser
1 5

<210> SEQ ID NO 475
<211> LENGTH: 7
<212> TYPE: PRT
<213> ORGANISM: Artificial Sequence
<220> FEATURE:
<223> OTHER INFORMATION: Synthetic peptide

<400> SEQUENCE: 475

Ser Tyr Phe Arg Ala Gly Arg
1 5

<210> SEQ ID NO 476

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 476

Ala Gly Leu Gly His Glu Gly
1               5

<210> SEQ ID NO 477
<211> LENGTH: 7
<212> TYPE: PRT
<213> ORGANISM: Artificial Sequence
<220> FEATURE:
<223> OTHER INFORMATION: Synthetic peptide

<400> SEQUENCE: 477

Ala Gly Gly Ser Leu Gly Ser
1               5

<210> SEQ ID NO 478
<211> LENGTH: 7
<212> TYPE: PRT
<213> ORGANISM: Artificial Sequence
<220> FEATURE:
<223> OTHER INFORMATION: Synthetic peptide

<400> SEQUENCE: 478

Tyr Gly Ile Gly Val Arg Leu
1               5

<210> SEQ ID NO 479
<211> LENGTH: 7
<212> TYPE: PRT
<213> ORGANISM: Artificial Sequence
<220> FEATURE:
<223> OTHER INFORMATION: Synthetic peptide

<400> SEQUENCE: 479

Arg Ala Asn Gly Val Leu Val
1               5

<210> SEQ ID NO 480
<211> LENGTH: 7
<212> TYPE: PRT
<213> ORGANISM: Artificial Sequence
<220> FEATURE:
<223> OTHER INFORMATION: Synthetic peptide

<400> SEQUENCE: 480

Leu Ala Ser Leu Gly Val Gly
1               5

<210> SEQ ID NO 481
<211> LENGTH: 7
<212> TYPE: PRT
<213> ORGANISM: Artificial Sequence
<220> FEATURE:
<223> OTHER INFORMATION: Synthetic peptide

<400> SEQUENCE: 481

Arg Ala Ala Val Gly Ala Arg
1               5

<210> SEQ ID NO 482
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 482

Gly Cys Asp Gly Gly Ser Ala
1 5

<210> SEQ ID NO 483
<211> LENGTH: 7
<212> TYPE: PRT
<213> ORGANISM: Artificial Sequence
<220> FEATURE:
<223> OTHER INFORMATION: Synthetic peptide

<400> SEQUENCE: 483

Gly Gly Ser Gly Glu Leu Gly
1 5

<210> SEQ ID NO 484
<211> LENGTH: 7
<212> TYPE: PRT
<213> ORGANISM: Artificial Sequence
<220> FEATURE:
<223> OTHER INFORMATION: Synthetic peptide

<400> SEQUENCE: 484

Leu Gly Gly Ser Gly Arg Arg
1 5

<210> SEQ ID NO 485
<211> LENGTH: 7
<212> TYPE: PRT
<213> ORGANISM: Artificial Sequence
<220> FEATURE:
<223> OTHER INFORMATION: Synthetic peptide

<400> SEQUENCE: 485

Ala Gly Gly Ser Leu Gly Ser
1 5

<210> SEQ ID NO 486
<211> LENGTH: 7
<212> TYPE: PRT
<213> ORGANISM: Artificial Sequence
<220> FEATURE:
<223> OTHER INFORMATION: Synthetic peptide

<400> SEQUENCE: 486

Ile Gly Gly Arg Glu Ile Thr
1 5

<210> SEQ ID NO 487
<211> LENGTH: 7
<212> TYPE: PRT
<213> ORGANISM: Artificial Sequence
<220> FEATURE:
<223> OTHER INFORMATION: Synthetic peptide

<400> SEQUENCE: 487

Gly Glu His Gly Leu Gly Ala
1 5

<210> SEQ ID NO 488
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 488

Arg Arg Gly Ser Gly Gly Leu
1 5

<210> SEQ ID NO 489
<211> LENGTH: 7
<212> TYPE: PRT
<213> ORGANISM: Artificial Sequence
<220> FEATURE:
<223> OTHER INFORMATION: Synthetic peptide

<400> SEQUENCE: 489

Arg Ser Gly Ser Ser Val Tyr
1 5

<210> SEQ ID NO 490
<211> LENGTH: 7
<212> TYPE: PRT
<213> ORGANISM: Artificial Sequence
<220> FEATURE:
<223> OTHER INFORMATION: Synthetic peptide

<400> SEQUENCE: 490

Gly Leu Glu Gly Ser Gly Gly
1 5

<210> SEQ ID NO 491
<211> LENGTH: 7
<212> TYPE: PRT
<213> ORGANISM: Artificial Sequence
<220> FEATURE:
<223> OTHER INFORMATION: Synthetic peptide

<400> SEQUENCE: 491

Leu Gly Gly Ser Gly Arg Arg
1 5

<210> SEQ ID NO 492
<211> LENGTH: 7
<212> TYPE: PRT
<213> ORGANISM: Artificial Sequence
<220> FEATURE:
<223> OTHER INFORMATION: Synthetic peptide

<400> SEQUENCE: 492

Thr Thr Gly Ser Val Ile Val
1 5

<210> SEQ ID NO 493
<211> LENGTH: 7
<212> TYPE: PRT
<213> ORGANISM: Artificial Sequence
<220> FEATURE:
<223> OTHER INFORMATION: Synthetic peptide

<400> SEQUENCE: 493

Val Arg Gly Ser Val Arg Ala
1 5

<210> SEQ ID NO 494
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 494

His Gly Arg Val His Arg Leu
1 5

<210> SEQ ID NO 495
<211> LENGTH: 7
<212> TYPE: PRT
<213> ORGANISM: Artificial Sequence
<220> FEATURE:
<223> OTHER INFORMATION: Synthetic peptide

<400> SEQUENCE: 495

Ala Arg Val Ser Gly Arg Val
1 5

<210> SEQ ID NO 496
<211> LENGTH: 7
<212> TYPE: PRT
<213> ORGANISM: Artificial Sequence
<220> FEATURE:
<223> OTHER INFORMATION: Synthetic peptide

<400> SEQUENCE: 496

Ser Gly His Gly Val Ser Ala
1 5

<210> SEQ ID NO 497
<211> LENGTH: 7
<212> TYPE: PRT
<213> ORGANISM: Artificial Sequence
<220> FEATURE:
<223> OTHER INFORMATION: Synthetic peptide

<400> SEQUENCE: 497

Ala Val Trp Arg Leu Ser His
1 5

<210> SEQ ID NO 498
<211> LENGTH: 7
<212> TYPE: PRT
<213> ORGANISM: Artificial Sequence
<220> FEATURE:
<223> OTHER INFORMATION: Synthetic peptide

<400> SEQUENCE: 498

Arg Gly Val Phe Tyr Gly Lys
1 5

<210> SEQ ID NO 499
<211> LENGTH: 7
<212> TYPE: PRT
<213> ORGANISM: Artificial Sequence
<220> FEATURE:
<223> OTHER INFORMATION: Synthetic peptide

<400> SEQUENCE: 499

Arg Gly Val Gly Trp Ala Lys
1 5

<210> SEQ ID NO 500
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 500

Ser Arg Gly Ser Thr Ala Gly
1 5

<210> SEQ ID NO 501
<211> LENGTH: 7
<212> TYPE: PRT
<213> ORGANISM: Artificial Sequence
<220> FEATURE:
<223> OTHER INFORMATION: Synthetic peptide

<400> SEQUENCE: 501

Ser Glu Asp Glu Gly Ala Gly
1 5

<210> SEQ ID NO 502
<211> LENGTH: 7
<212> TYPE: PRT
<213> ORGANISM: Artificial Sequence
<220> FEATURE:
<223> OTHER INFORMATION: Synthetic peptide

<400> SEQUENCE: 502

Ser Thr Ser Leu Gly Ala Gly
1 5

<210> SEQ ID NO 503
<211> LENGTH: 7
<212> TYPE: PRT
<213> ORGANISM: Artificial Sequence
<220> FEATURE:
<223> OTHER INFORMATION: Synthetic peptide

<400> SEQUENCE: 503

Asp Leu Leu Arg Tyr Leu Ala
1 5

<210> SEQ ID NO 504
<211> LENGTH: 7
<212> TYPE: PRT
<213> ORGANISM: Artificial Sequence
<220> FEATURE:
<223> OTHER INFORMATION: Synthetic peptide

<400> SEQUENCE: 504

Leu Arg Val Arg Tyr Ala Val
1 5

<210> SEQ ID NO 505
<211> LENGTH: 7
<212> TYPE: PRT
<213> ORGANISM: Artificial Sequence
<220> FEATURE:
<223> OTHER INFORMATION: Synthetic peptide

<400> SEQUENCE: 505

Leu Arg Ser Ser Gly Ala Thr
1 5

<210> SEQ ID NO 506
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 506

Leu Ser Met Leu Arg Ser Ala
1 5

<210> SEQ ID NO 507
<211> LENGTH: 7
<212> TYPE: PRT
<213> ORGANISM: Artificial Sequence
<220> FEATURE:
<223> OTHER INFORMATION: Synthetic peptide

<400> SEQUENCE: 507

Arg Glu Ala Glu Arg Val Ser
1 5

<210> SEQ ID NO 508
<211> LENGTH: 7
<212> TYPE: PRT
<213> ORGANISM: Artificial Sequence
<220> FEATURE:
<223> OTHER INFORMATION: Synthetic peptide

<400> SEQUENCE: 508

Leu Arg Ser Ser Gly Ala Thr
1 5

<210> SEQ ID NO 509
<211> LENGTH: 7
<212> TYPE: PRT
<213> ORGANISM: Artificial Sequence
<220> FEATURE:
<223> OTHER INFORMATION: Synthetic peptide

<400> SEQUENCE: 509

Thr Ala Gly Ser Ser Arg Leu
1 5

<210> SEQ ID NO 510
<211> LENGTH: 7
<212> TYPE: PRT
<213> ORGANISM: Artificial Sequence
<220> FEATURE:
<223> OTHER INFORMATION: Synthetic peptide

<400> SEQUENCE: 510

Ala Ala Gly Arg Ala Gly Cys
1 5

<210> SEQ ID NO 511
<211> LENGTH: 7
<212> TYPE: PRT
<213> ORGANISM: Artificial Sequence
<220> FEATURE:
<223> OTHER INFORMATION: Synthetic peptide

<400> SEQUENCE: 511

Gly Ala Gly Leu Ser Thr Ser
1 5

<210> SEQ ID NO 512
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 512

Pro Ser Val Gly Val Arg Ala
1 5

<210> SEQ ID NO 513
<211> LENGTH: 7
<212> TYPE: PRT
<213> ORGANISM: Artificial Sequence
<220> FEATURE:
<223> OTHER INFORMATION: Synthetic peptide

<400> SEQUENCE: 513

Val Gly Ala Val Tyr Phe Leu
1 5

<210> SEQ ID NO 514
<211> LENGTH: 7
<212> TYPE: PRT
<213> ORGANISM: Artificial Sequence
<220> FEATURE:
<223> OTHER INFORMATION: Synthetic peptide

<400> SEQUENCE: 514

Leu Gly Leu Arg Ala Phe Val
1 5

<210> SEQ ID NO 515
<211> LENGTH: 7
<212> TYPE: PRT
<213> ORGANISM: Artificial Sequence
<220> FEATURE:
<223> OTHER INFORMATION: Synthetic peptide

<400> SEQUENCE: 515

Thr Glu Leu Val Ser Trp Ser
1 5

<210> SEQ ID NO 516
<211> LENGTH: 7
<212> TYPE: PRT
<213> ORGANISM: Artificial Sequence
<220> FEATURE:
<223> OTHER INFORMATION: Synthetic peptide

<400> SEQUENCE: 516

Cys Gly Ala Arg Gly Ala Ala
1 5

<210> SEQ ID NO 517
<211> LENGTH: 7
<212> TYPE: PRT
<213> ORGANISM: Artificial Sequence
<220> FEATURE:
<223> OTHER INFORMATION: Synthetic peptide

<400> SEQUENCE: 517

Gly Gly Ser Arg Ala Ala Glu
1 5

<210> SEQ ID NO 518
<211> LENGTH: 7
<212> TYPE: PRT
<213> ORGANISM: Artificial Sequence
<220> FEATURE:
<223> OTHER INFORMATION: Synthetic peptide

<400> SEQUENCE: 518

Val Asn Leu Gly Gly Ser Trp
1 5

<210> SEQ ID NO 519
<211> LENGTH: 7
<212> TYPE: PRT
<213> ORGANISM: Artificial Sequence
<220> FEATURE:
<223> OTHER INFORMATION: Synthetic peptide

<400> SEQUENCE: 519

Leu Ile Gly Pro Gly Gly Arg
1 5

<210> SEQ ID NO 520
<211> LENGTH: 7
<212> TYPE: PRT
<213> ORGANISM: Artificial Sequence
<220> FEATURE:
<223> OTHER INFORMATION: Synthetic peptide

<400> SEQUENCE: 520

Leu Gly Gly Leu Ser Pro His
1 5

<210> SEQ ID NO 521
<211> LENGTH: 7
<212> TYPE: PRT
<213> ORGANISM: Artificial Sequence
<220> FEATURE:
<223> OTHER INFORMATION: Synthetic peptide

<400> SEQUENCE: 521

Trp Ser Gly Gly Leu Asn Val
1 5

<210> SEQ ID NO 522
<211> LENGTH: 7
<212> TYPE: PRT
<213> ORGANISM: Artificial Sequence
<220> FEATURE:
<223> OTHER INFORMATION: Synthetic peptide

<400> SEQUENCE: 522

Thr Ala Gly Ser Ser Arg Leu
1 5

<210> SEQ ID NO 523
<211> LENGTH: 7
<212> TYPE: PRT
<213> ORGANISM: Artificial Sequence
<220> FEATURE:
<223> OTHER INFORMATION: Synthetic peptide

<400> SEQUENCE: 523

Ser Asp Val Ser Gly Ser Ser
1 5

<210> SEQ ID NO 524
<211> LENGTH: 7
<212> TYPE: PRT
<213> ORGANISM: Artificial Sequence
<220> FEATURE:
<223> OTHER INFORMATION: Synthetic peptide

<400> SEQUENCE: 524

-continued

Trp Gly Ser Ser Thr Val Arg
1 5

<210> SEQ ID NO 525
<211> LENGTH: 7
<212> TYPE: PRT
<213> ORGANISM: Artificial Sequence
<220> FEATURE:
<223> OTHER INFORMATION: Synthetic peptide

<400> SEQUENCE: 525

Asn Leu Ala Asp Gly Ser Val
1 5

<210> SEQ ID NO 526
<211> LENGTH: 7
<212> TYPE: PRT
<213> ORGANISM: Artificial Sequence
<220> FEATURE:
<223> OTHER INFORMATION: Synthetic peptide

<400> SEQUENCE: 526

Ser Ser Gly Ser Val Asp Ser
1 5

<210> SEQ ID NO 527
<211> LENGTH: 7
<212> TYPE: PRT
<213> ORGANISM: Artificial Sequence
<220> FEATURE:
<223> OTHER INFORMATION: Synthetic peptide

<400> SEQUENCE: 527

Gly Arg Val Pro Gly Phe Glu
1 5

<210> SEQ ID NO 528
<211> LENGTH: 7
<212> TYPE: PRT
<213> ORGANISM: Artificial Sequence
<220> FEATURE:
<223> OTHER INFORMATION: Synthetic peptide

<400> SEQUENCE: 528

Gly Arg Val Val Gly Glu Ala
1 5

<210> SEQ ID NO 529
<211> LENGTH: 7
<212> TYPE: PRT
<213> ORGANISM: Artificial Sequence
<220> FEATURE:
<223> OTHER INFORMATION: Synthetic peptide

<400> SEQUENCE: 529

Ser Arg Phe Gly Pro Ser Val
1 5

<210> SEQ ID NO 530
<211> LENGTH: 7
<212> TYPE: PRT
<213> ORGANISM: Artificial Sequence
<220> FEATURE:
<223> OTHER INFORMATION: Synthetic peptide

<400> SEQUENCE: 530

Ala Arg Val Gly Val Ser Pro

-continued 1 5

<210> SEQ ID NO 531
<211> LENGTH: 7
<212> TYPE: PRT
<213> ORGANISM: Artificial Sequence
<220> FEATURE:
<223> OTHER INFORMATION: Synthetic peptide

<400> SEQUENCE: 531

Pro Gly Lys Arg Gly Val Gln
1 5

<210> SEQ ID NO 532
<211> LENGTH: 7
<212> TYPE: PRT
<213> ORGANISM: Artificial Sequence
<220> FEATURE:
<223> OTHER INFORMATION: Synthetic peptide

<400> SEQUENCE: 532

Arg Gly Val Ala Ser Arg Ser
1 5

<210> SEQ ID NO 533
<211> LENGTH: 7
<212> TYPE: PRT
<213> ORGANISM: Artificial Sequence
<220> FEATURE:
<223> OTHER INFORMATION: Synthetic peptide

<400> SEQUENCE: 533

Glu Arg Gly Ser Pro Ser Arg
1 5

<210> SEQ ID NO 534
<211> LENGTH: 7
<212> TYPE: PRT
<213> ORGANISM: Artificial Sequence
<220> FEATURE:
<223> OTHER INFORMATION: Synthetic peptide

<400> SEQUENCE: 534

Leu Ile Arg Ala Val Ser Ala
1 5

<210> SEQ ID NO 535
<211> LENGTH: 7
<212> TYPE: PRT
<213> ORGANISM: Artificial Sequence
<220> FEATURE:
<223> OTHER INFORMATION: Synthetic peptide

<400> SEQUENCE: 535

Arg Ala Val Glu Met Gly Thr
1 5

<210> SEQ ID NO 536
<211> LENGTH: 7
<212> TYPE: PRT
<213> ORGANISM: Artificial Sequence
<220> FEATURE:
<223> OTHER INFORMATION: Synthetic peptide

<400> SEQUENCE: 536

Trp Gly Ala Gly Phe Trp Met
1 5

-continued

<210> SEQ ID NO 537
<211> LENGTH: 7
<212> TYPE: PRT
<213> ORGANISM: Artificial Sequence
<220> FEATURE:
<223> OTHER INFORMATION: Synthetic peptide

<400> SEQUENCE: 537

Leu Ile Arg Ala Val Ser Ala
1               5

<210> SEQ ID NO 538
<211> LENGTH: 7
<212> TYPE: PRT
<213> ORGANISM: Artificial Sequence
<220> FEATURE:
<223> OTHER INFORMATION: Synthetic peptide

<400> SEQUENCE: 538

Asp Arg Tyr Met Leu Arg Ser
1               5

<210> SEQ ID NO 539
<211> LENGTH: 7
<212> TYPE: PRT
<213> ORGANISM: Artificial Sequence
<220> FEATURE:
<223> OTHER INFORMATION: Synthetic peptide

<400> SEQUENCE: 539

Pro Arg Ser Ser Tyr Asn Glu
1               5

<210> SEQ ID NO 540
<211> LENGTH: 7
<212> TYPE: PRT
<213> ORGANISM: Artificial Sequence
<220> FEATURE:
<223> OTHER INFORMATION: Synthetic peptide

<400> SEQUENCE: 540

Pro Arg Ser Ser Leu Val Val
1               5

<210> SEQ ID NO 541
<211> LENGTH: 7
<212> TYPE: PRT
<213> ORGANISM: Artificial Sequence
<220> FEATURE:
<223> OTHER INFORMATION: Synthetic peptide

<400> SEQUENCE: 541

Arg Arg Phe Trp Ala Gly Leu
1               5

<210> SEQ ID NO 542
<211> LENGTH: 7
<212> TYPE: PRT
<213> ORGANISM: Artificial Sequence
<220> FEATURE:
<223> OTHER INFORMATION: Synthetic peptide

<400> SEQUENCE: 542

Pro Val His Ser Ala Gly Gly
1               5

<210> SEQ ID NO 543
<211> LENGTH: 7
<212> TYPE: PRT
<213> ORGANISM: Artificial Sequence
<220> FEATURE:
<223> OTHER INFORMATION: Synthetic peptide

<400> SEQUENCE: 543

Phe Gly Gly Ser Gly Val Leu
1 5

<210> SEQ ID NO 544
<211> LENGTH: 7
<212> TYPE: PRT
<213> ORGANISM: Artificial Sequence
<220> FEATURE:
<223> OTHER INFORMATION: Synthetic peptide

<400> SEQUENCE: 544

Ser Ser Gly Gly Val Leu Gly
1 5

<210> SEQ ID NO 545
<211> LENGTH: 7
<212> TYPE: PRT
<213> ORGANISM: Artificial Sequence
<220> FEATURE:
<223> OTHER INFORMATION: Synthetic peptide

<400> SEQUENCE: 545

Gly Leu Val Gly Gly Ser Ser
1 5

<210> SEQ ID NO 546
<211> LENGTH: 7
<212> TYPE: PRT
<213> ORGANISM: Artificial Sequence
<220> FEATURE:
<223> OTHER INFORMATION: Synthetic peptide

<400> SEQUENCE: 546

Leu Ser Ser Gly Leu Val Ser
1 5

<210> SEQ ID NO 547
<211> LENGTH: 7
<212> TYPE: PRT
<213> ORGANISM: Artificial Sequence
<220> FEATURE:
<223> OTHER INFORMATION: Synthetic peptide

<400> SEQUENCE: 547

Leu Ser Ser Gly Leu Val Ser
1 5

<210> SEQ ID NO 548
<211> LENGTH: 7
<212> TYPE: PRT
<213> ORGANISM: Artificial Sequence
<220> FEATURE:
<223> OTHER INFORMATION: Synthetic peptide

<400> SEQUENCE: 548

Trp Phe Ser Trp Leu Val Ser
1 5

-continued

<210> SEQ ID NO 549
<211> LENGTH: 7
<212> TYPE: PRT
<213> ORGANISM: Artificial Sequence
<220> FEATURE:
<223> OTHER INFORMATION: Synthetic peptide

<400> SEQUENCE: 549

Gly Ala Ser Leu Thr Gly Asp
1 5

<210> SEQ ID NO 550
<211> LENGTH: 7
<212> TYPE: PRT
<213> ORGANISM: Artificial Sequence
<220> FEATURE:
<223> OTHER INFORMATION: Synthetic peptide

<400> SEQUENCE: 550

Trp Ser Ser Thr Ala Ser Leu
1 5

<210> SEQ ID NO 551
<211> LENGTH: 7
<212> TYPE: PRT
<213> ORGANISM: Artificial Sequence
<220> FEATURE:
<223> OTHER INFORMATION: Synthetic peptide

<400> SEQUENCE: 551

Phe Gly Gly Ser Gly Val Leu
1 5

<210> SEQ ID NO 552
<211> LENGTH: 7
<212> TYPE: PRT
<213> ORGANISM: Artificial Sequence
<220> FEATURE:
<223> OTHER INFORMATION: Synthetic peptide

<400> SEQUENCE: 552

Gly Leu Val Gly Gly Ser Ser
1 5

<210> SEQ ID NO 553
<211> LENGTH: 7
<212> TYPE: PRT
<213> ORGANISM: Artificial Sequence
<220> FEATURE:
<223> OTHER INFORMATION: Synthetic peptide

<400> SEQUENCE: 553

Gly Gly Leu Ser Pro His Arg
1 5

<210> SEQ ID NO 554
<211> LENGTH: 7
<212> TYPE: PRT
<213> ORGANISM: Artificial Sequence
<220> FEATURE:
<223> OTHER INFORMATION: Synthetic peptide

<400> SEQUENCE: 554

Gly Leu Val Gly Gly Ser Ser
1 5

<210> SEQ ID NO 555

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 555

Ser Val Leu Gly Ser Ser Leu
1 5

<210> SEQ ID NO 556
<211> LENGTH: 7
<212> TYPE: PRT
<213> ORGANISM: Artificial Sequence
<220> FEATURE:
<223> OTHER INFORMATION: Synthetic peptide

<400> SEQUENCE: 556

Phe Gly Gly Ser Gly Val Leu
1 5

<210> SEQ ID NO 557
<211> LENGTH: 7
<212> TYPE: PRT
<213> ORGANISM: Artificial Sequence
<220> FEATURE:
<223> OTHER INFORMATION: Synthetic peptide

<400> SEQUENCE: 557

Asp Val Arg Gly Arg Val Trp
1 5

<210> SEQ ID NO 558
<211> LENGTH: 7
<212> TYPE: PRT
<213> ORGANISM: Artificial Sequence
<220> FEATURE:
<223> OTHER INFORMATION: Synthetic peptide

<400> SEQUENCE: 558

Ala Glu Pro Arg Gly Arg Val
1 5

<210> SEQ ID NO 559
<211> LENGTH: 7
<212> TYPE: PRT
<213> ORGANISM: Artificial Sequence
<220> FEATURE:
<223> OTHER INFORMATION: Synthetic peptide

<400> SEQUENCE: 559

Ser Ile Gly Pro Ser Thr Asn
1 5

<210> SEQ ID NO 560
<211> LENGTH: 7
<212> TYPE: PRT
<213> ORGANISM: Artificial Sequence
<220> FEATURE:
<223> OTHER INFORMATION: Synthetic peptide

<400> SEQUENCE: 560

Gly Val Ser Ile Arg Gln Leu
1 5

<210> SEQ ID NO 561
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 561

Ala Val Ser Lys Arg Leu Pro
1 5

<210> SEQ ID NO 562
<211> LENGTH: 7
<212> TYPE: PRT
<213> ORGANISM: Artificial Sequence
<220> FEATURE:
<223> OTHER INFORMATION: Synthetic peptide

<400> SEQUENCE: 562

Arg Leu Ala Val Ser Gly Tyr
1 5

<210> SEQ ID NO 563
<211> LENGTH: 7
<212> TYPE: PRT
<213> ORGANISM: Artificial Sequence
<220> FEATURE:
<223> OTHER INFORMATION: Synthetic peptide

<400> SEQUENCE: 563

Arg Arg Glu Gly Leu Arg Ser
1 5

<210> SEQ ID NO 564
<211> LENGTH: 7
<212> TYPE: PRT
<213> ORGANISM: Artificial Sequence
<220> FEATURE:
<223> OTHER INFORMATION: Synthetic peptide

<400> SEQUENCE: 564

Ser Arg Tyr Trp Leu Arg Ser
1 5

<210> SEQ ID NO 565
<211> LENGTH: 7
<212> TYPE: PRT
<213> ORGANISM: Artificial Sequence
<220> FEATURE:
<223> OTHER INFORMATION: Synthetic peptide

<400> SEQUENCE: 565

Ala Val Tyr Arg Ala Gly Arg
1 5

<210> SEQ ID NO 566
<211> LENGTH: 7
<212> TYPE: PRT
<213> ORGANISM: Artificial Sequence
<220> FEATURE:
<223> OTHER INFORMATION: Synthetic peptide

<400> SEQUENCE: 566

Arg His Phe Gly Leu Arg Glu
1 5

<210> SEQ ID NO 567
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 567

Arg Arg Glu Gly Leu Arg Ser
1               5

<210> SEQ ID NO 568
<211> LENGTH: 7
<212> TYPE: PRT
<213> ORGANISM: Artificial Sequence
<220> FEATURE:
<223> OTHER INFORMATION: Synthetic peptide

<400> SEQUENCE: 568

Gly Gln Gly Ala Ala Ser Leu
1               5

<210> SEQ ID NO 569
<211> LENGTH: 7
<212> TYPE: PRT
<213> ORGANISM: Artificial Sequence
<220> FEATURE:
<223> OTHER INFORMATION: Synthetic peptide

<400> SEQUENCE: 569

Gly Gln Gly Ala Ala Ser Leu
1               5

<210> SEQ ID NO 570
<211> LENGTH: 7
<212> TYPE: PRT
<213> ORGANISM: Artificial Sequence
<220> FEATURE:
<223> OTHER INFORMATION: Synthetic peptide

<400> SEQUENCE: 570

Tyr Gly Ser Val Ala Leu Arg
1               5

<210> SEQ ID NO 571
<211> LENGTH: 7
<212> TYPE: PRT
<213> ORGANISM: Artificial Sequence
<220> FEATURE:
<223> OTHER INFORMATION: Synthetic peptide

<400> SEQUENCE: 571

Ala Arg Arg Gly Val Leu Gly
1               5

<210> SEQ ID NO 572
<211> LENGTH: 7
<212> TYPE: PRT
<213> ORGANISM: Artificial Sequence
<220> FEATURE:
<223> OTHER INFORMATION: Synthetic peptide

<400> SEQUENCE: 572

Leu Arg Ile Ala Arg Gly Val
1               5

<210> SEQ ID NO 573
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 573

Tyr Arg Gly Ser Met Val Gly
1               5

<210> SEQ ID NO 574
<211> LENGTH: 7
<212> TYPE: PRT
<213> ORGANISM: Artificial Sequence
<220> FEATURE:
<223> OTHER INFORMATION: Synthetic peptide

<400> SEQUENCE: 574

Gly Leu Arg Gly Ser Val Trp
1               5

<210> SEQ ID NO 575
<211> LENGTH: 7
<212> TYPE: PRT
<213> ORGANISM: Artificial Sequence
<220> FEATURE:
<223> OTHER INFORMATION: Synthetic peptide

<400> SEQUENCE: 575

Gly Pro Phe Arg Ala Val Pro
1               5

<210> SEQ ID NO 576
<211> LENGTH: 7
<212> TYPE: PRT
<213> ORGANISM: Artificial Sequence
<220> FEATURE:
<223> OTHER INFORMATION: Synthetic peptide

<400> SEQUENCE: 576

Ala His Tyr Thr Leu Arg Ser
1               5

<210> SEQ ID NO 577
<211> LENGTH: 7
<212> TYPE: PRT
<213> ORGANISM: Artificial Sequence
<220> FEATURE:
<223> OTHER INFORMATION: Synthetic peptide

<400> SEQUENCE: 577

Ser Glu Leu Arg Ser Ile Arg
1               5

<210> SEQ ID NO 578
<211> LENGTH: 7
<212> TYPE: PRT
<213> ORGANISM: Artificial Sequence
<220> FEATURE:
<223> OTHER INFORMATION: Synthetic peptide

<400> SEQUENCE: 578

Ser Val Tyr Ala Leu Arg Ser
1               5

<210> SEQ ID NO 579
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 579

Ala Arg Arg Gly Val Leu Gly
1 5

<210> SEQ ID NO 580
<211> LENGTH: 7
<212> TYPE: PRT
<213> ORGANISM: Artificial Sequence
<220> FEATURE:
<223> OTHER INFORMATION: Synthetic peptide

<400> SEQUENCE: 580

Pro Gly Ala Val Leu Thr Val
1 5

<210> SEQ ID NO 581
<211> LENGTH: 7
<212> TYPE: PRT
<213> ORGANISM: Artificial Sequence
<220> FEATURE:
<223> OTHER INFORMATION: Synthetic peptide

<400> SEQUENCE: 581

Gly Leu Val Gly Arg Arg Ala
1 5

<210> SEQ ID NO 582
<211> LENGTH: 7
<212> TYPE: PRT
<213> ORGANISM: Artificial Sequence
<220> FEATURE:
<223> OTHER INFORMATION: Synthetic peptide

<400> SEQUENCE: 582

Gly Leu Val Arg Cys Val Leu
1 5

<210> SEQ ID NO 583
<211> LENGTH: 7
<212> TYPE: PRT
<213> ORGANISM: Artificial Sequence
<220> FEATURE:
<223> OTHER INFORMATION: Synthetic peptide

<400> SEQUENCE: 583

Tyr Asp Gly Leu Val Ser Gly
1 5

<210> SEQ ID NO 584
<211> LENGTH: 7
<212> TYPE: PRT
<213> ORGANISM: Artificial Sequence
<220> FEATURE:
<223> OTHER INFORMATION: Synthetic peptide

<400> SEQUENCE: 584

Gly Leu Val Thr Ala Pro Leu
1 5

<210> SEQ ID NO 585
<211> LENGTH: 7
<212> TYPE: PRT
<213> ORGANISM: Artificial Sequence
<220> FEATURE:
<223> OTHER INFORMATION: Synthetic peptide

<400> SEQUENCE: 585

Arg Gly Leu Val Arg Val Val
1 5

<210> SEQ ID NO 586
<211> LENGTH: 7
<212> TYPE: PRT
<213> ORGANISM: Artificial Sequence
<220> FEATURE:
<223> OTHER INFORMATION: Synthetic peptide

<400> SEQUENCE: 586

Gly Leu Arg Gly Ser Val Trp
1 5

<210> SEQ ID NO 587
<211> LENGTH: 7
<212> TYPE: PRT
<213> ORGANISM: Artificial Sequence
<220> FEATURE:
<223> OTHER INFORMATION: Synthetic peptide

<400> SEQUENCE: 587

Asn Ser Phe Gly Leu Arg Tyr
1 5

<210> SEQ ID NO 588
<211> LENGTH: 7
<212> TYPE: PRT
<213> ORGANISM: Artificial Sequence
<220> FEATURE:
<223> OTHER INFORMATION: Synthetic peptide

<400> SEQUENCE: 588

Tyr Asp Gly Leu Val Ser Gly
1 5

<210> SEQ ID NO 589
<211> LENGTH: 7
<212> TYPE: PRT
<213> ORGANISM: Artificial Sequence
<220> FEATURE:
<223> OTHER INFORMATION: Synthetic peptide

<400> SEQUENCE: 589

Ala Ala Arg Gly Leu Glu Ala
1 5

<210> SEQ ID NO 590
<211> LENGTH: 7
<212> TYPE: PRT
<213> ORGANISM: Artificial Sequence
<220> FEATURE:
<223> OTHER INFORMATION: Synthetic peptide

<400> SEQUENCE: 590

Asp Asn Asp Gly Ala Arg Gly
1 5

<210> SEQ ID NO 591
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 591

Leu Arg Ile Ala Arg Gly Val
1               5

<210> SEQ ID NO 592
<211> LENGTH: 7
<212> TYPE: PRT
<213> ORGANISM: Artificial Sequence
<220> FEATURE:
<223> OTHER INFORMATION: Synthetic peptide

<400> SEQUENCE: 592

Met Ser Asn Leu Ala Ala Val
1               5

<210> SEQ ID NO 593
<211> LENGTH: 7
<212> TYPE: PRT
<213> ORGANISM: Artificial Sequence
<220> FEATURE:
<223> OTHER INFORMATION: Synthetic peptide

<400> SEQUENCE: 593

Tyr Ser Gly Ser Ser Asp Phe
1               5

<210> SEQ ID NO 594
<211> LENGTH: 7
<212> TYPE: PRT
<213> ORGANISM: Artificial Sequence
<220> FEATURE:
<223> OTHER INFORMATION: Synthetic peptide

<400> SEQUENCE: 594

Gly Ser Val Leu Gly Asp Tyr
1               5

<210> SEQ ID NO 595
<211> LENGTH: 7
<212> TYPE: PRT
<213> ORGANISM: Artificial Sequence
<220> FEATURE:
<223> OTHER INFORMATION: Synthetic peptide

<400> SEQUENCE: 595

Gly Leu Arg Gly Ser Val Trp
1               5

<210> SEQ ID NO 596
<211> LENGTH: 7
<212> TYPE: PRT
<213> ORGANISM: Artificial Sequence
<220> FEATURE:
<223> OTHER INFORMATION: Synthetic peptide

<400> SEQUENCE: 596

Asp Leu Asp Gly Arg Val Val
1               5

<210> SEQ ID NO 597
<211> LENGTH: 7
<212> TYPE: PRT
<213> ORGANISM: Artificial Sequence
<220> FEATURE:
<223> OTHER INFORMATION: Synthetic peptide

<400> SEQUENCE: 597

-continued

Trp Val Ser Gly Arg Leu Gly
1 5

<210> SEQ ID NO 598
<211> LENGTH: 7
<212> TYPE: PRT
<213> ORGANISM: Artificial Sequence
<220> FEATURE:
<223> OTHER INFORMATION: Synthetic peptide

<400> SEQUENCE: 598

Gly Pro Ser Ser Met Thr Phe
1 5

<210> SEQ ID NO 599
<211> LENGTH: 7
<212> TYPE: PRT
<213> ORGANISM: Artificial Sequence
<220> FEATURE:
<223> OTHER INFORMATION: Synthetic peptide

<400> SEQUENCE: 599

Asp Gly Val Ser Ser Asp Tyr
1 5

<210> SEQ ID NO 600
<211> LENGTH: 7
<212> TYPE: PRT
<213> ORGANISM: Artificial Sequence
<220> FEATURE:
<223> OTHER INFORMATION: Synthetic peptide

<400> SEQUENCE: 600

Phe Thr Ser Gly Val Ser Trp
1 5

<210> SEQ ID NO 601
<211> LENGTH: 7
<212> TYPE: PRT
<213> ORGANISM: Artificial Sequence
<220> FEATURE:
<223> OTHER INFORMATION: Synthetic peptide

<400> SEQUENCE: 601

Val Leu Thr Arg Ala Ser Thr
1 5

<210> SEQ ID NO 602
<211> LENGTH: 7
<212> TYPE: PRT
<213> ORGANISM: Artificial Sequence
<220> FEATURE:
<223> OTHER INFORMATION: Synthetic peptide

<400> SEQUENCE: 602

Leu Arg Ala Ser Leu Leu Trp
1 5

<210> SEQ ID NO 603
<211> LENGTH: 7
<212> TYPE: PRT
<213> ORGANISM: Artificial Sequence
<220> FEATURE:
<223> OTHER INFORMATION: Synthetic peptide

<400> SEQUENCE: 603

-continued

Trp Leu Leu Ser Ala Arg Leu
1 5

<210> SEQ ID NO 604
<211> LENGTH: 7
<212> TYPE: PRT
<213> ORGANISM: Artificial Sequence
<220> FEATURE:
<223> OTHER INFORMATION: Synthetic peptide

<400> SEQUENCE: 604

Leu Leu Arg Pro Gly Thr Val
1 5

<210> SEQ ID NO 605
<211> LENGTH: 7
<212> TYPE: PRT
<213> ORGANISM: Artificial Sequence
<220> FEATURE:
<223> OTHER INFORMATION: Synthetic peptide

<400> SEQUENCE: 605

Ala Ala Gly Gly Leu Leu Val
1 5

<210> SEQ ID NO 606
<211> LENGTH: 7
<212> TYPE: PRT
<213> ORGANISM: Artificial Sequence
<220> FEATURE:
<223> OTHER INFORMATION: Synthetic peptide

<400> SEQUENCE: 606

Leu Arg Ala Ser Leu Leu Trp
1 5

<210> SEQ ID NO 607
<211> LENGTH: 7
<212> TYPE: PRT
<213> ORGANISM: Artificial Sequence
<220> FEATURE:
<223> OTHER INFORMATION: Synthetic peptide

<400> SEQUENCE: 607

Leu Trp Gly Leu Gly Trp Leu
1 5

<210> SEQ ID NO 608
<211> LENGTH: 7
<212> TYPE: PRT
<213> ORGANISM: Artificial Sequence
<220> FEATURE:
<223> OTHER INFORMATION: Synthetic peptide

<400> SEQUENCE: 608

Arg Arg Ser Gly Leu Gly Asp
1 5

<210> SEQ ID NO 609
<211> LENGTH: 7
<212> TYPE: PRT
<213> ORGANISM: Artificial Sequence
<220> FEATURE:
<223> OTHER INFORMATION: Synthetic peptide

<400> SEQUENCE: 609

Trp Trp Gly Leu Gly Trp Leu

-continued 1 5

<210> SEQ ID NO 610
<211> LENGTH: 7
<212> TYPE: PRT
<213> ORGANISM: Artificial Sequence
<220> FEATURE:
<223> OTHER INFORMATION: Synthetic peptide

<400> SEQUENCE: 610

Ala Ala Gly Gly Leu Leu Val
1 5

<210> SEQ ID NO 611
<211> LENGTH: 7
<212> TYPE: PRT
<213> ORGANISM: Artificial Sequence
<220> FEATURE:
<223> OTHER INFORMATION: Synthetic peptide

<400> SEQUENCE: 611

Gly Leu Arg Gly Val Val Lys
1 5

<210> SEQ ID NO 612
<211> LENGTH: 7
<212> TYPE: PRT
<213> ORGANISM: Artificial Sequence
<220> FEATURE:
<223> OTHER INFORMATION: Synthetic peptide

<400> SEQUENCE: 612

Ala Val Glu Gly Arg Gly Ser
1 5

<210> SEQ ID NO 613
<211> LENGTH: 7
<212> TYPE: PRT
<213> ORGANISM: Artificial Sequence
<220> FEATURE:
<223> OTHER INFORMATION: Synthetic peptide

<400> SEQUENCE: 613

Asn Ala Val Arg Gly Ser Ala
1 5

<210> SEQ ID NO 614
<211> LENGTH: 7
<212> TYPE: PRT
<213> ORGANISM: Artificial Sequence
<220> FEATURE:
<223> OTHER INFORMATION: Synthetic peptide

<400> SEQUENCE: 614

Leu Leu Arg Ser Ser Leu Gly
1 5

<210> SEQ ID NO 615
<211> LENGTH: 7
<212> TYPE: PRT
<213> ORGANISM: Artificial Sequence
<220> FEATURE:
<223> OTHER INFORMATION: Synthetic peptide

<400> SEQUENCE: 615

Met Tyr Leu Arg Leu Leu Arg
1 5

-continued

<210> SEQ ID NO 616
<211> LENGTH: 7
<212> TYPE: PRT
<213> ORGANISM: Artificial Sequence
<220> FEATURE:
<223> OTHER INFORMATION: Synthetic peptide

<400> SEQUENCE: 616

Leu Leu Arg Ser Ser Leu Gly
1               5

<210> SEQ ID NO 617
<211> LENGTH: 7
<212> TYPE: PRT
<213> ORGANISM: Artificial Sequence
<220> FEATURE:
<223> OTHER INFORMATION: Synthetic peptide

<400> SEQUENCE: 617

Asp Glu Gly Leu Arg Ser Arg
1               5

<210> SEQ ID NO 618
<211> LENGTH: 7
<212> TYPE: PRT
<213> ORGANISM: Artificial Sequence
<220> FEATURE:
<223> OTHER INFORMATION: Synthetic peptide

<400> SEQUENCE: 618

Tyr Trp Gln His Arg Val Ser
1               5

<210> SEQ ID NO 619
<211> LENGTH: 7
<212> TYPE: PRT
<213> ORGANISM: Artificial Sequence
<220> FEATURE:
<223> OTHER INFORMATION: Synthetic peptide

<400> SEQUENCE: 619

Ala Arg Ser Ser His Arg Ala
1               5

<210> SEQ ID NO 620
<211> LENGTH: 7
<212> TYPE: PRT
<213> ORGANISM: Artificial Sequence
<220> FEATURE:
<223> OTHER INFORMATION: Synthetic peptide

<400> SEQUENCE: 620

Leu Leu Arg Ser Ser Leu Gly
1               5

<210> SEQ ID NO 621
<211> LENGTH: 7
<212> TYPE: PRT
<213> ORGANISM: Artificial Sequence
<220> FEATURE:
<223> OTHER INFORMATION: Synthetic peptide

<400> SEQUENCE: 621

Ala Gly Arg Ser Cys Asn Leu
1               5

-continued

<210> SEQ ID NO 622
<211> LENGTH: 7
<212> TYPE: PRT
<213> ORGANISM: Artificial Sequence
<220> FEATURE:
<223> OTHER INFORMATION: Synthetic peptide

<400> SEQUENCE: 622

Ala Gly Arg Pro Arg Ala Thr
1               5

<210> SEQ ID NO 623
<211> LENGTH: 7
<212> TYPE: PRT
<213> ORGANISM: Artificial Sequence
<220> FEATURE:
<223> OTHER INFORMATION: Synthetic peptide

<400> SEQUENCE: 623

Gly Gly Val Arg Ile Ala Ala
1               5

<210> SEQ ID NO 624
<211> LENGTH: 7
<212> TYPE: PRT
<213> ORGANISM: Artificial Sequence
<220> FEATURE:
<223> OTHER INFORMATION: Synthetic peptide

<400> SEQUENCE: 624

Gly Val Arg Tyr Leu Arg Thr
1               5

<210> SEQ ID NO 625
<211> LENGTH: 7
<212> TYPE: PRT
<213> ORGANISM: Artificial Sequence
<220> FEATURE:
<223> OTHER INFORMATION: Synthetic peptide

<400> SEQUENCE: 625

Pro Leu Ala Val Gly Leu Val
1               5

<210> SEQ ID NO 626
<211> LENGTH: 7
<212> TYPE: PRT
<213> ORGANISM: Artificial Sequence
<220> FEATURE:
<223> OTHER INFORMATION: Synthetic peptide

<400> SEQUENCE: 626

Gly Leu Arg Gly Val Val Lys
1               5

<210> SEQ ID NO 627
<211> LENGTH: 7
<212> TYPE: PRT
<213> ORGANISM: Artificial Sequence
<220> FEATURE:
<223> OTHER INFORMATION: Synthetic peptide

<400> SEQUENCE: 627

Asp Glu Gly Leu Arg Ser Arg
1               5

-continued

<210> SEQ ID NO 628
<211> LENGTH: 7
<212> TYPE: PRT
<213> ORGANISM: Artificial Sequence
<220> FEATURE:
<223> OTHER INFORMATION: Synthetic peptide

<400> SEQUENCE: 628

Gln Leu Val Ser Gly Ser Leu
1 5

<210> SEQ ID NO 629
<211> LENGTH: 7
<212> TYPE: PRT
<213> ORGANISM: Artificial Sequence
<220> FEATURE:
<223> OTHER INFORMATION: Synthetic peptide

<400> SEQUENCE: 629

Gly Trp Ser Ala Ser Leu Gly
1 5

<210> SEQ ID NO 630
<211> LENGTH: 7
<212> TYPE: PRT
<213> ORGANISM: Artificial Sequence
<220> FEATURE:
<223> OTHER INFORMATION: Synthetic peptide

<400> SEQUENCE: 630

Ile Ala Ala Val Trp Arg Ser
1 5

<210> SEQ ID NO 631
<211> LENGTH: 7
<212> TYPE: PRT
<213> ORGANISM: Artificial Sequence
<220> FEATURE:
<223> OTHER INFORMATION: Synthetic peptide

<400> SEQUENCE: 631

Gly Gly Ser Ser Leu Asp Ala
1 5

<210> SEQ ID NO 632
<211> LENGTH: 7
<212> TYPE: PRT
<213> ORGANISM: Artificial Sequence
<220> FEATURE:
<223> OTHER INFORMATION: Synthetic peptide

<400> SEQUENCE: 632

Leu Gly Gly Ser Arg Asp Leu
1 5

<210> SEQ ID NO 633
<211> LENGTH: 7
<212> TYPE: PRT
<213> ORGANISM: Artificial Sequence
<220> FEATURE:
<223> OTHER INFORMATION: Synthetic peptide

<400> SEQUENCE: 633

Leu Ile Gly Gly Arg Asn Ala
1 5

<210> SEQ ID NO 634

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 634

Leu Asp Arg Ser Gly Gly Leu
1               5

<210> SEQ ID NO 635
<211> LENGTH: 7
<212> TYPE: PRT
<213> ORGANISM: Artificial Sequence
<220> FEATURE:
<223> OTHER INFORMATION: Synthetic peptide

<400> SEQUENCE: 635

Gly Gly Ser Ser Leu Asp Ala
1               5

<210> SEQ ID NO 636
<211> LENGTH: 7
<212> TYPE: PRT
<213> ORGANISM: Artificial Sequence
<220> FEATURE:
<223> OTHER INFORMATION: Synthetic peptide

<400> SEQUENCE: 636

Gly Ser Ser Tyr Ser Gly Pro
1               5

<210> SEQ ID NO 637
<211> LENGTH: 7
<212> TYPE: PRT
<213> ORGANISM: Artificial Sequence
<220> FEATURE:
<223> OTHER INFORMATION: Synthetic peptide

<400> SEQUENCE: 637

Thr Val Gly Ser Gly Cys Leu
1               5

<210> SEQ ID NO 638
<211> LENGTH: 7
<212> TYPE: PRT
<213> ORGANISM: Artificial Sequence
<220> FEATURE:
<223> OTHER INFORMATION: Synthetic peptide

<400> SEQUENCE: 638

Leu Ser Gly Ser Val Leu Gln
1               5

<210> SEQ ID NO 639
<211> LENGTH: 7
<212> TYPE: PRT
<213> ORGANISM: Artificial Sequence
<220> FEATURE:
<223> OTHER INFORMATION: Synthetic peptide

<400> SEQUENCE: 639

Ala Ser Gly Arg Val Ala Asn
1               5

<210> SEQ ID NO 640
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 640

Lys Val Val Gly Arg Leu Gly
1 5

<210> SEQ ID NO 641
<211> LENGTH: 7
<212> TYPE: PRT
<213> ORGANISM: Artificial Sequence
<220> FEATURE:
<223> OTHER INFORMATION: Synthetic peptide

<400> SEQUENCE: 641

Gly Arg Leu Val Trp Gly Leu
1 5

<210> SEQ ID NO 642
<211> LENGTH: 7
<212> TYPE: PRT
<213> ORGANISM: Artificial Sequence
<220> FEATURE:
<223> OTHER INFORMATION: Synthetic peptide

<400> SEQUENCE: 642

Asn Glu Phe Leu Gly Arg Leu
1 5

<210> SEQ ID NO 643
<211> LENGTH: 7
<212> TYPE: PRT
<213> ORGANISM: Artificial Sequence
<220> FEATURE:
<223> OTHER INFORMATION: Synthetic peptide

<400> SEQUENCE: 643

Leu Cys Asp Ala Gly Pro Ser
1 5

<210> SEQ ID NO 644
<211> LENGTH: 7
<212> TYPE: PRT
<213> ORGANISM: Artificial Sequence
<220> FEATURE:
<223> OTHER INFORMATION: Synthetic peptide

<400> SEQUENCE: 644

Phe Arg Ala Gly Val Ser His
1 5

<210> SEQ ID NO 645
<211> LENGTH: 7
<212> TYPE: PRT
<213> ORGANISM: Artificial Sequence
<220> FEATURE:
<223> OTHER INFORMATION: Synthetic peptide

<400> SEQUENCE: 645

Ala Gly Asp Ser Arg Leu Ser
1 5

<210> SEQ ID NO 646
<211> LENGTH: 7
<212> TYPE: PRT

<213> ORGANISM: Artificial Sequence
<220> FEATURE:
<223> OTHER INFORMATION: Synthetic peptide

<400> SEQUENCE: 646

Asp Trp Arg Arg Arg Ala Val
1               5

<210> SEQ ID NO 647
<211> LENGTH: 7
<212> TYPE: PRT
<213> ORGANISM: Artificial Sequence
<220> FEATURE:
<223> OTHER INFORMATION: Synthetic peptide

<400> SEQUENCE: 647

Trp Thr Glu Arg Ala Ser Ala
1               5

<210> SEQ ID NO 648
<211> LENGTH: 7
<212> TYPE: PRT
<213> ORGANISM: Artificial Sequence
<220> FEATURE:
<223> OTHER INFORMATION: Synthetic peptide

<400> SEQUENCE: 648

Arg Leu Leu Ser Ala Phe Gly
1               5

<210> SEQ ID NO 649
<211> LENGTH: 7
<212> TYPE: PRT
<213> ORGANISM: Artificial Sequence
<220> FEATURE:
<223> OTHER INFORMATION: Synthetic peptide

<400> SEQUENCE: 649

Gly Phe Ala Ser Leu Leu Arg
1               5

<210> SEQ ID NO 650
<211> LENGTH: 7
<212> TYPE: PRT
<213> ORGANISM: Artificial Sequence
<220> FEATURE:
<223> OTHER INFORMATION: Synthetic peptide

<400> SEQUENCE: 650

Gly Ala Leu Arg Val Pro Trp
1               5

<210> SEQ ID NO 651
<211> LENGTH: 7
<212> TYPE: PRT
<213> ORGANISM: Artificial Sequence
<220> FEATURE:
<223> OTHER INFORMATION: Synthetic peptide

<400> SEQUENCE: 651

Ser Leu Arg Ser Asp Gly Ala
1               5

<210> SEQ ID NO 652
<211> LENGTH: 7
<212> TYPE: PRT
<213> ORGANISM: Artificial Sequence
<220> FEATURE:
<223> OTHER INFORMATION: Synthetic peptide

<400> SEQUENCE: 652

Asp Thr Leu Arg Ser Gln Trp
1 5

<210> SEQ ID NO 653
<211> LENGTH: 7
<212> TYPE: PRT
<213> ORGANISM: Artificial Sequence
<220> FEATURE:
<223> OTHER INFORMATION: Synthetic peptide

<400> SEQUENCE: 653

Leu Arg Ser Val Gly Ser Trp
1 5

<210> SEQ ID NO 654
<211> LENGTH: 7
<212> TYPE: PRT
<213> ORGANISM: Artificial Sequence
<220> FEATURE:
<223> OTHER INFORMATION: Synthetic peptide

<400> SEQUENCE: 654

Ile Ser Pro Arg Ser Ser Gly
1 5

<210> SEQ ID NO 655
<211> LENGTH: 7
<212> TYPE: PRT
<213> ORGANISM: Artificial Sequence
<220> FEATURE:
<223> OTHER INFORMATION: Synthetic peptide

<400> SEQUENCE: 655

Trp Arg Val Arg Ser Ser Gly
1 5

<210> SEQ ID NO 656
<211> LENGTH: 7
<212> TYPE: PRT
<213> ORGANISM: Artificial Sequence
<220> FEATURE:
<223> OTHER INFORMATION: Synthetic peptide

<400> SEQUENCE: 656

Ala Ala Gly Arg Ile Arg Pro
1 5

<210> SEQ ID NO 657
<211> LENGTH: 7
<212> TYPE: PRT
<213> ORGANISM: Artificial Sequence
<220> FEATURE:
<223> OTHER INFORMATION: Synthetic peptide

<400> SEQUENCE: 657

Arg Ala Ala Gly Arg Val Gly
1 5

<210> SEQ ID NO 658
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 658

Ala Gly Leu Gln His Ala Val
1 5

<210> SEQ ID NO 659
<211> LENGTH: 7
<212> TYPE: PRT
<213> ORGANISM: Artificial Sequence
<220> FEATURE:
<223> OTHER INFORMATION: Synthetic peptide

<400> SEQUENCE: 659

Ala Gly Gly Trp Trp Val Gly
1 5

<210> SEQ ID NO 660
<211> LENGTH: 7
<212> TYPE: PRT
<213> ORGANISM: Artificial Sequence
<220> FEATURE:
<223> OTHER INFORMATION: Synthetic peptide

<400> SEQUENCE: 660

Gly Val Arg Gly Ala Ala Arg
1 5

<210> SEQ ID NO 661
<211> LENGTH: 7
<212> TYPE: PRT
<213> ORGANISM: Artificial Sequence
<220> FEATURE:
<223> OTHER INFORMATION: Synthetic peptide

<400> SEQUENCE: 661

Gly Val Leu Pro Val Val Thr
1 5

<210> SEQ ID NO 662
<211> LENGTH: 7
<212> TYPE: PRT
<213> ORGANISM: Artificial Sequence
<220> FEATURE:
<223> OTHER INFORMATION: Synthetic peptide

<400> SEQUENCE: 662

Gly Leu Val Ser Ser Leu Pro
1 5

<210> SEQ ID NO 663
<211> LENGTH: 7
<212> TYPE: PRT
<213> ORGANISM: Artificial Sequence
<220> FEATURE:
<223> OTHER INFORMATION: Synthetic peptide

<400> SEQUENCE: 663

Ser Arg His Gly Leu Val Arg
1 5

<210> SEQ ID NO 664
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 664

Ser Asp Arg Gly Leu Val Val
1 5

<210> SEQ ID NO 665
<211> LENGTH: 7
<212> TYPE: PRT
<213> ORGANISM: Artificial Sequence
<220> FEATURE:
<223> OTHER INFORMATION: Synthetic peptide

<400> SEQUENCE: 665

Ser Asp Arg Gly Leu Val Val
1 5

<210> SEQ ID NO 666
<211> LENGTH: 7
<212> TYPE: PRT
<213> ORGANISM: Artificial Sequence
<220> FEATURE:
<223> OTHER INFORMATION: Synthetic peptide

<400> SEQUENCE: 666

Gly Leu Val Ser Ser Leu Pro
1 5

<210> SEQ ID NO 667
<211> LENGTH: 7
<212> TYPE: PRT
<213> ORGANISM: Artificial Sequence
<220> FEATURE:
<223> OTHER INFORMATION: Synthetic peptide

<400> SEQUENCE: 667

Leu Val Ser Val Trp Ser Arg
1 5

<210> SEQ ID NO 668
<211> LENGTH: 7
<212> TYPE: PRT
<213> ORGANISM: Artificial Sequence
<220> FEATURE:
<223> OTHER INFORMATION: Synthetic peptide

<400> SEQUENCE: 668

Gly Ser Trp Ala Arg Gly Tyr
1 5

<210> SEQ ID NO 669
<211> LENGTH: 7
<212> TYPE: PRT
<213> ORGANISM: Artificial Sequence
<220> FEATURE:
<223> OTHER INFORMATION: Synthetic peptide

<400> SEQUENCE: 669

Gly Phe Ala Ser Leu Leu Arg
1 5

<210> SEQ ID NO 670
<211> LENGTH: 7
<212> TYPE: PRT
<213> ORGANISM: Artificial Sequence
<220> FEATURE:
<223> OTHER INFORMATION: Synthetic peptide

<400> SEQUENCE: 670

His Ala Ala Val Met Ser Leu
1               5

<210> SEQ ID NO 671
<211> LENGTH: 7
<212> TYPE: PRT
<213> ORGANISM: Artificial Sequence
<220> FEATURE:
<223> OTHER INFORMATION: Synthetic peptide

<400> SEQUENCE: 671

Asp Gly Gly Arg Arg Thr Asp
1               5

<210> SEQ ID NO 672
<211> LENGTH: 7
<212> TYPE: PRT
<213> ORGANISM: Artificial Sequence
<220> FEATURE:
<223> OTHER INFORMATION: Synthetic peptide

<400> SEQUENCE: 672

Gly Arg Pro Leu Gly Gly Arg
1               5

<210> SEQ ID NO 673
<211> LENGTH: 7
<212> TYPE: PRT
<213> ORGANISM: Artificial Sequence
<220> FEATURE:
<223> OTHER INFORMATION: Synthetic peptide

<400> SEQUENCE: 673

Gly Arg Val Thr Gly Gly Arg
1               5

<210> SEQ ID NO 674
<211> LENGTH: 7
<212> TYPE: PRT
<213> ORGANISM: Artificial Sequence
<220> FEATURE:
<223> OTHER INFORMATION: Synthetic peptide

<400> SEQUENCE: 674

Arg Gly Gly Leu Pro Arg Gly
1               5

<210> SEQ ID NO 675
<211> LENGTH: 7
<212> TYPE: PRT
<213> ORGANISM: Artificial Sequence
<220> FEATURE:
<223> OTHER INFORMATION: Synthetic peptide

<400> SEQUENCE: 675

Tyr Gly Gln Tyr Gly Gly Leu
1               5

<210> SEQ ID NO 676
<211> LENGTH: 7
<212> TYPE: PRT
<213> ORGANISM: Artificial Sequence
<220> FEATURE:
<223> OTHER INFORMATION: Synthetic peptide

<400> SEQUENCE: 676

Gly Ser Ser Arg Pro Ser Ile
1 5

<210> SEQ ID NO 677
<211> LENGTH: 7
<212> TYPE: PRT
<213> ORGANISM: Artificial Sequence
<220> FEATURE:
<223> OTHER INFORMATION: Synthetic peptide

<400> SEQUENCE: 677

Pro Gly Ser Ser Phe Val Gly
1 5

<210> SEQ ID NO 678
<211> LENGTH: 7
<212> TYPE: PRT
<213> ORGANISM: Artificial Sequence
<220> FEATURE:
<223> OTHER INFORMATION: Synthetic peptide

<400> SEQUENCE: 678

Gly Ser Ser Arg Val Arg Trp
1 5

<210> SEQ ID NO 679
<211> LENGTH: 7
<212> TYPE: PRT
<213> ORGANISM: Artificial Sequence
<220> FEATURE:
<223> OTHER INFORMATION: Synthetic peptide

<400> SEQUENCE: 679

Arg Ala Ala Gly Arg Val Gly
1 5

<210> SEQ ID NO 680
<211> LENGTH: 7
<212> TYPE: PRT
<213> ORGANISM: Artificial Sequence
<220> FEATURE:
<223> OTHER INFORMATION: Synthetic peptide

<400> SEQUENCE: 680

Gly Arg Val Thr Gly Gly Arg
1 5

<210> SEQ ID NO 681
<211> LENGTH: 7
<212> TYPE: PRT
<213> ORGANISM: Artificial Sequence
<220> FEATURE:
<223> OTHER INFORMATION: Synthetic peptide

<400> SEQUENCE: 681

Tyr Val Arg Ile Gly Arg Val
1 5

<210> SEQ ID NO 682
<211> LENGTH: 7
<212> TYPE: PRT
<213> ORGANISM: Artificial Sequence
<220> FEATURE:
<223> OTHER INFORMATION: Synthetic peptide

<400> SEQUENCE: 682

-continued

Met Ile Thr Arg Gly Arg Leu
1 5

<210> SEQ ID NO 683
<211> LENGTH: 7
<212> TYPE: PRT
<213> ORGANISM: Artificial Sequence
<220> FEATURE:
<223> OTHER INFORMATION: Synthetic peptide

<400> SEQUENCE: 683

Ser Val Val Gly Val Ser Thr
1 5

<210> SEQ ID NO 684
<211> LENGTH: 7
<212> TYPE: PRT
<213> ORGANISM: Artificial Sequence
<220> FEATURE:
<223> OTHER INFORMATION: Synthetic peptide

<400> SEQUENCE: 684

Trp Ser Gly Val Ser Arg Leu
1 5

<210> SEQ ID NO 685
<211> LENGTH: 7
<212> TYPE: PRT
<213> ORGANISM: Artificial Sequence
<220> FEATURE:
<223> OTHER INFORMATION: Synthetic peptide

<400> SEQUENCE: 685

Arg Arg Leu Ser Tyr Phe His
1 5

<210> SEQ ID NO 686
<211> LENGTH: 7
<212> TYPE: PRT
<213> ORGANISM: Artificial Sequence
<220> FEATURE:
<223> OTHER INFORMATION: Synthetic peptide

<400> SEQUENCE: 686

Pro Arg Leu Ser Trp Val Leu
1 5

<210> SEQ ID NO 687
<211> LENGTH: 7
<212> TYPE: PRT
<213> ORGANISM: Artificial Sequence
<220> FEATURE:
<223> OTHER INFORMATION: Synthetic peptide

<400> SEQUENCE: 687

Arg Leu Ser Ala Leu Thr Asp
1 5

<210> SEQ ID NO 688
<211> LENGTH: 7
<212> TYPE: PRT
<213> ORGANISM: Artificial Sequence
<220> FEATURE:
<223> OTHER INFORMATION: Synthetic peptide

<400> SEQUENCE: 688

Gly Arg Gly Val Gly Thr Asp

-continued 1 5

<210> SEQ ID NO 689
<211> LENGTH: 7
<212> TYPE: PRT
<213> ORGANISM: Artificial Sequence
<220> FEATURE:
<223> OTHER INFORMATION: Synthetic peptide

<400> SEQUENCE: 689

Leu Lys Val Arg Gly Val Leu
1 5

<210> SEQ ID NO 690
<211> LENGTH: 7
<212> TYPE: PRT
<213> ORGANISM: Artificial Sequence
<220> FEATURE:
<223> OTHER INFORMATION: Synthetic peptide

<400> SEQUENCE: 690

Ser Ser Thr Arg Gly Val Tyr
1 5

<210> SEQ ID NO 691
<211> LENGTH: 7
<212> TYPE: PRT
<213> ORGANISM: Artificial Sequence
<220> FEATURE:
<223> OTHER INFORMATION: Synthetic peptide

<400> SEQUENCE: 691

Gln Val Arg Arg Gly Val Val
1 5

<210> SEQ ID NO 692
<211> LENGTH: 7
<212> TYPE: PRT
<213> ORGANISM: Artificial Sequence
<220> FEATURE:
<223> OTHER INFORMATION: Synthetic peptide

<400> SEQUENCE: 692

Gly Arg Gly Val Thr Ile Trp
1 5

<210> SEQ ID NO 693
<211> LENGTH: 7
<212> TYPE: PRT
<213> ORGANISM: Artificial Sequence
<220> FEATURE:
<223> OTHER INFORMATION: Synthetic peptide

<400> SEQUENCE: 693

Arg Gly Ser Val Ala Ser Ala
1 5

<210> SEQ ID NO 694
<211> LENGTH: 7
<212> TYPE: PRT
<213> ORGANISM: Artificial Sequence
<220> FEATURE:
<223> OTHER INFORMATION: Synthetic peptide

<400> SEQUENCE: 694

His Phe Ile Arg Gly Ser Val
1 5

<210> SEQ ID NO 695
<211> LENGTH: 7
<212> TYPE: PRT
<213> ORGANISM: Artificial Sequence
<220> FEATURE:
<223> OTHER INFORMATION: Synthetic peptide

<400> SEQUENCE: 695

Arg Gly Ser Trp Ala Gly Val
1               5

<210> SEQ ID NO 696
<211> LENGTH: 7
<212> TYPE: PRT
<213> ORGANISM: Artificial Sequence
<220> FEATURE:
<223> OTHER INFORMATION: Synthetic peptide

<400> SEQUENCE: 696

Val Arg Gly Ser Arg Trp Arg
1               5

<210> SEQ ID NO 697
<211> LENGTH: 7
<212> TYPE: PRT
<213> ORGANISM: Artificial Sequence
<220> FEATURE:
<223> OTHER INFORMATION: Synthetic peptide

<400> SEQUENCE: 697

Leu Glu Arg Ala Val Arg Thr
1               5

<210> SEQ ID NO 698
<211> LENGTH: 7
<212> TYPE: PRT
<213> ORGANISM: Artificial Sequence
<220> FEATURE:
<223> OTHER INFORMATION: Synthetic peptide

<400> SEQUENCE: 698

Gly Tyr Ser Arg Ala Ser Asp
1               5

<210> SEQ ID NO 699
<211> LENGTH: 7
<212> TYPE: PRT
<213> ORGANISM: Artificial Sequence
<220> FEATURE:
<223> OTHER INFORMATION: Synthetic peptide

<400> SEQUENCE: 699

Ser Arg Ala Ser Gly His Gly
1               5

<210> SEQ ID NO 700
<211> LENGTH: 7
<212> TYPE: PRT
<213> ORGANISM: Artificial Sequence
<220> FEATURE:
<223> OTHER INFORMATION: Synthetic peptide

<400> SEQUENCE: 700

Gly His Tyr Arg Ala Ser Val
1               5

-continued

<210> SEQ ID NO 701
<211> LENGTH: 7
<212> TYPE: PRT
<213> ORGANISM: Artificial Sequence
<220> FEATURE:
<223> OTHER INFORMATION: Synthetic peptide

<400> SEQUENCE: 701

Asp Trp Val Cys Arg Ala Ser
1               5

<210> SEQ ID NO 702
<211> LENGTH: 7
<212> TYPE: PRT
<213> ORGANISM: Artificial Sequence
<220> FEATURE:
<223> OTHER INFORMATION: Synthetic peptide

<400> SEQUENCE: 702

Gly Ala Gly Arg Gly Thr Pro
1               5

<210> SEQ ID NO 703
<211> LENGTH: 7
<212> TYPE: PRT
<213> ORGANISM: Artificial Sequence
<220> FEATURE:
<223> OTHER INFORMATION: Synthetic peptide

<400> SEQUENCE: 703

Leu Ser Leu Ala Gly Ala Gly
1               5

<210> SEQ ID NO 704
<211> LENGTH: 7
<212> TYPE: PRT
<213> ORGANISM: Artificial Sequence
<220> FEATURE:
<223> OTHER INFORMATION: Synthetic peptide

<400> SEQUENCE: 704

Ala Ser Ala Val Ser Gly Arg
1               5

<210> SEQ ID NO 705
<211> LENGTH: 7
<212> TYPE: PRT
<213> ORGANISM: Artificial Sequence
<220> FEATURE:
<223> OTHER INFORMATION: Synthetic peptide

<400> SEQUENCE: 705

Phe Ser Gly Asp Ala Val Ser
1               5

<210> SEQ ID NO 706
<211> LENGTH: 7
<212> TYPE: PRT
<213> ORGANISM: Artificial Sequence
<220> FEATURE:
<223> OTHER INFORMATION: Synthetic peptide

<400> SEQUENCE: 706

Leu Lys Leu Leu Ser Val Pro
1               5

-continued

<210> SEQ ID NO 707
<211> LENGTH: 7
<212> TYPE: PRT
<213> ORGANISM: Artificial Sequence
<220> FEATURE:
<223> OTHER INFORMATION: Synthetic peptide

<400> SEQUENCE: 707

Gly Thr Leu Arg Val Gly Ser
1 5

<210> SEQ ID NO 708
<211> LENGTH: 7
<212> TYPE: PRT
<213> ORGANISM: Artificial Sequence
<220> FEATURE:
<223> OTHER INFORMATION: Synthetic peptide

<400> SEQUENCE: 708

Glu His Tyr Arg Leu Arg Ser
1 5

<210> SEQ ID NO 709
<211> LENGTH: 7
<212> TYPE: PRT
<213> ORGANISM: Artificial Sequence
<220> FEATURE:
<223> OTHER INFORMATION: Synthetic peptide

<400> SEQUENCE: 709

Leu Arg Ser Trp Leu Leu Phe
1 5

<210> SEQ ID NO 710
<211> LENGTH: 7
<212> TYPE: PRT
<213> ORGANISM: Artificial Sequence
<220> FEATURE:
<223> OTHER INFORMATION: Synthetic peptide

<400> SEQUENCE: 710

Arg Arg Pro Gly Leu Arg Ser
1 5

<210> SEQ ID NO 711
<211> LENGTH: 7
<212> TYPE: PRT
<213> ORGANISM: Artificial Sequence
<220> FEATURE:
<223> OTHER INFORMATION: Synthetic peptide

<400> SEQUENCE: 711

Ser Lys Tyr Asn Leu Arg Ser
1 5

<210> SEQ ID NO 712
<211> LENGTH: 7
<212> TYPE: PRT
<213> ORGANISM: Artificial Sequence
<220> FEATURE:
<223> OTHER INFORMATION: Synthetic peptide

<400> SEQUENCE: 712

Trp Gln Val Ala Leu Arg Ser
1 5

<210> SEQ ID NO 713

<211> LENGTH: 7
<212> TYPE: PRT
<213> ORGANISM: Artificial Sequence
<220> FEATURE:
<223> OTHER INFORMATION: Synthetic peptide

<400> SEQUENCE: 713

Leu Arg Ser Asp Pro Arg Ser
1 5

<210> SEQ ID NO 714
<211> LENGTH: 7
<212> TYPE: PRT
<213> ORGANISM: Artificial Sequence
<220> FEATURE:
<223> OTHER INFORMATION: Synthetic peptide

<400> SEQUENCE: 714

Val Pro Leu Arg Ser Ser Ala
1 5

<210> SEQ ID NO 715
<211> LENGTH: 7
<212> TYPE: PRT
<213> ORGANISM: Artificial Sequence
<220> FEATURE:
<223> OTHER INFORMATION: Synthetic peptide

<400> SEQUENCE: 715

Gly Arg Ser Ser Gly Met Glu
1 5

<210> SEQ ID NO 716
<211> LENGTH: 7
<212> TYPE: PRT
<213> ORGANISM: Artificial Sequence
<220> FEATURE:
<223> OTHER INFORMATION: Synthetic peptide

<400> SEQUENCE: 716

Val Pro Leu Arg Ser Ser Ala
1 5

<210> SEQ ID NO 717
<211> LENGTH: 7
<212> TYPE: PRT
<213> ORGANISM: Artificial Sequence
<220> FEATURE:
<223> OTHER INFORMATION: Synthetic peptide

<400> SEQUENCE: 717

Ala Gly Ser Gly Phe Pro Phe
1 5

<210> SEQ ID NO 718
<211> LENGTH: 7
<212> TYPE: PRT
<213> ORGANISM: Artificial Sequence
<220> FEATURE:
<223> OTHER INFORMATION: Synthetic peptide

<400> SEQUENCE: 718

Gly Ala Gly Arg Gly Thr Pro
1 5

<210> SEQ ID NO 719
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 719

Ala Gly Arg Ile Ala Ser Lys
1               5

<210> SEQ ID NO 720
<211> LENGTH: 7
<212> TYPE: PRT
<213> ORGANISM: Artificial Sequence
<220> FEATURE:
<223> OTHER INFORMATION: Synthetic peptide

<400> SEQUENCE: 720

Trp Gly Val Ala Gly Leu Gly
1               5

<210> SEQ ID NO 721
<211> LENGTH: 7
<212> TYPE: PRT
<213> ORGANISM: Artificial Sequence
<220> FEATURE:
<223> OTHER INFORMATION: Synthetic peptide

<400> SEQUENCE: 721

Leu Ala Gly Leu Val Ser Gly
1               5

<210> SEQ ID NO 722
<211> LENGTH: 7
<212> TYPE: PRT
<213> ORGANISM: Artificial Sequence
<220> FEATURE:
<223> OTHER INFORMATION: Synthetic peptide

<400> SEQUENCE: 722

Asp Ala Gly Gly Met Asp Leu
1               5

<210> SEQ ID NO 723
<211> LENGTH: 7
<212> TYPE: PRT
<213> ORGANISM: Artificial Sequence
<220> FEATURE:
<223> OTHER INFORMATION: Synthetic peptide

<400> SEQUENCE: 723

Ala Gly Gly Arg Trp Asn Leu
1               5

<210> SEQ ID NO 724
<211> LENGTH: 7
<212> TYPE: PRT
<213> ORGANISM: Artificial Sequence
<220> FEATURE:
<223> OTHER INFORMATION: Synthetic peptide

<400> SEQUENCE: 724

Gly Cys Gly Gly Val Arg Asp
1               5

<210> SEQ ID NO 725
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 725

Ser Gly Val Arg Leu Thr Gly
1               5

<210> SEQ ID NO 726
<211> LENGTH: 7
<212> TYPE: PRT
<213> ORGANISM: Artificial Sequence
<220> FEATURE:
<223> OTHER INFORMATION: Synthetic peptide

<400> SEQUENCE: 726

Leu Lys Val Arg Gly Val Leu
1               5

<210> SEQ ID NO 727
<211> LENGTH: 7
<212> TYPE: PRT
<213> ORGANISM: Artificial Sequence
<220> FEATURE:
<223> OTHER INFORMATION: Synthetic peptide

<400> SEQUENCE: 727

Gly Leu Gly Ala Val Gly Trp
1               5

<210> SEQ ID NO 728
<211> LENGTH: 7
<212> TYPE: PRT
<213> ORGANISM: Artificial Sequence
<220> FEATURE:
<223> OTHER INFORMATION: Synthetic peptide

<400> SEQUENCE: 728

Pro Gly Ala Val Pro Gly Ala
1               5

<210> SEQ ID NO 729
<211> LENGTH: 7
<212> TYPE: PRT
<213> ORGANISM: Artificial Sequence
<220> FEATURE:
<223> OTHER INFORMATION: Synthetic peptide

<400> SEQUENCE: 729

Arg Ile Gly Ala Val Trp Tyr
1               5

<210> SEQ ID NO 730
<211> LENGTH: 7
<212> TYPE: PRT
<213> ORGANISM: Artificial Sequence
<220> FEATURE:
<223> OTHER INFORMATION: Synthetic peptide

<400> SEQUENCE: 730

Phe Ser Gly Leu Val Val Ala
1               5

<210> SEQ ID NO 731
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 731

Pro Gly Gly Leu Val Pro Gly
1 5

<210> SEQ ID NO 732
<211> LENGTH: 7
<212> TYPE: PRT
<213> ORGANISM: Artificial Sequence
<220> FEATURE:
<223> OTHER INFORMATION: Synthetic peptide

<400> SEQUENCE: 732

Leu Ala Gly Leu Val Ser Gly
1 5

<210> SEQ ID NO 733
<211> LENGTH: 7
<212> TYPE: PRT
<213> ORGANISM: Artificial Sequence
<220> FEATURE:
<223> OTHER INFORMATION: Synthetic peptide

<400> SEQUENCE: 733

Leu Gly Leu Val Ser Thr Thr
1 5

<210> SEQ ID NO 734
<211> LENGTH: 7
<212> TYPE: PRT
<213> ORGANISM: Artificial Sequence
<220> FEATURE:
<223> OTHER INFORMATION: Synthetic peptide

<400> SEQUENCE: 734

Gly Leu Arg Leu Gly Val Thr
1 5

<210> SEQ ID NO 735
<211> LENGTH: 7
<212> TYPE: PRT
<213> ORGANISM: Artificial Sequence
<220> FEATURE:
<223> OTHER INFORMATION: Synthetic peptide

<400> SEQUENCE: 735

Arg Arg Pro Gly Leu Arg Ser
1 5

<210> SEQ ID NO 736
<211> LENGTH: 7
<212> TYPE: PRT
<213> ORGANISM: Artificial Sequence
<220> FEATURE:
<223> OTHER INFORMATION: Synthetic peptide

<400> SEQUENCE: 736

Leu Ala Gly Leu Val Ser Gly
1 5

<210> SEQ ID NO 737
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 737

Leu Gly Leu Val Ser Thr Thr
1 5

<210> SEQ ID NO 738
<211> LENGTH: 7
<212> TYPE: PRT
<213> ORGANISM: Artificial Sequence
<220> FEATURE:
<223> OTHER INFORMATION: Synthetic peptide

<400> SEQUENCE: 738

Arg Gln Leu Val Ser Pro Ala
1 5

<210> SEQ ID NO 739
<211> LENGTH: 7
<212> TYPE: PRT
<213> ORGANISM: Artificial Sequence
<220> FEATURE:
<223> OTHER INFORMATION: Synthetic peptide

<400> SEQUENCE: 739

Leu Arg Ala Arg Gly Gly His
1 5

<210> SEQ ID NO 740
<211> LENGTH: 7
<212> TYPE: PRT
<213> ORGANISM: Artificial Sequence
<220> FEATURE:
<223> OTHER INFORMATION: Synthetic peptide

<400> SEQUENCE: 740

Glu Leu Trp Ala Ser Leu Gly
1 5

<210> SEQ ID NO 741
<211> LENGTH: 7
<212> TYPE: PRT
<213> ORGANISM: Artificial Sequence
<220> FEATURE:
<223> OTHER INFORMATION: Synthetic peptide

<400> SEQUENCE: 741

Asp Thr Leu Ala Ser Leu Arg
1 5

<210> SEQ ID NO 742
<211> LENGTH: 7
<212> TYPE: PRT
<213> ORGANISM: Artificial Sequence
<220> FEATURE:
<223> OTHER INFORMATION: Synthetic peptide

<400> SEQUENCE: 742

Val Val Ala Ser Leu Pro His
1 5

<210> SEQ ID NO 743
<211> LENGTH: 7
<212> TYPE: PRT
<213> ORGANISM: Artificial Sequence
<220> FEATURE:
<223> OTHER INFORMATION: Synthetic peptide

<400> SEQUENCE: 743

Val Leu Arg Ala Ala Ser Arg
1 5

<210> SEQ ID NO 744
<211> LENGTH: 7
<212> TYPE: PRT
<213> ORGANISM: Artificial Sequence
<220> FEATURE:
<223> OTHER INFORMATION: Synthetic peptide

<400> SEQUENCE: 744

Ala Ala Ser Gly Ser Tyr Tyr
1 5

<210> SEQ ID NO 745
<211> LENGTH: 7
<212> TYPE: PRT
<213> ORGANISM: Artificial Sequence
<220> FEATURE:
<223> OTHER INFORMATION: Synthetic peptide

<400> SEQUENCE: 745

Gly Gly Ser Ala Leu Phe Gly
1 5

<210> SEQ ID NO 746
<211> LENGTH: 7
<212> TYPE: PRT
<213> ORGANISM: Artificial Sequence
<220> FEATURE:
<223> OTHER INFORMATION: Synthetic peptide

<400> SEQUENCE: 746

Gly Arg Gly Gly Ser Gly Tyr
1 5

<210> SEQ ID NO 747
<211> LENGTH: 7
<212> TYPE: PRT
<213> ORGANISM: Artificial Sequence
<220> FEATURE:
<223> OTHER INFORMATION: Synthetic peptide

<400> SEQUENCE: 747

Tyr Gly Ser Gly Gly Arg Gly
1 5

<210> SEQ ID NO 748
<211> LENGTH: 7
<212> TYPE: PRT
<213> ORGANISM: Artificial Sequence
<220> FEATURE:
<223> OTHER INFORMATION: Synthetic peptide

<400> SEQUENCE: 748

Gly Thr Leu Gly Gly Arg Val
1 5

<210> SEQ ID NO 749
<211> LENGTH: 7
<212> TYPE: PRT
<213> ORGANISM: Artificial Sequence
<220> FEATURE:
<223> OTHER INFORMATION: Synthetic peptide

<400> SEQUENCE: 749

Ala Gly Gly Arg Trp Asn Leu
1 5

<210> SEQ ID NO 750
<211> LENGTH: 7
<212> TYPE: PRT
<213> ORGANISM: Artificial Sequence
<220> FEATURE:
<223> OTHER INFORMATION: Synthetic peptide

<400> SEQUENCE: 750

His Gly Gly Arg Ala Arg Leu
1 5

<210> SEQ ID NO 751
<211> LENGTH: 7
<212> TYPE: PRT
<213> ORGANISM: Artificial Sequence
<220> FEATURE:
<223> OTHER INFORMATION: Synthetic peptide

<400> SEQUENCE: 751

Arg Gly Gly Arg Ser Pro Ser
1 5

<210> SEQ ID NO 752
<211> LENGTH: 7
<212> TYPE: PRT
<213> ORGANISM: Artificial Sequence
<220> FEATURE:
<223> OTHER INFORMATION: Synthetic peptide

<400> SEQUENCE: 752

Arg Lys Pro Gly Gly Gly Arg
1 5

<210> SEQ ID NO 753
<211> LENGTH: 7
<212> TYPE: PRT
<213> ORGANISM: Artificial Sequence
<220> FEATURE:
<223> OTHER INFORMATION: Synthetic peptide

<400> SEQUENCE: 753

Glu Gly Gly Arg Thr His Trp
1 5

<210> SEQ ID NO 754
<211> LENGTH: 7
<212> TYPE: PRT
<213> ORGANISM: Artificial Sequence
<220> FEATURE:
<223> OTHER INFORMATION: Synthetic peptide

<400> SEQUENCE: 754

Gly Glu Val Gly Leu Gly Val
1 5

<210> SEQ ID NO 755
<211> LENGTH: 7
<212> TYPE: PRT
<213> ORGANISM: Artificial Sequence
<220> FEATURE:
<223> OTHER INFORMATION: Synthetic peptide

<400> SEQUENCE: 755

-continued

Gly Leu Gly Ala Val Gly Trp
1 5

<210> SEQ ID NO 756
<211> LENGTH: 7
<212> TYPE: PRT
<213> ORGANISM: Artificial Sequence
<220> FEATURE:
<223> OTHER INFORMATION: Synthetic peptide

<400> SEQUENCE: 756

Pro Gly Gly Leu Val Pro Gly
1 5

<210> SEQ ID NO 757
<211> LENGTH: 7
<212> TYPE: PRT
<213> ORGANISM: Artificial Sequence
<220> FEATURE:
<223> OTHER INFORMATION: Synthetic peptide

<400> SEQUENCE: 757

Val Arg Gly Gly Leu Thr Gly
1 5

<210> SEQ ID NO 758
<211> LENGTH: 7
<212> TYPE: PRT
<213> ORGANISM: Artificial Sequence
<220> FEATURE:
<223> OTHER INFORMATION: Synthetic peptide

<400> SEQUENCE: 758

Arg Gln Lys Cys Gly Gly Leu
1 5

<210> SEQ ID NO 759
<211> LENGTH: 7
<212> TYPE: PRT
<213> ORGANISM: Artificial Sequence
<220> FEATURE:
<223> OTHER INFORMATION: Synthetic peptide

<400> SEQUENCE: 759

Arg Tyr Gly Val Gly Gly Leu
1 5

<210> SEQ ID NO 760
<211> LENGTH: 7
<212> TYPE: PRT
<213> ORGANISM: Artificial Sequence
<220> FEATURE:
<223> OTHER INFORMATION: Synthetic peptide

<400> SEQUENCE: 760

Glu Met Gly Ser Ser Arg Gly
1 5

<210> SEQ ID NO 761
<211> LENGTH: 7
<212> TYPE: PRT
<213> ORGANISM: Artificial Sequence
<220> FEATURE:
<223> OTHER INFORMATION: Synthetic peptide

<400> SEQUENCE: 761

-continued

Ala Gly Ser Gly Phe Pro Phe
1 5

<210> SEQ ID NO 762
<211> LENGTH: 7
<212> TYPE: PRT
<213> ORGANISM: Artificial Sequence
<220> FEATURE:
<223> OTHER INFORMATION: Synthetic peptide

<400> SEQUENCE: 762

Gly Arg Gly Gly Ser Gly Tyr
1 5

<210> SEQ ID NO 763
<211> LENGTH: 7
<212> TYPE: PRT
<213> ORGANISM: Artificial Sequence
<220> FEATURE:
<223> OTHER INFORMATION: Synthetic peptide

<400> SEQUENCE: 763

Gly Ser Val Ser Ala Gly Ala
1 5

<210> SEQ ID NO 764
<211> LENGTH: 7
<212> TYPE: PRT
<213> ORGANISM: Artificial Sequence
<220> FEATURE:
<223> OTHER INFORMATION: Synthetic peptide

<400> SEQUENCE: 764

Arg Gly Ser Val Ala Ser Ala
1 5

<210> SEQ ID NO 765
<211> LENGTH: 7
<212> TYPE: PRT
<213> ORGANISM: Artificial Sequence
<220> FEATURE:
<223> OTHER INFORMATION: Synthetic peptide

<400> SEQUENCE: 765

Asp Leu Gly Ser Val Gln His
1 5

<210> SEQ ID NO 766
<211> LENGTH: 7
<212> TYPE: PRT
<213> ORGANISM: Artificial Sequence
<220> FEATURE:
<223> OTHER INFORMATION: Synthetic peptide

<400> SEQUENCE: 766

His Phe Ile Arg Gly Ser Val
1 5

<210> SEQ ID NO 767
<211> LENGTH: 7
<212> TYPE: PRT
<213> ORGANISM: Artificial Sequence
<220> FEATURE:
<223> OTHER INFORMATION: Synthetic peptide

<400> SEQUENCE: 767

Gly Ser Val Leu Gly Ala Leu

-continued 1 5

<210> SEQ ID NO 768
<211> LENGTH: 7
<212> TYPE: PRT
<213> ORGANISM: Artificial Sequence
<220> FEATURE:
<223> OTHER INFORMATION: Synthetic peptide

<400> SEQUENCE: 768

Gly Thr Leu Gly Gly Arg Val
1 5

<210> SEQ ID NO 769
<211> LENGTH: 7
<212> TYPE: PRT
<213> ORGANISM: Artificial Sequence
<220> FEATURE:
<223> OTHER INFORMATION: Synthetic peptide

<400> SEQUENCE: 769

Leu Gly Arg Val His Val Trp
1 5

<210> SEQ ID NO 770
<211> LENGTH: 7
<212> TYPE: PRT
<213> ORGANISM: Artificial Sequence
<220> FEATURE:
<223> OTHER INFORMATION: Synthetic peptide

<400> SEQUENCE: 770

Leu Val Gly Arg Val Lys Leu
1 5

<210> SEQ ID NO 771
<211> LENGTH: 7
<212> TYPE: PRT
<213> ORGANISM: Artificial Sequence
<220> FEATURE:
<223> OTHER INFORMATION: Synthetic peptide

<400> SEQUENCE: 771

Arg Trp Arg Ser Gly Arg Val
1 5

<210> SEQ ID NO 772
<211> LENGTH: 7
<212> TYPE: PRT
<213> ORGANISM: Artificial Sequence
<220> FEATURE:
<223> OTHER INFORMATION: Synthetic peptide

<400> SEQUENCE: 772

Arg Asn Pro Gly Arg Leu Ala
1 5

<210> SEQ ID NO 773
<211> LENGTH: 7
<212> TYPE: PRT
<213> ORGANISM: Artificial Sequence
<220> FEATURE:
<223> OTHER INFORMATION: Synthetic peptide

<400> SEQUENCE: 773

Pro Arg Gly Arg Leu Phe Asp
1 5

-continued

<210> SEQ ID NO 774
<211> LENGTH: 7
<212> TYPE: PRT
<213> ORGANISM: Artificial Sequence
<220> FEATURE:
<223> OTHER INFORMATION: Synthetic peptide

<400> SEQUENCE: 774

Gly Arg Leu Ala Val Val Ala
1 5

<210> SEQ ID NO 775
<211> LENGTH: 7
<212> TYPE: PRT
<213> ORGANISM: Artificial Sequence
<220> FEATURE:
<223> OTHER INFORMATION: Synthetic peptide

<400> SEQUENCE: 775

Leu Ala Gln Gly Arg Leu Ala
1 5

<210> SEQ ID NO 776
<211> LENGTH: 7
<212> TYPE: PRT
<213> ORGANISM: Artificial Sequence
<220> FEATURE:
<223> OTHER INFORMATION: Synthetic peptide

<400> SEQUENCE: 776

Gly Gly Met Asn Gly Arg Leu
1 5

<210> SEQ ID NO 777
<211> LENGTH: 7
<212> TYPE: PRT
<213> ORGANISM: Artificial Sequence
<220> FEATURE:
<223> OTHER INFORMATION: Synthetic peptide

<400> SEQUENCE: 777

Arg Ser Thr Leu Gly Pro Ser
1 5

<210> SEQ ID NO 778
<211> LENGTH: 7
<212> TYPE: PRT
<213> ORGANISM: Artificial Sequence
<220> FEATURE:
<223> OTHER INFORMATION: Synthetic peptide

<400> SEQUENCE: 778

Gly Val Ser Ala Leu Ser Leu
1 5

<210> SEQ ID NO 779
<211> LENGTH: 7
<212> TYPE: PRT
<213> ORGANISM: Artificial Sequence
<220> FEATURE:
<223> OTHER INFORMATION: Synthetic peptide

<400> SEQUENCE: 779

Ser Arg Leu Ser Tyr Tyr Ala
1 5

-continued

<210> SEQ ID NO 780
<211> LENGTH: 7
<212> TYPE: PRT
<213> ORGANISM: Artificial Sequence
<220> FEATURE:
<223> OTHER INFORMATION: Synthetic peptide

<400> SEQUENCE: 780

Ala Arg Gly Val Ser Ala Pro
1 5

<210> SEQ ID NO 781
<211> LENGTH: 7
<212> TYPE: PRT
<213> ORGANISM: Artificial Sequence
<220> FEATURE:
<223> OTHER INFORMATION: Synthetic peptide

<400> SEQUENCE: 781

Gly Arg Gly Val Leu Ala Phe
1 5

<210> SEQ ID NO 782
<211> LENGTH: 7
<212> TYPE: PRT
<213> ORGANISM: Artificial Sequence
<220> FEATURE:
<223> OTHER INFORMATION: Synthetic peptide

<400> SEQUENCE: 782

Met Arg Gly Ser Gly Arg Asn
1 5

<210> SEQ ID NO 783
<211> LENGTH: 7
<212> TYPE: PRT
<213> ORGANISM: Artificial Sequence
<220> FEATURE:
<223> OTHER INFORMATION: Synthetic peptide

<400> SEQUENCE: 783

Arg Asp Gly Arg Ala Val Arg
1 5

<210> SEQ ID NO 784
<211> LENGTH: 7
<212> TYPE: PRT
<213> ORGANISM: Artificial Sequence
<220> FEATURE:
<223> OTHER INFORMATION: Synthetic peptide

<400> SEQUENCE: 784

Gly Arg Ala Val Trp Met Val
1 5

<210> SEQ ID NO 785
<211> LENGTH: 7
<212> TYPE: PRT
<213> ORGANISM: Artificial Sequence
<220> FEATURE:
<223> OTHER INFORMATION: Synthetic peptide

<400> SEQUENCE: 785

Leu Arg Val Pro Gly Gly Pro
1 5

-continued

<210> SEQ ID NO 786
<211> LENGTH: 7
<212> TYPE: PRT
<213> ORGANISM: Artificial Sequence
<220> FEATURE:
<223> OTHER INFORMATION: Synthetic peptide

<400> SEQUENCE: 786

Ala Tyr Tyr Ser Leu Arg Ser
1 5

<210> SEQ ID NO 787
<211> LENGTH: 7
<212> TYPE: PRT
<213> ORGANISM: Artificial Sequence
<220> FEATURE:
<223> OTHER INFORMATION: Synthetic peptide

<400> SEQUENCE: 787

Val Leu Arg Ser Ala Leu Gln
1 5

<210> SEQ ID NO 788
<211> LENGTH: 7
<212> TYPE: PRT
<213> ORGANISM: Artificial Sequence
<220> FEATURE:
<223> OTHER INFORMATION: Synthetic peptide

<400> SEQUENCE: 788

Val Tyr Tyr Ala Leu Arg Ser
1 5

<210> SEQ ID NO 789
<211> LENGTH: 7
<212> TYPE: PRT
<213> ORGANISM: Artificial Sequence
<220> FEATURE:
<223> OTHER INFORMATION: Synthetic peptide

<400> SEQUENCE: 789

Arg Tyr Arg Val Ser Val Tyr
1 5

<210> SEQ ID NO 790
<211> LENGTH: 7
<212> TYPE: PRT
<213> ORGANISM: Artificial Sequence
<220> FEATURE:
<223> OTHER INFORMATION: Synthetic peptide

<400> SEQUENCE: 790

Ala Gly Gly Ile Trp Ile Arg
1 5

<210> SEQ ID NO 791
<211> LENGTH: 7
<212> TYPE: PRT
<213> ORGANISM: Artificial Sequence
<220> FEATURE:
<223> OTHER INFORMATION: Synthetic peptide

<400> SEQUENCE: 791

Trp Gln Val Ser Gly Val Arg
1 5

<210> SEQ ID NO 792

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 792

Gly Arg Gly Val Leu Ala Phe
1               5

<210> SEQ ID NO 793
<211> LENGTH: 7
<212> TYPE: PRT
<213> ORGANISM: Artificial Sequence
<220> FEATURE:
<223> OTHER INFORMATION: Synthetic peptide

<400> SEQUENCE: 793

His Ala Glu Leu Val Ser Leu
1               5

<210> SEQ ID NO 794
<211> LENGTH: 7
<212> TYPE: PRT
<213> ORGANISM: Artificial Sequence
<220> FEATURE:
<223> OTHER INFORMATION: Synthetic peptide

<400> SEQUENCE: 794

Ala Arg Gly Val Ser Ala Pro
1               5

<210> SEQ ID NO 795
<211> LENGTH: 7
<212> TYPE: PRT
<213> ORGANISM: Artificial Sequence
<220> FEATURE:
<223> OTHER INFORMATION: Synthetic peptide

<400> SEQUENCE: 795

Arg Val Ala Arg Gly Asp Arg
1               5

<210> SEQ ID NO 796
<211> LENGTH: 7
<212> TYPE: PRT
<213> ORGANISM: Artificial Sequence
<220> FEATURE:
<223> OTHER INFORMATION: Synthetic peptide

<400> SEQUENCE: 796

Val Met Trp Val Ala Arg Gly
1               5

<210> SEQ ID NO 797
<211> LENGTH: 7
<212> TYPE: PRT
<213> ORGANISM: Artificial Sequence
<220> FEATURE:
<223> OTHER INFORMATION: Synthetic peptide

<400> SEQUENCE: 797

Ala Ala Val Thr Val Val Arg
1               5

<210> SEQ ID NO 798
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 798

Thr Arg Glu Gly Gly Leu Asp
1 5

<210> SEQ ID NO 799
<211> LENGTH: 7
<212> TYPE: PRT
<213> ORGANISM: Artificial Sequence
<220> FEATURE:
<223> OTHER INFORMATION: Synthetic peptide

<400> SEQUENCE: 799

Leu Gly Gly Gly Gly Leu Leu
1 5

<210> SEQ ID NO 800
<211> LENGTH: 7
<212> TYPE: PRT
<213> ORGANISM: Artificial Sequence
<220> FEATURE:
<223> OTHER INFORMATION: Synthetic peptide

<400> SEQUENCE: 800

Gly Ser Gly His Ser Phe Ala
1 5

<210> SEQ ID NO 801
<211> LENGTH: 7
<212> TYPE: PRT
<213> ORGANISM: Artificial Sequence
<220> FEATURE:
<223> OTHER INFORMATION: Synthetic peptide

<400> SEQUENCE: 801

Met Arg Gly Ser Gly Arg Asn
1 5

<210> SEQ ID NO 802
<211> LENGTH: 7
<212> TYPE: PRT
<213> ORGANISM: Artificial Sequence
<220> FEATURE:
<223> OTHER INFORMATION: Synthetic peptide

<400> SEQUENCE: 802

Arg Val Gly Ser Val Gln Trp
1 5

<210> SEQ ID NO 803
<211> LENGTH: 7
<212> TYPE: PRT
<213> ORGANISM: Artificial Sequence
<220> FEATURE:
<223> OTHER INFORMATION: Synthetic peptide

<400> SEQUENCE: 803

Glu Gly Thr Ser Gly Ser Val
1 5

<210> SEQ ID NO 804
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 804

Gly Arg Val Pro Thr Val Val
1 5

<210> SEQ ID NO 805
<211> LENGTH: 7
<212> TYPE: PRT
<213> ORGANISM: Artificial Sequence
<220> FEATURE:
<223> OTHER INFORMATION: Synthetic peptide

<400> SEQUENCE: 805

Ala Asp Gly Arg Leu Arg Tyr
1 5

<210> SEQ ID NO 806
<211> LENGTH: 7
<212> TYPE: PRT
<213> ORGANISM: Artificial Sequence
<220> FEATURE:
<223> OTHER INFORMATION: Synthetic peptide

<400> SEQUENCE: 806

Ala Arg Gly Val Ser Ala Pro
1 5

<210> SEQ ID NO 807
<211> LENGTH: 7
<212> TYPE: PRT
<213> ORGANISM: Artificial Sequence
<220> FEATURE:
<223> OTHER INFORMATION: Synthetic peptide

<400> SEQUENCE: 807

Arg Gly Val Lys Leu Gly Asp
1 5

<210> SEQ ID NO 808
<211> LENGTH: 7
<212> TYPE: PRT
<213> ORGANISM: Artificial Sequence
<220> FEATURE:
<223> OTHER INFORMATION: Synthetic peptide

<400> SEQUENCE: 808

Leu Arg Gly Ser Tyr Val Leu
1 5

<210> SEQ ID NO 809
<211> LENGTH: 7
<212> TYPE: PRT
<213> ORGANISM: Artificial Sequence
<220> FEATURE:
<223> OTHER INFORMATION: Synthetic peptide

<400> SEQUENCE: 809

Arg Arg Gly Ser Leu Met Phe
1 5

<210> SEQ ID NO 810
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 810

Arg Gly Ser Val Gly Pro Ser
1 5

<210> SEQ ID NO 811
<211> LENGTH: 7
<212> TYPE: PRT
<213> ORGANISM: Artificial Sequence
<220> FEATURE:
<223> OTHER INFORMATION: Synthetic peptide

<400> SEQUENCE: 811

Ser Arg Ala Ser Asp Val Thr
1 5

<210> SEQ ID NO 812
<211> LENGTH: 7
<212> TYPE: PRT
<213> ORGANISM: Artificial Sequence
<220> FEATURE:
<223> OTHER INFORMATION: Synthetic peptide

<400> SEQUENCE: 812

Ala Ala Lys Thr Leu Leu Ser
1 5

<210> SEQ ID NO 813
<211> LENGTH: 7
<212> TYPE: PRT
<213> ORGANISM: Artificial Sequence
<220> FEATURE:
<223> OTHER INFORMATION: Synthetic peptide

<400> SEQUENCE: 813

Arg Ser Tyr Pro Leu Arg Ser
1 5

<210> SEQ ID NO 814
<211> LENGTH: 7
<212> TYPE: PRT
<213> ORGANISM: Artificial Sequence
<220> FEATURE:
<223> OTHER INFORMATION: Synthetic peptide

<400> SEQUENCE: 814

Tyr Leu Gly Arg Arg Val Ser
1 5

<210> SEQ ID NO 815
<211> LENGTH: 7
<212> TYPE: PRT
<213> ORGANISM: Artificial Sequence
<220> FEATURE:
<223> OTHER INFORMATION: Synthetic peptide

<400> SEQUENCE: 815

Arg Ser Ser Pro Val Trp Thr
1 5

<210> SEQ ID NO 816
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 816

Asp Leu Arg Arg Ala Gly Ser
1               5

<210> SEQ ID NO 817
<211> LENGTH: 7
<212> TYPE: PRT
<213> ORGANISM: Artificial Sequence
<220> FEATURE:
<223> OTHER INFORMATION: Synthetic peptide

<400> SEQUENCE: 817

Gly Val Ala Gly Leu Arg Trp
1               5

<210> SEQ ID NO 818
<211> LENGTH: 7
<212> TYPE: PRT
<213> ORGANISM: Artificial Sequence
<220> FEATURE:
<223> OTHER INFORMATION: Synthetic peptide

<400> SEQUENCE: 818

Arg Ile Asp Ala Gly Gly Gly
1               5

<210> SEQ ID NO 819
<211> LENGTH: 7
<212> TYPE: PRT
<213> ORGANISM: Artificial Sequence
<220> FEATURE:
<223> OTHER INFORMATION: Synthetic peptide

<400> SEQUENCE: 819

Gly Val Ala Gly Gly Ala Thr
1               5

<210> SEQ ID NO 820
<211> LENGTH: 7
<212> TYPE: PRT
<213> ORGANISM: Artificial Sequence
<220> FEATURE:
<223> OTHER INFORMATION: Synthetic peptide

<400> SEQUENCE: 820

Thr Ala Gly Gly Ala Val Gly
1               5

<210> SEQ ID NO 821
<211> LENGTH: 7
<212> TYPE: PRT
<213> ORGANISM: Artificial Sequence
<220> FEATURE:
<223> OTHER INFORMATION: Synthetic peptide

<400> SEQUENCE: 821

Trp Arg Leu Gly Ala Val Gly
1               5

<210> SEQ ID NO 822
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 822

Ser Gly Leu Val Ala Met Val
1 5

<210> SEQ ID NO 823
<211> LENGTH: 7
<212> TYPE: PRT
<213> ORGANISM: Artificial Sequence
<220> FEATURE:
<223> OTHER INFORMATION: Synthetic peptide

<400> SEQUENCE: 823

Val Gly Leu Arg Asp Trp Gly
1 5

<210> SEQ ID NO 824
<211> LENGTH: 7
<212> TYPE: PRT
<213> ORGANISM: Artificial Sequence
<220> FEATURE:
<223> OTHER INFORMATION: Synthetic peptide

<400> SEQUENCE: 824

Gly Val Ala Gly Leu Arg Trp
1 5

<210> SEQ ID NO 825
<211> LENGTH: 7
<212> TYPE: PRT
<213> ORGANISM: Artificial Sequence
<220> FEATURE:
<223> OTHER INFORMATION: Synthetic peptide

<400> SEQUENCE: 825

Ala Arg Gly Ile Val Arg Val
1 5

<210> SEQ ID NO 826
<211> LENGTH: 7
<212> TYPE: PRT
<213> ORGANISM: Artificial Sequence
<220> FEATURE:
<223> OTHER INFORMATION: Synthetic peptide

<400> SEQUENCE: 826

Ala Ser Leu His His Arg Arg
1 5

<210> SEQ ID NO 827
<211> LENGTH: 7
<212> TYPE: PRT
<213> ORGANISM: Artificial Sequence
<220> FEATURE:
<223> OTHER INFORMATION: Synthetic peptide

<400> SEQUENCE: 827

Gly Ala Ala Ala Ser Gly Tyr
1 5

<210> SEQ ID NO 828
<211> LENGTH: 7
<212> TYPE: PRT
<213> ORGANISM: Artificial Sequence
<220> FEATURE:
<223> OTHER INFORMATION: Synthetic peptide

<400> SEQUENCE: 828

Leu Ala Ile Arg Gly Leu Gly
1               5

<210> SEQ ID NO 829
<211> LENGTH: 7
<212> TYPE: PRT
<213> ORGANISM: Artificial Sequence
<220> FEATURE:
<223> OTHER INFORMATION: Synthetic peptide

<400> SEQUENCE: 829

Gly Gly Leu Ser Asn Val Val
1               5

<210> SEQ ID NO 830
<211> LENGTH: 7
<212> TYPE: PRT
<213> ORGANISM: Artificial Sequence
<220> FEATURE:
<223> OTHER INFORMATION: Synthetic peptide

<400> SEQUENCE: 830

Pro Pro Gly Gly Leu Lys Trp
1               5

<210> SEQ ID NO 831
<211> LENGTH: 7
<212> TYPE: PRT
<213> ORGANISM: Artificial Sequence
<220> FEATURE:
<223> OTHER INFORMATION: Synthetic peptide

<400> SEQUENCE: 831

Glu Gly Ser Val Asp Ala His
1               5

<210> SEQ ID NO 832
<211> LENGTH: 7
<212> TYPE: PRT
<213> ORGANISM: Artificial Sequence
<220> FEATURE:
<223> OTHER INFORMATION: Synthetic peptide

<400> SEQUENCE: 832

Arg Gly Ser Val Gly Pro Ser
1               5

<210> SEQ ID NO 833
<211> LENGTH: 7
<212> TYPE: PRT
<213> ORGANISM: Artificial Sequence
<220> FEATURE:
<223> OTHER INFORMATION: Synthetic peptide

<400> SEQUENCE: 833

Leu Val Tyr Ser Gly Arg Leu
1               5

<210> SEQ ID NO 834
<211> LENGTH: 7
<212> TYPE: PRT
<213> ORGANISM: Artificial Sequence
<220> FEATURE:
<223> OTHER INFORMATION: Synthetic peptide

<400> SEQUENCE: 834

-continued

Val Glu Glu Gly Arg Leu Arg
1 5

<210> SEQ ID NO 835
<211> LENGTH: 7
<212> TYPE: PRT
<213> ORGANISM: Artificial Sequence
<220> FEATURE:
<223> OTHER INFORMATION: Synthetic peptide

<400> SEQUENCE: 835

Arg Gly Ser Val Gly Pro Ser
1 5

<210> SEQ ID NO 836
<211> LENGTH: 7
<212> TYPE: PRT
<213> ORGANISM: Artificial Sequence
<220> FEATURE:
<223> OTHER INFORMATION: Synthetic peptide

<400> SEQUENCE: 836

Ser Pro Gly Val Ser Gly Arg
1 5

<210> SEQ ID NO 837
<211> LENGTH: 7
<212> TYPE: PRT
<213> ORGANISM: Artificial Sequence
<220> FEATURE:
<223> OTHER INFORMATION: Synthetic peptide

<400> SEQUENCE: 837

Arg Val Gly Arg Gly Val Leu
1 5

<210> SEQ ID NO 838
<211> LENGTH: 7
<212> TYPE: PRT
<213> ORGANISM: Artificial Sequence
<220> FEATURE:
<223> OTHER INFORMATION: Synthetic peptide

<400> SEQUENCE: 838

Trp Ile Trp Arg Ala Val Ser
1 5

<210> SEQ ID NO 839
<211> LENGTH: 7
<212> TYPE: PRT
<213> ORGANISM: Artificial Sequence
<220> FEATURE:
<223> OTHER INFORMATION: Synthetic peptide

<400> SEQUENCE: 839

Val Thr Asp Gly Ala Gly Gln
1 5

<210> SEQ ID NO 840
<211> LENGTH: 7
<212> TYPE: PRT
<213> ORGANISM: Artificial Sequence
<220> FEATURE:
<223> OTHER INFORMATION: Synthetic peptide

<400> SEQUENCE: 840

-continued

Leu Gly Thr Ala Val Ser Ser
1 5

<210> SEQ ID NO 841
<211> LENGTH: 7
<212> TYPE: PRT
<213> ORGANISM: Artificial Sequence
<220> FEATURE:
<223> OTHER INFORMATION: Synthetic peptide

<400> SEQUENCE: 841

Trp Ile Trp Arg Ala Val Ser
1 5

<210> SEQ ID NO 842
<211> LENGTH: 7
<212> TYPE: PRT
<213> ORGANISM: Artificial Sequence
<220> FEATURE:
<223> OTHER INFORMATION: Synthetic peptide

<400> SEQUENCE: 842

Asp Thr Pro Ser Ala Val Ser
1 5

<210> SEQ ID NO 843
<211> LENGTH: 7
<212> TYPE: PRT
<213> ORGANISM: Artificial Sequence
<220> FEATURE:
<223> OTHER INFORMATION: Synthetic peptide

<400> SEQUENCE: 843

Gly Leu Leu Ser Ala Gly Ile
1 5

<210> SEQ ID NO 844
<211> LENGTH: 7
<212> TYPE: PRT
<213> ORGANISM: Artificial Sequence
<220> FEATURE:
<223> OTHER INFORMATION: Synthetic peptide

<400> SEQUENCE: 844

Tyr Leu Leu Arg Ala Leu Gly
1 5

<210> SEQ ID NO 845
<211> LENGTH: 7
<212> TYPE: PRT
<213> ORGANISM: Artificial Sequence
<220> FEATURE:
<223> OTHER INFORMATION: Synthetic peptide

<400> SEQUENCE: 845

Leu Arg Ser Gly Ser Leu Gly
1 5

<210> SEQ ID NO 846
<211> LENGTH: 7
<212> TYPE: PRT
<213> ORGANISM: Artificial Sequence
<220> FEATURE:
<223> OTHER INFORMATION: Synthetic peptide

<400> SEQUENCE: 846

Pro Leu Arg Ser Val Trp Ser

-continued 1 5

<210> SEQ ID NO 847
<211> LENGTH: 7
<212> TYPE: PRT
<213> ORGANISM: Artificial Sequence
<220> FEATURE:
<223> OTHER INFORMATION: Synthetic peptide

<400> SEQUENCE: 847

Ala Arg Ser Ser Ile Val Arg
1 5

<210> SEQ ID NO 848
<211> LENGTH: 7
<212> TYPE: PRT
<213> ORGANISM: Artificial Sequence
<220> FEATURE:
<223> OTHER INFORMATION: Synthetic peptide

<400> SEQUENCE: 848

Ala Gly Gly Arg Leu Gly Leu
1 5

<210> SEQ ID NO 849
<211> LENGTH: 7
<212> TYPE: PRT
<213> ORGANISM: Artificial Sequence
<220> FEATURE:
<223> OTHER INFORMATION: Synthetic peptide

<400> SEQUENCE: 849

Ala Gly Gly Trp Arg Gly Arg
1 5

<210> SEQ ID NO 850
<211> LENGTH: 7
<212> TYPE: PRT
<213> ORGANISM: Artificial Sequence
<220> FEATURE:
<223> OTHER INFORMATION: Synthetic peptide

<400> SEQUENCE: 850

Leu Val Gly Arg Gly Val Arg
1 5

<210> SEQ ID NO 851
<211> LENGTH: 7
<212> TYPE: PRT
<213> ORGANISM: Artificial Sequence
<220> FEATURE:
<223> OTHER INFORMATION: Synthetic peptide

<400> SEQUENCE: 851

Asp Val Val Gly Val Leu Lys
1 5

<210> SEQ ID NO 852
<211> LENGTH: 7
<212> TYPE: PRT
<213> ORGANISM: Artificial Sequence
<220> FEATURE:
<223> OTHER INFORMATION: Synthetic peptide

<400> SEQUENCE: 852

Arg Val Gly Arg Gly Val Leu
1 5

-continued

<210> SEQ ID NO 853
<211> LENGTH: 7
<212> TYPE: PRT
<213> ORGANISM: Artificial Sequence
<220> FEATURE:
<223> OTHER INFORMATION: Synthetic peptide

<400> SEQUENCE: 853

Gly Ala Val Thr Gly Tyr Pro
1               5

<210> SEQ ID NO 854
<211> LENGTH: 7
<212> TYPE: PRT
<213> ORGANISM: Artificial Sequence
<220> FEATURE:
<223> OTHER INFORMATION: Synthetic peptide

<400> SEQUENCE: 854

Trp Gly Leu Val Arg His Ala
1               5

<210> SEQ ID NO 855
<211> LENGTH: 7
<212> TYPE: PRT
<213> ORGANISM: Artificial Sequence
<220> FEATURE:
<223> OTHER INFORMATION: Synthetic peptide

<400> SEQUENCE: 855

Leu Gly Leu Arg Gly Gly Ala
1               5

<210> SEQ ID NO 856
<211> LENGTH: 7
<212> TYPE: PRT
<213> ORGANISM: Artificial Sequence
<220> FEATURE:
<223> OTHER INFORMATION: Synthetic peptide

<400> SEQUENCE: 856

Ile Gly Ala Ser Leu Leu Gly
1               5

<210> SEQ ID NO 857
<211> LENGTH: 7
<212> TYPE: PRT
<213> ORGANISM: Artificial Sequence
<220> FEATURE:
<223> OTHER INFORMATION: Synthetic peptide

<400> SEQUENCE: 857

Ala Ala Val Glu Thr Gly Val
1               5

<210> SEQ ID NO 858
<211> LENGTH: 7
<212> TYPE: PRT
<213> ORGANISM: Artificial Sequence
<220> FEATURE:
<223> OTHER INFORMATION: Synthetic peptide

<400> SEQUENCE: 858

Gly Leu Gly Gly Gly Gly Ser
1               5

-continued

<210> SEQ ID NO 859
<211> LENGTH: 7
<212> TYPE: PRT
<213> ORGANISM: Artificial Sequence
<220> FEATURE:
<223> OTHER INFORMATION: Synthetic peptide

<400> SEQUENCE: 859

Glu Val Leu Trp Gly Gly Arg
1 5

<210> SEQ ID NO 860
<211> LENGTH: 7
<212> TYPE: PRT
<213> ORGANISM: Artificial Sequence
<220> FEATURE:
<223> OTHER INFORMATION: Synthetic peptide

<400> SEQUENCE: 860

Ala Gly Gly Arg Leu Gly Leu
1 5

<210> SEQ ID NO 861
<211> LENGTH: 7
<212> TYPE: PRT
<213> ORGANISM: Artificial Sequence
<220> FEATURE:
<223> OTHER INFORMATION: Synthetic peptide

<400> SEQUENCE: 861

Gly Gly Arg Ser Lys Lys Val
1 5

<210> SEQ ID NO 862
<211> LENGTH: 7
<212> TYPE: PRT
<213> ORGANISM: Artificial Sequence
<220> FEATURE:
<223> OTHER INFORMATION: Synthetic peptide

<400> SEQUENCE: 862

Gly Leu Gly Gly Gly Gly Ser
1 5

<210> SEQ ID NO 863
<211> LENGTH: 7
<212> TYPE: PRT
<213> ORGANISM: Artificial Sequence
<220> FEATURE:
<223> OTHER INFORMATION: Synthetic peptide

<400> SEQUENCE: 863

Ser Gly Gly Gly Gly Leu Gly
1 5

<210> SEQ ID NO 864
<211> LENGTH: 7
<212> TYPE: PRT
<213> ORGANISM: Artificial Sequence
<220> FEATURE:
<223> OTHER INFORMATION: Synthetic peptide

<400> SEQUENCE: 864

Gly Ala Tyr Gly Gly Leu Leu
1 5

-continued

<210> SEQ ID NO 865
<211> LENGTH: 7
<212> TYPE: PRT
<213> ORGANISM: Artificial Sequence
<220> FEATURE:
<223> OTHER INFORMATION: Synthetic peptide

<400> SEQUENCE: 865

Gly Gly Leu Ser Arg Ser Asn
1 5

<210> SEQ ID NO 866
<211> LENGTH: 7
<212> TYPE: PRT
<213> ORGANISM: Artificial Sequence
<220> FEATURE:
<223> OTHER INFORMATION: Synthetic peptide

<400> SEQUENCE: 866

Phe Gly Ser Ser Asn Arg Ser
1 5

<210> SEQ ID NO 867
<211> LENGTH: 7
<212> TYPE: PRT
<213> ORGANISM: Artificial Sequence
<220> FEATURE:
<223> OTHER INFORMATION: Synthetic peptide

<400> SEQUENCE: 867

Gly Ser Val Ser Asp Arg Phe
1 5

<210> SEQ ID NO 868
<211> LENGTH: 7
<212> TYPE: PRT
<213> ORGANISM: Artificial Sequence
<220> FEATURE:
<223> OTHER INFORMATION: Synthetic peptide

<400> SEQUENCE: 868

Ala Gly Gly Arg Leu Gly Leu
1 5

<210> SEQ ID NO 869
<211> LENGTH: 7
<212> TYPE: PRT
<213> ORGANISM: Artificial Sequence
<220> FEATURE:
<223> OTHER INFORMATION: Synthetic peptide

<400> SEQUENCE: 869

Trp Phe Lys Gly Pro Ser Val
1 5

<210> SEQ ID NO 870
<211> LENGTH: 7
<212> TYPE: PRT
<213> ORGANISM: Artificial Sequence
<220> FEATURE:
<223> OTHER INFORMATION: Synthetic peptide

<400> SEQUENCE: 870

Leu Ser Glu Arg Arg Gly Val
1 5

<210> SEQ ID NO 871

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 871

Ala Arg Gly Val Ala Glu Tyr
1 5

<210> SEQ ID NO 872
<211> LENGTH: 7
<212> TYPE: PRT
<213> ORGANISM: Artificial Sequence
<220> FEATURE:
<223> OTHER INFORMATION: Synthetic peptide

<400> SEQUENCE: 872

Phe Asp Arg Gly Ser Leu Thr
1 5

<210> SEQ ID NO 873
<211> LENGTH: 7
<212> TYPE: PRT
<213> ORGANISM: Artificial Sequence
<220> FEATURE:
<223> OTHER INFORMATION: Synthetic peptide

<400> SEQUENCE: 873

Gly Arg Leu Arg Ala Ser Leu
1 5

<210> SEQ ID NO 874
<211> LENGTH: 7
<212> TYPE: PRT
<213> ORGANISM: Artificial Sequence
<220> FEATURE:
<223> OTHER INFORMATION: Synthetic peptide

<400> SEQUENCE: 874

Arg Asp Gly Arg Gly Ala Gly
1 5

<210> SEQ ID NO 875
<211> LENGTH: 7
<212> TYPE: PRT
<213> ORGANISM: Artificial Sequence
<220> FEATURE:
<223> OTHER INFORMATION: Synthetic peptide

<400> SEQUENCE: 875

Gly Ala Val Ser Val Leu Ala
1 5

<210> SEQ ID NO 876
<211> LENGTH: 7
<212> TYPE: PRT
<213> ORGANISM: Artificial Sequence
<220> FEATURE:
<223> OTHER INFORMATION: Synthetic peptide

<400> SEQUENCE: 876

Thr Arg Gly Asp Ala Val Ser
1 5

<210> SEQ ID NO 877
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 877

Leu Leu Ser Pro Arg Gly Thr
1 5

<210> SEQ ID NO 878
<211> LENGTH: 7
<212> TYPE: PRT
<213> ORGANISM: Artificial Sequence
<220> FEATURE:
<223> OTHER INFORMATION: Synthetic peptide

<400> SEQUENCE: 878

Leu Leu Arg Ser His Gly Val
1 5

<210> SEQ ID NO 879
<211> LENGTH: 7
<212> TYPE: PRT
<213> ORGANISM: Artificial Sequence
<220> FEATURE:
<223> OTHER INFORMATION: Synthetic peptide

<400> SEQUENCE: 879

Pro Leu Arg Val Leu Lys Arg
1 5

<210> SEQ ID NO 880
<211> LENGTH: 7
<212> TYPE: PRT
<213> ORGANISM: Artificial Sequence
<220> FEATURE:
<223> OTHER INFORMATION: Synthetic peptide

<400> SEQUENCE: 880

Gly Arg Leu Arg Leu Arg Val
1 5

<210> SEQ ID NO 881
<211> LENGTH: 7
<212> TYPE: PRT
<213> ORGANISM: Artificial Sequence
<220> FEATURE:
<223> OTHER INFORMATION: Synthetic peptide

<400> SEQUENCE: 881

Leu Leu Arg Ser His Gly Val
1 5

<210> SEQ ID NO 882
<211> LENGTH: 7
<212> TYPE: PRT
<213> ORGANISM: Artificial Sequence
<220> FEATURE:
<223> OTHER INFORMATION: Synthetic peptide

<400> SEQUENCE: 882

Val Leu Arg Ser Gly Glu Leu
1 5

<210> SEQ ID NO 883
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 883

Val Leu Arg Ser Ile Pro Ser
1 5

<210> SEQ ID NO 884
<211> LENGTH: 7
<212> TYPE: PRT
<213> ORGANISM: Artificial Sequence
<220> FEATURE:
<223> OTHER INFORMATION: Synthetic peptide

<400> SEQUENCE: 884

Gly Ser Met His Arg Val Ser
1 5

<210> SEQ ID NO 885
<211> LENGTH: 7
<212> TYPE: PRT
<213> ORGANISM: Artificial Sequence
<220> FEATURE:
<223> OTHER INFORMATION: Synthetic peptide

<400> SEQUENCE: 885

Tyr Ser Ile Met Arg Val Ser
1 5

<210> SEQ ID NO 886
<211> LENGTH: 7
<212> TYPE: PRT
<213> ORGANISM: Artificial Sequence
<220> FEATURE:
<223> OTHER INFORMATION: Synthetic peptide

<400> SEQUENCE: 886

Arg Ala Gly Ser Arg Val Gln
1 5

<210> SEQ ID NO 887
<211> LENGTH: 7
<212> TYPE: PRT
<213> ORGANISM: Artificial Sequence
<220> FEATURE:
<223> OTHER INFORMATION: Synthetic peptide

<400> SEQUENCE: 887

Arg Arg Asp Ala Gly Arg Met
1 5

<210> SEQ ID NO 888
<211> LENGTH: 7
<212> TYPE: PRT
<213> ORGANISM: Artificial Sequence
<220> FEATURE:
<223> OTHER INFORMATION: Synthetic peptide

<400> SEQUENCE: 888

Gly Ala Gly Arg Gly Asp Arg
1 5

<210> SEQ ID NO 889
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 889

Arg Trp Ala Gly Leu Val Ala
1               5

<210> SEQ ID NO 890
<211> LENGTH: 7
<212> TYPE: PRT
<213> ORGANISM: Artificial Sequence
<220> FEATURE:
<223> OTHER INFORMATION: Synthetic peptide

<400> SEQUENCE: 890

Gln Thr Leu Ser Ala Gly Gly
1               5

<210> SEQ ID NO 891
<211> LENGTH: 7
<212> TYPE: PRT
<213> ORGANISM: Artificial Sequence
<220> FEATURE:
<223> OTHER INFORMATION: Synthetic peptide

<400> SEQUENCE: 891

Leu Ala Gly Gly Trp Gly Ser
1               5

<210> SEQ ID NO 892
<211> LENGTH: 7
<212> TYPE: PRT
<213> ORGANISM: Artificial Sequence
<220> FEATURE:
<223> OTHER INFORMATION: Synthetic peptide

<400> SEQUENCE: 892

Arg His Gly Val Arg Ser Lys
1               5

<210> SEQ ID NO 893
<211> LENGTH: 7
<212> TYPE: PRT
<213> ORGANISM: Artificial Sequence
<220> FEATURE:
<223> OTHER INFORMATION: Synthetic peptide

<400> SEQUENCE: 893

Gly Ala Val Ser Val Leu Ala
1               5

<210> SEQ ID NO 894
<211> LENGTH: 7
<212> TYPE: PRT
<213> ORGANISM: Artificial Sequence
<220> FEATURE:
<223> OTHER INFORMATION: Synthetic peptide

<400> SEQUENCE: 894

Arg Trp Ala Gly Leu Val Ala
1               5

<210> SEQ ID NO 895
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 895

Gly Arg Gly Leu Arg Thr Asp
1 5

<210> SEQ ID NO 896
<211> LENGTH: 7
<212> TYPE: PRT
<213> ORGANISM: Artificial Sequence
<220> FEATURE:
<223> OTHER INFORMATION: Synthetic peptide

<400> SEQUENCE: 896

Thr Leu Gly Gly Leu Arg Thr
1 5

<210> SEQ ID NO 897
<211> LENGTH: 7
<212> TYPE: PRT
<213> ORGANISM: Artificial Sequence
<220> FEATURE:
<223> OTHER INFORMATION: Synthetic peptide

<400> SEQUENCE: 897

Ala Leu Val Ser Val Ala Gly
1 5

<210> SEQ ID NO 898
<211> LENGTH: 7
<212> TYPE: PRT
<213> ORGANISM: Artificial Sequence
<220> FEATURE:
<223> OTHER INFORMATION: Synthetic peptide

<400> SEQUENCE: 898

Ala Arg Gly Val Ala Glu Tyr
1 5

<210> SEQ ID NO 899
<211> LENGTH: 7
<212> TYPE: PRT
<213> ORGANISM: Artificial Sequence
<220> FEATURE:
<223> OTHER INFORMATION: Synthetic peptide

<400> SEQUENCE: 899

Gly Gly Ala Ser Leu Thr Gln
1 5

<210> SEQ ID NO 900
<211> LENGTH: 7
<212> TYPE: PRT
<213> ORGANISM: Artificial Sequence
<220> FEATURE:
<223> OTHER INFORMATION: Synthetic peptide

<400> SEQUENCE: 900

Gly Arg Leu Arg Ala Ser Leu
1 5

<210> SEQ ID NO 901
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 901

Ser Asn His Thr Ala Ser Leu
1               5

<210> SEQ ID NO 902
<211> LENGTH: 7
<212> TYPE: PRT
<213> ORGANISM: Artificial Sequence
<220> FEATURE:
<223> OTHER INFORMATION: Synthetic peptide

<400> SEQUENCE: 902

Tyr Ala Asp Gly Ala Ala Val
1               5

<210> SEQ ID NO 903
<211> LENGTH: 7
<212> TYPE: PRT
<213> ORGANISM: Artificial Sequence
<220> FEATURE:
<223> OTHER INFORMATION: Synthetic peptide

<400> SEQUENCE: 903

Leu Gly Gly Leu Gly Ile His
1               5

<210> SEQ ID NO 904
<211> LENGTH: 7
<212> TYPE: PRT
<213> ORGANISM: Artificial Sequence
<220> FEATURE:
<223> OTHER INFORMATION: Synthetic peptide

<400> SEQUENCE: 904

Gly Gly Phe Thr Gly Gly Leu
1               5

<210> SEQ ID NO 905
<211> LENGTH: 7
<212> TYPE: PRT
<213> ORGANISM: Artificial Sequence
<220> FEATURE:
<223> OTHER INFORMATION: Synthetic peptide

<400> SEQUENCE: 905

His Ile Gly Leu Gly Gly Leu
1               5

<210> SEQ ID NO 906
<211> LENGTH: 7
<212> TYPE: PRT
<213> ORGANISM: Artificial Sequence
<220> FEATURE:
<223> OTHER INFORMATION: Synthetic peptide

<400> SEQUENCE: 906

Thr Arg Leu Gly Gly Leu Thr
1               5

<210> SEQ ID NO 907
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 907

Val Met Pro Gly Ser Val Val
1 5

<210> SEQ ID NO 908
<211> LENGTH: 7
<212> TYPE: PRT
<213> ORGANISM: Artificial Sequence
<220> FEATURE:
<223> OTHER INFORMATION: Synthetic peptide

<400> SEQUENCE: 908

Gly Arg Leu Arg Ala Ser Leu
1 5

<210> SEQ ID NO 909
<211> LENGTH: 7
<212> TYPE: PRT
<213> ORGANISM: Artificial Sequence
<220> FEATURE:
<223> OTHER INFORMATION: Synthetic peptide

<400> SEQUENCE: 909

Gly Arg Leu Tyr Leu Gly Ile
1 5

<210> SEQ ID NO 910
<211> LENGTH: 7
<212> TYPE: PRT
<213> ORGANISM: Artificial Sequence
<220> FEATURE:
<223> OTHER INFORMATION: Synthetic peptide

<400> SEQUENCE: 910

Gly Arg Leu Arg Leu Arg Val
1 5

<210> SEQ ID NO 911
<211> LENGTH: 7
<212> TYPE: PRT
<213> ORGANISM: Artificial Sequence
<220> FEATURE:
<223> OTHER INFORMATION: Synthetic peptide

<400> SEQUENCE: 911

Ser His Cys Gly Pro Ser Asn
1 5

<210> SEQ ID NO 912
<211> LENGTH: 7
<212> TYPE: PRT
<213> ORGANISM: Artificial Sequence
<220> FEATURE:
<223> OTHER INFORMATION: Synthetic peptide

<400> SEQUENCE: 912

Val Arg Leu Ser Gly Arg Ala
1 5

<210> SEQ ID NO 913
<211> LENGTH: 7
<212> TYPE: PRT
<213> ORGANISM: Artificial Sequence
<220> FEATURE:
<223> OTHER INFORMATION: Synthetic peptide

<400> SEQUENCE: 913

-continued

Arg Leu Ser Thr Phe Ala Gly
1 5

<210> SEQ ID NO 914
<211> LENGTH: 7
<212> TYPE: PRT
<213> ORGANISM: Artificial Sequence
<220> FEATURE:
<223> OTHER INFORMATION: Synthetic peptide

<400> SEQUENCE: 914

Ala Arg Gly Ser Leu Arg Val
1 5

<210> SEQ ID NO 915
<211> LENGTH: 7
<212> TYPE: PRT
<213> ORGANISM: Artificial Sequence
<220> FEATURE:
<223> OTHER INFORMATION: Synthetic peptide

<400> SEQUENCE: 915

Phe Ser Pro Arg Gly Ser Val
1 5

<210> SEQ ID NO 916
<211> LENGTH: 7
<212> TYPE: PRT
<213> ORGANISM: Artificial Sequence
<220> FEATURE:
<223> OTHER INFORMATION: Synthetic peptide

<400> SEQUENCE: 916

Gly Gly Arg Leu Arg Ala Val
1 5

<210> SEQ ID NO 917
<211> LENGTH: 7
<212> TYPE: PRT
<213> ORGANISM: Artificial Sequence
<220> FEATURE:
<223> OTHER INFORMATION: Synthetic peptide

<400> SEQUENCE: 917

Val Leu Ser Ala Val Ser Ser
1 5

<210> SEQ ID NO 918
<211> LENGTH: 7
<212> TYPE: PRT
<213> ORGANISM: Artificial Sequence
<220> FEATURE:
<223> OTHER INFORMATION: Synthetic peptide

<400> SEQUENCE: 918

Ala Arg Gly Ser Leu Arg Val
1 5

<210> SEQ ID NO 919
<211> LENGTH: 7
<212> TYPE: PRT
<213> ORGANISM: Artificial Sequence
<220> FEATURE:
<223> OTHER INFORMATION: Synthetic peptide

<400> SEQUENCE: 919

-continued

Leu Arg Ser Tyr Ala Trp Ser
1 5

<210> SEQ ID NO 920
<211> LENGTH: 7
<212> TYPE: PRT
<213> ORGANISM: Artificial Sequence
<220> FEATURE:
<223> OTHER INFORMATION: Synthetic peptide

<400> SEQUENCE: 920

Lys Gly Arg Val Ser Ala Gly
1 5

<210> SEQ ID NO 921
<211> LENGTH: 7
<212> TYPE: PRT
<213> ORGANISM: Artificial Sequence
<220> FEATURE:
<223> OTHER INFORMATION: Synthetic peptide

<400> SEQUENCE: 921

Ala Gly Leu Thr Ile Gly Ile
1 5

<210> SEQ ID NO 922
<211> LENGTH: 7
<212> TYPE: PRT
<213> ORGANISM: Artificial Sequence
<220> FEATURE:
<223> OTHER INFORMATION: Synthetic peptide

<400> SEQUENCE: 922

Ala Trp Arg His Ala Gly Gly
1 5

<210> SEQ ID NO 923
<211> LENGTH: 7
<212> TYPE: PRT
<213> ORGANISM: Artificial Sequence
<220> FEATURE:
<223> OTHER INFORMATION: Synthetic peptide

<400> SEQUENCE: 923

Trp Ala Arg Ala Gly Gly Phe
1 5

<210> SEQ ID NO 924
<211> LENGTH: 7
<212> TYPE: PRT
<213> ORGANISM: Artificial Sequence
<220> FEATURE:
<223> OTHER INFORMATION: Synthetic peptide

<400> SEQUENCE: 924

Met Gly Val Leu Thr Ala Glu
1 5

<210> SEQ ID NO 925
<211> LENGTH: 7
<212> TYPE: PRT
<213> ORGANISM: Artificial Sequence
<220> FEATURE:
<223> OTHER INFORMATION: Synthetic peptide

<400> SEQUENCE: 925

Phe Ala Gly Tyr Gly Val Leu

-continued 1 5

<210> SEQ ID NO 926
<211> LENGTH: 7
<212> TYPE: PRT
<213> ORGANISM: Artificial Sequence
<220> FEATURE:
<223> OTHER INFORMATION: Synthetic peptide

<400> SEQUENCE: 926

Arg Ile Phe His Gly Ala Val
1 5

<210> SEQ ID NO 927
<211> LENGTH: 7
<212> TYPE: PRT
<213> ORGANISM: Artificial Sequence
<220> FEATURE:
<223> OTHER INFORMATION: Synthetic peptide

<400> SEQUENCE: 927

Glu Gly Leu Val Val Phe Glu
1 5

<210> SEQ ID NO 928
<211> LENGTH: 7
<212> TYPE: PRT
<213> ORGANISM: Artificial Sequence
<220> FEATURE:
<223> OTHER INFORMATION: Synthetic peptide

<400> SEQUENCE: 928

Arg Glu Val Pro Gly Leu Arg
1 5

<210> SEQ ID NO 929
<211> LENGTH: 7
<212> TYPE: PRT
<213> ORGANISM: Artificial Sequence
<220> FEATURE:
<223> OTHER INFORMATION: Synthetic peptide

<400> SEQUENCE: 929

Leu Val Ser Val Asn Gly Ala
1 5

<210> SEQ ID NO 930
<211> LENGTH: 7
<212> TYPE: PRT
<213> ORGANISM: Artificial Sequence
<220> FEATURE:
<223> OTHER INFORMATION: Synthetic peptide

<400> SEQUENCE: 930

His Ser Leu Val Ser Gln Pro
1 5

<210> SEQ ID NO 931
<211> LENGTH: 7
<212> TYPE: PRT
<213> ORGANISM: Artificial Sequence
<220> FEATURE:
<223> OTHER INFORMATION: Synthetic peptide

<400> SEQUENCE: 931

Ala Arg Gly Ser Leu Arg Val
1 5

<210> SEQ ID NO 932
<211> LENGTH: 7
<212> TYPE: PRT
<213> ORGANISM: Artificial Sequence
<220> FEATURE:
<223> OTHER INFORMATION: Synthetic peptide

<400> SEQUENCE: 932

Ser Ser Val Ala Ser Leu Val
1               5

<210> SEQ ID NO 933
<211> LENGTH: 7
<212> TYPE: PRT
<213> ORGANISM: Artificial Sequence
<220> FEATURE:
<223> OTHER INFORMATION: Synthetic peptide

<400> SEQUENCE: 933

Ala Ala Val Trp Gln Met Lys
1               5

<210> SEQ ID NO 934
<211> LENGTH: 7
<212> TYPE: PRT
<213> ORGANISM: Artificial Sequence
<220> FEATURE:
<223> OTHER INFORMATION: Synthetic peptide

<400> SEQUENCE: 934

Gln Arg Ala Ala Val Ile Val
1               5

<210> SEQ ID NO 935
<211> LENGTH: 7
<212> TYPE: PRT
<213> ORGANISM: Artificial Sequence
<220> FEATURE:
<223> OTHER INFORMATION: Synthetic peptide

<400> SEQUENCE: 935

Pro Gly Gly Ser Asp Ala Ala
1               5

<210> SEQ ID NO 936
<211> LENGTH: 7
<212> TYPE: PRT
<213> ORGANISM: Artificial Sequence
<220> FEATURE:
<223> OTHER INFORMATION: Synthetic peptide

<400> SEQUENCE: 936

Gly Gly Arg Leu Arg Ala Val
1               5

<210> SEQ ID NO 937
<211> LENGTH: 7
<212> TYPE: PRT
<213> ORGANISM: Artificial Sequence
<220> FEATURE:
<223> OTHER INFORMATION: Synthetic peptide

<400> SEQUENCE: 937

Leu Pro Cys Gly Gly Leu Ala
1               5

-continued

<210> SEQ ID NO 938
<211> LENGTH: 7
<212> TYPE: PRT
<213> ORGANISM: Artificial Sequence
<220> FEATURE:
<223> OTHER INFORMATION: Synthetic peptide

<400> SEQUENCE: 938

Gly Ser Ser His Asp Ala Leu
1 5

<210> SEQ ID NO 939
<211> LENGTH: 7
<212> TYPE: PRT
<213> ORGANISM: Artificial Sequence
<220> FEATURE:
<223> OTHER INFORMATION: Synthetic peptide

<400> SEQUENCE: 939

Thr Gln Tyr Tyr Gly Ser Ser
1 5

<210> SEQ ID NO 940
<211> LENGTH: 7
<212> TYPE: PRT
<213> ORGANISM: Artificial Sequence
<220> FEATURE:
<223> OTHER INFORMATION: Synthetic peptide

<400> SEQUENCE: 940

Phe Ser Pro Arg Gly Ser Val
1 5

<210> SEQ ID NO 941
<211> LENGTH: 7
<212> TYPE: PRT
<213> ORGANISM: Artificial Sequence
<220> FEATURE:
<223> OTHER INFORMATION: Synthetic peptide

<400> SEQUENCE: 941

Lys Gly Arg Val Ser Ala Gly
1 5

<210> SEQ ID NO 942
<211> LENGTH: 7
<212> TYPE: PRT
<213> ORGANISM: Artificial Sequence
<220> FEATURE:
<223> OTHER INFORMATION: Synthetic peptide

<400> SEQUENCE: 942

Gln Gly Arg Val Asn Val Lys
1 5

<210> SEQ ID NO 943
<211> LENGTH: 7
<212> TYPE: PRT
<213> ORGANISM: Artificial Sequence
<220> FEATURE:
<223> OTHER INFORMATION: Synthetic peptide

<400> SEQUENCE: 943

Gly Gly Arg Leu Arg Ala Val
1 5

-continued

<210> SEQ ID NO 944
<211> LENGTH: 7
<212> TYPE: PRT
<213> ORGANISM: Artificial Sequence
<220> FEATURE:
<223> OTHER INFORMATION: Synthetic peptide

<400> SEQUENCE: 944

Tyr Asp Gly Arg Leu Ala Arg
1               5

<210> SEQ ID NO 945
<211> LENGTH: 7
<212> TYPE: PRT
<213> ORGANISM: Artificial Sequence
<220> FEATURE:
<223> OTHER INFORMATION: Synthetic peptide

<400> SEQUENCE: 945

Pro Gln Gly Arg Gly Val Lys
1               5

<210> SEQ ID NO 946
<211> LENGTH: 7
<212> TYPE: PRT
<213> ORGANISM: Artificial Sequence
<220> FEATURE:
<223> OTHER INFORMATION: Synthetic peptide

<400> SEQUENCE: 946

Met Val Leu Arg Gly Ser Tyr
1               5

<210> SEQ ID NO 947
<211> LENGTH: 7
<212> TYPE: PRT
<213> ORGANISM: Artificial Sequence
<220> FEATURE:
<223> OTHER INFORMATION: Synthetic peptide

<400> SEQUENCE: 947

Gly Gly Trp Ala Arg Ala Val
1               5

<210> SEQ ID NO 948
<211> LENGTH: 7
<212> TYPE: PRT
<213> ORGANISM: Artificial Sequence
<220> FEATURE:
<223> OTHER INFORMATION: Synthetic peptide

<400> SEQUENCE: 948

Val Arg Ala Val Cys Leu Met
1               5

<210> SEQ ID NO 949
<211> LENGTH: 7
<212> TYPE: PRT
<213> ORGANISM: Artificial Sequence
<220> FEATURE:
<223> OTHER INFORMATION: Synthetic peptide

<400> SEQUENCE: 949

Thr Arg Ala Ser Arg Arg Gly
1               5

<210> SEQ ID NO 950

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 950

Leu Gly Ala Gly Glu Gly Asp
1 5

<210> SEQ ID NO 951
<211> LENGTH: 7
<212> TYPE: PRT
<213> ORGANISM: Artificial Sequence
<220> FEATURE:
<223> OTHER INFORMATION: Synthetic peptide

<400> SEQUENCE: 951

Ile Gly Ala Val Ser Gly Trp
1 5

<210> SEQ ID NO 952
<211> LENGTH: 7
<212> TYPE: PRT
<213> ORGANISM: Artificial Sequence
<220> FEATURE:
<223> OTHER INFORMATION: Synthetic peptide

<400> SEQUENCE: 952

Leu Leu Ser Arg Arg Val Gly
1 5

<210> SEQ ID NO 953
<211> LENGTH: 7
<212> TYPE: PRT
<213> ORGANISM: Artificial Sequence
<220> FEATURE:
<223> OTHER INFORMATION: Synthetic peptide

<400> SEQUENCE: 953

Leu Glu Leu Leu Ser Val Val
1 5

<210> SEQ ID NO 954
<211> LENGTH: 7
<212> TYPE: PRT
<213> ORGANISM: Artificial Sequence
<220> FEATURE:
<223> OTHER INFORMATION: Synthetic peptide

<400> SEQUENCE: 954

Arg Leu Leu Ser Glu Gly Tyr
1 5

<210> SEQ ID NO 955
<211> LENGTH: 7
<212> TYPE: PRT
<213> ORGANISM: Artificial Sequence
<220> FEATURE:
<223> OTHER INFORMATION: Synthetic peptide

<400> SEQUENCE: 955

Gln Leu Pro Gly Leu Leu Arg
1 5

<210> SEQ ID NO 956
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 956

Tyr Gly Glu Ser Leu Leu Arg
1               5

<210> SEQ ID NO 957
<211> LENGTH: 7
<212> TYPE: PRT
<213> ORGANISM: Artificial Sequence
<220> FEATURE:
<223> OTHER INFORMATION: Synthetic peptide

<400> SEQUENCE: 957

Leu Arg Val Tyr Gly Glu Gly
1               5

<210> SEQ ID NO 958
<211> LENGTH: 7
<212> TYPE: PRT
<213> ORGANISM: Artificial Sequence
<220> FEATURE:
<223> OTHER INFORMATION: Synthetic peptide

<400> SEQUENCE: 958

Tyr Arg Val Ser Ser Gly Ser
1               5

<210> SEQ ID NO 959
<211> LENGTH: 7
<212> TYPE: PRT
<213> ORGANISM: Artificial Sequence
<220> FEATURE:
<223> OTHER INFORMATION: Synthetic peptide

<400> SEQUENCE: 959

Arg Ser Ser Ser Ser Thr Arg
1               5

<210> SEQ ID NO 960
<211> LENGTH: 7
<212> TYPE: PRT
<213> ORGANISM: Artificial Sequence
<220> FEATURE:
<223> OTHER INFORMATION: Synthetic peptide

<400> SEQUENCE: 960

Trp Ala Gly Ser Asn Tyr Ser
1               5

<210> SEQ ID NO 961
<211> LENGTH: 7
<212> TYPE: PRT
<213> ORGANISM: Artificial Sequence
<220> FEATURE:
<223> OTHER INFORMATION: Synthetic peptide

<400> SEQUENCE: 961

Cys Ala Gly Arg Ala Arg Arg
1               5

<210> SEQ ID NO 962
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 962

Ile Ala Gly Leu Ala Val Val
1               5

<210> SEQ ID NO 963
<211> LENGTH: 7
<212> TYPE: PRT
<213> ORGANISM: Artificial Sequence
<220> FEATURE:
<223> OTHER INFORMATION: Synthetic peptide

<400> SEQUENCE: 963

Asp Gly Glu Gly Ala Gly Leu
1               5

<210> SEQ ID NO 964
<211> LENGTH: 7
<212> TYPE: PRT
<213> ORGANISM: Artificial Sequence
<220> FEATURE:
<223> OTHER INFORMATION: Synthetic peptide

<400> SEQUENCE: 964

Ala Leu Ala Gly Gly Gly Leu
1               5

<210> SEQ ID NO 965
<211> LENGTH: 7
<212> TYPE: PRT
<213> ORGANISM: Artificial Sequence
<220> FEATURE:
<223> OTHER INFORMATION: Synthetic peptide

<400> SEQUENCE: 965

Gly Val Arg Arg Ser Leu Leu
1               5

<210> SEQ ID NO 966
<211> LENGTH: 7
<212> TYPE: PRT
<213> ORGANISM: Artificial Sequence
<220> FEATURE:
<223> OTHER INFORMATION: Synthetic peptide

<400> SEQUENCE: 966

Ala Asp Trp Gly Val Leu Glu
1               5

<210> SEQ ID NO 967
<211> LENGTH: 7
<212> TYPE: PRT
<213> ORGANISM: Artificial Sequence
<220> FEATURE:
<223> OTHER INFORMATION: Synthetic peptide

<400> SEQUENCE: 967

Ile Gly Ala Val Ser Gly Trp
1               5

<210> SEQ ID NO 968
<211> LENGTH: 7
<212> TYPE: PRT
<213> ORGANISM: Artificial Sequence
<220> FEATURE:
<223> OTHER INFORMATION: Synthetic peptide

<400> SEQUENCE: 968

Ala Ser Gly Leu Val Val Thr
1 5

<210> SEQ ID NO 969
<211> LENGTH: 7
<212> TYPE: PRT
<213> ORGANISM: Artificial Sequence
<220> FEATURE:
<223> OTHER INFORMATION: Synthetic peptide

<400> SEQUENCE: 969

Ile Gly Leu Arg Gly Glu Asn
1 5

<210> SEQ ID NO 970
<211> LENGTH: 7
<212> TYPE: PRT
<213> ORGANISM: Artificial Sequence
<220> FEATURE:
<223> OTHER INFORMATION: Synthetic peptide

<400> SEQUENCE: 970

Arg Arg Ala Arg Gly Ala Cys
1 5

<210> SEQ ID NO 971
<211> LENGTH: 7
<212> TYPE: PRT
<213> ORGANISM: Artificial Sequence
<220> FEATURE:
<223> OTHER INFORMATION: Synthetic peptide

<400> SEQUENCE: 971

Tyr Ala Ala Ser Leu Met Gly
1 5

<210> SEQ ID NO 972
<211> LENGTH: 7
<212> TYPE: PRT
<213> ORGANISM: Artificial Sequence
<220> FEATURE:
<223> OTHER INFORMATION: Synthetic peptide

<400> SEQUENCE: 972

Leu Thr Ala Ala Val Met Val
1 5

<210> SEQ ID NO 973
<211> LENGTH: 7
<212> TYPE: PRT
<213> ORGANISM: Artificial Sequence
<220> FEATURE:
<223> OTHER INFORMATION: Synthetic peptide

<400> SEQUENCE: 973

Tyr Ala Ala Ser Leu Met Gly
1 5

<210> SEQ ID NO 974
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 974

Arg Ala Arg Thr Gly Gly Ser
1 5

<210> SEQ ID NO 975
<211> LENGTH: 7
<212> TYPE: PRT
<213> ORGANISM: Artificial Sequence
<220> FEATURE:
<223> OTHER INFORMATION: Synthetic peptide

<400> SEQUENCE: 975

Val Ser Gly Asp Gly Gly Ser
1 5

<210> SEQ ID NO 976
<211> LENGTH: 7
<212> TYPE: PRT
<213> ORGANISM: Artificial Sequence
<220> FEATURE:
<223> OTHER INFORMATION: Synthetic peptide

<400> SEQUENCE: 976

Phe Gly Gly Arg Ser Leu Ser
1 5

<210> SEQ ID NO 977
<211> LENGTH: 7
<212> TYPE: PRT
<213> ORGANISM: Artificial Sequence
<220> FEATURE:
<223> OTHER INFORMATION: Synthetic peptide

<400> SEQUENCE: 977

Ser Leu Gly Gly Arg Thr Phe
1 5

<210> SEQ ID NO 978
<211> LENGTH: 7
<212> TYPE: PRT
<213> ORGANISM: Artificial Sequence
<220> FEATURE:
<223> OTHER INFORMATION: Synthetic peptide

<400> SEQUENCE: 978

Ala Arg Arg Gly Leu Gly Leu
1 5

<210> SEQ ID NO 979
<211> LENGTH: 7
<212> TYPE: PRT
<213> ORGANISM: Artificial Sequence
<220> FEATURE:
<223> OTHER INFORMATION: Synthetic peptide

<400> SEQUENCE: 979

Ala Leu Ala Gly Gly Gly Leu
1 5

<210> SEQ ID NO 980
<211> LENGTH: 7
<212> TYPE: PRT
<213> ORGANISM: Artificial Sequence
<220> FEATURE:
<223> OTHER INFORMATION: Synthetic peptide

<400> SEQUENCE: 980

Phe Arg Ala Leu Gly Gly Leu
1 5

<210> SEQ ID NO 981
<211> LENGTH: 7
<212> TYPE: PRT
<213> ORGANISM: Artificial Sequence
<220> FEATURE:
<223> OTHER INFORMATION: Synthetic peptide

<400> SEQUENCE: 981

Phe Thr Arg Gly Gly Leu Ser
1 5

<210> SEQ ID NO 982
<211> LENGTH: 7
<212> TYPE: PRT
<213> ORGANISM: Artificial Sequence
<220> FEATURE:
<223> OTHER INFORMATION: Synthetic peptide

<400> SEQUENCE: 982

Ser Gly Ser Ser Val Arg Tyr
1 5

<210> SEQ ID NO 983
<211> LENGTH: 7
<212> TYPE: PRT
<213> ORGANISM: Artificial Sequence
<220> FEATURE:
<223> OTHER INFORMATION: Synthetic peptide

<400> SEQUENCE: 983

Trp Gly Ser Val Ala Gly Ile
1 5

<210> SEQ ID NO 984
<211> LENGTH: 7
<212> TYPE: PRT
<213> ORGANISM: Artificial Sequence
<220> FEATURE:
<223> OTHER INFORMATION: Synthetic peptide

<400> SEQUENCE: 984

Ser Gly Gly Asp Gly Ser Val
1 5

<210> SEQ ID NO 985
<211> LENGTH: 7
<212> TYPE: PRT
<213> ORGANISM: Artificial Sequence
<220> FEATURE:
<223> OTHER INFORMATION: Synthetic peptide

<400> SEQUENCE: 985

Asn Glu Gly Arg Leu Gly Ile
1 5

<210> SEQ ID NO 986
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 986

Tyr Ser Gly Arg Leu Val Met
1               5

<210> SEQ ID NO 987
<211> LENGTH: 7
<212> TYPE: PRT
<213> ORGANISM: Artificial Sequence
<220> FEATURE:
<223> OTHER INFORMATION: Synthetic peptide

<400> SEQUENCE: 987

Asp Gly Pro Ser Gly Cys Ser
1               5

<210> SEQ ID NO 988
<211> LENGTH: 7
<212> TYPE: PRT
<213> ORGANISM: Artificial Sequence
<220> FEATURE:
<223> OTHER INFORMATION: Synthetic peptide

<400> SEQUENCE: 988

Arg Gly Ser Arg Thr Gly Pro
1               5

<210> SEQ ID NO 989
<211> LENGTH: 7
<212> TYPE: PRT
<213> ORGANISM: Artificial Sequence
<220> FEATURE:
<223> OTHER INFORMATION: Synthetic peptide

<400> SEQUENCE: 989

Gly Ser Ser Ala Cys Gly Ala
1               5

<210> SEQ ID NO 990
<211> LENGTH: 7
<212> TYPE: PRT
<213> ORGANISM: Artificial Sequence
<220> FEATURE:
<223> OTHER INFORMATION: Synthetic peptide

<400> SEQUENCE: 990

Val Arg Leu Ser Gly Arg Ala
1               5

<210> SEQ ID NO 991
<211> LENGTH: 7
<212> TYPE: PRT
<213> ORGANISM: Artificial Sequence
<220> FEATURE:
<223> OTHER INFORMATION: Synthetic peptide

<400> SEQUENCE: 991

Arg Leu Ser Thr Phe Ala Gly
1               5

<210> SEQ ID NO 992
<211> LENGTH: 7
<212> TYPE: PRT
<213> ORGANISM: Artificial Sequence
<220> FEATURE:
<223> OTHER INFORMATION: Synthetic peptide

<400> SEQUENCE: 992

-continued

```
Ala Arg Gly Ser Leu Arg Val
1               5


<210> SEQ ID NO 993
<211> LENGTH: 7
<212> TYPE: PRT
<213> ORGANISM: Artificial Sequence
<220> FEATURE:
<223> OTHER INFORMATION: Synthetic peptide

<400> SEQUENCE: 993

Phe Ser Pro Arg Gly Ser Val
1               5


<210> SEQ ID NO 994
<211> LENGTH: 7
<212> TYPE: PRT
<213> ORGANISM: Artificial Sequence
<220> FEATURE:
<223> OTHER INFORMATION: Synthetic peptide

<400> SEQUENCE: 994

Gly Gly Arg Leu Arg Ala Val
1               5


<210> SEQ ID NO 995
<211> LENGTH: 7
<212> TYPE: PRT
<213> ORGANISM: Artificial Sequence
<220> FEATURE:
<223> OTHER INFORMATION: Synthetic peptide

<400> SEQUENCE: 995

Val Leu Ser Ala Val Ser Ser
1               5


<210> SEQ ID NO 996
<211> LENGTH: 7
<212> TYPE: PRT
<213> ORGANISM: Artificial Sequence
<220> FEATURE:
<223> OTHER INFORMATION: Synthetic peptide

<400> SEQUENCE: 996

Ala Arg Gly Ser Leu Arg Val
1               5


<210> SEQ ID NO 997
<211> LENGTH: 7
<212> TYPE: PRT
<213> ORGANISM: Artificial Sequence
<220> FEATURE:
<223> OTHER INFORMATION: Synthetic peptide

<400> SEQUENCE: 997

Leu Arg Ser Tyr Ala Trp Ser
1               5


<210> SEQ ID NO 998
<211> LENGTH: 7
<212> TYPE: PRT
<213> ORGANISM: Artificial Sequence
<220> FEATURE:
<223> OTHER INFORMATION: Synthetic peptide

<400> SEQUENCE: 998
```

-continued

Lys Gly Arg Val Ser Ala Gly
1 5

<210> SEQ ID NO 999
<211> LENGTH: 7
<212> TYPE: PRT
<213> ORGANISM: Artificial Sequence
<220> FEATURE:
<223> OTHER INFORMATION: Synthetic peptide

<400> SEQUENCE: 999

Ala Gly Leu Thr Ile Gly Ile
1 5

<210> SEQ ID NO 1000
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1000

Ala Trp Arg His Ala Gly Gly
1 5

<210> SEQ ID NO 1001
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1001

Trp Ala Arg Ala Gly Gly Phe
1 5

<210> SEQ ID NO 1002
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1002

Met Gly Val Leu Thr Ala Glu
1 5

<210> SEQ ID NO 1003
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1003

Phe Ala Gly Tyr Gly Val Leu
1 5

<210> SEQ ID NO 1004
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1004

Arg Ile Phe His Gly Ala Val

-continued 1 5

<210> SEQ ID NO 1005
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1005

Glu Gly Leu Val Val Phe Glu
1 5

<210> SEQ ID NO 1006
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1006

Arg Glu Val Pro Gly Leu Arg
1 5

<210> SEQ ID NO 1007
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1007

Leu Val Ser Val Asn Gly Ala
1 5

<210> SEQ ID NO 1008
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1008

His Ser Leu Val Ser Gln Pro
1 5

<210> SEQ ID NO 1009
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1009

Ala Arg Gly Ser Leu Arg Val
1 5

<210> SEQ ID NO 1010
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1010

Ser Ser Val Ala Ser Leu Val
1 5

-continued

<210> SEQ ID NO 1011
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1011

Ala Ala Val Trp Gln Met Lys
1               5

<210> SEQ ID NO 1012
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1012

Gln Arg Ala Ala Val Ile Val
1               5

<210> SEQ ID NO 1013
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1013

Gly Gly Arg Leu Arg Ala Val
1               5

<210> SEQ ID NO 1014
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1014

Leu Pro Cys Gly Gly Leu Ala
1               5

<210> SEQ ID NO 1015
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1015

Gly Ser Ser His Asp Ala Leu
1               5

<210> SEQ ID NO 1016
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1016

Thr Gln Tyr Tyr Gly Ser Ser
1               5

-continued

<210> SEQ ID NO 1017
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1017

Phe Ser Pro Arg Gly Ser Val
1               5

<210> SEQ ID NO 1018
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1018

Lys Gly Arg Val Ser Ala Gly
1               5

<210> SEQ ID NO 1019
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1019

Gln Gly Arg Val Asn Val Lys
1               5

<210> SEQ ID NO 1020
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1020

Gly Gly Arg Leu Arg Ala Val
1               5

<210> SEQ ID NO 1021
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1021

Tyr Asp Gly Arg Leu Ala Arg
1               5

<210> SEQ ID NO 1022
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1022

Ser Arg Leu Ser Tyr Trp Gln
1               5

-continued

<210> SEQ ID NO 1023
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1023

Phe Val Gly Ser Arg Gly Val
1 5

<210> SEQ ID NO 1024
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1024

Ser Val Asp Arg Gly Val Ile
1 5

<210> SEQ ID NO 1025
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1025

Gly Arg Gly Ser Gly Gly Phe
1 5

<210> SEQ ID NO 1026
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1026

Ile Phe Gly Ala Gly Leu Arg
1 5

<210> SEQ ID NO 1027
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1027

Gly Trp Val Ala Val Ser Cys
1 5

<210> SEQ ID NO 1028
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1028

Leu Leu Ser Gly Val Ile Leu
1 5

<210> SEQ ID NO 1029

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1029

Gly Ser Thr Leu Leu Ser Arg
1               5

<210> SEQ ID NO 1030
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1030

Gln Trp Tyr Ser Leu Arg Ser
1               5

<210> SEQ ID NO 1031
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1031

Thr Trp Ile Gly Arg Val Ser
1               5

<210> SEQ ID NO 1032
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1032

Ser Val Val Leu Ala Gly Ser
1               5

<210> SEQ ID NO 1033
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1033

Ile Phe Gly Ala Gly Leu Arg
1               5

<210> SEQ ID NO 1034
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1034

Ser Ala Gly Gly Trp Cys Ala
1               5

<210> SEQ ID NO 1035
<211> LENGTH: 7

<212> TYPE: PRT
<213> ORGANISM: Artificial Sequence
<220> FEATURE:
<223> OTHER INFORMATION: Synthetic peptide

<400> SEQUENCE: 1035

Arg Asp Gly Val Arg Val Gly
1 5

<210> SEQ ID NO 1036
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1036

Val Ser Arg Ile Gly Val Arg
1 5

<210> SEQ ID NO 1037
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1037

Gly Val Arg Ser Met Pro Val
1 5

<210> SEQ ID NO 1038
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1038

Gly Gly Val Leu Gly Ser Asp
1 5

<210> SEQ ID NO 1039
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1039

Trp Gly Val Leu Gln Leu Glu
1 5

<210> SEQ ID NO 1040
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1040

His Gly Gly Pro Gly Ala Val
1 5

<210> SEQ ID NO 1041
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1041

Asp Ser Gly Leu Val Gly Gly
1 5

<210> SEQ ID NO 1042
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1042

Ile Phe Gly Ala Gly Leu Arg
1 5

<210> SEQ ID NO 1043
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1043

Arg Met Gly Phe Gly Leu Arg
1 5

<210> SEQ ID NO 1044
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1044

Trp Leu Asp Ala Ala Val Lys
1 5

<210> SEQ ID NO 1045
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1045

Ile Ala Ala Ser Tyr Arg Gly
1 5

<210> SEQ ID NO 1046
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1046

Ala Thr Ile Pro Gly Gly Ser
1 5

<210> SEQ ID NO 1047
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1047

Asp Gly Gly Ser Leu Val Val
1               5

<210> SEQ ID NO 1048
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1048

Phe Gly Gly Ser Gly Arg Gly
1               5

<210> SEQ ID NO 1049
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1049

Ser Pro Thr Gly Gly Arg Arg
1               5

<210> SEQ ID NO 1050
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1050

Thr Trp Ser Thr Gly Gly Arg
1               5

<210> SEQ ID NO 1051
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1051

Ser Arg Ser Cys Gly Gly Leu
1               5

<210> SEQ ID NO 1052
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1052

Cys Pro Gly Ser Gly Ile Ile
1               5

<210> SEQ ID NO 1053
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1053

Phe Gly Gly Ser Gly Arg Gly
1 5

<210> SEQ ID NO 1054
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1054

Ser Gly Ser Val Val Gln Arg
1 5

<210> SEQ ID NO 1055
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1055

Thr Trp Ile Gly Arg Val Ser
1 5

<210> SEQ ID NO 1056
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1056

Gly Pro Ser Trp Ala Thr Val
1 5

<210> SEQ ID NO 1057
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1057

Ala Arg Arg Gly Ser Gly Leu
1 5

<210> SEQ ID NO 1058
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1058

Arg Ala Val Gly Tyr Asn Ala
1 5

<210> SEQ ID NO 1059
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1059

Leu Arg Ala Val Glu Phe Leu
1               5

<210> SEQ ID NO 1060
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1060

Phe Glu Asp Leu Leu Ser Leu
1               5

<210> SEQ ID NO 1061
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1061

Arg Trp Leu Ser Leu Leu Ser
1               5

<210> SEQ ID NO 1062
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1062

His Ala Pro Gly Leu Arg Val
1               5

<210> SEQ ID NO 1063
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1063

Leu Arg Ser Ser Met Met Leu
1               5

<210> SEQ ID NO 1064
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1064

Arg Pro Lys Leu Arg Ser Val
1               5

<210> SEQ ID NO 1065
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1065

Ser Arg Val Ser Phe His Glu
1 5

<210> SEQ ID NO 1066
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1066

Leu Arg Ser Ser Met Met Leu
1 5

<210> SEQ ID NO 1067
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1067

Ser Ser Gly Gly Arg Ser Ser
1 5

<210> SEQ ID NO 1068
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1068

Val Ala Gly Arg Val Gly Ile
1 5

<210> SEQ ID NO 1069
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1069

Ala Gly Leu Ala Leu Thr Val
1 5

<210> SEQ ID NO 1070
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1070

Ile Gly Val Arg Gly Ala Val
1 5

<210> SEQ ID NO 1071
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1071

-continued

Leu Val Arg Asp Gly Val Leu
1 5

<210> SEQ ID NO 1072
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1072

Ile Gly Val Arg Gly Ala Val
1 5

<210> SEQ ID NO 1073
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1073

His Gly Leu Val Thr His Asn
1 5

<210> SEQ ID NO 1074
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1074

His Ala Pro Gly Leu Arg Val
1 5

<210> SEQ ID NO 1075
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1075

Val Ser Ser Thr Ala Arg Gly
1 5

<210> SEQ ID NO 1076
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1076

Arg Ala Ala Val Ile His Thr
1 5

<210> SEQ ID NO 1077
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1077

-continued

Ala Ala Ser Thr Arg Ser Leu
1 5

<210> SEQ ID NO 1078
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1078

Gly Trp Gly Gly Gly Ser Ala
1 5

<210> SEQ ID NO 1079
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1079

Ser Ser Arg Gly Gly Ser Ser
1 5

<210> SEQ ID NO 1080
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1080

Ser Ser Gly Gly Arg Ser Ser
1 5

<210> SEQ ID NO 1081
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1081

Ser Ser Arg Gly Gly Ser Ser
1 5

<210> SEQ ID NO 1082
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1082

Ala Arg Arg Gly Ser Gly Leu
1 5

<210> SEQ ID NO 1083
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1083

Val Ala Gly Arg Val Gly Ile

-continued 1 5

<210> SEQ ID NO 1084
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1084

Glu Gly Arg Leu Met Leu Ala
1 5

<210> SEQ ID NO 1085
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1085

Arg Leu Ser Ser Ala Pro Ser
1 5

<210> SEQ ID NO 1086
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1086

Arg Arg Leu Ser Tyr His Ser
1 5

<210> SEQ ID NO 1087
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1087

Phe Leu His Met Arg Leu Ser
1 5

<210> SEQ ID NO 1088
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1088

Leu Ala Arg Gly Val Pro Pro
1 5

<210> SEQ ID NO 1089
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1089

Leu Ser Arg Gly Ser Val Ala
1 5

-continued

<210> SEQ ID NO 1090
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1090

Val Trp Leu Arg Gly Ser Thr
1               5

<210> SEQ ID NO 1091
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1091

Arg Gly Gly Gln Arg Ala Ser
1               5

<210> SEQ ID NO 1092
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1092

Ala Val Ser Gly Arg Ser Leu
1               5

<210> SEQ ID NO 1093
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1093

Gly Leu Leu Ser Ser Phe Ser
1               5

<210> SEQ ID NO 1094
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1094

Arg Met Gly Leu Leu Arg Gln
1               5

<210> SEQ ID NO 1095
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1095

Arg Leu His Tyr Leu Arg Ser
1               5

-continued

<210> SEQ ID NO 1096
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1096

Gly Gly Tyr Trp Leu Arg Ser
1 5

<210> SEQ ID NO 1097
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1097

Asn Arg Ser Ser His Cys Gly
1 5

<210> SEQ ID NO 1098
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1098

Gln Arg Ser Ser Asp Leu Thr
1 5

<210> SEQ ID NO 1099
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1099

Ala Ala Gly Arg Ser Arg Ile
1 5

<210> SEQ ID NO 1100
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1100

Gly Arg Ala Gly Gly Asn Gly
1 5

<210> SEQ ID NO 1101
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1101

Ala Asn Ala Ser Gly Val Arg
1 5

-continued

<210> SEQ ID NO 1102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1102

Trp Ala His Gly Val Leu Ser
1 5

<210> SEQ ID NO 1103
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1103

Ser Leu Tyr Gly Leu Arg Trp
1 5

<210> SEQ ID NO 1104
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1104

Gly Asn Gly Gly Ala Arg Gly
1 5

<210> SEQ ID NO 1105
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1105

Leu Ala Arg Gly Val Pro Pro
1 5

<210> SEQ ID NO 1106
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1106

Asn Trp Asp Ala Arg Gly Arg
1 5

<210> SEQ ID NO 1107
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1107

Ala Ser Leu Pro Val Leu Asp
1 5

<210> SEQ ID NO 1108

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1108

Pro Pro Gly Ala Ser Leu Tyr
1 5

<210> SEQ ID NO 1109
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1109

Ala Ala Val Gly Gly Arg Val
1 5

<210> SEQ ID NO 1110
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1110

Ala Ala Ser Ser Trp Ala Val
1 5

<210> SEQ ID NO 1111
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1111

Ala Phe Lys Thr Gly Gly Ser
1 5

<210> SEQ ID NO 1112
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1112

Phe Glu Gly Gly Arg Ser Gly
1 5

<210> SEQ ID NO 1113
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1113

Arg Thr Trp Gly Gly Arg Met
1 5

<210> SEQ ID NO 1114
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1114

Ser Ala Arg Gln Gly Gly Arg
1               5

<210> SEQ ID NO 1115
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1115

Ala Ala Val Gly Gly Arg Val
1               5

<210> SEQ ID NO 1116
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1116

Ala Arg His Gly Ser Ser Val
1               5

<210> SEQ ID NO 1117
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1117

Ser Asn Phe Tyr Gly Ser Ser
1               5

<210> SEQ ID NO 1118
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1118

Gly Ser Gly Gln Leu Ile Pro
1               5

<210> SEQ ID NO 1119
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1119

Leu Ser Arg Gly Ser Val Ala
1               5

<210> SEQ ID NO 1120
<211> LENGTH: 7
<212> TYPE: PRT

<213> ORGANISM: Artificial Sequence
<220> FEATURE:
<223> OTHER INFORMATION: Synthetic peptide

<400> SEQUENCE: 1120

Ala Glu Tyr Gly Arg Val Leu
1               5

<210> SEQ ID NO 1121
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1121

Arg Gly Arg Val Leu Leu Pro
1               5

<210> SEQ ID NO 1122
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1122

Ala Ala Val Gly Gly Arg Val
1               5

<210> SEQ ID NO 1123
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1123

Arg Gly Arg Leu Ala Leu Leu
1               5

<210> SEQ ID NO 1124
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1124

Ser Gly Pro Gly Arg Leu Pro
1               5

<210> SEQ ID NO 1125
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1125

Thr Ser Gly Arg Leu Trp Val
1               5

<210> SEQ ID NO 1126
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1126

Met Val Tyr Ser Gly Val Ser
1 5

<210> SEQ ID NO 1127
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1127

Trp Arg Leu Ser Arg Glu Gly
1 5

<210> SEQ ID NO 1128
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1128

Leu Leu Arg Arg Leu Ser Trp
1 5

<210> SEQ ID NO 1129
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1129

Ala Ala Arg Gly Val Met Val
1 5

<210> SEQ ID NO 1130
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1130

Ala Leu Ala Arg Gly Ser Gly
1 5

<210> SEQ ID NO 1131
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1131

Asn Leu Arg Gly Ser Arg Ser
1 5

<210> SEQ ID NO 1132
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1132

Arg Ala Val Trp Arg Ala Ser
1               5

<210> SEQ ID NO 1133
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1133

Gly Ala Gly Ser Phe Ser Ser
1               5

<210> SEQ ID NO 1134
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1134

Leu Leu Ser Ser Arg Arg Cys
1               5

<210> SEQ ID NO 1135
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1135

Leu Leu Ser Leu Asp Pro Gly
1               5

<210> SEQ ID NO 1136
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1136

Ser Ser Leu Leu Ser Ser Leu
1               5

<210> SEQ ID NO 1137
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1137

Leu Leu Arg Pro Ala His Gly
1               5

<210> SEQ ID NO 1138
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1138

Leu Leu Arg Arg Leu Ser Trp
1 5

<210> SEQ ID NO 1139
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1139

Cys Met Leu Arg Ser Ala Thr
1 5

<210> SEQ ID NO 1140
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1140

Ser Lys Ala Val Leu Arg Ser
1 5

<210> SEQ ID NO 1141
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1141

Ser Arg Val Ser Asn Pro Ser
1 5

<210> SEQ ID NO 1142
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1142

Cys Arg Arg Ser Ser Leu Leu
1 5

<210> SEQ ID NO 1143
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1143

Gly Ala Gly Ser Phe Ser Ser
1 5

<210> SEQ ID NO 1144
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1144

Ser Ala Ala Gly Arg Thr Phe
1 5

<210> SEQ ID NO 1145
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1145

Pro Ala Gly Arg Met Leu Ser
1 5

<210> SEQ ID NO 1146
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1146

Ile Ala Met Ala Gly Leu Arg
1 5

<210> SEQ ID NO 1147
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1147

Ala Gly Gly Phe Arg Phe Ile
1 5

<210> SEQ ID NO 1148
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1148

Ser Gly Val Arg Pro Val Ile
1 5

<210> SEQ ID NO 1149
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1149

Gly Val Leu Ser Asp Arg Ser
1 5

<210> SEQ ID NO 1150
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1150

-continued

Gly Ala Val Thr Ser Ala Asp
1 5

<210> SEQ ID NO 1151
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1151

Gly Ala Val Thr Ser Ala Asp
1 5

<210> SEQ ID NO 1152
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1152

Gly Ala Val Asn Thr Pro Ala
1 5

<210> SEQ ID NO 1153
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1153

Gly Gly Leu Val Lys Arg Leu
1 5

<210> SEQ ID NO 1154
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1154

Glu Val Ala Ser Gly Leu Val
1 5

<210> SEQ ID NO 1155
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1155

Ile Ala Met Ala Gly Leu Arg
1 5

<210> SEQ ID NO 1156
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1156

-continued

Gly Thr His Ser Gly Leu Arg
1 5

<210> SEQ ID NO 1157
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1157

Leu Val Ser Thr Ser Asn Arg
1 5

<210> SEQ ID NO 1158
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1158

Phe Ser Leu Val Ser Phe Val
1 5

<210> SEQ ID NO 1159
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1159

Ala Leu Val Ser Ser His Val
1 5

<210> SEQ ID NO 1160
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1160

Ala Ala Arg Gly Val Met Val
1 5

<210> SEQ ID NO 1161
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1161

Ala Leu Ala Arg Gly Ser Gly
1 5

<210> SEQ ID NO 1162
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1162

Leu Arg Tyr Trp Ala Ala Val

-continued 1 5

<210> SEQ ID NO 1163
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1163

Phe Thr Arg Gly Ala Ala Ser
1 5

<210> SEQ ID NO 1164
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1164

Glu Trp His Ala Ala Ser Gly
1 5

<210> SEQ ID NO 1165
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1165

Phe Gly Gly Ser Met Ala Pro
1 5

<210> SEQ ID NO 1166
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1166

Gly Gly Ser Leu Lys Trp Val
1 5

<210> SEQ ID NO 1167
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1167

Arg Gly Leu Gln Gly Gly Arg
1 5

<210> SEQ ID NO 1168
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1168

Thr Cys Gly Gly Arg Ser Tyr
1 5

-continued

<210> SEQ ID NO 1169
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1169

Gly Glu Ala Leu Gly Leu Gly
1               5

<210> SEQ ID NO 1170
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1170

Pro Arg Gly Leu Gly Val Gly
1               5

<210> SEQ ID NO 1171
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1171

Val Gly Leu Gly Asn Ser Ala
1               5

<210> SEQ ID NO 1172
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1172

Gly Gly Leu Val Lys Arg Leu
1               5

<210> SEQ ID NO 1173
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1173

Gly Ser Gly Arg Ala Leu Ala
1               5

<210> SEQ ID NO 1174
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1174

Ser Arg Ser Gly Arg Leu Asn
1               5

-continued

<210> SEQ ID NO 1175
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1175

Ser Ala Gly Val Ser Asp Ser
1               5

<210> SEQ ID NO 1176
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1176

Pro Arg Leu Ser Asp Lys Ser
1               5

<210> SEQ ID NO 1177
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1177

Gly Arg Gly Asp Arg Gly Val
1               5

<210> SEQ ID NO 1178
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1178

Arg Gly Val Ser Gly Arg Leu
1               5

<210> SEQ ID NO 1179
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1179

Ile Asn Arg Gly Ser Arg Glu
1               5

<210> SEQ ID NO 1180
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1180

Leu Arg Gly Ser Arg Gln Phe
1               5

-continued

<210> SEQ ID NO 1181
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1181

Leu Arg Gly Ser Val Gly Arg
1 5

<210> SEQ ID NO 1182
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1182

Gly Leu Trp Tyr Arg Ala Val
1 5

<210> SEQ ID NO 1183
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1183

Arg Val Arg Ala Val Leu Gly
1 5

<210> SEQ ID NO 1184
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1184

Arg Ala Val Leu Glu Leu Trp
1 5

<210> SEQ ID NO 1185
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1185

Leu Val Arg Ala Ser Asn Gly
1 5

<210> SEQ ID NO 1186
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1186

Ala Ser Gly Thr Leu Leu Arg
1 5

<210> SEQ ID NO 1187

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1187

Gly Ser Gly Val Arg Val Ser
1 5

<210> SEQ ID NO 1188
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1188

Val Gly Ser Thr Arg Ser Ser
1 5

<210> SEQ ID NO 1189
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1189

Arg Ala Gly Ser Arg Tyr Ile
1 5

<210> SEQ ID NO 1190
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1190

Val Gly Val Arg Phe Ser Arg
1 5

<210> SEQ ID NO 1191
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1191

Gly Ser Gly Val Arg Val Ser
1 5

<210> SEQ ID NO 1192
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1192

Ile Gly Val Leu Ala Ser Ala
1 5

<210> SEQ ID NO 1193
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1193

Gly Leu Val Ala Arg Val Arg
1               5

<210> SEQ ID NO 1194
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1194

Leu Leu Gly Ile Gly Gly Ser
1               5

<210> SEQ ID NO 1195
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1195

Gln Leu Gly Gly Ser Phe Arg
1               5

<210> SEQ ID NO 1196
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1196

Leu Phe Arg Trp Gly Gly Arg
1               5

<210> SEQ ID NO 1197
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1197

Arg Phe Ser Gly Gly Leu Gln
1               5

<210> SEQ ID NO 1198
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1198

Val Gly Ser Ser His Gly Leu
1               5

<210> SEQ ID NO 1199
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1199

Ser Val Arg Val Gly Ser Gly
1 5

<210> SEQ ID NO 1200
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1200

Gly Val Asn Gly Ser Val Ser
1 5

<210> SEQ ID NO 1201
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1201

Leu Arg Gly Ser Val Gly Arg
1 5

<210> SEQ ID NO 1202
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1202

His Val Lys Asn Gly Arg Val
1 5

<210> SEQ ID NO 1203
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1203

Phe Gln Arg Ser Gly Arg Leu
1 5

<210> SEQ ID NO 1204
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1204

His Gly Arg Leu Ala Phe Gly
1 5

<210> SEQ ID NO 1205
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1205

Arg Gly Val Ser Gly Arg Leu
1 5

<210> SEQ ID NO 1206
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1206

Arg Gly Val Ser Gly Arg Leu
1 5

<210> SEQ ID NO 1207
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1207

Phe Gly Ile Gly Arg Gly Val
1 5

<210> SEQ ID NO 1208
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1208

Gly Val Val Gln Ala Val Ser
1 5

<210> SEQ ID NO 1209
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1209

Leu Ser Ala Val Ser Val Lys
1 5

<210> SEQ ID NO 1210
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1210

Leu Tyr Leu Leu Ser Ser Ala
1 5

<210> SEQ ID NO 1211
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1211

Leu Ile Gly Gly Leu Leu Ser
1 5

<210> SEQ ID NO 1212
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1212

Leu Leu Arg Arg Gly Ile Gly
1 5

<210> SEQ ID NO 1213
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1213

Phe Leu Arg Ser Leu Ser Leu
1 5

<210> SEQ ID NO 1214
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1214

Val Arg Val Ser Gly Leu Thr
1 5

<210> SEQ ID NO 1215
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1215

Ala Gly Ser Val Asp Leu Val
1 5

<210> SEQ ID NO 1216
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1216

Gly Phe Val Ala Gly Arg Thr
1 5

<210> SEQ ID NO 1217
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1217

Thr Arg Gly Ala Val Phe Gly
1 5

<210> SEQ ID NO 1218
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1218

Ile Tyr Gly Gly Leu Val Ile
1 5

<210> SEQ ID NO 1219
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1219

Pro Thr Gly Glu Gly Leu Arg
1 5

<210> SEQ ID NO 1220
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1220

Lys Val Ser Val Ala Ser Leu
1 5

<210> SEQ ID NO 1221
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1221

Arg Tyr Ser Met Ala Ser Leu
1 5

<210> SEQ ID NO 1222
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1222

Ala Asn Ala Ala Ser Ser Pro
1 5

<210> SEQ ID NO 1223
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1223

Pro Gly Gly Ser Arg His Ala
1               5

<210> SEQ ID NO 1224
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1224

Gly Gly Ser Pro Gly Val Trp
1               5

<210> SEQ ID NO 1225
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1225

Ile Tyr Gly Gly Leu Val Ile
1               5

<210> SEQ ID NO 1226
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1226

Leu Ile Gly Gly Leu Leu Ser
1               5

<210> SEQ ID NO 1227
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1227

Ala Cys Gly Ser Gly Leu Asp
1               5

<210> SEQ ID NO 1228
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1228

Ala Gly Ser Val Asp Leu Val
1               5

<210> SEQ ID NO 1229
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1229

-continued

Thr Leu Gly Ser Val Arg Val
1 5

<210> SEQ ID NO 1230
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1230

His Val Arg Gly Arg Val Ala
1 5

<210> SEQ ID NO 1231
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1231

Ile Asp Leu Gly Arg Val Asn
1 5

<210> SEQ ID NO 1232
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1232

Gly Arg Leu Asp Ala Phe Gly
1 5

<210> SEQ ID NO 1233
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1233

Trp Val Gly Pro Ser Gly Gly
1 5

<210> SEQ ID NO 1234
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1234

Asp Leu Arg Leu Ser Phe Pro
1 5

<210> SEQ ID NO 1235
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1235

-continued

Ser Ala Arg Leu Ser His Val
1               5

<210> SEQ ID NO 1236
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1236

Val Met Asp Arg Gly Val Ala
1               5

<210> SEQ ID NO 1237
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1237

Arg Gly Ser Leu Leu Trp Ala
1               5

<210> SEQ ID NO 1238
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1238

Arg Gly Ser Pro Leu Thr Lys
1               5

<210> SEQ ID NO 1239
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1239

Arg Ala Ser Ile Gly Ile Glu
1               5

<210> SEQ ID NO 1240
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1240

Val His Ser Leu Arg Ala Ser
1               5

<210> SEQ ID NO 1241
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1241

Ala Trp Leu Leu Ser Gly Arg

-continued 1 5

<210> SEQ ID NO 1242
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1242

Leu Trp Leu Arg Ser Arg Glu
1 5

<210> SEQ ID NO 1243
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1243

Val Thr Arg Ile Arg Val Ser
1 5

<210> SEQ ID NO 1244
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1244

Asn Ser Gln Arg Ser Ser Val
1 5

<210> SEQ ID NO 1245
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1245

Ala Ala Thr Arg Ala Gly Ser
1 5

<210> SEQ ID NO 1246
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1246

Thr Asp Gly Val Arg Ala Phe
1 5

<210> SEQ ID NO 1247
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1247

Phe Ala Ala Ser Gly Val Leu
1 5

<210> SEQ ID NO 1248
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1248

Gly Val Leu Glu Gly Arg Arg
1               5

<210> SEQ ID NO 1249
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1249

Glu Ala Asp Pro Gly Ala Val
1               5

<210> SEQ ID NO 1250
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1250

Asp Gly Ala Val Ile Leu His
1               5

<210> SEQ ID NO 1251
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1251

Arg Asp Gly Ala Val Asn Leu
1               5

<210> SEQ ID NO 1252
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1252

Gly Leu Arg Pro His Gly Ala
1               5

<210> SEQ ID NO 1253
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1253

Thr Ser Arg Gly Leu Arg Leu
1               5

-continued

<210> SEQ ID NO 1254
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1254

Arg Met Leu Val Ser Ser Phe
1 5

<210> SEQ ID NO 1255
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1255

Asp Val Ile Ala Arg Gly Trp
1 5

<210> SEQ ID NO 1256
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1256

Thr Leu Thr Ala Ala Val Phe
1 5

<210> SEQ ID NO 1257
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1257

Gly Trp Leu Asn Ala Ala Val
1 5

<210> SEQ ID NO 1258
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1258

Phe Ala Ala Ser Gly Val Leu
1 5

<210> SEQ ID NO 1259
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1259

Gly Gly Ser Lys Gly Ser Ala
1 5

-continued

<210> SEQ ID NO 1260
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1260

Ala Val Ala Leu Gly Gly Ser
1               5

<210> SEQ ID NO 1261
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1261

His Gly Gly Arg Tyr Arg His
1               5

<210> SEQ ID NO 1262
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1262

Ser Gly Val Gly Gly Arg Tyr
1               5

<210> SEQ ID NO 1263
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1263

Ser Gly Gly Leu Ala Val Ala
1               5

<210> SEQ ID NO 1264
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1264

Gly Arg Leu Ala Lys Ser Ile
1               5

<210> SEQ ID NO 1265
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1265

Ala Gly Pro Ser Arg Gly Pro
1               5

<210> SEQ ID NO 1266

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1266

Gly Leu Met Arg Leu Ser His
1               5

<210> SEQ ID NO 1267
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1267

Val Arg Val Gly Arg Leu Ser
1               5

<210> SEQ ID NO 1268
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1268

Thr Gly Arg Leu Ser Ala Ala
1               5

<210> SEQ ID NO 1269
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1269

Ser Leu Arg Gly Val Arg Val
1               5

<210> SEQ ID NO 1270
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1270

Asp Asn Cys Glu Arg Gly Val
1               5

<210> SEQ ID NO 1271
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1271

Thr Thr Gln Leu Arg Gly Val
1               5

<210> SEQ ID NO 1272
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1272

Gly Val Ile Gly Arg Gly Ser
1 5

<210> SEQ ID NO 1273
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1273

Leu Ala Gly Met Arg Gly Ser
1 5

<210> SEQ ID NO 1274
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1274

Val Arg Pro Arg Ala Val Leu
1 5

<210> SEQ ID NO 1275
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1275

Pro Pro Arg Ala Val Thr Asn
1 5

<210> SEQ ID NO 1276
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1276

Trp Arg Ala Arg Ala Ser Pro
1 5

<210> SEQ ID NO 1277
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1277

Phe Gly Arg Leu Leu Ser Pro
1 5

<210> SEQ ID NO 1278
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1278

Pro Ser Leu Leu Arg Gly Phe
1 5

<210> SEQ ID NO 1279
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1279

Arg Asp Leu Arg Val His Leu
1 5

<210> SEQ ID NO 1280
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1280

Leu Arg Val Ser Asn Pro Arg
1 5

<210> SEQ ID NO 1281
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1281

Leu Arg Val Asp Gln Leu Tyr
1 5

<210> SEQ ID NO 1282
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1282

His Arg Leu Arg Ser Met Ser
1 5

<210> SEQ ID NO 1283
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1283

Leu Arg Val Ser Asn Pro Arg
1 5

<210> SEQ ID NO 1284
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1284

Pro Gly Phe Met Ala Gly Ser
1 5

<210> SEQ ID NO 1285
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1285

Ala Gly Arg Gly Ile Ser Gln
1 5

<210> SEQ ID NO 1286
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1286

Arg Ala Gly Arg Asp Ala Pro
1 5

<210> SEQ ID NO 1287
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1287

Arg Ala Gly Arg Gly Phe Glu
1 5

<210> SEQ ID NO 1288
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1288

His Gln Ala Gly Gly Val Thr
1 5

<210> SEQ ID NO 1289
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1289

Ser Leu Arg Gly Val Arg Val
1 5

<210> SEQ ID NO 1290
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1290

Asp Trp Val Gly Val Leu Met
1 5

<210> SEQ ID NO 1291
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1291

Gly Thr Leu Gly Val Leu Ser
1 5

<210> SEQ ID NO 1292
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1292

Gly Val Leu Leu Trp Arg Pro
1 5

<210> SEQ ID NO 1293
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1293

Gly Leu Arg Glu Ala His Val
1 5

<210> SEQ ID NO 1294
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1294

Ala Ala Arg Gly Glu Leu Arg
1 5

<210> SEQ ID NO 1295
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1295

Ala Ala Ser Leu Arg Gly Thr
1 5

<210> SEQ ID NO 1296
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1296

Pro Val Gly Ala Ala Val Ala
1               5

<210> SEQ ID NO 1297
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1297

Ala Ala Ser Leu Arg Gly Thr
1               5

<210> SEQ ID NO 1298
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1298

Ser Asn Pro Gly Ser Gly Ser
1               5

<210> SEQ ID NO 1299
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1299

Gly Arg Val Arg Glu Thr Pro
1               5

<210> SEQ ID NO 1300
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1300

Phe Gly Arg Leu Leu Ser Pro
1               5

<210> SEQ ID NO 1301
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1301

Val Arg Val Gly Arg Leu Ser
1               5

<210> SEQ ID NO 1302
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1302

Thr Gly Arg Leu Ser Ala Ala
1 5

<210> SEQ ID NO 1303
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1303

Val Gly Arg Leu Gln Thr Thr
1 5

<210> SEQ ID NO 1304
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1304

Asp Gly Pro Ser Cys Val Ile
1 5

<210> SEQ ID NO 1305
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1305

Arg Phe Ser Ser Arg Ala Val
1 5

<210> SEQ ID NO 1306
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1306

His Ala Gly Ser Arg Ala Ser
1 5

<210> SEQ ID NO 1307
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1307

Gly Ala Gly Leu Gly Val Ser
1 5

<210> SEQ ID NO 1308
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1308

-continued

Leu Leu Gly Ala Gly Thr Pro
1 5

<210> SEQ ID NO 1309
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1309

Leu Leu Ser Ile Leu Lys Ala
1 5

<210> SEQ ID NO 1310
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1310

Gly Leu Leu Ser Gly Gly Thr
1 5

<210> SEQ ID NO 1311
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1311

Leu Ser Val Leu Arg Val Leu
1 5

<210> SEQ ID NO 1312
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1312

Ser Arg Tyr Thr Leu Arg Ser
1 5

<210> SEQ ID NO 1313
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1313

Leu Phe His Thr Arg Ser Ser
1 5

<210> SEQ ID NO 1314
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1314

-continued

Val Ala Arg Ser Ser Phe Arg
1               5

<210> SEQ ID NO 1315
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1315

Cys Thr Ala Gly Ser Val Ser
1               5

<210> SEQ ID NO 1316
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1316

Arg Ala Ala Gly Ser Ala Gly
1               5

<210> SEQ ID NO 1317
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1317

His Ala Gly Ser Arg Ala Ser
1               5

<210> SEQ ID NO 1318
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1318

Gly Ala Gly Leu Gly Val Ser
1               5

<210> SEQ ID NO 1319
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1319

Pro Thr Gly Ala Gly Leu Leu
1               5

<210> SEQ ID NO 1320
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1320

Ala Ser Tyr Ala Gly Leu Val

-continued 1 5

<210> SEQ ID NO 1321
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1321

Ala Gly Gly Phe Gly Val Leu
1 5

<210> SEQ ID NO 1322
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1322

Asn Met Ala Gly Gly Gln Glu
1 5

<210> SEQ ID NO 1323
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1323

Leu Arg Ala Gly Gly Ser Tyr
1 5

<210> SEQ ID NO 1324
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1324

Tyr Leu Ala Gly Gly Lys Ala
1 5

<210> SEQ ID NO 1325
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1325

Pro Tyr Tyr Asn Gly Val Arg
1 5

<210> SEQ ID NO 1326
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1326

Ala Gly Gly Phe Gly Val Leu
1 5

-continued

<210> SEQ ID NO 1327
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1327

Leu Ile Gly Gly Val Leu His
1 5

<210> SEQ ID NO 1328
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1328

Asp Gly Leu Val Pro Val Ala
1 5

<210> SEQ ID NO 1329
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1329

Gly Leu Val Ala Ser Met Pro
1 5

<210> SEQ ID NO 1330
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1330

Ala Ser Tyr Ala Gly Leu Val
1 5

<210> SEQ ID NO 1331
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1331

Leu Val Arg Leu Val Ser Leu
1 5

<210> SEQ ID NO 1332
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1332

Val Leu Ala Ser Leu Ser Gly
1 5

-continued

<210> SEQ ID NO 1333
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1333

Gly Ser Ile Thr Gly Gly Ser
1               5

<210> SEQ ID NO 1334
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1334

Leu Arg Ala Gly Gly Ser Tyr
1               5

<210> SEQ ID NO 1335
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1335

Thr Gly Gly Ser Leu Leu Gly
1               5

<210> SEQ ID NO 1336
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1336

Asp Glu Gly Gly Ser Arg Trp
1               5

<210> SEQ ID NO 1337
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1337

Gly Ala Gly Leu Gly Val Ser
1               5

<210> SEQ ID NO 1338
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1338

Trp Gly Ser Ser Ala Val Lys
1               5

-continued

<210> SEQ ID NO 1339
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1339

Gln Gly Ser Ser Asn Ser Val
1 5

<210> SEQ ID NO 1340
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1340

Cys Thr Ala Gly Ser Val Ser
1 5

<210> SEQ ID NO 1341
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1341

Ser Val Thr Gly Ser Val Gly
1 5

<210> SEQ ID NO 1342
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1342

Ser Pro Gly Arg Val Ala Asp
1 5

<210> SEQ ID NO 1343
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1343

Asp Ala Val Arg Gly Pro Ser
1 5

<210> SEQ ID NO 1344
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1344

Gly Ala Gly Leu Gly Val Ser
1 5

<210> SEQ ID NO 1345

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1345

Gly Val Ser Gly Thr Val Ser
1               5

<210> SEQ ID NO 1346
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1346

Ser Gly Val Ser Ile Ser Cys
1               5

<210> SEQ ID NO 1347
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1347

Arg Arg Leu Ser Tyr His Ser
1               5

<210> SEQ ID NO 1348
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1348

Arg Arg Glu Gly Leu Arg Ser
1               5

<210> SEQ ID NO 1349
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1349

Glu Arg Val Ser Ala Ala Val
1               5

<210> SEQ ID NO 1350
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1350

Ala Gly Ser Met Met Glu Phe
1               5

<210> SEQ ID NO 1351
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1351

Arg His Gly Pro Gly Val Leu
1 5

<210> SEQ ID NO 1352
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1352

Gly Leu Arg Arg Asp Asn Gly
1 5

<210> SEQ ID NO 1353
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1353

Arg Arg Glu Gly Leu Arg Ser
1 5

<210> SEQ ID NO 1354
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1354

Glu Arg Val Ser Ala Ala Val
1 5

<210> SEQ ID NO 1355
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1355

Val Ala Ala Ser Val Arg Glu
1 5

<210> SEQ ID NO 1356
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1356

Pro Trp Tyr Asp Gly Ser Val
1 5

<210> SEQ ID NO 1357
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1357

Gly Arg Val Thr Leu Glu Ser
1               5

<210> SEQ ID NO 1358
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1358

Gly Arg Leu Ser Arg Ala Pro
1               5

<210> SEQ ID NO 1359
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1359

Ser Arg Leu Ser Tyr Cys Asn
1               5

<210> SEQ ID NO 1360
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1360

Gln Ala Arg Gly Ser Trp Leu
1               5

<210> SEQ ID NO 1361
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1361

Phe Val Pro Arg Gly Ser Tyr
1               5

<210> SEQ ID NO 1362
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1362

Ala Ala Leu Leu Arg Ala Val
1               5

<210> SEQ ID NO 1363
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1363

Leu Ala Gly Arg Ala Ser Glu
1 5

<210> SEQ ID NO 1364
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1364

Ala Ala Gly Ala Gly Trp Arg
1 5

<210> SEQ ID NO 1365
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1365

Ala Asp Leu Gly Ala Gly Trp
1 5

<210> SEQ ID NO 1366
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1366

Ala Asp Leu Gly Ala Gly Trp
1 5

<210> SEQ ID NO 1367
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1367

Gly Gly Ala Gly Arg Gly Ala
1 5

<210> SEQ ID NO 1368
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1368

Asp Val Trp Val Ala Val Ser
1 5

<210> SEQ ID NO 1369
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1369

Ala Ala Leu Leu Arg Ala Val
1               5

<210> SEQ ID NO 1370
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1370

Asn Leu Arg Val Gly Ala Glu
1               5

<210> SEQ ID NO 1371
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1371

Asn Cys Tyr Ser Leu Arg Ser
1               5

<210> SEQ ID NO 1372
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1372

Leu Ala Gly Ser Arg Val Ser
1               5

<210> SEQ ID NO 1373
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1373

Ser Gly Pro Ala Gly Ser Phe
1               5

<210> SEQ ID NO 1374
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1374

Leu Ala Gly Ser Arg Val Ser
1               5

<210> SEQ ID NO 1375
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1375

Gly Gly Ala Gly Arg Gly Ala
1 5

<210> SEQ ID NO 1376
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1376

Leu Ala Gly Arg Ala Ser Glu
1 5

<210> SEQ ID NO 1377
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1377

Val Ala Gly Arg Leu Gln Met
1 5

<210> SEQ ID NO 1378
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1378

Trp Gly Ala Gly Leu Asp Ala
1 5

<210> SEQ ID NO 1379
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1379

Trp Gly Ala Gly Leu Asp Ala
1 5

<210> SEQ ID NO 1380
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1380

Ala Gly Arg Gly Ala Gly Gly
1 5

<210> SEQ ID NO 1381
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1381

Glu Ala Gly Val Arg Leu Asn
1               5

<210> SEQ ID NO 1382
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1382

Met Gln Leu Arg Gly Ala Val
1               5

<210> SEQ ID NO 1383
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1383

Gly Gly Pro Gly Leu Val Met
1               5

<210> SEQ ID NO 1384
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1384

Gln Gly Leu Val Arg Gly Gly
1               5

<210> SEQ ID NO 1385
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1385

Pro Gly Leu Arg Gly Pro Ala
1               5

<210> SEQ ID NO 1386
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1386

Pro Gly Leu Arg Gly Pro Ala
1               5

<210> SEQ ID NO 1387
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1387

-continued

Gly Arg Met Leu Val Ser Gly
1 5

<210> SEQ ID NO 1388
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1388

Glu Ser Ala Arg Gly Ala Leu
1 5

<210> SEQ ID NO 1389
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1389

Gln Ala Arg Gly Ser Trp Leu
1 5

<210> SEQ ID NO 1390
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1390

Gly Gly Gly Ser Gly Gly Gly
1 5

<210> SEQ ID NO 1391
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1391

Asn Asn Val Gly Gly Ser Ser
1 5

<210> SEQ ID NO 1392
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1392

Gly Gly Arg Val Leu Gly Gln
1 5

<210> SEQ ID NO 1393
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1393

-continued

Gly Gly Arg Val Arg Gly Gly
1 5

<210> SEQ ID NO 1394
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1394

Gly Gly Arg Val Arg Gly Gly
1 5

<210> SEQ ID NO 1395
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1395

Trp Tyr Gly Gly Arg Gly Asn
1 5

<210> SEQ ID NO 1396
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1396

Cys Val Gly Leu Gly Cys His
1 5

<210> SEQ ID NO 1397
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1397

Asn Asn Val Gly Gly Ser Ser
1 5

<210> SEQ ID NO 1398
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1398

Phe Met Thr Tyr Gly Ser Gly
1 5

<210> SEQ ID NO 1399
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1399

Gly Gly Gly Ser Gly Gly Gly

-continued 1 5

<210> SEQ ID NO 1400
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1400

Trp Asp Gln Gly Ser Gly Tyr
1 5

<210> SEQ ID NO 1401
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1401

Gly Ser Val Leu Met Arg Gly
1 5

<210> SEQ ID NO 1402
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1402

Gly Gly Arg Val Leu Gly Gln
1 5

<210> SEQ ID NO 1403
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1403

Gly Gly Arg Val Arg Gly Gly
1 5

<210> SEQ ID NO 1404
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1404

Gly Gly Arg Val Arg Gly Gly
1 5

<210> SEQ ID NO 1405
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1405

Tyr Met Tyr His Gly Arg Val
1 5

-continued

<210> SEQ ID NO 1406
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1406

Gly Arg Leu Ser Arg Ala Pro
1               5

<210> SEQ ID NO 1407
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1407

Val Ala Gly Arg Leu Gln Met
1               5

<210> SEQ ID NO 1408
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1408

Ala Pro Gly Arg Leu Gly Pro
1               5

<210> SEQ ID NO 1409
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1409

Ala Pro Gly Arg Leu Gly Pro
1               5

<210> SEQ ID NO 1410
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1410

Arg Asp Leu Ala Gly Pro Ser
1               5

<210> SEQ ID NO 1411
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1411

Arg Leu Ser Gly Ala Gly Asp
1               5

-continued

<210> SEQ ID NO 1412
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1412

Leu Gln Arg Gly Val Ala Arg
1 5

<210> SEQ ID NO 1413
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1413

Arg Ala Val Gly Arg Gln Leu
1 5

<210> SEQ ID NO 1414
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1414

Ser Arg Ala Val Ile Arg Leu
1 5

<210> SEQ ID NO 1415
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1415

Val Arg Ala Ser Ser Lys Arg
1 5

<210> SEQ ID NO 1416
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1416

Asp Gly Ala Gly Ser Leu Arg
1 5

<210> SEQ ID NO 1417
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1417

Ser Val Ser Gly Ala Gly Ser
1 5

-continued

<210> SEQ ID NO 1418
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1418

Thr Thr Leu Leu Ser Arg Gln
1 5

<210> SEQ ID NO 1419
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1419

Val Ala Glu Leu Leu Ser Met
1 5

<210> SEQ ID NO 1420
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1420

Leu Pro Gly Arg Leu Arg Val
1 5

<210> SEQ ID NO 1421
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1421

Leu Lys Ala Gly Leu Arg Ser
1 5

<210> SEQ ID NO 1422
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1422

His Arg Val Ser Glu Ser Val
1 5

<210> SEQ ID NO 1423
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1423

Tyr Tyr Gly Glu Arg Ser Ser
1 5

<210> SEQ ID NO 1424

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1424

Asp Gly Ala Gly Ser Leu Arg
1               5

<210> SEQ ID NO 1425
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1425

Ser Val Ser Gly Ala Gly Ser
1               5

<210> SEQ ID NO 1426
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1426

Ala Gly Ser Val Tyr Ser Val
1               5

<210> SEQ ID NO 1427
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1427

Ser Ala Gly Leu Leu Pro Ser
1               5

<210> SEQ ID NO 1428
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1428

Leu Lys Ala Gly Leu Arg Ser
1               5

<210> SEQ ID NO 1429
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1429

Arg Arg Ala Gly Gly Ser Val
1               5

<210> SEQ ID NO 1430
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1430

Ser Trp Ala Gly Val Arg Phe
1 5

<210> SEQ ID NO 1431
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1431

Ile Tyr Pro Gly Ala Val Leu
1 5

<210> SEQ ID NO 1432
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1432

Leu Lys Ala Gly Leu Arg Ser
1 5

<210> SEQ ID NO 1433
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1433

Ser Leu Val Ser Pro Arg Thr
1 5

<210> SEQ ID NO 1434
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1434

His Ala Ala Val Glu Pro Ser
1 5

<210> SEQ ID NO 1435
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1435

Thr Ala Ala Ala Val Leu Leu
1 5

<210> SEQ ID NO 1436
<211> LENGTH: 7
<212> TYPE: PRT

<213> ORGANISM: Artificial Sequence
<220> FEATURE:
<223> OTHER INFORMATION: Synthetic peptide

<400> SEQUENCE: 1436

Phe His Phe Gly Gly Ser Gly
1 5

<210> SEQ ID NO 1437
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1437

Gly Glu Gly Gly Ser Gly Gly
1 5

<210> SEQ ID NO 1438
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1438

Arg Arg Ala Gly Gly Ser Val
1 5

<210> SEQ ID NO 1439
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1439

Ala Leu Pro Gly Gly Gly Arg
1 5

<210> SEQ ID NO 1440
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1440

Tyr Val Gly Gly Arg Leu Arg
1 5

<210> SEQ ID NO 1441
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1441

Gly Lys Gly Met Gly Leu Gly
1 5

<210> SEQ ID NO 1442
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1442

Ser Leu Gly Leu Gly Gly Leu
1               5

<210> SEQ ID NO 1443
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1443

Asp Gly Gly Leu Asn Asp Cys
1               5

<210> SEQ ID NO 1444
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1444

Leu Gly Gly Leu Gly Leu Ser
1               5

<210> SEQ ID NO 1445
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1445

Phe His Phe Gly Gly Ser Gly
1               5

<210> SEQ ID NO 1446
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1446

Gly Glu Gly Gly Ser Gly Gly
1               5

<210> SEQ ID NO 1447
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1447

Arg Arg Ala Gly Gly Ser Val
1               5

<210> SEQ ID NO 1448
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1448

Ser Gly Ala Gly Ser Val Ser
1               5

<210> SEQ ID NO 1449
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1449

Ala Gly Ser Val Tyr Ser Val
1               5

<210> SEQ ID NO 1450
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1450

Gly Arg Val Thr Trp Arg Ser
1               5

<210> SEQ ID NO 1451
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1451

Leu Pro Gly Arg Leu Arg Val
1               5

<210> SEQ ID NO 1452
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1452

Tyr Val Gly Gly Arg Leu Arg
1               5

<210> SEQ ID NO 1453
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1453

Gly Pro Ser Ser Ala Val Glu
1               5

<210> SEQ ID NO 1454
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1454

Arg Arg Leu Ser Tyr Arg Glu
1 5

<210> SEQ ID NO 1455
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1455

His Thr Arg Ala Val Ser Glu
1 5

<210> SEQ ID NO 1456
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1456

Asn Val Ser Arg Ala Val Gly
1 5

<210> SEQ ID NO 1457
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1457

Pro Arg His Arg Ala Ser Gln
1 5

<210> SEQ ID NO 1458
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1458

Leu Gly Ala Gly Met Ile Ala
1 5

<210> SEQ ID NO 1459
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1459

Ala Val Ser Leu Val Val Leu
1 5

<210> SEQ ID NO 1460
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1460

His Thr Arg Ala Val Ser Glu
1 5

<210> SEQ ID NO 1461
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1461

Glu Leu Gly Leu Arg Val Pro
1 5

<210> SEQ ID NO 1462
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1462

Gly Arg Ser Ser Val Ser Asp
1 5

<210> SEQ ID NO 1463
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1463

Tyr Ala Gly Ser Gly Gln Leu
1 5

<210> SEQ ID NO 1464
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1464

Ala Gly Arg Phe Gly Ala Arg
1 5

<210> SEQ ID NO 1465
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1465

Ala Ile Met Gly Ala Gly Leu
1 5

<210> SEQ ID NO 1466
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1466

-continued

Thr His Val Gly Gly Val Arg
1               5

<210> SEQ ID NO 1467
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1467

Gly Val Leu Thr Arg Gly Asn
1               5

<210> SEQ ID NO 1468
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1468

Glu Leu Gly Leu Arg Val Pro
1               5

<210> SEQ ID NO 1469
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1469

Gly Leu Gly Leu Arg Leu Gly
1               5

<210> SEQ ID NO 1470
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1470

Ile Asp Leu Val Ser Pro Gly
1               5

<210> SEQ ID NO 1471
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1471

Gly Gly Ser Thr Val Pro Gln
1               5

<210> SEQ ID NO 1472
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1472

-continued

```
Gly Leu Gly Leu Arg Leu Gly
1               5


<210> SEQ ID NO 1473
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1473

Thr Ala Thr Gly Gly Leu Leu
1               5


<210> SEQ ID NO 1474
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1474

Gly Ser Asn Gly Ser Ser His
1               5


<210> SEQ ID NO 1475
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1475

Leu Gln Gly Ser Gly Ala Tyr
1               5


<210> SEQ ID NO 1476
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1476

Leu Gln His Leu Gly Ser Gly
1               5


<210> SEQ ID NO 1477
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1477

Gly Pro Ser Val Leu Asp Ile
1               5


<210> SEQ ID NO 1478
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1478

Gly Ala Thr Gly Val Ser Ser
```

-continued 1 5

<210> SEQ ID NO 1479
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1479

Thr Arg Leu Ser Phe Arg His
1 5

<210> SEQ ID NO 1480
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1480

Phe Leu Arg Gly Val Glu Leu
1 5

<210> SEQ ID NO 1481
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1481

Asn Ser Val Arg Gly Ser Arg
1 5

<210> SEQ ID NO 1482
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1482

Asn Arg Ala Val Leu Ser Ala
1 5

<210> SEQ ID NO 1483
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1483

Leu Ile Gly Arg Ala Ser Met
1 5

<210> SEQ ID NO 1484
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1484

Arg Val Gly Ala Gly Ala Phe
1 5

-continued

<210> SEQ ID NO 1485
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1485

Trp Ile Ser Ala Val Ser Lys
1 5

<210> SEQ ID NO 1486
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1486

Ser Ala Val Ser Glu Ser Pro
1 5

<210> SEQ ID NO 1487
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1487

Arg Val Gly Thr Leu Arg Val
1 5

<210> SEQ ID NO 1488
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1488

Arg Val Ser Gly Asp Gly Lys
1 5

<210> SEQ ID NO 1489
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1489

Arg Ser Gly Arg Val Ser Asn
1 5

<210> SEQ ID NO 1490
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1490

Arg Val Ser Asn Glu Ala Leu
1 5

-continued

<210> SEQ ID NO 1491
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1491

Arg Val Ser Ser Asp Pro Ile
1               5

<210> SEQ ID NO 1492
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1492

Val Arg Ser Ser Gly Val Leu
1               5

<210> SEQ ID NO 1493
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1493

Ser Gly Trp Phe Ala Gly Ser
1               5

<210> SEQ ID NO 1494
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1494

Ala Gly Leu Gly Leu Leu Asp
1               5

<210> SEQ ID NO 1495
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1495

Ser Ala Ala Gly Leu Ala Arg
1               5

<210> SEQ ID NO 1496
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1496

Phe Ala Gly Ala Gly Val Arg
1               5

-continued

<210> SEQ ID NO 1497
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1497

Val Arg Leu Thr Gly Val Arg
1 5

<210> SEQ ID NO 1498
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1498

Val Arg Ser Ser Gly Val Leu
1 5

<210> SEQ ID NO 1499
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1499

Arg Pro Trp Gly Ala Val Ala
1 5

<210> SEQ ID NO 1500
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1500

Pro Val Ser Asp Gly Leu Val
1 5

<210> SEQ ID NO 1501
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1501

Asn Lys Gly Gly Leu Arg Gln
1 5

<210> SEQ ID NO 1502
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1502

Gly Gly Phe Leu Leu Val Ser
1 5

<210> SEQ ID NO 1503

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1503

Leu Val Pro Leu Val Ser Gly
1 5

<210> SEQ ID NO 1504
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1504

Ala Arg Gly Gly Glu Ser Ala
1 5

<210> SEQ ID NO 1505
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1505

Met Ser Ala Arg Gly Ile Leu
1 5

<210> SEQ ID NO 1506
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1506

Ala Ser Leu Val Ala Arg Asn
1 5

<210> SEQ ID NO 1507
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1507

Arg Val Glu Ala Ala Val Pro
1 5

<210> SEQ ID NO 1508
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1508

Arg Ala Leu Gly Ala Ala Ser
1 5

<210> SEQ ID NO 1509
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1509

Ala Ser Glu Gly Gly Arg Ala
1               5

<210> SEQ ID NO 1510
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1510

Ile Gly Gly Arg Trp Val Val
1               5

<210> SEQ ID NO 1511
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1511

Ala Gly Leu Gly Leu Leu Asp
1               5

<210> SEQ ID NO 1512
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1512

Leu Gly Gly Leu Ser Glu Arg
1               5

<210> SEQ ID NO 1513
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1513

Asn Lys Gly Gly Leu Arg Gln
1               5

<210> SEQ ID NO 1514
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1514

Leu Val Gly Ser Ser Arg Val
1               5

<210> SEQ ID NO 1515
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1515

Tyr Thr Gly Ser Ser Pro Ser
1 5

<210> SEQ ID NO 1516
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1516

Gly Ser Val Leu Pro Val Leu
1 5

<210> SEQ ID NO 1517
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1517

Lys Gly Asp Gly Ser Val Arg
1 5

<210> SEQ ID NO 1518
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1518

Gly Ser Val Ser His Arg Arg
1 5

<210> SEQ ID NO 1519
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1519

Arg Leu Trp Gly Ser Val Val
1 5

<210> SEQ ID NO 1520
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1520

Met Gln Gly Arg Val Ile Val
1 5

<210> SEQ ID NO 1521
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1521

Arg Ser Gly Arg Val Ser Asn
1 5

<210> SEQ ID NO 1522
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1522

Leu Glu Val Gly Arg Leu Phe
1 5

<210> SEQ ID NO 1523
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1523

Ser Gln Phe Gly Pro Ser Phe
1 5

<210> SEQ ID NO 1524
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1524

Ala Thr Leu Asp Gly Val Ser
1 5

<210> SEQ ID NO 1525
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1525

Arg Leu Ser Trp Thr Val Leu
1 5

<210> SEQ ID NO 1526
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1526

Leu Arg Phe Arg Arg Gly Val
1 5

<210> SEQ ID NO 1527
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1527

Ala Arg Gly Arg Gly Ser Gln
1 5

<210> SEQ ID NO 1528
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1528

Val Leu Arg Gly Ser Thr Pro
1 5

<210> SEQ ID NO 1529
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1529

Ala Arg Leu Arg Ala Ser Arg
1 5

<210> SEQ ID NO 1530
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1530

Arg Ile Gly Ala Gly His Arg
1 5

<210> SEQ ID NO 1531
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1531

Trp Leu Leu Ser Ser Glu Ile
1 5

<210> SEQ ID NO 1532
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1532

Gly Gly Leu Arg Val Gly Gly
1 5

<210> SEQ ID NO 1533
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1533

Gly Leu Arg Val Tyr Glu Pro
1 5

<210> SEQ ID NO 1534
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1534

Tyr Leu Arg Ser Ala Gly Met
1 5

<210> SEQ ID NO 1535
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1535

Arg Val Ser Arg Ala Gly Gly
1 5

<210> SEQ ID NO 1536
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1536

Ala Gly Arg Pro Gly Gly Tyr
1 5

<210> SEQ ID NO 1537
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1537

Tyr Gly Ala Leu Ala Gly Leu
1 5

<210> SEQ ID NO 1538
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1538

Arg Val Ser Arg Ala Gly Gly
1 5

<210> SEQ ID NO 1539
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1539

Ser His Thr Ala Gly Gly Gly
1 5

<210> SEQ ID NO 1540
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1540

Ala Gly Gly Val Arg Asp Leu
1 5

<210> SEQ ID NO 1541
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1541

Arg Pro Ala Gly Gly Arg Thr
1 5

<210> SEQ ID NO 1542
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1542

Gly Gly Val Arg Leu Gly Gly
1 5

<210> SEQ ID NO 1543
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1543

Ala Gly Gly Val Arg Asp Leu
1 5

<210> SEQ ID NO 1544
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1544

Gly Val Leu Gly Cys Asp Gly
1 5

<210> SEQ ID NO 1545
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1545

-continued

Cys Gly Ala Val Ala Glu Trp
1               5

<210> SEQ ID NO 1546
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1546

Gly Asp Cys Gly Leu Val Gly
1               5

<210> SEQ ID NO 1547
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1547

Gly Gly Leu Arg Val Gly Gly
1               5

<210> SEQ ID NO 1548
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1548

Gly Leu Arg Val Tyr Glu Pro
1               5

<210> SEQ ID NO 1549
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1549

Ala Arg Gly Arg Gly Ser Gln
1               5

<210> SEQ ID NO 1550
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1550

Gly Gly Arg Glu Leu Lys Ala
1               5

<210> SEQ ID NO 1551
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1551

-continued

Gly Gly Gly Arg Arg Ala Leu
1 5

<210> SEQ ID NO 1552
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1552

Arg Pro Ala Gly Gly Arg Thr
1 5

<210> SEQ ID NO 1553
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1553

Gly Gly Leu Lys Val Trp Arg
1 5

<210> SEQ ID NO 1554
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1554

Gly Gly Leu Arg Val Gly Gly
1 5

<210> SEQ ID NO 1555
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1555

Gly Gly Leu Pro Val Gln Met
1 5

<210> SEQ ID NO 1556
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1556

Arg Gln Asp Gly Gly Leu Tyr
1 5

<210> SEQ ID NO 1557
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1557

Tyr Ala Thr Leu Gly Ser Ser

-continued 1 5

<210> SEQ ID NO 1558
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1558

Ser Gly Ser Gly Cys Val Phe
1 5

<210> SEQ ID NO 1559
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1559

Val Ser Gly Ser Gly Thr Ala
1 5

<210> SEQ ID NO 1560
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1560

Val Gly Ser Val Lys Ala Ser
1 5

<210> SEQ ID NO 1561
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1561

Ala Thr Gly Ser Gly Ser Val
1 5

<210> SEQ ID NO 1562
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1562

Pro Thr Ser Gly Arg Leu Val
1 5

<210> SEQ ID NO 1563
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1563

Leu Ala Cys Arg Gly Pro Ser
1 5

-continued

<210> SEQ ID NO 1564
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1564

Arg Gly Pro Ser Gln Val Leu
1               5

<210> SEQ ID NO 1565
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1565

Thr Leu Gly Arg Leu Ser Ser
1               5

<210> SEQ ID NO 1566
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1566

Ala Gly Asp Arg Gly Val Ala
1               5

<210> SEQ ID NO 1567
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1567

Leu Pro Arg Arg Ala Val Phe
1               5

<210> SEQ ID NO 1568
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1568

Arg Ala Ser Cys Val Trp Arg
1               5

<210> SEQ ID NO 1569
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1569

Phe Ser Lys Met Arg Ala Ser
1               5

-continued

<210> SEQ ID NO 1570
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1570

Asp Tyr Val Gly Ala Gly Thr
1               5

<210> SEQ ID NO 1571
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1571

Ala Arg Leu Leu Arg Gly Gly
1               5

<210> SEQ ID NO 1572
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1572

Leu Leu Arg Ser Val Gly Tyr
1               5

<210> SEQ ID NO 1573
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1573

His Leu Arg Ser Gly Phe Ser
1               5

<210> SEQ ID NO 1574
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1574

Leu Leu Arg Ser Val Gly Tyr
1               5

<210> SEQ ID NO 1575
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1575

Ala Gly Arg Pro Asp Gly Val
1               5

-continued

<210> SEQ ID NO 1576
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1576

Asp Glu Asn Arg Ala Gly Leu
1               5

<210> SEQ ID NO 1577
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1577

Ala Trp Ala Gly Gly Asp Met
1               5

<210> SEQ ID NO 1578
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1578

Leu Asn Ala Gly Gly Ser Gly
1               5

<210> SEQ ID NO 1579
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1579

Asn Met Gly Ala Val Gly Ser
1               5

<210> SEQ ID NO 1580
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1580

Pro Ile Gly Ala Val Met Asn
1               5

<210> SEQ ID NO 1581
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1581

Leu Thr Gly Gly Leu Val Phe
1               5

<210> SEQ ID NO 1582

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1582

Cys Gly Glu Gly Leu Val Val
1 5

<210> SEQ ID NO 1583
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1583

Ser Asp Leu Gly Leu Arg Arg
1 5

<210> SEQ ID NO 1584
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1584

His Ala Asp Val Leu Val Ser
1 5

<210> SEQ ID NO 1585
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1585

Phe Ser Asn Ala Arg Gly Tyr
1 5

<210> SEQ ID NO 1586
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1586

Ala Ala Val Trp Trp Ala Ala
1 5

<210> SEQ ID NO 1587
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1587

Leu Asn Ala Gly Gly Ser Gly
1 5

<210> SEQ ID NO 1588
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1588

Gly Gly Ser Ala Trp Trp Gly
1 5

<210> SEQ ID NO 1589
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1589

Val Tyr Gly Trp Gly Gly Ser
1 5

<210> SEQ ID NO 1590
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1590

Gly Gly Arg Leu Leu Arg Ala
1 5

<210> SEQ ID NO 1591
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1591

Leu Gly Gly Arg Thr Ile Ser
1 5

<210> SEQ ID NO 1592
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1592

Tyr Leu Gly Leu Gly Gly Leu
1 5

<210> SEQ ID NO 1593
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1593

Ser Ile Thr Arg Gly Gly Leu
1 5

<210> SEQ ID NO 1594
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1594

Leu Thr Gly Gly Leu Val Phe
1               5

<210> SEQ ID NO 1595
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1595

Leu Gly Gly Leu Gly Leu Tyr
1               5

<210> SEQ ID NO 1596
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1596

Gly Ser Ser Glu Leu Ser Arg
1               5

<210> SEQ ID NO 1597
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1597

Gly Ser Gly Gly Ala Asn Leu
1               5

<210> SEQ ID NO 1598
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1598

Val Asp Gly Ser Gly Asp Asp
1               5

<210> SEQ ID NO 1599
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1599

Arg Ser Leu Gly Ser Val Gly
1               5

<210> SEQ ID NO 1600
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1600

Gly Arg Val Lys Pro Gly Ala
1 5

<210> SEQ ID NO 1601
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1601

Gly Gly Arg Leu Leu Arg Ala
1 5

<210> SEQ ID NO 1602
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1602

Gly Arg Leu Trp Tyr Val Ala
1 5

<210> SEQ ID NO 1603
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1603

Thr Leu Gly Arg Leu Ser Ser
1 5

<210> SEQ ID NO 1604
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1604

Gly Val Ser Gly Leu Ser Arg
1 5

<210> SEQ ID NO 1605
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1605

Tyr Gly Val Ser Arg Leu Leu
1 5

<210> SEQ ID NO 1606
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1606

Ser Arg Leu Ser Tyr Arg Ala
1 5

<210> SEQ ID NO 1607
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1607

Ile His Arg Gly Val Trp Gly
1 5

<210> SEQ ID NO 1608
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1608

Tyr Phe Arg Ala Arg Gly Ser
1 5

<210> SEQ ID NO 1609
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1609

Gly Ala Gly Arg Phe Pro His
1 5

<210> SEQ ID NO 1610
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1610

Ser Gly Ala Gly Ala Ala Phe
1 5

<210> SEQ ID NO 1611
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1611

Val Asp Val Gly Gly Ala Gly
1 5

<210> SEQ ID NO 1612
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1612

Ala Ser Ala Gly Ala Val Ser
1 5

<210> SEQ ID NO 1613
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1613

Ala Arg Tyr Ser Leu Arg Ser
1 5

<210> SEQ ID NO 1614
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1614

Arg Leu Arg Ser Tyr Val Ala
1 5

<210> SEQ ID NO 1615
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1615

Ser Arg Lys Gly Leu Arg Ser
1 5

<210> SEQ ID NO 1616
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1616

Ser Val Thr Gly Arg Val Ser
1 5

<210> SEQ ID NO 1617
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1617

Ala Gly Ser Ala Phe Trp Ala
1 5

<210> SEQ ID NO 1618
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1618

Asp Gln Gln Glu Ala Gly Ser
1 5

<210> SEQ ID NO 1619
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1619

Phe Ala Ala Gly Ala Gly Ser
1 5

<210> SEQ ID NO 1620
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1620

Gly Ala Gly Arg Phe Pro His
1 5

<210> SEQ ID NO 1621
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1621

Gly Ala Gly Gly Val Asp Val
1 5

<210> SEQ ID NO 1622
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1622

Ala Ser Ala Gly Ala Val Ser
1 5

<210> SEQ ID NO 1623
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1623

Arg Arg Asp Gly Leu Val Glu
1 5

<210> SEQ ID NO 1624
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1624

-continued

Ser Arg Lys Gly Leu Arg Ser
1               5

<210> SEQ ID NO 1625
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1625

Gly Asp Ala Thr Leu Val Ser
1               5

<210> SEQ ID NO 1626
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1626

Gly Asp Ala Thr Leu Val Ser
1               5

<210> SEQ ID NO 1627
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1627

Tyr Phe Arg Ala Arg Gly Ser
1               5

<210> SEQ ID NO 1628
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1628

Asp Arg Gly Leu Gly Met Ser
1               5

<210> SEQ ID NO 1629
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1629

Gly Ser Gly Tyr Phe Ile Thr
1               5

<210> SEQ ID NO 1630
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1630

-continued

```
Ser Val Thr Gly Arg Val Ser
1               5


<210> SEQ ID NO 1631
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1631

Val Gly Pro Ser Val His Leu
1               5


<210> SEQ ID NO 1632
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1632

Glu Gly Val Arg Gly Val Phe
1               5


<210> SEQ ID NO 1633
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1633

Gly Asp Arg Gly Val Arg Gly
1               5


<210> SEQ ID NO 1634
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1634

Met Arg Gly Val Ala Arg Lys
1               5


<210> SEQ ID NO 1635
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1635

Lys Arg Ala Val Gly Arg Met
1               5


<210> SEQ ID NO 1636
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1636

Asp Arg Ala Ser Ser Trp Ala
```

-continued 1 5

<210> SEQ ID NO 1637
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1637

Leu Gln Gly Ala Gly Ile His
1 5

<210> SEQ ID NO 1638
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1638

Trp Leu Leu Arg Gly Phe Gly
1 5

<210> SEQ ID NO 1639
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1639

Ala Ser Pro Pro Leu Arg Ser
1 5

<210> SEQ ID NO 1640
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1640

Arg Val Ser Ser Glu Thr Phe
1 5

<210> SEQ ID NO 1641
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1641

Ala Arg Ala Gly Ser Thr Phe
1 5

<210> SEQ ID NO 1642
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1642

Thr Phe Ala Gly Arg Ser Leu
1 5

-continued

<210> SEQ ID NO 1643
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1643

Tyr Ala Ala Gly Gly Ser Thr
1 5

<210> SEQ ID NO 1644
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1644

Glu Gly Val Arg Gly Val Phe
1 5

<210> SEQ ID NO 1645
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1645

Gly Asp Arg Gly Val Arg Gly
1 5

<210> SEQ ID NO 1646
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1646

Pro Gly Val Leu Arg Glu Pro
1 5

<210> SEQ ID NO 1647
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1647

Gly Leu Arg Asp Gly Val Glu
1 5

<210> SEQ ID NO 1648
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1648

Phe Pro Ala Arg Gly Glu Asp
1 5

-continued

<210> SEQ ID NO 1649
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1649

Met Leu Gly Ser Ala Ser Leu
1               5

<210> SEQ ID NO 1650
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1650

His Gly Gly Ser Asn Asp Arg
1               5

<210> SEQ ID NO 1651
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1651

Tyr Ala Ala Gly Gly Ser Thr
1               5

<210> SEQ ID NO 1652
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1652

Gln Gly Gly Arg Ser Gly Val
1               5

<210> SEQ ID NO 1653
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1653

Trp Thr Val Gly Gly Arg Val
1               5

<210> SEQ ID NO 1654
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1654

Val Lys Gly Ser Ser Met Arg
1               5

-continued

<210> SEQ ID NO 1655
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1655

Phe Val Gly Arg Val Gly Glu
1 5

<210> SEQ ID NO 1656
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1656

Gly Arg Val Gly Arg Asp Gly
1 5

<210> SEQ ID NO 1657
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1657

Ser Val Ser Arg Gly Arg Val
1 5

<210> SEQ ID NO 1658
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1658

Trp Thr Val Gly Gly Arg Val
1 5

<210> SEQ ID NO 1659
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1659

Gly Phe Gly Arg Leu Leu Trp
1 5

<210> SEQ ID NO 1660
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1660

Ala Ala Tyr Trp Gly Pro Ser
1 5

<210> SEQ ID NO 1661

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1661

Met Asp Gly Val Ser Thr Glu
1               5

<210> SEQ ID NO 1662
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1662

Val Tyr Trp Trp Gly Val Ser
1               5

<210> SEQ ID NO 1663
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1663

Arg Leu Ser Met Ala Ser Arg
1               5

<210> SEQ ID NO 1664
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1664

Gly Arg Leu Ser Phe Gly Val
1               5

<210> SEQ ID NO 1665
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1665

Gly Leu Ser Arg Gly Val Leu
1               5

<210> SEQ ID NO 1666
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1666

Leu Arg Gly Ser His Val Ala
1               5

<210> SEQ ID NO 1667
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1667

Asn Met Gly Arg Gly Ser Leu
1               5

<210> SEQ ID NO 1668
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1668

Ser Val Val Arg Arg Gly Ser
1               5

<210> SEQ ID NO 1669
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1669

Val Met Gly Ala Gly Val Gln
1               5

<210> SEQ ID NO 1670
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1670

Pro Leu Leu Arg Gln Gln Leu
1               5

<210> SEQ ID NO 1671
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1671

Ser Asn Gly Leu Arg Val Val
1               5

<210> SEQ ID NO 1672
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1672

Leu Arg Ser Met Ala Val Met
1               5

<210> SEQ ID NO 1673
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1673

Val Asp Leu Arg Ser Ala Phe
1 5

<210> SEQ ID NO 1674
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1674

Phe Arg Val Ser Leu Gly Tyr
1 5

<210> SEQ ID NO 1675
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1675

Arg Ser Ser Tyr Ala Pro Pro
1 5

<210> SEQ ID NO 1676
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1676

Phe Pro Gly Ser Ala Gly Ser
1 5

<210> SEQ ID NO 1677
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1677

Phe Ala Gly Arg Ala Pro Arg
1 5

<210> SEQ ID NO 1678
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1678

Phe Ile Ala Gly Gly Val Gly
1 5

<210> SEQ ID NO 1679
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1679

Leu Ile His Ala Gly Gly Gln
1 5

<210> SEQ ID NO 1680
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1680

Arg Ala Gly Gly Gly Ala Pro
1 5

<210> SEQ ID NO 1681
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1681

Thr Trp His Ala Gly Gly Ile
1 5

<210> SEQ ID NO 1682
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1682

Gly Val Arg Ser Ile Thr Leu
1 5

<210> SEQ ID NO 1683
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1683

Gly Leu Ser Arg Gly Val Leu
1 5

<210> SEQ ID NO 1684
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1684

Arg Val Val Gly Ala Val Leu
1 5

<210> SEQ ID NO 1685
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1685

Phe Gly Leu Arg Met Ser Asn
1 5

<210> SEQ ID NO 1686
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1686

Leu Gly Leu Arg Gly Trp Thr
1 5

<210> SEQ ID NO 1687
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1687

Ala Phe Phe Met Gly Leu Arg
1 5

<210> SEQ ID NO 1688
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1688

Ser Asn Gly Leu Arg Val Val
1 5

<210> SEQ ID NO 1689
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1689

Ala Arg Gly Thr Met Thr Gly
1 5

<210> SEQ ID NO 1690
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1690

Arg Pro Ala Arg Gly Ala Phe
1 5

<210> SEQ ID NO 1691
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1691

Ala Ser Leu Pro Met Leu His
1 5

<210> SEQ ID NO 1692
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1692

Gly Gly Ser Val Glu Gly Gln
1 5

<210> SEQ ID NO 1693
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1693

Leu Gly Gly Arg Gln Glu Ser
1 5

<210> SEQ ID NO 1694
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1694

Asn Gly Gly Arg Val Leu Ser
1 5

<210> SEQ ID NO 1695
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1695

Pro Ile Gly Gly Leu Phe Gly
1 5

<210> SEQ ID NO 1696
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1696

Ala Glu Cys Cys Gly Gly Leu
1 5

<210> SEQ ID NO 1697
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1697

Ser Glu Gln Arg Gly Gly Leu
1 5

<210> SEQ ID NO 1698
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1698

Asp Arg Phe Gly Ser Ser Ala
1 5

<210> SEQ ID NO 1699
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1699

Gly His Gly Ser Gly Ser Arg
1 5

<210> SEQ ID NO 1700
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1700

Gly Gly Ser Val Glu Gly Gln
1 5

<210> SEQ ID NO 1701
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1701

Gly Ser Val Val Ser Ser Trp
1 5

<210> SEQ ID NO 1702
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1702

Asn Gly Gly Arg Val Leu Ser
1 5

<210> SEQ ID NO 1703
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1703

-continued

Gly Arg Leu Met Pro Gly Gly
1 5

<210> SEQ ID NO 1704
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1704

Thr Trp Gly Arg Leu Gly Leu
1 5

<210> SEQ ID NO 1705
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1705

Ala Val His Ser Gly Arg Leu
1 5

<210> SEQ ID NO 1706
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1706

Gly Arg Leu Ser Phe Gly Val
1 5

<210> SEQ ID NO 1707
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1707

Pro Gln Gly Pro Ser Ser Val
1 5

<210> SEQ ID NO 1708
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1708

Ala Gly Trp Arg Leu Ser Gln
1 5

<210> SEQ ID NO 1709
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1709

-continued

```
Arg Val Asp Arg Gly Ser Leu
1               5


<210> SEQ ID NO 1710
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1710

Arg Ala Val Cys Glu Trp Asp
1               5


<210> SEQ ID NO 1711
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1711

Arg Ala Val Glu Arg Val Ala
1               5


<210> SEQ ID NO 1712
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1712

Ala Val Phe Arg Ala Ser Arg
1               5


<210> SEQ ID NO 1713
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1713

Gly Ala Gly Ser Ser Val Trp
1               5


<210> SEQ ID NO 1714
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1714

Gly Ala Gly Ser Ser Val Trp
1               5


<210> SEQ ID NO 1715
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1715

Trp Leu Leu Arg Ser Trp Ser
```

-continued 1 5

<210> SEQ ID NO 1716
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1716

Arg Lys Glu Ala Leu Arg Val
1 5

<210> SEQ ID NO 1717
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1717

Arg Leu Arg Val Ser Val Arg
1 5

<210> SEQ ID NO 1718
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1718

Leu Arg Pro Gly Leu Arg Ser
1 5

<210> SEQ ID NO 1719
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1719

Gln Arg Tyr His Leu Arg Ser
1 5

<210> SEQ ID NO 1720
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1720

Trp Leu Leu Arg Ser Trp Ser
1 5

<210> SEQ ID NO 1721
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1721

Gly Arg Glu Arg Val Ser His
1 5

<210> SEQ ID NO 1722
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1722

Arg Val Ser Val Arg Leu Arg
1 5

<210> SEQ ID NO 1723
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1723

Gly Ala Gly Ser Ser Val Trp
1 5

<210> SEQ ID NO 1724
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1724

Gly Ala Gly Ser Ser Val Trp
1 5

<210> SEQ ID NO 1725
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1725

Ala Gly Leu Trp Pro Trp Asn
1 5

<210> SEQ ID NO 1726
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1726

Gly Val Arg Gly Gly Gly Asp
1 5

<210> SEQ ID NO 1727
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1727

Gly Leu Val Arg Arg Val Val
1 5

-continued

<210> SEQ ID NO 1728
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1728

Leu Arg Pro Gly Leu Arg Ser
1 5

<210> SEQ ID NO 1729
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1729

Trp Ala His Ala Ala Ser Tyr
1 5

<210> SEQ ID NO 1730
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1730

Asp Gly Gly Gly Arg Val Gly
1 5

<210> SEQ ID NO 1731
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1731

Val Gly Val Met Gly Gly Arg
1 5

<210> SEQ ID NO 1732
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1732

Val Tyr Gly Gly Arg Ser Glu
1 5

<210> SEQ ID NO 1733
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1733

Thr Ile Cys Leu Gly Leu Gly
1 5

<210> SEQ ID NO 1734
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1734

Gly Ala Gly Ser Ser Val Trp
1 5

<210> SEQ ID NO 1735
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1735

Gly Ala Gly Ser Ser Val Trp
1 5

<210> SEQ ID NO 1736
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1736

Asp His Val Ser Gly Ser Val
1 5

<210> SEQ ID NO 1737
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1737

Asp Gly Gly Gly Arg Val Gly
1 5

<210> SEQ ID NO 1738
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1738

Gly Glu Gly Arg Leu Cys Gly
1 5

<210> SEQ ID NO 1739
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1739

Gly Val Ala Ile Gly Arg Leu
1 5

<210> SEQ ID NO 1740

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1740

Phe Gly Val Ser Gln Val His
1 5

<210> SEQ ID NO 1741
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1741

Gly Gly Val Ser Arg Met Arg
1 5

<210> SEQ ID NO 1742
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1742

Gly Arg Ile Arg Leu Ser Phe
1 5

<210> SEQ ID NO 1743
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1743

Arg Gly Val Asn Tyr Arg Ser
1 5

<210> SEQ ID NO 1744
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1744

Thr Glu Gly Thr Arg Gly Val
1 5

<210> SEQ ID NO 1745
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1745

Gly Tyr Ala Arg Gly Ser Gly
1 5

<210> SEQ ID NO 1746
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1746

Gly Val Trp Leu Arg Gly Ser
1 5

<210> SEQ ID NO 1747
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1747

Ala Ala Arg Ala Val Trp Gly
1 5

<210> SEQ ID NO 1748
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1748

Arg Ala Ser Tyr Tyr Gly Val
1 5

<210> SEQ ID NO 1749
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1749

Gly Ala Gly Val Glu Tyr Phe
1 5

<210> SEQ ID NO 1750
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1750

Leu Leu Leu Leu Ser Gly Ser
1 5

<210> SEQ ID NO 1751
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1751

Val Leu Leu Ser Ala Gly Leu
1 5

<210> SEQ ID NO 1752
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1752

Thr Gly Leu Leu Arg Leu Tyr
1               5

<210> SEQ ID NO 1753
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1753

Leu Arg Ser Ser Leu Val Ser
1               5

<210> SEQ ID NO 1754
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1754

Leu Arg Ser Ser Leu Val Ser
1               5

<210> SEQ ID NO 1755
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1755

Pro Arg Ser Ser Gly Pro Met
1               5

<210> SEQ ID NO 1756
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1756

Thr Ala Gly Arg Leu Glu Val
1               5

<210> SEQ ID NO 1757
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1757

Ala Gly Leu Glu Asp Leu Gly
1               5

<210> SEQ ID NO 1758
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1758

Met Pro Ala Gly Leu Gly Val
1               5

<210> SEQ ID NO 1759
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1759

Val Leu Leu Ser Ala Gly Leu
1               5

<210> SEQ ID NO 1760
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1760

Gly Val Arg Trp Asn Trp Ser
1               5

<210> SEQ ID NO 1761
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1761

Thr Arg Asp Gly Val Arg Trp
1               5

<210> SEQ ID NO 1762
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1762

Arg Ala His Gly Leu Val Cys
1               5

<210> SEQ ID NO 1763
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1763

Leu Gly Ser Ser Gly Leu Arg
1               5

<210> SEQ ID NO 1764
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1764

Leu Leu Val Ser Leu Ser Ser
1               5

<210> SEQ ID NO 1765
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1765

Leu Arg Ser Ser Leu Val Ser
1               5

<210> SEQ ID NO 1766
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1766

Leu Val Ser Thr Arg Trp Ala
1               5

<210> SEQ ID NO 1767
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1767

Leu Val Ser Tyr Ser Ala Val
1               5

<210> SEQ ID NO 1768
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1768

Gly Tyr Ala Arg Gly Ser Gly
1               5

<210> SEQ ID NO 1769
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1769

Leu Gly Ala Ser Leu Leu Val
1               5

<210> SEQ ID NO 1770
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1770

Gly Thr Gly Ala Ala Val Phe
1               5

<210> SEQ ID NO 1771
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1771

Ala Ala Val Gly Thr Ala Leu
1               5

<210> SEQ ID NO 1772
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1772

Val Ser Ala Ala Ser Ser Val
1               5

<210> SEQ ID NO 1773
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1773

Arg Gly Gly Ser Pro Pro Val
1               5

<210> SEQ ID NO 1774
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1774

Val Pro Pro Ser Gly Gly Arg
1               5

<210> SEQ ID NO 1775
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1775

Gly Leu Gly Ser Cys Ala Pro
1               5

<210> SEQ ID NO 1776
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1776

Met Pro Ala Gly Leu Gly Val
1 5

<210> SEQ ID NO 1777
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1777

Met Pro Gly Ser Ser Arg Pro
1 5

<210> SEQ ID NO 1778
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1778

Gly Ser Ser Leu Ser Arg Pro
1 5

<210> SEQ ID NO 1779
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1779

Arg Leu Gly Ser Ser Gly Leu
1 5

<210> SEQ ID NO 1780
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1780

Gly Tyr Ala Arg Gly Ser Gly
1 5

<210> SEQ ID NO 1781
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1781

Ser Gly Arg Leu Trp Val Gly
1 5

<210> SEQ ID NO 1782
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1782

-continued

Thr Ala Gly Arg Leu Glu Val
1 5

<210> SEQ ID NO 1783
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1783

Gly Pro Ser Phe Asp Ala Lys
1 5

<210> SEQ ID NO 1784
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1784

Ala Cys Thr Gly Val Ser Arg
1 5

<210> SEQ ID NO 1785
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1785

Leu Gly Met Gly Arg Gly Val
1 5

<210> SEQ ID NO 1786
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1786

Met Leu Gly Arg Gly Ser Val
1 5

<210> SEQ ID NO 1787
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1787

Pro Arg Ala Ser Ser Thr Gly
1 5

<210> SEQ ID NO 1788
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1788

-continued

Arg Ala Ser Cys Phe Trp Asp
1 5

<210> SEQ ID NO 1789
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1789

Arg Ala Ser Cys Phe Trp Asp
1 5

<210> SEQ ID NO 1790
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1790

Phe Leu Leu Leu Ser His Arg
1 5

<210> SEQ ID NO 1791
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1791

Leu Leu Ser Val Thr Ser Xaa
1 5

<210> SEQ ID NO 1792
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1792

Pro Leu Leu Arg Glu Val Gly
1 5

<210> SEQ ID NO 1793
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1793

Leu Arg Val Gly His Ala Gly
1 5

<210> SEQ ID NO 1794
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1794

Asn Glu Leu Arg Val Cys Arg
1 5

<210> SEQ ID NO 1795
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1795

Met Arg Tyr Glu Leu Arg Ser
1 5

<210> SEQ ID NO 1796
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1796

Arg Val Ser Val Trp Trp Ala
1 5

<210> SEQ ID NO 1797
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1797

Phe Ala Gln Arg Arg Val Ser
1 5

<210> SEQ ID NO 1798
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1798

Ser His His Arg Ser Ser Ile
1 5

<210> SEQ ID NO 1799
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1799

Cys Met Ala Gly Ser Gln Asp
1 5

<210> SEQ ID NO 1800
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1800

Arg Tyr Gly Thr Ala Gly Ser
1 5

<210> SEQ ID NO 1801
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1801

Ser Ala Gly Ser His Pro Ala
1 5

<210> SEQ ID NO 1802
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1802

Pro Asn Ser Ala Gly Ser Val
1 5

<210> SEQ ID NO 1803
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1803

Lys Met Arg Ile Ala Gly Arg
1 5

<210> SEQ ID NO 1804
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1804

Met Glu Arg Val Ala Gly Arg
1 5

<210> SEQ ID NO 1805
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1805

Trp Ala Gly Leu Ser Arg Pro
1 5

<210> SEQ ID NO 1806
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1806

-continued

Gly Ala His Gly Val Arg Leu
1 5

<210> SEQ ID NO 1807
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1807

Arg Val Pro Thr Gly Val Arg
1 5

<210> SEQ ID NO 1808
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1808

Arg Gly Ala Val Arg Glu Met
1 5

<210> SEQ ID NO 1809
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1809

Phe Asp Pro Gly Gly Leu Arg
1 5

<210> SEQ ID NO 1810
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1810

Ile Leu Ser Asp Leu Val Ser
1 5

<210> SEQ ID NO 1811
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1811

Leu Leu Asn Pro Ala Arg Gly
1 5

<210> SEQ ID NO 1812
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1812

-continued

Trp Trp Ala Ala Val Pro Gly
1 5

<210> SEQ ID NO 1813
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1813

Lys Ala Ala Ser Thr Glu Asp
1 5

<210> SEQ ID NO 1814
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1814

Ser Tyr Met Gly Ala Ala Ser
1 5

<210> SEQ ID NO 1815
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1815

Gly Gly Ser Ile Asp Cys Cys
1 5

<210> SEQ ID NO 1816
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1816

Gly Pro Gly Gly Ser Lys Arg
1 5

<210> SEQ ID NO 1817
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1817

Ala Phe Gly Gly Gly Ser Met
1 5

<210> SEQ ID NO 1818
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1818

Pro Glu Gly Gly Arg Arg Pro

-continued 1 5

<210> SEQ ID NO 1819
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1819

Gly Gly Leu Glu Gln Asp Gly
1 5

<210> SEQ ID NO 1820
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1820

Phe Asp Pro Gly Gly Leu Arg
1 5

<210> SEQ ID NO 1821
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1821

Leu Phe Gly Ser Ser Val Ser
1 5

<210> SEQ ID NO 1822
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1822

Trp Asp Gly Ser Ser Val Ser
1 5

<210> SEQ ID NO 1823
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1823

Pro Asn Ser Ala Gly Ser Val
1 5

<210> SEQ ID NO 1824
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1824

Met Leu Gly Arg Gly Ser Val
1 5

<210> SEQ ID NO 1825
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1825

Thr Arg Arg Gly Arg Leu Asp
1               5

<210> SEQ ID NO 1826
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1826

Gly Val Ser Ile Ser Asp Gly
1               5

<210> SEQ ID NO 1827
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1827

Gly Val Ser Ile Tyr Asp Leu
1               5

<210> SEQ ID NO 1828
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1828

Ala Arg Leu Ser Leu Glu Leu
1               5

<210> SEQ ID NO 1829
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1829

Arg Leu Arg Leu Ser Ser Trp
1               5

<210> SEQ ID NO 1830
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1830

Arg Arg Leu Ser Ser Ile Ala
1               5

<210> SEQ ID NO 1831
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1831

Ser Arg Leu Ser Tyr Arg Thr
1               5

<210> SEQ ID NO 1832
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1832

Ala Arg Gly Ser Trp Arg Glu
1               5

<210> SEQ ID NO 1833
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1833

Val Arg Leu Arg Ala Val Phe
1               5

<210> SEQ ID NO 1834
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1834

Arg Ala Ser Arg Ile Gly Leu
1               5

<210> SEQ ID NO 1835
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1835

Gly Ala Gly Thr Ser Glu Gly
1               5

<210> SEQ ID NO 1836
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1836

Leu Leu Ser Thr Val Trp Val
1               5

-continued

<210> SEQ ID NO 1837
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1837

Glu Leu Arg Arg Leu Leu Ser
1               5

<210> SEQ ID NO 1838
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1838

Leu Leu Arg Gly Leu Arg Pro
1               5

<210> SEQ ID NO 1839
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1839

Ser Leu Leu Arg Arg Leu Glu
1               5

<210> SEQ ID NO 1840
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1840

Leu Arg Val Ser Arg Gly Leu
1               5

<210> SEQ ID NO 1841
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1841

Thr Leu Gly Leu Arg Val Pro
1               5

<210> SEQ ID NO 1842
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1842

Phe Val Ala Arg Leu Arg Val
1               5

<210> SEQ ID NO 1843

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1843

Gly Val Tyr Trp Leu Arg Ser
1 5

<210> SEQ ID NO 1844
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1844

Ser Phe Trp Trp Leu Arg Ser
1 5

<210> SEQ ID NO 1845
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1845

Thr Arg Tyr Ser Leu Arg Ser
1 5

<210> SEQ ID NO 1846
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1846

Leu Arg Val Ser Arg Gly Leu
1 5

<210> SEQ ID NO 1847
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1847

Arg Ser Ser Ser Gly Ser Gly
1 5

<210> SEQ ID NO 1848
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1848

Thr Arg Ser Ser Leu Thr His
1 5

<210> SEQ ID NO 1849
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1849

Thr Gly Arg Ser Ser Phe Trp
1 5

<210> SEQ ID NO 1850
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1850

Asn Ala Gly Arg Gly Ala Ser
1 5

<210> SEQ ID NO 1851
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1851

His Ala Gly Leu Leu Val Val
1 5

<210> SEQ ID NO 1852
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1852

His Thr Tyr Gly Val Arg Phe
1 5

<210> SEQ ID NO 1853
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1853

Gly Ala Val Arg Ser Val Met
1 5

<210> SEQ ID NO 1854
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1854

Val Leu Val Glu Gly Ala Val
1 5

<210> SEQ ID NO 1855
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1855

Leu Leu Arg Gly Leu Arg Pro
1 5

<210> SEQ ID NO 1856
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1856

Thr Leu Gly Leu Arg Val Pro
1 5

<210> SEQ ID NO 1857
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1857

Ala Arg Gly Ser Trp Arg Glu
1 5

<210> SEQ ID NO 1858
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1858

Gly Leu Trp Ala Ala Val Leu
1 5

<210> SEQ ID NO 1859
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1859

Gly Trp Thr Met Ala Ala Ser
1 5

<210> SEQ ID NO 1860
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1860

Leu Tyr Met Gly Gly Ser His
1 5

<210> SEQ ID NO 1861
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1861

Gly Val Gly Gly Arg Gln Ser
1               5

<210> SEQ ID NO 1862
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1862

Arg Arg Gly Leu Gly Asp Ala
1               5

<210> SEQ ID NO 1863
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1863

Thr Gly Gly Leu His Trp Tyr
1               5

<210> SEQ ID NO 1864
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1864

Gly Ser Gly Ser Ser Ser Arg
1               5

<210> SEQ ID NO 1865
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1865

Gly Ser Ser Thr Leu Gln Trp
1               5

<210> SEQ ID NO 1866
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1866

Arg Ser Ser Ser Gly Ser Gly
1               5

<210> SEQ ID NO 1867
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1867

Asp Glu Leu Gly Ser Val Gln
1 5

<210> SEQ ID NO 1868
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1868

Gly Arg Leu Arg Pro Phe Ser
1 5

<210> SEQ ID NO 1869
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1869

Pro Arg Leu Gly Arg Leu Leu
1 5

<210> SEQ ID NO 1870
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1870

Val Gly Val Ser Gln Glu Trp
1 5

<210> SEQ ID NO 1871
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1871

Asp Gly Val Ser Pro Leu Trp
1 5

<210> SEQ ID NO 1872
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1872

Pro Arg Gly Ser Leu Phe Ala
1 5

<210> SEQ ID NO 1873
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1873

Val Ile Val Arg Gly Ser Leu
1 5

<210> SEQ ID NO 1874
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1874

Gly Asp Arg Ala Val Gly Leu
1 5

<210> SEQ ID NO 1875
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1875

Val His Lys Arg Ala Val Leu
1 5

<210> SEQ ID NO 1876
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1876

Gly Gly Ala Gly Ser Arg Arg
1 5

<210> SEQ ID NO 1877
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1877

Arg Leu Glu Thr Leu Leu Ser
1 5

<210> SEQ ID NO 1878
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1878

Leu Leu Arg Ala Gly Val Arg
1 5

<210> SEQ ID NO 1879
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1879

Pro Ala Ile Leu Arg Val Arg
1               5

<210> SEQ ID NO 1880
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1880

Gly Asp Leu Arg Val Ser Val
1               5

<210> SEQ ID NO 1881
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1881

Gly Asp Leu Arg Val Ser Val
1               5

<210> SEQ ID NO 1882
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1882

Gly Gly Ala Gly Ser Arg Arg
1               5

<210> SEQ ID NO 1883
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1883

Ala Gly Ser Val Thr Glu Gln
1               5

<210> SEQ ID NO 1884
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1884

Ser Ser Ser Leu Ala Gly Ser
1               5

<210> SEQ ID NO 1885
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1885

-continued

Arg Ser Trp Asn Ala Gly Arg
1 5

<210> SEQ ID NO 1886
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1886

Ala Gly Leu Pro His Arg Phe
1 5

<210> SEQ ID NO 1887
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1887

Arg Asn Ser Arg Ala Gly Leu
1 5

<210> SEQ ID NO 1888
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1888

Arg Arg Ser Gly Ala Gly Gly
1 5

<210> SEQ ID NO 1889
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1889

Ala Gly Gly Pro Ser Ser Tyr
1 5

<210> SEQ ID NO 1890
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1890

Thr Gly Val Arg Asn Ser Pro
1 5

<210> SEQ ID NO 1891
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1891

-continued

Leu Leu Arg Ala Gly Val Arg
1 5

<210> SEQ ID NO 1892
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1892

Ala Leu Val Ser Thr Ile Leu
1 5

<210> SEQ ID NO 1893
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1893

Ala Arg Gly Arg Asp Glu Gly
1 5

<210> SEQ ID NO 1894
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1894

Ala Ser Leu Ser Val Val Ile
1 5

<210> SEQ ID NO 1895
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1895

Gly Gly Ser Arg Gly Tyr Arg
1 5

<210> SEQ ID NO 1896
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1896

Tyr Trp Gly Gly Ser Val Pro
1 5

<210> SEQ ID NO 1897
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1897

Gly Gly Arg Pro Val Glu Arg

-continued 1 5

<210> SEQ ID NO 1898
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1898

Gly Gly Arg Ser Gln Glu Gly
1 5

<210> SEQ ID NO 1899
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1899

Pro Gly Gly Gly Arg Gly Arg
1 5

<210> SEQ ID NO 1900
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1900

Phe Ser Leu Gly Ser Ser Pro
1 5

<210> SEQ ID NO 1901
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1901

Gly Ser Val Phe Gly Thr Pro
1 5

<210> SEQ ID NO 1902
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1902

Ala Gly Ser Val Thr Glu Gln
1 5

<210> SEQ ID NO 1903
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1903

Tyr Trp Gly Gly Ser Val Pro
1 5

-continued

<210> SEQ ID NO 1904
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1904

Leu Ser Gly Arg Val Ile Val
1 5

<210> SEQ ID NO 1905
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1905

Leu Ser Thr Pro Gly Arg Val
1 5

<210> SEQ ID NO 1906
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1906

Ala Gly Gly Pro Ser Ser Tyr
1 5

<210> SEQ ID NO 1907
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1907

Arg Val Met Arg Gly Ser Leu
1 5

<210> SEQ ID NO 1908
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1908

Arg Ala Ser Cys Val Trp Ala
1 5

<210> SEQ ID NO 1909
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1909

Gln Leu Leu Ser Gln Val Tyr
1 5

-continued

<210> SEQ ID NO 1910
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1910

Glu Arg Tyr Tyr Leu Arg Ser
1 5

<210> SEQ ID NO 1911
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1911

Gly Leu Val Lys Leu Arg Ser
1 5

<210> SEQ ID NO 1912
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1912

Gly Arg Leu Ala Ala Gly Ser
1 5

<210> SEQ ID NO 1913
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1913

Gly Leu Val Lys Leu Arg Ser
1 5

<210> SEQ ID NO 1914
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1914

Leu Trp Phe Glu Leu Val Ser
1 5

<210> SEQ ID NO 1915
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1915

Ile Gly Ala Ala Ser Trp Phe
1 5

-continued

<210> SEQ ID NO 1916
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1916

Gly Gly Arg Arg Gly Thr Ser
1               5

<210> SEQ ID NO 1917
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1917

Arg Asp Leu Gly Gly Arg Trp
1               5

<210> SEQ ID NO 1918
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1918

Trp Arg Gly Gly Leu Asp Arg
1               5

<210> SEQ ID NO 1919
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1919

Gly Arg Trp Thr Gly Ser Ser
1               5

<210> SEQ ID NO 1920
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1920

Ser Tyr Trp Val Gly Ser Ser
1               5

<210> SEQ ID NO 1921
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1921

Gly Arg Leu Ala Ala Gly Ser
1               5

<210> SEQ ID NO 1922

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1922

Ala Lys Ala Gly Val Ser Arg
1 5

<210> SEQ ID NO 1923
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1923

Leu Arg Leu Ser Gly His Asp
1 5

<210> SEQ ID NO 1924
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1924

Arg Gly Val Gly Ala Lys Ala
1 5

<210> SEQ ID NO 1925
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1925

Leu Arg Gly Val Tyr Val Ala
1 5

<210> SEQ ID NO 1926
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1926

Gly Thr Pro Ala Val Ser Tyr
1 5

<210> SEQ ID NO 1927
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1927

Phe Leu Leu Ser Arg Ser Ala
1 5

<210> SEQ ID NO 1928
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1928

Ala Gly Leu Leu Ser Asp Val
1               5

<210> SEQ ID NO 1929
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1929

Leu Arg Val Gly Xaa Pro Gly
1               5

<210> SEQ ID NO 1930
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1930

Arg Val Ser Gly Ser Pro Val
1               5

<210> SEQ ID NO 1931
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1931

Arg Ser Ser Ile Asp Val Gly
1               5

<210> SEQ ID NO 1932
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1932

Ala Gly Arg Arg Leu Arg Asp
1               5

<210> SEQ ID NO 1933
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1933

Trp Arg Leu Ala Gly Leu Gly
1               5

-continued

<210> SEQ ID NO 1934
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1934

Pro Thr Val Ser Ala Gly Leu
1               5

<210> SEQ ID NO 1935
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1935

Ala Gly Leu Leu Ser Asp Val
1               5

<210> SEQ ID NO 1936
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1936

Thr Leu Gly Val Leu Val Thr
1               5

<210> SEQ ID NO 1937
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1937

Gly Asp Arg Arg Leu Val Ser
1               5

<210> SEQ ID NO 1938
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1938

Leu Met Leu Val Ser Gly Lys
1               5

<210> SEQ ID NO 1939
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1939

Asp Val His Ala Arg Gly Asp
1               5

-continued

<210> SEQ ID NO 1940
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1940

Arg Glu Gly Gly Ser Asp Thr
1 5

<210> SEQ ID NO 1941
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1941

Gly Gly Arg Arg Val Val Val
1 5

<210> SEQ ID NO 1942
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1942

Asn Val Gly Gly Gly Arg Phe
1 5

<210> SEQ ID NO 1943
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1943

Gly Leu Gly Ala Leu Arg Trp
1 5

<210> SEQ ID NO 1944
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1944

Leu Gly Leu Ser Gly Leu Gly
1 5

<210> SEQ ID NO 1945
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1945

Arg Gly Leu Gly Arg Pro Val
1 5

<210> SEQ ID NO 1946

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 1946

Gly Ser Ser Gly Leu Leu Ala
1               5

<210> SEQ ID NO 1947
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1947

Leu Gly Ser Ser Ser His Ile
1               5

<210> SEQ ID NO 1948
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1948

Ile Gly Ser Gly Val Gly Val
1               5

<210> SEQ ID NO 1949
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1949

Lys Gly Ser Val Leu Met Leu
1               5

<210> SEQ ID NO 1950
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1950

Val Pro Ser Gly Ser Val Arg
1               5

<210> SEQ ID NO 1951
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1951

Gly Tyr Leu Gly Arg Leu Pro
1               5

<210> SEQ ID NO 1952
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 1952

Ala Val Tyr Val Gly Arg Leu
1 5

<210> SEQ ID NO 1953
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1953

Leu Gly Gly Arg Leu Ser Leu
1 5

<210> SEQ ID NO 1954
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1954

Arg Gly Val Gly Lys Thr Lys
1 5

<210> SEQ ID NO 1955
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1955

Leu Gly Gly Ala Arg Gly Val
1 5

<210> SEQ ID NO 1956
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1956

His Ala Trp Asp Arg Gly Val
1 5

<210> SEQ ID NO 1957
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1957

Asp Trp Gly Ser Arg Gly Val
1 5

<210> SEQ ID NO 1958
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 1958

Pro Tyr Arg Arg Gly Ser Cys
1 5

<210> SEQ ID NO 1959
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1959

Ala Leu Asn Arg Gly Ser Arg
1 5

<210> SEQ ID NO 1960
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1960

Thr Phe Arg Gly Ala Gly Val
1 5

<210> SEQ ID NO 1961
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1961

Leu Leu Ser Ala Ala Arg Phe
1 5

<210> SEQ ID NO 1962
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1962

Met Arg Pro Gly Leu Arg Ser
1 5

<210> SEQ ID NO 1963
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1963

Pro Arg Val Ser Ala Leu Val
1 5

<210> SEQ ID NO 1964
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 1964

Val Arg Val Ser Leu Asn Ser
1               5

<210> SEQ ID NO 1965
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1965

Gly Arg Ser Ser Ala Gly Pro
1               5

<210> SEQ ID NO 1966
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1966

Leu His Ala Gly Ser Ser Val
1               5

<210> SEQ ID NO 1967
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1967

Val Val Met Ile Ala Gly Ser
1               5

<210> SEQ ID NO 1968
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1968

Asp Thr Pro Ala Gly Arg Leu
1               5

<210> SEQ ID NO 1969
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1969

Val Gly Ala Gly Arg Phe Thr
1               5

<210> SEQ ID NO 1970
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 1970

Ala Gly Gly Thr Asp Arg Thr
1               5

<210> SEQ ID NO 1971
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1971

Phe Ile Ser Ala Gly Gly Trp
1               5

<210> SEQ ID NO 1972
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1972

Thr Ile Pro Ala Gly Gly Gly
1               5

<210> SEQ ID NO 1973
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1973

Val Gly Arg Ala Gly Gly Leu
1               5

<210> SEQ ID NO 1974
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1974

Asn Pro Gly Leu Val Trp Asn
1               5

<210> SEQ ID NO 1975
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1975

Leu Gly Leu Val His Trp Val
1               5

<210> SEQ ID NO 1976
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 1976

Met Arg Pro Gly Leu Arg Ser
1 5

<210> SEQ ID NO 1977
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1977

Ala Arg Gly Asn Val Arg Phe
1 5

<210> SEQ ID NO 1978
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1978

Leu Gly Gly Ala Arg Gly Val
1 5

<210> SEQ ID NO 1979
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1979

Phe Arg Ala Ala Ser Leu Leu
1 5

<210> SEQ ID NO 1980
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1980

Ala Ala Ser Val Gly Val Ala
1 5

<210> SEQ ID NO 1981
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1981

Phe Arg Ala Ala Ser Leu Leu
1 5

<210> SEQ ID NO 1982
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1982

Pro Val Phe Arg Gly Gly Ser
1 5

<210> SEQ ID NO 1983
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1983

Ser Gly Gly Ser Val Gly Phe
1 5

<210> SEQ ID NO 1984
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1984

Val Arg Ala Asn Gly Gly Ser
1 5

<210> SEQ ID NO 1985
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1985

Phe His Ile Trp Gly Gly Arg
1 5

<210> SEQ ID NO 1986
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1986

Leu Gly Gly Arg Leu Ser Leu
1 5

<210> SEQ ID NO 1987
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1987

Ser Gly Gly Arg Phe Val Pro
1 5

<210> SEQ ID NO 1988
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1988

-continued

Gly Gly Gly Leu Pro Val Asp
1 5

<210> SEQ ID NO 1989
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1989

Leu Ser Leu Arg Gly Gly Leu
1 5

<210> SEQ ID NO 1990
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1990

Val Gly Arg Ala Gly Gly Leu
1 5

<210> SEQ ID NO 1991
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1991

Ala Asn Gly Ser Ser Lys Lys
1 5

<210> SEQ ID NO 1992
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1992

Asp Phe Thr Leu Gly Ser Ser
1 5

<210> SEQ ID NO 1993
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1993

Leu His Ala Gly Ser Ser Val
1 5

<210> SEQ ID NO 1994
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1994

-continued

Asn Ser Gly Ser Val Val Ser
1 5

<210> SEQ ID NO 1995
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1995

Ser Gly Gly Ser Val Gly Phe
1 5

<210> SEQ ID NO 1996
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1996

Trp Ser Ile Ser Gly Ser Val
1 5

<210> SEQ ID NO 1997
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1997

Asp Thr Pro Ala Gly Arg Leu
1 5

<210> SEQ ID NO 1998
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1998

Leu Gly Gly Arg Leu Ser Leu
1 5

<210> SEQ ID NO 1999
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1999

Ala Val Gly Val Ser Ala Ala
1 5

<210> SEQ ID NO 2000
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2000

Ser Gly Val Ser Asn Pro Gly

-continued 1 5

<210> SEQ ID NO 2001
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2001

Phe Gly Val Ser Gly Gly Ser
1 5

<210> SEQ ID NO 2002
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2002

Glu Ser Ala Thr Gly Val Ser
1 5

<210> SEQ ID NO 2003
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2003

Ala Ala Ile Val Gly Val Ser
1 5

<210> SEQ ID NO 2004
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2004

Leu Arg Ser Gly Arg Gly Ser
1 5

<210> SEQ ID NO 2005
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2005

Leu Arg Ser Gly Arg Gly Ser
1 5

<210> SEQ ID NO 2006
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2006

Arg Gly Arg Gly Ser Thr Leu
1 5

-continued

<210> SEQ ID NO 2007
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2007

Arg Gly Ser Pro Ala Ala Ala
1 5

<210> SEQ ID NO 2008
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2008

Ser Arg Gly Ser Tyr Gly Ser
1 5

<210> SEQ ID NO 2009
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2009

Gly Val Gly Gly Gly Ala Gly
1 5

<210> SEQ ID NO 2010
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2010

Leu Arg Ser Gly Arg Gly Ser
1 5

<210> SEQ ID NO 2011
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2011

Ala Gly Gly Gly Gly Tyr His
1 5

<210> SEQ ID NO 2012
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2012

Gly Ala Gly Gly Gly Val Gly
1 5

-continued

<210> SEQ ID NO 2013
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2013

Tyr Arg Ala Leu Ala Gly Gly
1 5

<210> SEQ ID NO 2014
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2014

Leu Tyr Val Asp Ala Ser Leu
1 5

<210> SEQ ID NO 2015
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2015

Gly Glu Gly Ser Gly Ser Ala
1 5

<210> SEQ ID NO 2016
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2016

Arg Val Arg Gly Val Leu Asp
1 5

<210> SEQ ID NO 2017
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2017

Ser Met Arg Gly Val Leu Ser
1 5

<210> SEQ ID NO 2018
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2018

Glu Ala Gly Pro Arg Gly Val
1 5

-continued

<210> SEQ ID NO 2019
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2019

Cys Arg Gly Ser Ile Gly Ala
1 5

<210> SEQ ID NO 2020
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2020

Pro Leu Gln Arg Gly Ser Gly
1 5

<210> SEQ ID NO 2021
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2021

Arg Gly Ser Arg Trp Ser Ser
1 5

<210> SEQ ID NO 2022
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2022

Arg Gly Ser Tyr Val Glu Arg
1 5

<210> SEQ ID NO 2023
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2023

Thr Tyr Cys Asp Arg Ala Val
1 5

<210> SEQ ID NO 2024
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2024

Leu Gly Val Arg Ala Ser Pro
1 5

<210> SEQ ID NO 2025

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 2025

Trp Arg Ala Ser Pro Gly Met
1               5

<210> SEQ ID NO 2026
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2026

Pro Arg Ala Ser Asp Ile Leu
1               5

<210> SEQ ID NO 2027
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2027

Arg Val Gly Ala Gly Trp Pro
1               5

<210> SEQ ID NO 2028
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2028

Leu Leu Ser Arg Ala Gln Ala
1               5

<210> SEQ ID NO 2029
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2029

Ser Ala Leu Arg Val Gly Leu
1               5

<210> SEQ ID NO 2030
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2030

Val Gly Leu Arg Val Arg Phe
1               5

<210> SEQ ID NO 2031
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 2031

Tyr Gly Leu Arg Ser Leu Val
1 5

<210> SEQ ID NO 2032
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2032

Thr Arg Val Ser Gly Ser Gly
1 5

<210> SEQ ID NO 2033
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2033

Val Arg Arg Ser Ser Lys Phe
1 5

<210> SEQ ID NO 2034
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2034

Thr Phe Ala Gly Leu Ala Gln
1 5

<210> SEQ ID NO 2035
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2035

Leu Gly Val Arg Ala Ser Pro
1 5

<210> SEQ ID NO 2036
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2036

Leu Gly Val Arg Leu Ala Ser
1 5

<210> SEQ ID NO 2037
<211> LENGTH: 7
<212> TYPE: PRT

<213> ORGANISM: Artificial Sequence
<220> FEATURE:
<223> OTHER INFORMATION: Synthetic peptide

<400> SEQUENCE: 2037

Pro Trp Gly Ala Gly Val Arg
1               5

<210> SEQ ID NO 2038
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2038

Gly Val Leu Thr Ile Gly Ala
1               5

<210> SEQ ID NO 2039
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2039

Arg Val Arg Gly Val Leu Asp
1               5

<210> SEQ ID NO 2040
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2040

Ile Gly Trp Gly Val Leu Gly
1               5

<210> SEQ ID NO 2041
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2041

Ser Met Arg Gly Val Leu Ser
1               5

<210> SEQ ID NO 2042
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2042

Gly Ala Val Leu Thr Ser Cys
1               5

<210> SEQ ID NO 2043
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2043

Gly Leu Val Ser Thr Leu Ile
1 5

<210> SEQ ID NO 2044
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2044

Gly Leu Val Gly Trp Gly Ile
1 5

<210> SEQ ID NO 2045
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2045

Val Gly Leu Arg Cys Ser Val
1 5

<210> SEQ ID NO 2046
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2046

Val Gly Leu Arg Val Arg Phe
1 5

<210> SEQ ID NO 2047
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2047

Tyr Gly Leu Arg Ser Leu Val
1 5

<210> SEQ ID NO 2048
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2048

Gly Leu Val Ser Thr Leu Ile
1 5

<210> SEQ ID NO 2049
<211> LENGTH: 7
<212> TYPE: PRT
<213> ORGANISM: Artificial Sequence
<220> FEATURE:

-continued

<223> OTHER INFORMATION: Synthetic peptide

<400> SEQUENCE: 2049

Pro Arg Gly Met Ala Arg Gly
1 5

<210> SEQ ID NO 2050
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2050

Arg Gly Gly Ser Asp Glu Ala
1 5

<210> SEQ ID NO 2051
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2051

Ala Glu Asp Ser Gly Gly Arg
1 5

<210> SEQ ID NO 2052
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2052

Gly Gly Arg Cys Gly Ala Glu
1 5

<210> SEQ ID NO 2053
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2053

Gly Gly Leu Met Pro Arg Tyr
1 5

<210> SEQ ID NO 2054
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2054

Gly Ser Ser Val Ser Leu Gly
1 5

<210> SEQ ID NO 2055
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 2055

Gly Ser Gly Arg Gln Leu Pro
1               5

<210> SEQ ID NO 2056
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2056

Arg Lys Gly Ser Gly Thr Ala
1               5

<210> SEQ ID NO 2057
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2057

Thr Arg Val Ser Gly Ser Gly
1               5

<210> SEQ ID NO 2058
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2058

Gly Ser Gly Ser Val Arg Thr
1               5

<210> SEQ ID NO 2059
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2059

Asp Asp Gly Arg Val His Arg
1               5

<210> SEQ ID NO 2060
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2060

Asp Leu Val Gly Arg Val Arg
1               5

<210> SEQ ID NO 2061
<211> LENGTH: 7
<212> TYPE: PRT
<213> ORGANISM: Artificial Sequence
<220> FEATURE:
<223> OTHER INFORMATION: Synthetic peptide -continued

<400> SEQUENCE: 2061

Trp Gly Arg Leu Glu Ser Thr
1               5

<210> SEQ ID NO 2062
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2062

Met Gly Pro Ser Ala Arg Trp
1               5

<210> SEQ ID NO 2063
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2063

Ile Ser Gly Val Ser Asp Asp
1               5

<210> SEQ ID NO 2064
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2064

Gly His Ser Glu Arg Leu Ser
1               5

<210> SEQ ID NO 2065
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2065

Glu Arg Gly Val Phe Val Tyr
1               5

<210> SEQ ID NO 2066
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2066

Thr Arg Gly Val Ile Gly Gly
1               5

<210> SEQ ID NO 2067
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2067

-continued

Arg Gly Ser Phe Gly Leu Gly
1               5

<210> SEQ ID NO 2068
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2068

Pro Phe His Arg Arg Ala Val
1               5

<210> SEQ ID NO 2069
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2069

Val Gly Ile Gly Ala Gly Gly
1               5

<210> SEQ ID NO 2070
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2070

Ala Val Ser Leu Ala Trp Gln
1               5

<210> SEQ ID NO 2071
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2071

Phe Pro Ala Val Ser Thr Glu
1               5

<210> SEQ ID NO 2072
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2072

Ser Gly Ala Arg Leu Arg Ser
1               5

<210> SEQ ID NO 2073
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2073

-continued

Ser His Arg Ser Ser Thr Gly
1 5

<210> SEQ ID NO 2074
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2074

Ser Arg Leu Arg Ala Gly Ser
1 5

<210> SEQ ID NO 2075
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2075

Ser Phe Ala Gly Arg Ile Leu
1 5

<210> SEQ ID NO 2076
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2076

Arg Val Ala Ala Gly Gly Leu
1 5

<210> SEQ ID NO 2077
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2077

Val Gly Ile Gly Ala Gly Gly
1 5

<210> SEQ ID NO 2078
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2078

Val Gly Ile Gly Ala Gly Gly
1 5

<210> SEQ ID NO 2079
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2079

Gln Lys Pro Gly Ala Val Gly

-continued 1 5

<210> SEQ ID NO 2080
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2080

Leu Gly Tyr Tyr Gly Ala Val
1 5

<210> SEQ ID NO 2081
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2081

Leu Pro Leu Gly Leu Val Ser
1 5

<210> SEQ ID NO 2082
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2082

Leu Gly Leu Val Phe Thr Arg
1 5

<210> SEQ ID NO 2083
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2083

Leu Pro Leu Gly Leu Val Ser
1 5

<210> SEQ ID NO 2084
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2084

Asn Ser Lys Pro Leu Val Ser
1 5

<210> SEQ ID NO 2085
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2085

Thr Asn Arg Phe Ala Arg Gly
1 5

<210> SEQ ID NO 2086
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2086

Leu Ala Ser Leu Ala Arg Pro
1 5

<210> SEQ ID NO 2087
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2087

Leu Gly Gly Ala Ala Val Arg
1 5

<210> SEQ ID NO 2088
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2088

Ala Ala Ser Pro His Pro Gly
1 5

<210> SEQ ID NO 2089
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2089

Leu Ser Lys Gly Gly Ser Glu
1 5

<210> SEQ ID NO 2090
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2090

Gly Leu Gly Arg Ser Val Asn
1 5

<210> SEQ ID NO 2091
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2091

Pro Gly Leu Gly Tyr Ala Leu
1 5

-continued

<210> SEQ ID NO 2092
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2092

Arg Gly Ser Phe Gly Leu Gly
1 5

<210> SEQ ID NO 2093
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2093

Gly Arg Asp Trp Gly Gly Leu
1 5

<210> SEQ ID NO 2094
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2094

Arg Val Ala Ala Gly Gly Leu
1 5

<210> SEQ ID NO 2095
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2095

Thr Val Gly Ser Ser Leu Gly
1 5

<210> SEQ ID NO 2096
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2096

Gly Arg Val Asp Pro Val Asp
1 5

<210> SEQ ID NO 2097
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2097

Ser Leu Tyr Arg Gly Arg Leu
1 5

-continued

<210> SEQ ID NO 2098
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2098

Val Ala Leu Gly Val Ser Ser
1 5

<210> SEQ ID NO 2099
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2099

Val Ser Val Thr Arg Leu Ser
1 5

<210> SEQ ID NO 2100
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2100

Ala Gly Ala Thr Arg Gly Ser
1 5

<210> SEQ ID NO 2101
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2101

Arg Arg Gly Ser Val Ala Glu
1 5

<210> SEQ ID NO 2102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2102

Phe Arg Phe Val Arg Gly Ser
1 5

<210> SEQ ID NO 2103
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2103

Thr Arg Gly Ser Gly Ala Gly
1 5

<210> SEQ ID NO 2104

-continued

<211> LENGTH: 7
<212> TYPE: PRT
<213> ORGANISM: Artificial Sequence
<220> FEATURE:
<223> OTHER INFORMATION: Synthetic peptide

<400> SEQUENCE: 2104

Gly Ala Arg Ala Val Ala Pro
1               5

<210> SEQ ID NO 2105
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2105

Thr Arg Gly Ser Gly Ala Gly
1               5

<210> SEQ ID NO 2106
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2106

Glu Ala Val Ser Gly Arg Arg
1               5

<210> SEQ ID NO 2107
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2107

Pro Val Arg Arg Val Ser Ser
1               5

<210> SEQ ID NO 2108
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2108

Ile Arg Val Ser Ala Val Val
1               5

<210> SEQ ID NO 2109
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2109

His Val Arg Ser Ser Tyr Ala
1               5

<210> SEQ ID NO 2110
<211> LENGTH: 7

-continued

<212> TYPE: PRT
<213> ORGANISM: Artificial Sequence
<220> FEATURE:
<223> OTHER INFORMATION: Synthetic peptide

<400> SEQUENCE: 2110

Arg Val Arg Ser Ser Leu Ala
1 5

<210> SEQ ID NO 2111
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2111

Thr Ala Ala Gly Ser Ser Phe
1 5

<210> SEQ ID NO 2112
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2112

Gly Ala Gly Ser Gly Arg Thr
1 5

<210> SEQ ID NO 2113
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2113

Pro Ala Val Ala Gly Ser Thr
1 5

<210> SEQ ID NO 2114
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2114

Ala Gly Arg His Leu Asp Ala
1 5

<210> SEQ ID NO 2115
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2115

Asp Arg Gln Leu Ala Gly Arg
1 5

<210> SEQ ID NO 2116
<211> LENGTH: 7
<212> TYPE: PRT

-continued

<213> ORGANISM: Artificial Sequence
<220> FEATURE:
<223> OTHER INFORMATION: Synthetic peptide

<400> SEQUENCE: 2116

Leu Gly Val Arg Glu Val Gly
1 5

<210> SEQ ID NO 2117
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2117

Val Ala Val Gly Val Arg Ser
1 5

<210> SEQ ID NO 2118
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2118

Ser Phe Gly Val Leu Ser Gly
1 5

<210> SEQ ID NO 2119
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2119

Thr Ser Gly Ala Val Ala Pro
1 5

<210> SEQ ID NO 2120
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2120

Gly Leu Arg Glu Val Gln Asp
1 5

<210> SEQ ID NO 2121
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2121

Ser Leu Val Ser Glu Arg Ala
1 5

<210> SEQ ID NO 2122
<211> LENGTH: 7
<212> TYPE: PRT
<213> ORGANISM: Artificial Sequence -continued
<220> FEATURE:
<223> OTHER INFORMATION: Synthetic peptide

<400> SEQUENCE: 2122

Ser Val His Leu Val Ser Gly
1 5

<210> SEQ ID NO 2123
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2123

Thr Gln Val Glu Ala Arg Gly
1 5

<210> SEQ ID NO 2124
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2124

Gly Gly Arg Pro Thr Val Thr
1 5

<210> SEQ ID NO 2125
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2125

Val Val Gly Gly Arg Arg Thr
1 5

<210> SEQ ID NO 2126
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2126

Gly Val Gly Gly Leu Ser Ser
1 5

<210> SEQ ID NO 2127
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2127

Thr Ala Ala Gly Ser Ser Phe
1 5

<210> SEQ ID NO 2128
<211> LENGTH: 7
<212> TYPE: PRT
<213> ORGANISM: Artificial Sequence
<220> FEATURE:

<223> OTHER INFORMATION: Synthetic peptide

<400> SEQUENCE: 2128

Thr Arg Gly Ser Gly Ala Gly
1 5

<210> SEQ ID NO 2129
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2129

Arg Arg Gly Ser Val Ala Glu
1 5

<210> SEQ ID NO 2130
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2130

Gly Ser Val Leu His Val Ser
1 5

<210> SEQ ID NO 2131
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2131

Ser Gly Arg Val Phe Arg Phe
1 5

<210> SEQ ID NO 2132
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2132

Trp Ser Ala Thr Gly Val Ser
1 5

<210> SEQ ID NO 2133
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2133

Cys Ala Gly Leu Ser Gly Gly Thr Cys
1 5

<210> SEQ ID NO 2134
<211> LENGTH: 9
<212> TYPE: PRT
<213> ORGANISM: Artificial Sequence
<220> FEATURE:
<223> OTHER INFORMATION: Synthetic peptide -continued

<400> SEQUENCE: 2134

Cys Ser Gly Ile Gly Ser Gly Gly Cys
1 5

<210> SEQ ID NO 2135
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2135

Cys Ser Ser Gly Gly Val Leu Gly Cys
1 5

<210> SEQ ID NO 2136
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2136

Cys Ser Trp Gly Ser Gly Gly Ser Cys
1 5

<210> SEQ ID NO 2137
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2137

Cys Thr Leu Val Leu Gly Gly Ser Cys
1 5

<210> SEQ ID NO 2138
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2138

Cys Arg Phe Glu Ser Ser Gly Gly Cys
1 5

<210> SEQ ID NO 2139
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2139

Cys His Val Ser Gly Gly Ser Gly Cys
1 5

<210> SEQ ID NO 2140
<211> LENGTH: 9
<212> TYPE: PRT
<213> ORGANISM: Artificial Sequence -continued

```
<220> FEATURE:
<223> OTHER INFORMATION: Synthetic peptide

<400> SEQUENCE: 2140

Cys Thr Gly Gly Ser Leu Gly Ala Cys
1               5
```